(12) United States Patent
Blum et al.

(10) Patent No.: US 11,938,218 B2
(45) Date of Patent: *Mar. 26, 2024

(54) HIGH DENSITY PEPTIDE POLYMERS

(71) Applicant: The Regents of the University of California, Oakland, CA (US)

(72) Inventors: Angela P. Blum, San Diego, CA (US); Jacquelin K. Kammeyer, San Diego, CA (US); Nathan C. Gianneschi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/160,588

(22) Filed: Jan. 28, 2021

(65) Prior Publication Data

US 2021/0283054 A1 Sep. 16, 2021

Related U.S. Application Data

(63) Continuation of application No. 15/502,166, filed as application No. PCT/US2015/044515 on Aug. 10, 2015, now Pat. No. 10,980,744.

(60) Provisional application No. 62/035,313, filed on Aug. 8, 2014.

(51) Int. Cl.
| | |
|---|---|
| *A61K 9/107* | (2006.01) |
| *A61K 9/14* | (2006.01) |
| *A61K 47/42* | (2017.01) |
| *A61K 47/58* | (2017.01) |
| *C07K 14/00* | (2006.01) |
| *C08G 61/08* | (2006.01) |

(52) U.S. Cl.
CPC ............ *A61K 9/1075* (2013.01); *A61K 9/146* (2013.01); *A61K 47/42* (2013.01); *A61K 47/58* (2017.08); *C07K 14/001* (2013.01); *C08G 61/08* (2013.01); *C08G 2261/126* (2013.01); *C08G 2261/1424* (2013.01); *C08G 2261/1432* (2013.01); *C08G 2261/148* (2013.01); *C08G 2261/164* (2013.01); *C08G 2261/1644* (2013.01); *C08G 2261/1646* (2013.01); *C08G 2261/3324* (2013.01); *C08G 2261/334* (2013.01); *C08G 2261/418* (2013.01); *C08G 2261/80* (2013.01); *C08G 2261/90* (2013.01); *C08G 2261/94* (2013.01)

(58) Field of Classification Search
CPC ...... A61K 9/1075; A61K 9/146; A61K 47/42; A61K 47/58; C07K 14/001; C08G 61/08; C08G 2261/126; C08G 2261/1424; C08G 2261/1432; C08G 2261/148; C08G 2261/164; C08G 2261/1644; C08G 2261/1646; C08G 2261/3324; C08G 2261/334; C08G 2261/418; C08G 2261/80; C08G 2261/90; C08G 2261/94

See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,034,506 | A | 7/1991 | Summerton et al. |
| 5,212,162 | A | 5/1993 | Missel et al. |
| 5,235,033 | A | 8/1993 | Summerton et al. |
| 5,403,841 | A | 4/1995 | Lang et al. |
| 5,830,658 | A | 11/1998 | Gryaznov |
| 6,306,993 | B1 | 10/2001 | Rothbard et al. |
| 8,232,360 | B2 | 7/2012 | Sampson et al. |
| 9,040,626 | B2 | 5/2015 | Chien et al. |
| 10,980,744 | B2 | 4/2021 | Blum et al. |
| 2003/0113740 | A1 | 6/2003 | Mirkin et al. |
| 2011/0166063 | A1 | 7/2011 | Bossard et al. |
| 2011/0251363 | A1 | 10/2011 | Sampson et al. |
| 2012/0149843 | A1 | 6/2012 | Chien et al. |
| 2014/0105896 | A1 | 4/2014 | Cload et al. |
| 2017/0327633 | A1 | 11/2017 | Rush et al. |
| 2018/0042843 | A1 | 2/2018 | Blum et al. |
| 2018/0092845 | A1* | 4/2018 | Gianneschi ............... A61P 9/04 |
| 2021/0301078 | A1* | 9/2021 | Rush .................... C07K 14/003 |

FOREIGN PATENT DOCUMENTS

| | | |
|---|---|---|
| WO | WO 2016/018917 | 2/2016 |
| WO | WO 2016/023036 | 2/2016 |
| WO | WO 2021/030326 | 2/2021 |

OTHER PUBLICATIONS

Hahn et al. Polymerization of a peptide-based enzyme substrate. Chem. Commun., 2013, vol. 49, pp. 2873-2875. (Year: 2013).*

Al-Muhammed et al. (1996) "In-vivo studies on dexamethasone sodium phosphate liposomes," J. Microencapsul. 13(3): 293-305.

Barbieri et al. (2013) "Peptide Receptor Targeting in Cancer: The Somatostatin Paradigm," Int. J. Pept. 2013, 926295: 20 pp.

Belitsky et al. (2002) "Cellular uptake of N-methylpyrrole/N-methylimidazole polyamide-dye conjugates," Bioorg. Med. Chem. 10(10): 3313-3318.

Berge et al. (1977) "Pharmaceutical Salts," Journal of Pharmaceutical Science 66(1): 1-19.

Bertin et al. (2005) "High-density doxorubicin-conjugated polymeric nanoparticles via ring-opening metathesis polymerization," Chem. Commun., issue 30: 3793-3795.

Biron et al. (2008) "Improving Oral Bioavailability of Peptides by Multiple N-Methylation: Somatostatin Analogues," Angew. Chem., Int. Ed. 47(14): 2595-2599.

Blackwell et al. (1998) "Highly Efficient Synthesis of Covalently Cross-Linked Peptide Helices by Ring-Closing Metathesis," Angew. Chem., Int. Ed. 37(23): 3281-3284.

Blum et al. (2019) "Peptide Brush Polymers for Efficient Delivery of a Gene Editing Protein to Stem Cells," Angew. Chem. Int. Ed. 58: 15646-15649.

(Continued)

*Primary Examiner* — Marcela M Cordero Garcia

(74) *Attorney, Agent, or Firm* — Leydig, Voit & Mayer, Ltd.

(57) ABSTRACT

Described herein, inter alia, are peptide containing polymers, and methods of making and using the same.

28 Claims, 46 Drawing Sheets

Specification includes a Sequence Listing.

(56) References Cited

OTHER PUBLICATIONS

Blum et al. (Oct. 2014) "Peptides Displayed as High Density Brush Polymers Resist Proteolysis and Retain Bioactivity," J. Am. Chem. Soc. 136: 15422-15437.
Bolli et al. (1994) "α-Bicyclo-DNA: Synthesis, Characterization, and Pairing Properties of α-DNA-Analogues with Restricted Conformational Flexibility in the Sugar—Phosphate Backbone," Chapter 7 in Carbohydrate Modifications in Antisense Research, Sanghvi and Cook, eds. pp. 100-117.
Brinckerhoff et al. (1999) "Terminal modifications inhibit proteolytic degradation of an immunogenic mart-127-35 peptide: Implications for peptide vaccines," Int. J. Cancer 83(3): 326-334.
Bulte et al. (2004) "Iron oxide MR contrast agents for molecular and cellular imaging," NMR Biomed. 17(7): 484-499.
Burke et al. (2010) "Synthesis and Characterization of Biodegradable HPMA-Oligolysine Copolymers for Improved Gene Delivery," Bioconjugate Chem. 21(1): 140-150.
Busseron et al. (May 2013) "Supramolecular self-assemblies as functional nanomaterials," Nanoscale 5: 7098-7140.
Cardarelli (2011) "Quantitative Analysis of Tat Peptide Binding to Import Carriers Reveals Unconventional Nuclear Transport Properties," The Journal of Biological Chemistry 286(14): 12292-12299.
Cartier et al. (2002) "Utilization of synthetic peptides containing nuclear localization signals for nonviral gene transfer systems," Gene Ther. 9: 157-167.
Chatterjee et al. (2008) "N-Methylation of Peptides: A New Perspective in Medicinal Chemistry," Acc. Chem. Res. 41(10): 1331-1342.
Chien et al. (2012) "Fluorogenic enzyme-responsive micellar nanoparticles," Chem. Sci. 3(9): 2690-2694.
Chien et al. (Dec. 2013) "Enzyme-Directed Assembly of Nanoparticles in Tumors Monitored by in Vivo Whole Animal Imaging and ex Vivo Super-Resolution Fluorescence Imaging," J. Am. Chem. Soc. 135(50): 18710-18713.
Chien et al. (publicly available May 2013) "Enzyme-Directed Assembly of a Nanoparticle Probe in Tumor Tissue," Adv. Mater. (Jul. 2013), 25(26): 3599-3604.
Chonn et al. (1995) "Recent advances in liposomal drug-delivery systems," Curr. Opin. Biotechnol. 6:698-708.
Chu et al. (2012) "Cathepsin B-sensitive polymers for compartment-specific degradation and nucleic acid release," J. Controlled Release 157(3): 445-454.
Conrad et al. (2009) "Tunable, Temperature-Responsive Polynorbornenes with Side Chains Based on an Elastin Peptide Sequence," Angew. Chem. Int. Edit. 48(44): 8328-8330.
Craik et al. (publicly available Dec. 2012) "The Future of Peptide-based Drugs," Chem. Biol. Drug Des. (Jan. 2013), 81(1): 136-147.
Darden et al. (1993) "Particle mesh Ewald: An N•log(N) method for Ewald sums in large systems," J. Chem. Phys. 98(12): 10089-10092.
Doherty et al. (2009) "Mechanisms of Endocytosis," Annu. Rev. Biochem. 78: 31.1-31.46 and Supplementary Information (69 pp. total).
Escriou et al. (2003) "NLS bioconjugates for targeting therapeutic genes to the nucleus," Adv. Drug Delivery Rev. 55(2): 295-306.
Essmann et al. (1995) "A smooth particle mesh Ewald method," J. Chem. Phys. 103(19): 8577-8593.
Eyles et al. (1997) "Oral Delivery and Fate of Poly(lactic acid) Microsphere-encapsulated Interferon in Rats," J. Pharm. Pharmacol. 49: 669-674.
Falciani et al. (2007) "Molecular Basis of Branched Peptides Resistance to Enzyme Proteolysis," Chem. Biol. Drug Des. 69(3): 216-221.
Frankel et al. (1988) "Cellular uptake of the tat protein from human immunodeficiency virus," Cell 55(6): 1189-1193.
Futaki et al. (2001) "Arginine-rich Peptides: an Abundant Source of Membrane-Permeable Peptides Having Potential as Carriers for Intracellular Protein Delivery," J. Biol. Chem. 276(8): 5836-5840.

Gao et al. (1995) "Controlled Release of a Contraceptive Steroid from Biodegradable and Injectable Gel Formulations: In Vitro Evaluation," Pharm. Res. 12(6): 857-863.
Gordon et al. (2001) "Inhibition of β-Amyloid(40) Fibrillogenesis and Disassembly of β-Amyloid(40) Fibrils by Short β-Amyloid Congeners Containing N-Methyl Amino Acids at Alternate Residues," Biochemistry 40(28): 8237-8245.
Green et al. (1988) "Autonomous functional domains of chemically synthesized human immunodeficiency virus tat trans-activator protein," Cell 55(6): 1179-1188.
Hahn et al. (Apr. 2013) "Polymerization of a peptide-based enzyme substrate," Chem Commun (Camb) 49(28): 2873-2875 (8 pp.).
Hamamoto et al. (2002) "Antimicrobial Activity and Stability to Proteolysis of Small Linear Cationic Peptides with D-Amino Acid Substitutions," Microbiol. Immunol. 46(11): 741-749.
Hanover et al. (1984) "Kinetics of transit of transferrin and epidermal growth factor through clathrin-coated membranes," Cell 39(2): 283-293.
Heitz et al. (2009) "Twenty years of cell-penetrating peptides: from molecular mechanisms to therapeutics," Br. J. Pharmacol. 157(2): 195-206.
Henikoff et al. (1992) "Amino acid substitution matrices from protein blocks," Proc. Nat'l Acad. Sci. USA 89(22):10915-10919.
Herdewijn et al. (1994) "Hexopyranosyl-Like Oligonucleotides," Chapter 6 in Carbohydrate Modifications in Antisense Research, Sanghvi and Cook, eds. pp. 80-99.
Huh et al. (2005) "In Vivo Magnetic Resonance Detection of Cancer by Using Multifunctional Magnetic Nanocrystals," J. Am. Chem. Soc. 127(35): 12387-12391.
Humphrey et al. (1996) "VMD: Visual Molecular Dynamics," J. Malec. Graphics 14: 33-38.
Jakalian et al. (2000) "Fast, efficient generation of high-quality atomic charges. AM1-BCC model: I. Method," J. Comput. Chem. 21(2): 132-146.
Jakalian et al. (2002) "Fast, efficient generation of high-quality atomic charges. AM1-BCC model: II. Parameterization and validation," J. Comput. Chem. 23(16): 1623-1641.
James et al. (Jul. 2014) "Poly(oligonucleotides)," Journal of the American Chemical Society 136: 11216-11219.
Johnson et al. (2010) "Drug-Loaded, Bivalent-Bottle-Brush Polymers by Graft-through ROMP," Macromolecules 43(24): 10326-10335.
Johnson et al. (2010) "Synthesis of Statistical Copolymers Containing Multiple Functional Peptides for Nucleic Acid Delivery," Biomacromolecules 11(11): 3007-3013.
Johnson et al. (2011) "Core-Clickable PEG-Branch-Azide Bivalent-Bottle-Brush Polymers by ROMP: Grafting-Through and Clicking-To," J. Am. Chem. Soc. 133(3): 559-566.
Jun et al. (2005) "Nanoscale Size Effect of Magnetic Nanocrystals and Their Utilization for Cancer Diagnosis via Magnetic Resonance Imaging," J. Am. Chem. Soc. 127(16): 5732-5733.
Kammeyer et al. (May 2013) "Polymerization of protecting-group-free peptides via ROMP," Polymer Chemistry 4(14): 3929-3933.
Kaplan et al. (2005) "Cationic TAT peptide transduction domain enters cells by macropinocytosis," J. Controlled Release 102(1): 247-253.
Kaspar et al. (Sep. 2013) "Future directions for peptide therapeutics development," Drug Discovery Today 18(17-18): 807-817.
Kim et al. (2011) "Synthesis of all-hydrocarbon stapled α-helical peptides by ring-closing olefin metathesis," Nat. Protoc. 6(6): 761-771.
Kolonko et al. (2008) "A Polymeric Domain That Promotes Cellular Internalization," J. Am. Chem. Soc. 130(17): 5626-5627.
Kolonko et al. (2009) "General Synthetic Route to Cell-Permeable Block Copolymers via Romp," J. Am. Chem. Soc. 131(21): 7327-7333.
Koren et al. (2012) "Cell-penetrating peptides: breaking through to the other side," Trends Mol. Med. 18(7): 385-393.
Ku et al. (2011) "Controlling and Switching the Morphology of Micellar Nanoparticles with Enzymes," J. Am. Chem. Soc. 133: 8392-8395.
Lange et al. (2007) "Classical Nuclear Localization Signals: Definition, Function, and Interaction with Importin α," J. Biol. Chem. 282(8): 5101-5105.

(56) References Cited

OTHER PUBLICATIONS

Lee et al. (2003) "N-Terminal Site-Specific Mono-PEGylation of Epidermal Growth Factor," Pharm. Res. 20(5): 818-825.
Lei et al. (1995) "Structure-Function Analysis of Human Glucose-6-phosphatase, the Enzyme Deficient in Glycogen Storage Disease Type 1a," J. Biol. Chem. 270(20): 11882-11886.
Leicher et al. (1998) "Coexpression of the KCNA3B Gene Product with Kv1.5 Leads to a Novel A-type Potassium Channel," J. Biol. Chem. 273(52):35095-35101.
Li et al. (2002) "Preparation and characterization of PEGylated adducts of recombinant human tumor necrosis factor-α from *Escherichia coli*," Biotechnol. 92(3): 251-258.
Lindorff-Larsen et al. (2010) "Improved side-chain torsion potentials for the Amber ff99SB protein force field," Proteins 78(8): 1950-1958.
Livant et al. (2000) "The PHSRN sequence induces extracellular matrix invasion and accelerates wound healing in obese diabetic mice," J. Clin. Invest. 105(11):1537-1545.
Lopez et al. (2011) "Molecular Mechanism of Cyclodextrin Mediated Cholesterol Extraction," PLoS Comp. Biol. 7(3): e1002020, pp. 1-11.
Lu et al. (2009) "One-Pot Synthesis of Brush-Like Polymers via Integrated Ring-Opening Metathesis Polymerization and Polymerization of Amino Acid N-Carboxyanhydrides," JACS 131(38): 13582-13583.
Matson et al. (2010) "Monotelechelic Poly(oxa)norbornenes by Ring-Opening Metathesis Polymerization using Direct End-Capping and Cross Metathesis," Macromolecules 43(1): 213-221.
Maynard et al. (2000) "Synthesis of Norbornenyl Polymers with Bioactive Oligopeptides by Ring-Opening Metathesis Polymerization," Macromolecules 33(17):6239-6248.
Maynard et al. (2001) "Inhibition of Cell Adhesion to Fibronectin by Oligopeptide-Substituted Polynorbornenes," J. Am. Chem. Soc. 123(7): 1275-1279.
McGregor (2008) "Discovering and improving novel peptide therapeutics," Curr. Opin. Pharmacol. 8(5): 616-619.
Miller et al. (1994) "Proteolytic studies of homologous peptide and N-substituted glycine peptoid oligomers," Bioorg. Med. Chem. Lett. 4(22): 2657-2662.
Mitchell et al. (2000) "Polyarginine enters cells more efficiently than other polycationic homopolymers," J. Pept. Res. 56(5): 318-325.
Monfardini et al. (1995) "A Branched Monomethoxypoly(ethylene glycol) for Protein Modification," Bioconjugate Chem. 6(1): 62-69.
Murata et al. (1997) "Syntheses and Radical Polymerization Behavior of Methacrylamides Having Peptide Moieties: Effect of the Methylene Chain Introduced between the Methacrylamide and Peptide Moieties on the Polymerizability and Polymer Structure," Macromolecules 30(10): 2902-2906.
Nakase et al. (2004) "Cellular Uptake of Arginine-Rich Peptides: Roles for Macropinocytosis and Actin Rearrangement," Mol. Ther. 10(6): 1011-1022.
Needleman et al. (1970) "A general method applicable to the search for similarities in the amino acid sequence of two proteins," J. Mol. Biol. 48: 443-453.
Nischan et al. (publicly available Aug. 2013) "Stabilization of Peptides for Intracellular Applications by Phosphoramidate-Linked Polyethylene Glycol Chains," Angew. Chem., Int. Ed. (Nov. 2013), 52(45): 11920-11924.
O'Brien-Simpson et al. (1997) "Polymerization of Unprotected Synthetic Peptides: A View toward Synthetic Peptide Vaccines," J. Am. Chem. Soc. 119(6): 1183-1188.
Osapay et al. (1997) "Lanthionine-somatostatin analogs: synthesis, characterization, biological activity, and enzymatic stability studies," J. Med. Chem. 40(14): 2241-2251.
Ostro et al. (1989) "Use of liposomes as injectable-drug delivery systems," Am. J. Hosp. Pharm. 46: 1576-1587.
Ouyang et al. (2010) "Simultaneous Visualization of Protumorigenic Src and MT1-MMP Activities with Fluorescence Resonance Energy Transfer," Cancer Res. 70(6): 2204-2212.
Patel et al. (2007) "Cell Penetrating Peptides: Intracellular Pathways and Pharmaceutical Perspectives," Pharm. Res. 24(11): 1977-1992.
Patel et al. (2012) "Synthesis and Cell Adhesive Properties of Linear and Cyclic RGD Functionalized Polynorbornene Thin Films," Biomacromolecules 13(8): 2546-2553.
Pazos et al. (2009) "Peptide-based fluorescent biosensors," Chem. Soc. Rev. 38(12): 3348-3359.
Pearson et al. (1988) "Improved tools for biological sequence comparison," Proc. Nat'l. Acad. Sci. USA 85(8):2444-2448.
Phillips et al. (2005) "Scalable molecular dynamics with NAMD," Journal of Computational Chemistry 26(16): 1781-1802.
Pini et al. (2008) "Branched Peptides as Therapeutics," Curr. Protein Pept. Sci. 9(5): 468-477.
Powell et al. (1993) "Peptide Stability in Drug Development. II. Effect of Single Amino Acid Substitution and Glycosylation on Peptide Reactivity in Human Serum," Pharm. Res. 10(9): 1268-1273.
Price et al. (2004) "A modified TIP3P water potential for simulation with Ewald summation," J. Chem. Phys. 121(20): 10096-10103.
Pronk et al. (publicly available Feb. 2013) "GROMACS 4.5: a high-throughput and highly parallel open source molecular simulation toolkit," Bioinformatics (Apr. 2013) 29(7): 845-854.
Puglisi et al. (1995) "Solution Structure of a Bovine Immunodeficiency Virus Tat-TAR Peptide-RNA Complex," Science 270(5239): 1200-1203, (Machine Generated Copy).
Ramon et al. (2005) "PEGylated Interferon-α2b: A Branched 40K Polyethylene Glycol Derivative," Pharm. Res. 22(8): 1374-1386.
Rankin et al. (2007) "The controlled homogeneous organic solution polymerization of new hydrophilic cationic exo-7-oxanorbornenes via ROMP with RuCl2(PCy3)2CHPh in a novel 2,2,2-trifluoroethanol/methylenechloride solvent mixture," J. Polym. Sci. A Polym. Chem. 45(11): 2113-2128.
Rao (1995) "Recent developments of collagen-based materials for medical applications and drug delivery systems," J. Biomater Sci. Polym. Ed. 7(7): 623-645.
Rao et al. (2012) "Norbornene Derived Doxorubicin Copolymers as Drug Carriers with pH Responsive Hydrazone Linker," Biomacromolecules 13(1): 221-230.
Reissmann et al. (2000) "The LHRH antagonist Cetrorelix: a review," Human Reproduction Update 6(4): 322-331.
Richard et al. (2003) "Cell-penetrating Peptides: A Reevaluation of the Mechanism of Cellular Uptake," J. Biol. Chem. 278(1): 585-590.
Rodal et al. (1999) "Extraction of Cholesterol with Methyl-β-Cyclodextrin Perturbs Formation of Clathrin-coated Endocytic Vesicles," Mol. Biol. Cell 10(4): 961-974.
Rozek et al. (2003) "Structure-Based Design of an Indolicidin Peptide Analogue with Increased Protease Stability," Biochemistry 42(48): 14130-14138.
Ruijtenbeek et al. (2001) "Peptoid-Peptide Hybrids That Bind Syk SH2 Domains Involved in Signal Transduction," ChemBioChem 2(3): 171-179.
Rush et al. (May 2014) "Intracellular mRNA Regulation with Self-Assembled Locked Nucleic Acid Polymer Nanoparticles," J. Am. Chem. Soc. 136: 7615-7618.
Ruttekolk et al. (2011) "Coupling to Polymeric Scaffolds Stabilizes Biofunctional Peptides for Intracellular Applications," Mol. Pharmacol. 79(4): 692-700.
Samarajeewa et al. (publicly available Dec. 2013) "Programmed hydrolysis of nanoassemblies by electrostatic interaction-mediated enzymatic-degradation," Chem. Commun. (Jan. 2014), 50(8): 968-970.
Sanford et al. (2001) "A Versatile Precursor for the Synthesis of New Ruthenium Olefin Metathesis Catalysts," Organometallics 20(25): 5314-5318.
Schafmeister et al. (2000) "An All-Hydrocarbon Cross-Linking System for Enhancing the Helicity and Metabolic Stability of Peptides," J. Am. Chem. Soc. 122(24): 5891-5892.
Schellinger et al. (Jul. 2013) "Block Copolymers Containing a Hydrophobic Domain of Membrane-Lytic Peptides Form Micellar Structures and Are Effective Gene Delivery Agents," ACS Macro Lett. 2(8): 725-730.

(56) References Cited

OTHER PUBLICATIONS

Scholl et al. (1999) "Synthesis and Activity of a New Generation of Ruthenium-Based Olefin Metathesis Catalysts Coordinated with 1,3-Dimesityl-4,5-dihydroimidazol-2-ylidene Ligands," Org. Lett. 1(6): 953-956.
Schuster et al. (1997) "Neoglycopolymers produced by aqueous ring-opening metathesis polymerization: decreasing saccharide density increases activity," J. Mol. Catal. 116(1-2): 209-216.
Search Report and Written Opinion, dated Feb. 16, 2016, corresponding to International Application No. PCT/US2015/042482, 15 pp.
Search Report and Written Opinion, dated Jan. 21, 2021, corresponding to International Application No. PCT/US2020/045729, 15 pp.
Search Report and Written Opinion, dated Nov. 27, 2015, corresponding to International Application No. PCT/US2015/044515, 8 pp.
Shi et al. (Oct. 2013) "Engineering biodegradable and multifunctional peptide-based polymers for gene delivery," J. Biol. Eng. 7: 25, pp. 1-10.
Smith et al. (1981) "Comparison of Biosequences," Adv. Appl. Math. 2:482-489.
Som et al. (2011) "Self-Activation in De Novo Designed Mimics of Cell-Penetrating Peptides," Angew. Chem., Int. Ed. 123: 6271-6274.
Spring et al. (publicly available May 2014) "The preparation of well-controlled poly(N-cyclohexyl-exo-norbornene-5, 6-dicarboximide) polymers," Polymer Journal (Sep. 2014) 46: 576-583.
Steer et al. (2002) "β-Amino Acids: Versatile Peptidomimetics," Curr. Med. Chem. 9(8): 811-822.
Stickle et al. (1992) "Hydrogen bonding in globular proteins," J. Mol. Biol. 226(4): 1143-1159.
Su et al. (1991) "In Vitro Stability of Growth Hormone Releasing Factor (GRF) Analogs in Porcine Plasma," Horm. Metab. Res. 23(1): 15-21.
Sutthasupa et al. (2010) "Recent advances in ring-opening metathesis polymerization, and application to synthesis of functional materials," Polymer Journal 42: 905-915.
Thompson et al. (publicly available Dec. 2013) "Labelling Polymers and Micellar Nanoparticles via Initiation, Propagation and Termination with ROMP," Polym Chem, Mar. 2014 5(6):1954-1964.
Thundimadathil (Dec. 2012) "Cancer Treatment Using Peptides: Current Therapies and Future Prospects," Journal of Amino Acids 2012(967347): 1-13.
Tijssen (1993) "Overview of principles of hybridization and the strategy of nucleic acid probe assays," in Techniques in Biochemistry and Molecular Biology—Hybridization with Nucleic Probes, 19-78.
Toti et al. (2010) "Interfacial Activity Assisted Surface Functionalization: A Novel Approach To Incorporate Maleimide Functional Groups and cRGD Peptide on Polymeric Nanoparticles for Targeted Drug Delivery," Mol Pharm. 7(4): 1108-1117.
Trabulo et al. (2010) "Cell-Penetrating Peptides—Mechanisms of Cellular Uptake and Generation of Delivery Systems," Pharmaceuticals 3(4): 961-993.
Trnka et al. (2001) "The Development of L2X2RuCHR Olefin Metathesis Catalysts: An Organometallic Success Story," Acc. Chem. Res. 34(1): 18-29.
Tymoczko ed. (2010) Biochemistry: A Short Course, 2nd ed., W.H. Freeman and Company: 13-15.
U.S. Office Action, dated Dec. 19, 2019, in U.S. Appl. No. 15/329,526, 7 pp.
U.S. Office Action, dated Jul. 14, 2020, in U.S. Appl. No. 15/329,526, 11 pp.
U.S. Office Action, dated May 20, 2019, in U.S. Appl. No. 15/329,526, 5 pp.
Vanommeslaeghe et al. (2010) "CHARMM general force field: A force field for drug-like molecules compatible with the CHARMM all-atom additive biological force fields," J. Comput. Chem. 31(4): 671-690.
Vanommeslaeghe et al. (2012) "Automation of the CHARMM General Force Field (CGenFF) I: Bond Perception and Atom Typing," J. Chem. Inf. Model. 52(12): 3144-3154.
Vanommeslaeghe et al. (2012) "Automation of the CHARMM General Force Field (CGenFF) II: Assignment of Bonded Parameters and Partial Atomic Charges," J. Chem. Inf Model. 52(12): 3155-3168.
Verdine et al. (2012) "Chapter one—Stapled Peptides for Intracellular Drug Targets," Methods Enzymol. 503: 3-33.
Vlieghe et al. (2010) "Synthetic therapeutic peptides: science and market," Drug Discovery Today 15(1-2): 40-56.
Vonderheit et al. (2005) "Rab7 Associates with Early Endosomes to Mediate Sorting and Transport of Semliki Forest Virus to Late Endosomes," PLoS Biol. 3(7): 1225-1238.
Wang et al. (2004) "Development and testing of a general amber force field," J. Comput. Chem. 25(9): 1157-1174.
Wang et al. (publicly available Dec. 2013) "Recent progress of cell-penetrating peptides as new carriers for intracellular cargo delivery," J. Controlled Release (Jan. 2014) 174: 126-136.
Weinstock et al. (2012) "Protease-resistant peptide design—empowering nature's fragile warriors against HIV," Pept. Sci. 98(5): 431-442.
Wender et al. (2000) "The design, synthesis, and evaluation of molecules that enable or enhance cellular uptake: Peptoid molecular transporters," Proc. Natl. Acad. Sci. U. S. A. 97(24): 13003-13008.
Woodley (1994) "Enzymatic barriers for GI peptide and protein delivery," Crit. Rev. Ther. Drug Carrier Syst. 11(2-3): 61-95.
Yamaguchi et al. (2003) "Effect of α,α-Dialkyl Amino Acids on the Protease Resistance of Peptides," Biosci., Biotechnol., Biochem. 67(10): 2269-2272.
Zhao et al. (publicly available Aug. 2013) "Mimicry of High-Density Lipoprotein: Functional Peptide—Lipid Nanoparticles Based on Multivalent Peptide Constructs," J. Am. Chem. Soc. (Sep. 2013) 135(36): 13414-13424.
Zidovetzki et al. (2007) "Use of cyclodextrins to manipulate plasma membrane cholesterol content: Evidence, misconceptions and control strategies," Biochim. Biophys. Acta 1768(6): 1311-1324.
U.S. Appl. No. 15/329,526, filed Jan. 26, 2017.
U.S. Appl. No. 17/172,793, filed Feb. 10, 2021.
U.S. Appl. No. 15/502,166, filed Feb. 6, 2017.

* cited by examiner

A

*thrombin substrate monomer*

HIGH DENSITY PEPTIDE POLYMERS

CROSS-REFERENCES TO RELATED APPLICATIONS

This application is a continuation of U.S. patent application Ser. No. 15/502,166, filed Feb. 6, 2017, which application is a U.S. National Stage Application of International Application Serial No. PCT/US2015/044515, filed Aug. 10, 2015, which claims the benefit of and priority to U.S. Provisional Patent Application No. 62/035,313, filed Aug. 8, 2014; all of which are incorporated herein by reference in their entireties and for all purposes.

REFERENCE TO A "SEQUENCE LISTING," A TABLE, OR A COMPUTER PROGRAM LISTING APPENDIX SUBMITTED AS AN ASCII FILE

The Sequence Listing, written in file "338701_139-19A-US_SequenceListing_text-file", created on Jan. 26, 2021, 26,571 bytes, containing SEQ ID Nos: 1-77, is hereby incorporated by reference.

STATEMENT AS TO RIGHTS TO INVENTIONS MADE UNDER FEDERALLY SPONSORED RESEARCH AND DEVELOPMENT

This invention was made with government support under 1DP2OD008724, 1R01EB011633, and R01HL117326, awarded by the National Institutes of Health. The government has certain rights in this invention.

BACKGROUND

Peptides have been developed for decades for use as therapeutics, signaling agents, and sensors. However, significant problems limit their use in vivo, notably the short duration of their activity, due to expeditious digestion by endogenous proteases and efficient renal clearance due to their generally low molecular weights. Proteolytic digestion of circulating peptides can be rapid, occurring with half-lives of less than a few minutes, owing to the abundance of active proteases in both serum and tissues. The greatest threats to peptide integrity are found in the lumen of the small intestine, which contains gram quantities of proteases secreted by the pancreas (i.e. α-chymotrypsin, trypsin, and carboxypeptidases), as well as in the brush border membrane of epithelial cells, which houses some 15 peptidases that together cleave amide bonds in peptides and proteins with little specificity. In practice, unmodified therapeutic peptides are typically directly injected at the site of interest to minimize proteolytic degradation, and many are used only as last-resort, salvage treatments in patients with multi-drug resistant afflictions. Harnessing the inherent specificity, affinity, and low immunogenicity of peptides in therapeutic and diagnostic applications will require the development of simple, widely applicable, and easy-to-access methods that protect active peptides from proteolysis, but do not hinder their function.

Traditional strategies for limiting enzymatic degradation typically involve chemical modification of the peptide, such as by incorporating unnatural amino acids (including the use of D-amino acids), terminal capping via acetylation of the N-terminus or amidation of the C-terminus, introduction of backbone modifications such as N-methylation, use of stabilizing linkers, and conjugation to polyethylene glycol (PEG). Hence, chemistries are chosen such that peptides are no longer recognized by, or become inaccessible to, the active site of a proteolytic enzyme. However, because these strategies modify the connectivity or amino acid identity of the peptide, each modification has the potential to impact the ability of the peptide to elicit its intended response, often necessitating multiple rounds of structure-function studies to verify the activity of the material. Strategies that do not require direct modification of the peptide chemical structure typically involve manipulation of their three-dimensional spatial arrangement via chemical conjugation of the peptide to a higher molecular weight structure. Architectures of this type include polymeric, or nanoparticle conjugates or systems involving the display of multiple copies of the peptide on a small molecule scaffold. However, in practice syntheses of these materials often require multiple conjugation and purification steps or the preparation of complicated scaffolds that are not generalizable or convenient.

In addition to proteolysis, there are two other problems that often limit the bioavailability and clinical efficacy of peptide-based therapeutics: rapid renal clearance and inefficiencies in cellular uptake. Regarding the former, it should be noted that the exclusion limit for glomerular filtration includes molecules or assemblies whose molecular weight exceeds 50 kDa.

Provided herein are solutions to these and other problems.

BRIEF SUMMARY OF THE DISCLOSURE

The disclosure herein describes, inter alia, a methodology for protecting active peptides from proteolysis by packaging them into high-density brush polymers via ring opening metathesis polymerization (ROMP), using an easily-prepared catalyst initiator. The graft-through polymerization of norbornyl-peptide monomers via ROMP can result in structures that resist proteolysis relative to their monomeric analogues in a manner dependent on their degree of polymerization (REFS). Polymerized peptides, while protected from proteolysis, maintain their intended biological function and this phenomenon is a general feature of peptides arranged in this manner. Such an approach provides a general, accessible route to the development of proteolytically-resistant peptide displays, capable of any of the functions inherent to the peptide, such as binding a receptor or ligand, initiating a signaling pathway, penetrating a cell, or inducing a therapeutic effect. Thus, the current disclosure provides, inter alia, compositions of cell penetrating high density brush peptide polymer, drug delivery vehicles for delivering cell penetrating peptides and drugs, and methods of preparing the same.

In an aspect is provided a polymer having the formula: $R^1$-[M(O)]$_n$—$R^2$ wherein, n is an integer from 2 to 1000; M is a polymerized monomer; O is independently a polypeptide (a polypeptide moiety) covalently attached to M through a covalent linker; and $R^1$ and $R^2$ are independently terminal polymer moieties.

In an aspect is provided a block copolymer having the formula: $R^1$-[M(O)]$_n$-[M(P)]$_m$—$R^2$ or $R^1$-[M(P)]$_m$-[M(O)]$_n$—$R^2$ wherein, n is an integer from 2 to 1000; m is an integer from 2 to 1000; M is a polymerized monomer; O is independently a polypeptide (a polypeptide moiety) covalently attached to M through a covalent linker; P is independently a non-polypeptide moiety; and $R^1$ and $R^2$ are independently terminal polymer moieties.

In an aspect is provided a blend copolymer having the formula: $R^1$-([M(O)]$_n$-[M(P)]$_m$)$_z$—$R^2$ or $R^1$—([M(P)]$_m$-[M(O)]$_n$)$_z$—$R^2$ wherein, n is an integer from 2 to 1000; m is an integer from 2 to 1000; M is a polymerized monomer; O is independently a polypeptide (a polypeptide moiety) covalently attached to M through a covalent linker; P is independently a non-polypeptide moiety; z is an integer from 2 to 100; and $R^1$ and $R^2$ are independently terminal polymer moieties.

In an aspect is provided a micelle including a polymer (e.g., copolymer) described herein.

In an aspect is provided a nanoparticle including a polymer (e.g., copolymer) described herein.

In another aspect is provided a pharmaceutical composition including a pharmaceutically acceptable excipient and a polymer (e.g., polypeptide polymer, copolymer, block copolymer, blend copolymer), micelle, or nanoparticle (e.g., each as described herein).

In an aspect is provided a method of administering a polypeptide to the interior of a cell including contacting the cell with a polymer (e.g., polypeptide polymer, copolymer, block copolymer, blend copolymer), micelle, or nanoparticle (e.g., each as described herein).

In an aspect is provided a method of internalizing polypeptides (e.g., polypeptides copolymers, block copolymers, blend copolymers) into a cell including contacting the cell with a polymer.

In an aspect is provided a method of treating a disease in a subject, including administering to the subject an effective amount of a polymer described herein (e.g., polypeptide polymer, copolymer, block copolymer, blend copolymer), micelle, or nanoparticle (e.g., each as described herein).

In one aspect, the present disclosure provides a composition including a cell penetrating high density brush peptide polymer. The peptide polymer may include a polypeptide (i.e. polypeptide moiety) with arginine or lysine residues appended at the N- or at the C-terminus, and the polypeptide is pendant to polymerized norbornene moieties (the polymerized monomer).

In one aspect, the present disclosure provides a drug delivery vehicle for delivering a therapeutic agent into a cell, including a cell penetrating high density brush peptide polymer, where the peptide polymer includes polypeptide (polypeptide moiety) with arginine or lysine residues appended at the N- or at the C-terminus, and polypeptide is pendant to polymerized norbornene moieties (the polymerized monomer).

In another aspect, the present disclosure provides a method of preparing a cell penetrating high density brush peptide polymer, where the peptide polymer includes a polypeptide (polypeptide moiety) with an arginine or a lysine residue appended to the N- or at the C-terminus, and is pendant to a polymerized norbornene moieties (the polymerized monomer). The method involves combining a plurality of polypeptide monomers (i.e. an unpolymerized monomer attached to a polypetide) with a ruthenium catalyst into a mixture for ring opening metathesis polymerization (ROMP).

In another aspect, the present disclosure provides a method of delivering a peptide, a pharmaceutically active agent or an oligonucleotide to a cell. The method includes contacting a cell with a polymer provided herein. The method may employa delivery device disclosed herein.

Other features and advantages of the disclosure will be apparent from the following detailed description and claims.

Unless noted to the contrary, all publications, references, patents and/or patent applications reference herein are hereby incorporated by reference in their entirety for all purposes.

DETAILED DESCRIPTION OF THE DISCLOSURE

Figure 1A:
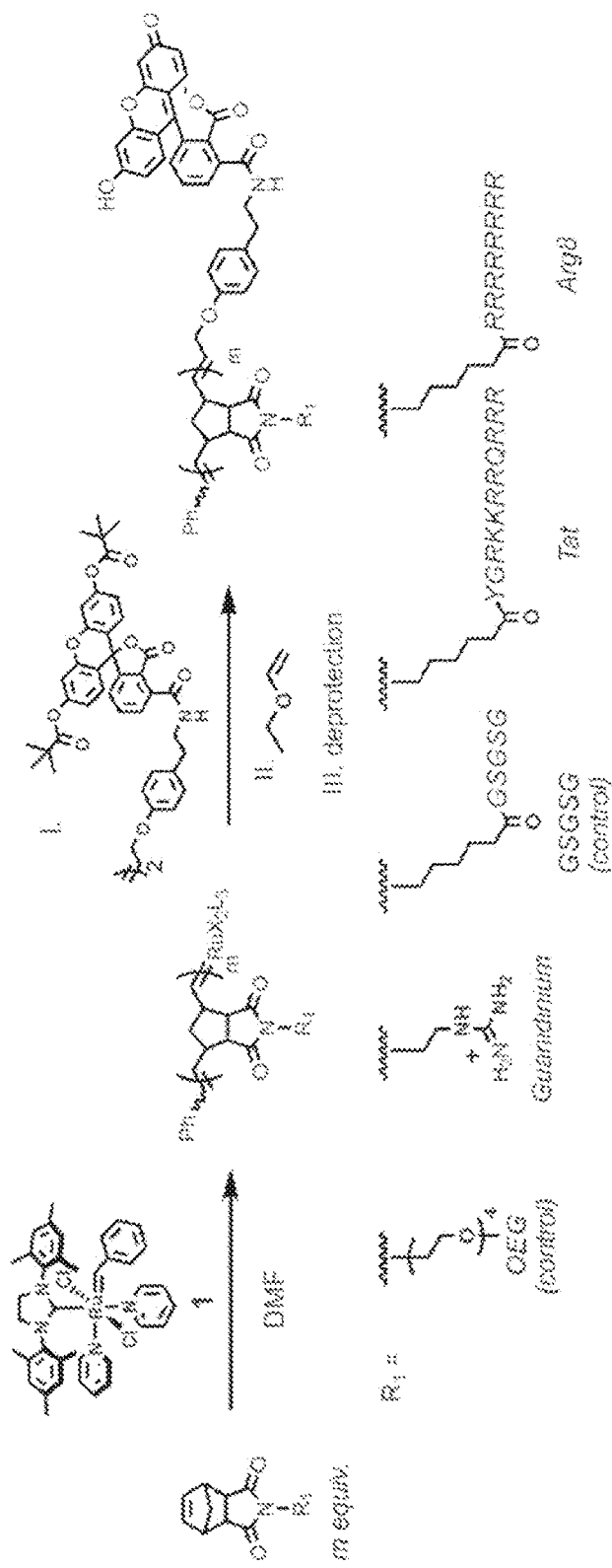
FIG. 1A is a schematic showing synthetic routes for the polymerization of cell penetrating polymers and controls, and routes to the preparation of homopolymers. Sequence legend: GSGSG (SEQ ID NO:1); YGRKKRRQRRR (SEQ ID NO:2); RRRRRRRR (SEQ ID NO:3).

Provided herein, inter alia, are cell penetrating high density brush peptide polymer compositions and/or delivery vehicles for delivering cell penetrating peptides and drugs, and methods of preparing the same.

Definitions

The following definitions are included for the purpose of understanding the present subject matter and for constructing the appended patent claims. Abbreviations used herein have their conventional meaning within the chemical and biological arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this disclosure. The following definitions are provided to facilitate understanding of certain terms used frequently herein and are not meant to limit the scope of the present disclosure.

The term "polypeptide polymer" refers to a polymer of polypeptides that contains a polymer backbone with a polypeptide attached to a polymerized monomer at multiple positions (e.g., every position, periodic position) of the backbone (i.e., a polypeptide connected at one end of the polypeptide to the polymer monomer moiety). In embodiments, the polypeptide polymer is a polymer of norbornyl monomer(the polymerized monomer) attached to apolypeptide (e.g., 2-2000 amino acids) (also referred to herein as a polypeptide moiety) forming a brush polymer where multiple (e.g., every, periodic, a majority) branch is a polypeptide (e.g., 2-2000 amino acids). In embodiments, the polypeptide polymer is a polymer of a polymerized monomer attached to apolypeptide (e.g., 2-2000 amino acids) forming a brush polymer where multiple (e.g., every, periodic, a majority) branches are a polypeptide (e.g., 2-2000 amino acids). The term may include a polymerized polypeptide containing material generated through direct polymerization of monomers including a polypeptide.

"Brush polymers," as used herein are polymers of monomers (e.g., monomers attached to a polypeptide that ultimately form a polymerized monomer). There are three main methodologies for the synthesis of brush-like polymeric architectures in general basis: the grafting onto, the grafting from, and the grafting through approach. The grafting onto approach is based on the attachment of already synthesized secondary chains onto a polymeric backbone with reactive sites usually randomly distributed. In the grafting from approach, the polymer backbone containing initiating sites is used as macroinitiator for the polymerization of a second monomer. In the grafting through approach, or macromonomer approach, a polymer chain bearing a monomer unit is polymerized with a second monomer to lead graft copolymers. In embodiments of the present disclosure, the brush polymers are prepared from the graft through polymerization of norbornyl-peptide monomers via ring opening metathesis polymerization (ROMP), using a catalyst initiator. In embodiments, the graft through polymerization of norbornyl-peptide monomers via ring opening metathesis polymerization (ROMP), using a catalyst initiator results in high density polypeptide polymers with structures that resist proteolysis dependent on their degree of polymerization. In embodiments, the peptides in the high density brush polymers also maintain their intended biological function. In embodiments, the polymers described herein are not made using a grafting onto approach.

The term "graft-through polymerization" is used in accordance with its plain meaning in the art of polymer chemistry and refers to a macromonomer method of graft polymer (e.g., polymer or copolymer) synthesis. The method forms the graft polymer (also referred to in the polymer chemistry arts as the macromolecule) by polymerizing macromonomer molecules having one polymerizable monomer end-group which enables it to act as a monomer molecule, contributing a single monomeric unit to a chain of the final macromolecule (graft polymer) (also referred to herein as a polymerized monomer). Unlike graft polymers assembled by graft-to (also commonly referred to as "graft-onto") polymerization, graft polymers assembled by graft-through polymerization do not include unreacted functional groups (or chemical vestiges thereof) within the linear backbone used to graft side chain polymers to the linear backbone. Graft-through polymerization includes methods of polymerization for synthesizing a polymer with monomer side chains (e.g., polypeptides) using a known polymerization strategy amenable to the functional groups involved, including protected and unprotected forms (e.g., of amino acid sidechains). Graft-through polymerization may include synthesizing a polymer with monomer side chains (e.g., polypeptide monomers) wherein the monomer side chains are not further derivatized or modified after synthesis of the polymer. Thus, graft polymers assembled by graft-through polymerization include high density polymers having smaller distances between side chains relative to graft polymers assembled by graft-to polymerization. In embodiments, the graft polymer is a polypeptide polymer. In embodiments, the graft polymer is a brush polymer. In embodiments, the graft polymer synthesis is a brush polymer synthesis. In embodiments, the graft-through polymerization employs atom transfer radical polymerization (ATRP), ring-opening metathesis polymerization (ROMP), anionic and cationic polymerizations, free radical living polymerization, radiation-induced polymerization, ring-opening olefin metathesis polymerization, polycondensation reactions, or iniferter-induced polymerization.

"Cell penetrating," when used to describe the various polypeptide polymers or brush polymers disclosed herein, means polypeptide polymers or brush polymers that are capable of entering into the interior of a cell. Canonical cell penetrating peptides (CPPs or CCPs, used interchangeably herein), are Tat (YGRKKRRQRRR, SEQ ID NO:2) and Arg8 (RRRRRRRR, SEQ ID NO:3).

"Pendant," when used to describe a peptide, an amino acid, or a non-peptidic moiety attached to a polypeptide polymers means, that the peptide, the amino acid, or the non-peptidic moiety is covalently bound to a monomer (polymerized monomer) in the polymer. "High density" is based on weight percentage of the pendant moiety in the polypeptide polymer. For example a polypeptide polymer may be high density in polypeptides (polypeptide moieties) when 100% of the constituent monomers (polymerized monomers) are attached to a polypeptide (polypeptide moiety). In embodiments, a polypeptide polymer is high density when about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the constituent monomers are attached to a polypeptide. In embodiments, a polypeptide polymer is high density when greater than about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the constituent monomers are attached to a polypeptide. In embodiments, a polypeptide polymer is high density when 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the constituent monomers are attached to a polypeptide. In embodiments, a polypeptide polymer is high density when greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the constituent monomers are attached to a polypeptide. In embodiments, a polypeptide polymer is high density when greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the constituent monomers are attached to a polypeptide. In embodiments, a polypeptide polymer is high density when greater than 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the constituent monomers are attached to a polypeptide. In embodiments, a polypeptide polymer is high density when greater than 80, 81, 82, 83, 84, 85, 86, 87, 88, 89, 90, 91, 92, 93, 94, 95, 96, 97, 98, or 99% of the constituent monomers are attached to a polypeptide. In embodiments, a polypeptide polymer is high density when greater than 90, 91, 92, 93, 94, 95, 96, 97, 98, or 99% of the constituent monomers are attached to a polypeptide. In embodiments, a polypeptide polymer is high density when greater than 95, 96, 97, 98, or 99% of the constituent monomers are attached to a polypeptide. In embodiments, a polypeptide polymer is high density when greater than 99% of the constituent monomers are attached to a polypeptide.

As used herein, the term "living polymerization" is used in accordance with its common meaning in the chemical sciences and refers to a form of chain growth polymerization where the ability of a growing polymer chain to terminate has been removed. Chain termination and chain transfer reactions may be absent and the rate of chain initiation may be much larger than the rate of chain propagation. The result is that the polymer chains may grow at a more constant rate than seen in traditional chain polymerization and their lengths may remain very similar (i.e. they have a very low polydispersity index). Additional advantages may include predetermined molar mass and control over end-groups.

The term "polymerizable monomer" is used in accordance with its meaning in the art of polymer chemistry and refers to a compound that may covalently bind chemically to other monomer molecules to form a polymer thereby forming a polymerized monomer. An example of a polymerizable monomer is a ROMP polymerizable monomer, which is a polymerizable monomer capable of binding chemically to other ROMP polymerizable monomers through a ROMP chemical reaction to form a polymer. It will be understood that a polymerizable monomer may be chemically modified in the polymerization reaction to differ from the free polymerizable monomer when forming the polymerized monomer moiety. In embodiments, the ROMP polymerizable monomer includes an olefin. In embodiments, the ROMP polymerizable monomer includes a cyclic olefin. In embodiments, the ROMP polymerizable monomer includes a cyclic olefin with ring strain (e.g., norbornene or cyclopentene or derivatives thereof). In embodiments, the ROMP polymerizable monomer is attached to a polypeptide. In embodiments, the ROMP polymerizable monomer is attached to a hydrophobic moiety. In embodiments, the ROMP polymerizable monomer is or includes a substituted or unsubstituted norbornenyl. In embodiments, the ROMP polymerizable monomer is

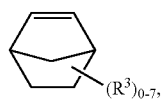

(IA)

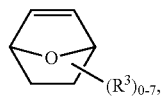

(IB)

-continued

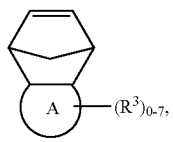 (IC)

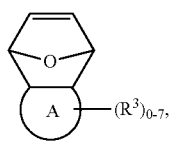 (ID)

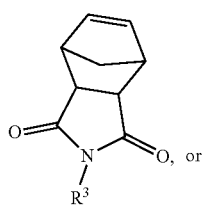 (IE)

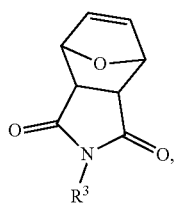 (IF)

wherein Ring A is substituted or unsubstituted cycloalkyl, substituted or unsubstituted heterocycloalkyl, substituted or unsubstituted aryl, or substituted or unsubstituted heteroaryl; $R^3$ is independently a polypeptide, non-polypeptide, detectable moiety, therapeutic moiety, functional moiety, therapeutic polypeptide hydrophobic moiety, hydrogen, halogen, oxo, —C(halo)$_3$, —CH(halo)$_2$, —CH$_2$(halo), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently a polypeptide. In embodiments, $R^3$ is independently a non-polypeptide. In embodiments, at least one $R^3$ is independently a polypeptide. In embodiments, $R^3$ is independently a halogen, oxo, —C(halo)$_3$, —CH(halo)$_2$, —CH$_2$(halo), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, at least one $R^3$ is independently a polypeptide. In embodiments, $R^3$ is independently a hydrogen, halogen, oxo, —C(halo)$_3$, —CH(halo)$_2$, —CH$_2$(halo), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, the ROMP polymerizable monomer is

 (IIA)

 (IIB)

 (IIC)

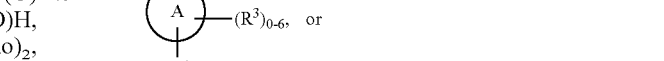 (IID)

 (IIE)

 (IIF)

In formula (IIA-IIF), Ring A, $L^1$, $R^3$ and $R^4$ are as defined herein. In embodiments of formula (IIA)-(IIF), $R^3$ is not a polypeptide. In embodiments, the ROMP polymerizable monomer is

 (IIIA)

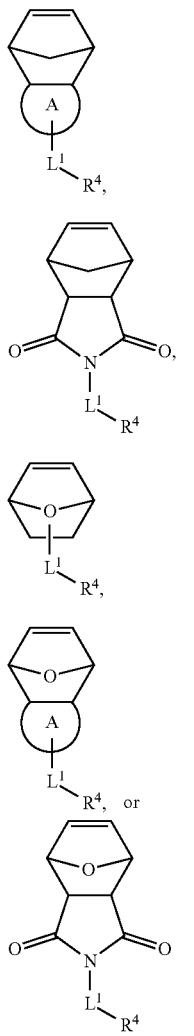

(IIIB)

(IIIC)

(IIID)

(IIIE)

(IIIF). In formula (IIIA)-(IIIF), Ring A, L¹ and R⁴ is as defined herein.

L¹ is independently a bond, —O—, —NH—, —COO—, —S—, —SO₂—, —SO₃—, —SO₄—, —SO₂NH—, —NHC(O)—, —C(O)NH—, —NHC(O)O—, —NHC(O)NH—, C(O), substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L¹ is independently a bond.

In embodiments, L¹ is independently a bond, —C(O)O—, —C(O)NH—, —C(O)NHCH₂CH₂NH—, —CH₂—, —CH₂CH₂O—, —CH₂CH₂—, —CH₂NHC(O)—, —CH₂CH₂NHC(O)—, —CH₂CH₂NH—, —CH₂O—, —CH₂CH₂N(CH₃)₂CH₂—, —CH₂C(O)—, or —CH₂CH₂C(O)—. In embodiments, L¹ is independently —C(O)O—, —C(O)NH—, —C(O)NHCH₂CH₂NH—, —CH₂—, —CH₂CH₂O—, —CH₂CH₂—, —CH₂NHC(O)—, —CH₂CH₂NHC(O)—, —CH₂CH₂NH—, —CH₂O—, —CH₂CH₂N(CH₃)₂CH₂—, —CH₂C(O)—, or —CH₂CH₂C(O)—. In embodiments, L¹ is independently —CH₂CH₂CH₂CH₂CH₂C(O)—. In embodiments, L¹ is independently —CH₂CH₂CH₂CH₂CH₂C(O)NH—. In embodiments, L¹ is a cleavable linker. In embodiments, L¹ is cleaved upon entering a cell. In embodiments, L¹ is cleaved by the environment inside a cell but not outside the cell. In embodiments, L¹ is cleaved by a change in pH. In embodiments, L¹ is cleaved by acidic pH. In embodiments, L¹ is cleaved by the pH of a lysosome. In embodiments, L¹ is cleaved by reducing conditions. In embodiments, L₁ is an enzyme substrate and is cleaved by the enzyme. In embodiments, L¹ is cleavable by radiation. In embodiments, L¹ is light. In embodiments, L¹ includes a prodrug cleavable linkage.

R⁴ is independently a polypeptide, hydrogen, halogen, oxo, —C(halo)₃, —CH(halo)₂, —CH₂(halo), —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OC(halo)₃, —OCH(halo)₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R⁴ may independently be an amino acid or polypeptide as described herein. R⁴ may be a polypeptide as described herein. R⁴ may be an amino acid as described herein.

In embodiments, a polymerizable monomer is selected from:

1

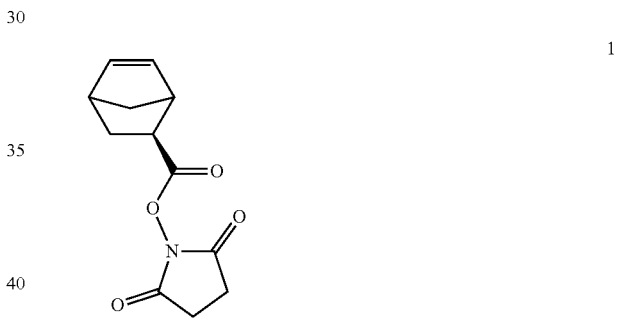

2

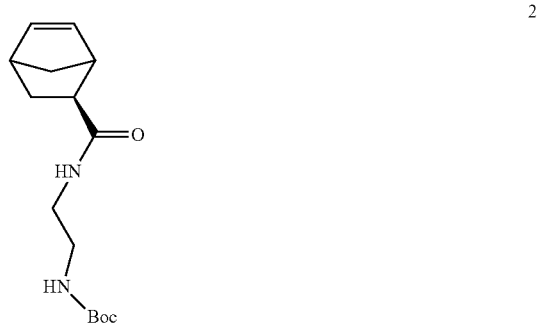

3

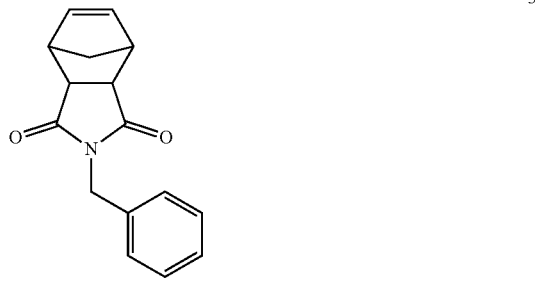

17
-continued
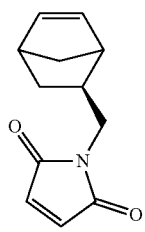
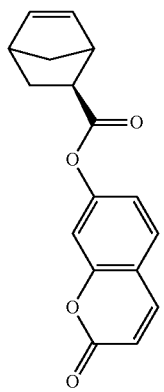
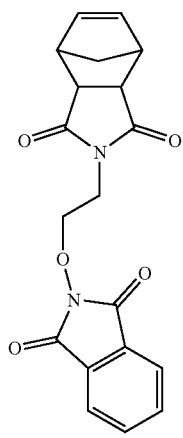
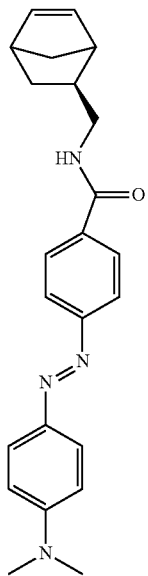
18
-continued
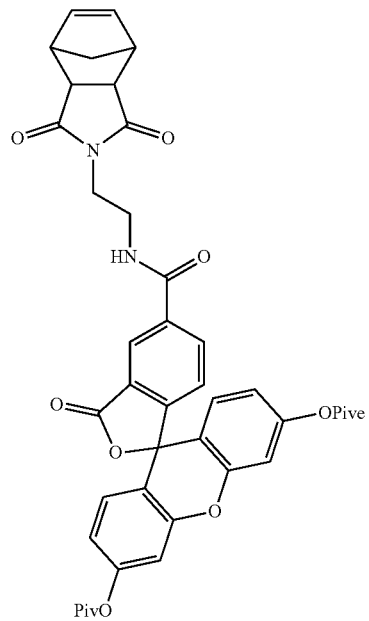
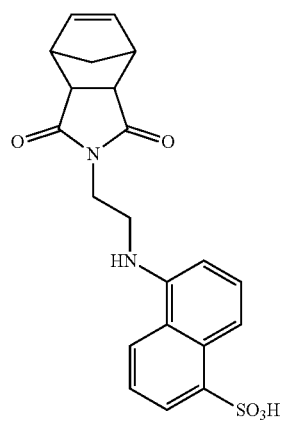
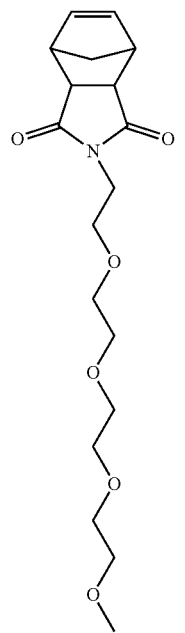

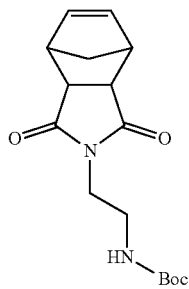

11

The above polymerizable monomers form the polymerized monomers within the polymers disclosed herein.

A "terminal polymer moiety" as used herein, refers to a chemical moiety that results from termination of a polymerization reaction (e.g., by addition of a chain terminator or transfer agent that may be modified to form the terminal polymer moiety in the termination reaction). Terminal polymer moieties may include a solid support, nanoparticle or appropriate termination moiety (e.g. substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl). In embodiments, a terminal polymer moiety includes a functional moiety, for example a detectable moiety. In embodiments, a terminal polymer moiety includes a therapeutic moiety. In embodiments, a terminal polymer moiety includes a label. In embodiments, a terminal polymer moiety is the polymerization product of an ethyl vinyl ether. In embodiments, a terminal polymer moiety is the polymerization product of an alkene containing substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, a terminal polymer moiety is the polymerization product of an alkene containing compound (e.g., also including a function group, substituted or unsubstituted alkyl, substituted or unsubstituted heteroalkyl, substituted or unsubstituted cycloalkyl, substituted or unsubstituted heterocycloalkyl, substituted or unsubstituted aryl or unsubstituted heteroaryl, therapeutic moiety, label, or detectable moiety). In embodiments, a terminal polymer moiety is selected from:

35

Carboxylic acid

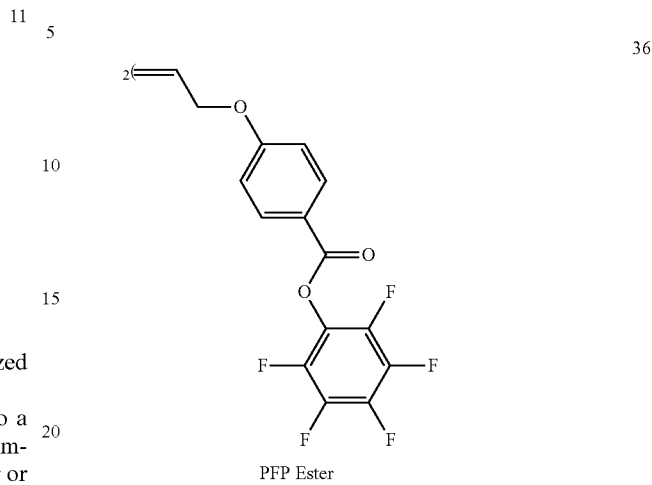

PFP Ester

36

Boc-Amine

37

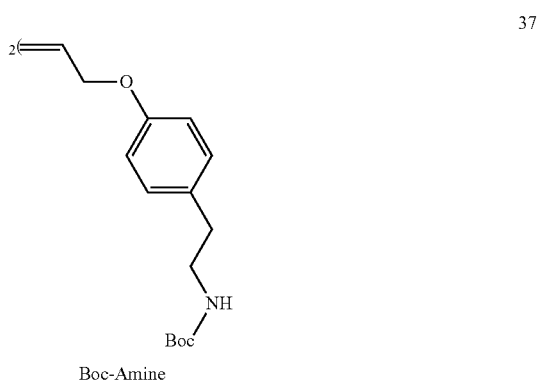

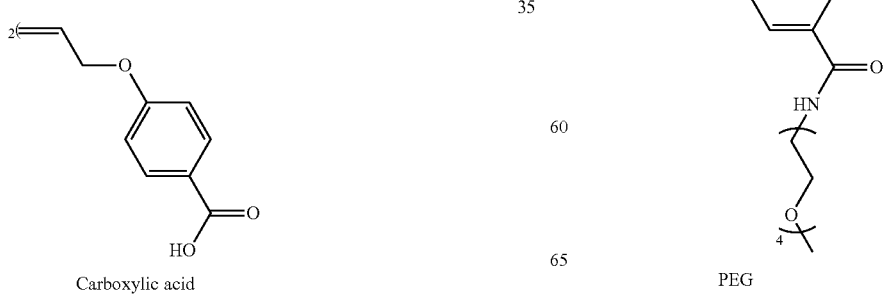

PEG

38

-continued

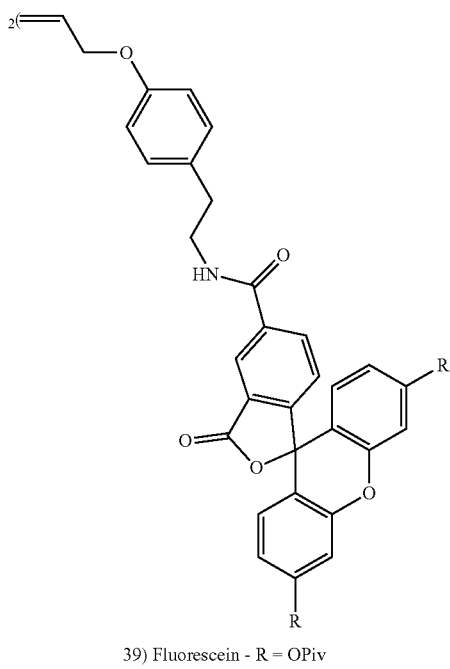

39) Fluorescein - R = OPiv
40) Rhodamine - R = N(Me)₂

41

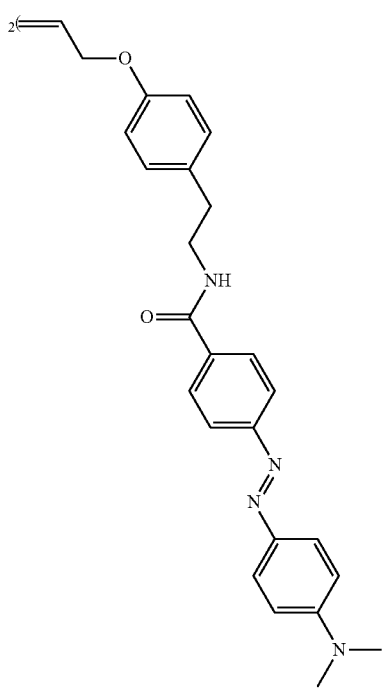

DABCYL

42

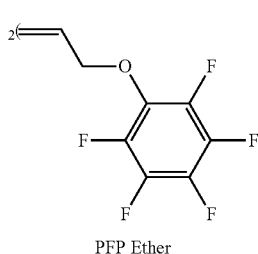

PFP Ether

-continued 39, 40

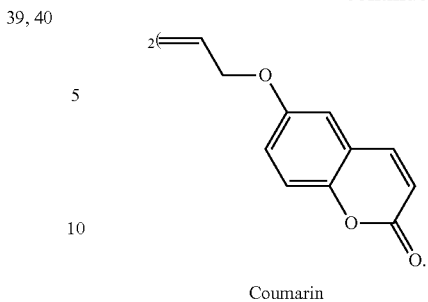

Coumarin

43

The term "ring-opening metathesis polymerization" or "ROMP" is used in accordance with its meaning in polymer chemistry and refers to a chain-growth polymerization (e.g., olefin metathesis chain-growth polymerization). In embodiments, the reaction is driven by relief of ring strain in cyclic olegins (e.g., norbornene or cyclopentene). In embodiments, the ROMP uses a ruthenium catalyst. In embodiments, the ROMP uses a Grubbs' catalyst. In embodiments, the ROMP uses a Mo catalyst. In embodiments, the ROMP uses [Mo(=CHBut)(Nar)(OR)2]. In embodiments, the ROMP uses a transition metal catalyst. In embodiments, the ROMP uses a transition metal carbine complex catalyst. In embodiments, the ROMP uses Benzylidene-bis(tricyclohexylphosphine)-dichlororuthenium. In embodiments, the ROMP uses [1,3-bis-(2,4,6-trimethylphenyl)-2-imidazolidinylidene]dichloro (phenylmethylene)(tricyclohexylphosphine)ruthenium. In embodiments, the ROMP uses Dichloro(o-isopropoxyphenylmethylene)(tricyclohexylphosphine)ruthenium(II). In embodiments, the ROMP uses [1,3-Bis-(2,4,6-trimethylphenyl)-2-imidazolidinylidene]dichloro(o-isopropoxyphenylmethylene)ruthenium. In embodiments, the ROMP uses a third generation Grubbs' catalyst. In embodiments, the ROMP uses (IMesH₂)(C₅H₅N)₂(Cl)₂Ru=CHPh.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C₁-C₁₀ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH₂CH₂CH₂CH₂—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —$CO_2$R', —CONR'R", —OC(O)N R'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —$NO_2$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC (O)NR'R", —NR"C(O)R', —NR'—C(O)NR"R''', —NR"C(O)$_2$R', —NR—C(NR'R"R''')=NR'''', —NR—C(NR' R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —$CF_3$, —CN, —OH, —$NH_2$, —COOH, —$CONH_2$, —$NO_2$, —SH, —$SO_2$Cl, —$SO_3$H, —$SO_4$H, —$SO_2NH_2$, —$NHNH_2$, —$ONH_2$, —NHC=(O)$NHNH_2$, —NHC=(O) $NH_2$, —$NHSO_2$H, —NHC=(O)H, —NHC(O)—OH, —NHOH, —$OCF_3$, —$OCHF_2$, —$NHSO_2CH_3$, —$N_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
 (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and
 (ii) alkyl, heteroalkyl, cycloalkyl, heterocycloalkyl, aryl, heteroaryl, substituted with at least one substituent selected from:
  (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and
  (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium (H), iodine-125 ($^{125}$I), or carbon-14 ($^{14}$C). All isotopic variations of the compounds of the present invention, whether radioactive or not, are encompassed within the scope of the present invention.

The symbol "⟿" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

An "effective amount" is an amount sufficient to accomplish a stated purpose (e.g. achieve the effect for which it is administered, treat a disease, reduce enzyme activity, increase enzyme activity, reduce transcriptional activity, increase transcriptional activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein (e.g. transcription factor) relative to the absence of the antagonist. An "activity increasing amount," as used herein, refers to an amount of agonist (activator) required to increase the activity of an enzyme or protein (e.g. transcription factor) relative to the absence of the agonist. A "function disrupting amount," as used herein, refers to the amount of antagonist (inhibitor) required to disrupt the function of an enzyme or protein (e.g. transcription factor) relative to the absence of the antagonist. A "function increasing amount," as used herein, refers to the amount of agonist (activator) required to increase the function of an enzyme or protein (e.g. transcription factor) relative to the absence of the agonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein The term "modulator" refers to a composition that increases or decreases the level of a target molecule or the function of a target molecule.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a mammal. In some embodiments, a patient is a mouse. In some embodiments, a patient is an experimental animal. In some embodiments, a patient is a rat. In some embodiments, a patient is a test animal.

"Disease" or "condition" refer to a state of being or health status of a patient or subject capable of being treated with a compound, pharmaceutical composition, or method provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). In embodiments, administration includes direct administration to a tumor. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. anti-cancer agent or chemotherapeutic). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions of the present invention can also be delivered as nanoparticles.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments. the nucleic acids herein contain phosphodiester bonds. In other embodiments, nucleic acid analogs are included that may have alternate backbones (e.g. phosphodiester derivatives), including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, peptide nucleic acid linkages, or O-methylphosphoroamidite linkages (see Eckstein, Oligonucleotides and Analogues: A Practical Approach, Oxford University Press), and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester A "label" or a "detectable moiety" is a composition detectable by spectroscopic, photochemical, biochemical, immunochemical, chemical, magnetic resonance imaging, or other physical means. For example, useful detectable moieties include peptide tags, protein tags, $^{32}$P, fluorescent dyes, electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline SPIO, monochrystalline SPIO aggregates, monochrystalline iron oxide nanoparticles, monochrystalline iron oxide, other nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. Detectable moieties also include any of the above compositions encapsulated in nanoparticles, particles, aggregates, coated with additional compositions, derivatized for binding to a targeting agent (e.g. compound described herein). Any method known in the art for conjugating an oligonucleotide or protein to the label may be employed, e.g., using methods described in Hermanson, Bioconjugate Techniques 1996, Academic Press, Inc., San Diego.

MRI can be used to non-invasively acquire tissue images with high resolution. Paramagnetic agents or USPIO nanoparticles or aggregates thereof enhance signal attenuation on $T_2$-weighted magnetic resonance images, and conjugation of such nanoparticles to binding ligands permits the detection of specific molecules at the cellular level. For example, MRI with nanoparticle detection agents can detect small foci of cancer. See e.g., Y. W. Jun et al., 2005, J. Am. Chern. Soc. 127:5732-5733; Y. M. Huh et al., 2005, J. Am. Chern. Soc. 127:12387-12391. Contrast-enhanced MRI is well-suited for the dynamic non-invasive imaging of macromolecules or of molecular events, but it requires ligands that specifically bind to the molecule of interest. J. W. Bulte et al., 2004, NMR Biomed. 17:484-499. Fluorescent dyes and fluorophores (e.g. fluorescein, fluorescein isothiocyanate, and fluorescein derivatives) can be used to non-invasively acquire tissue images with high resolution, with for example spectrophotometry, two-photon fluorescence, two-photon laser microscopy, or fluorescence microscopy (e.g. of tissue biopsies). MRI can be used to non-invasively acquire tissue images with high resolution, with for example paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, other nanoparticle contrast agents. MRI can be used to non-invasively acquire tissue images with high resolution, with for example Gadolinium, including liposomes or other delivery vehicles containing Gadolinium chelate ("Gd-chelate") molecules. Positron emission tomography (PET), PET/computed tomography (CT), single photon emission computed tomography (SPECT), and SPECT/CT can be used to non-invasively acquire tissue images with high resolution, with for example radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia. Ultrasound (ultrasonography) and contrast enhanced ultrasound (contrast enhanced ultrasonography) can be used to non-invasively acquire tissue images with high resolution, with for example biocolloids or microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.). X-ray imaging (radiography) or CT can be used to non-invasively acquire tissue images with high resolution, with for example iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, or gold nanoparticle aggregates. These detection methods and instruments and detectable moieties capable of being measured or detected by the corresponding method are non-limiting examples.

In embodiments, the peptide tags are: AviTag, a peptide allowing biotinylation by the enzyme BirA and so the protein can be isolated by streptavidin (GLNDIFEAQK-IEWHE, SEQ ID NO:25), Calmodulin-tag, a peptide bound by the protein calmodulin (KRRWKKNFIAVSAANRFK-KISSSGAL, SEQ ID NO:26), polyglutamate tag, a peptide binding efficiently to anion-exchange resin such as Mono-Q (EEEEEE, SEQ ID NO:27), E-tag, a peptide recognized by an antibody (GAPVPYPDPLEPR, SEQ ID NO:28), FLAG-tag, a peptide recognized by an antibody (DYKDDDDK, SEQ ID NO:29), HA-tag, a peptide recognized by an antibody (YPYDVPDYA, SEQ ID NO:30), His-tag, 5-10 histidines bound by a nickel or cobalt chelate (HHHHHH, SEQ ID NO:31), Myc-tag, a short peptide recognized by an antibody (EQKLISEEDL, SEQ ID NO:32), S-tag (KET-AAAKFERQHMDS, SEQ ID NO:33), SBP-tag, a peptide which binds to streptavidin (MDEKTTGWRGGHVVEG-LAGELEQLRARLEHHPQGQREP, SEQ ID NO:34), Softag 1, for mammalian expression (SLAELLNAGLGGS, SEQ ID NO:35), Softag 3, for prokaryotic expression (TQDPSRVG, SEQ ID NO:36), Strep-tag, a peptide which binds to streptavidin or the modified streptavidin called streptactin (Strep-tag II: WSHPQFEK, SEQ ID NO:37), TC tag, a tetracysteine tag that is recognized by FlAsH and ReAsH biarsenical compounds (CCPGCC. SEQ ID NO:38), V5 tag, a peptide recognized by an antibody (GKPIPN- PLLGLDST, SEQ ID NO:39), VSV-tag, a peptide recognized by an antibody (YTDIEMNRLGK, SEQ ID NO:40), Xpress tag (DLYDDDDK, SEQ ID NO:41). In embodiments, covalent peptide tags are: Isopeptag, a peptide which binds covalently to pilin-C protein (TDKDMTITFTNKK-DAE, SEQ ID NO:42), SpyTag, a peptide which binds covalently to SpyCatcher protein (AHIVMVDAYKPTK, SEQ ID NO:43). In embodiments, protein tags are: BCCP (Biotin Carboxyl Carrier Protein), a protein domain biotinylated by BirA enabling recognition by streptavidin, Glutathione-S-transferase-tag, a protein which binds to immobilized glutathione, Green fluorescent protein-tag, a protein which is spontaneously fluorescent and can be bound by nanobodies, Halo-tag, a mutated hydrolase that covalently attaches to the HaloLink™ Resin (Promega), Maltose binding protein-tag, a protein which binds to amylose agarose, Nus-tag, Thioredoxin-tag, Fc-tag, derived from immunoglobulin Fc domain, allow dimerization and solubilization.

"Therapeutic moiety" as used herein refers to a monovalent agent capable of treating a disease. In embodiments, the therapeutic moiety may be active when included in a graft polymer (e.g., polypeptide polymer). In embodiments, the therapeutic moiety may be active when released from the graft polymer (e.g., polypeptide polymer) as a therapeutic agent, for example through a chemical reaction. In embodiments, the active therapeutic agent is modified from the therapeutic moiety through the addition of a chemical moiety or removal of a portion of the therapeutic moiety during the release reaction. Examples of therapeutic agents or moieties include anti-cancer agents, cytotoxic agents, cytostatic agents, anti-inflammatory agents, analgesics, anti-infective agents, growth inhibitory agent; cytotoxic agents; immunogenic agent; immunomodulatory agents; agents that modulate T-cell activity; chemokines. A "therapeutic polypeptide" is a polypeptide capable of treating a disease.

A "small molecule" is defined herein to have a molecular weight below about 500 Daltons.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond(s), polar bond(s), or combinations or mixtures thereof).

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature. Examples of amino acid mimetics and polypeptide mimetics include peptoids, D-peptides, and β-peptides. Amino acids may be modified amino acids (natural or mimetics) including additional moieties, for example function, therapeutic, or detectable moieties. Modified amino acids may be modified in the side chain by the addition of additional moieties.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

| Example of amino acid classification | |
|---|---|
| Small/Aliphatic residues: | Gly, Ala, Val, Leu, Ile |
| Cyclic Imino Acid: | Pro |
| Hydroxyl-containing Residues: | Ser, Thr |
| Acidic Residues: | Asp, Glu |
| Amide Residues: | Asn, Gln |
| Basic Residues: | Lys, Arg |
| Imidazole Residue: | His |
| Aromatic Residues: | Phe, Tyr, Trp |
| Sulfur-containing Residues: | Met, Cys |

In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMIS- TRY at pp. 13-15, 2nd ed. Lubert Stryer ed. (Stanford University); Henikoff et al., Proc. Nat'l Acad. Sci. USA (1992) 89:10915-10919; Lei et al., J. Biol. Chem. (1995) 270(20):11882-11886).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative. The terms apply to amino acid polymers in which one or more amino acid residue is an artificial chemical mimetic of a corresponding naturally occurring amino acid, as well as to naturally occurring amino acid polymers and non-naturally occurring amino acid polymer. When a polypeptide includes amino acid mimetics or modified amino acids, the monomer may be connected through bonds that are different from or derivatives of peptide links.

"Isolated," when used to describe the various polypeptides disclosed herein, means a polypeptide that has been identified and separated and/or recovered from a component of its natural environment for example, that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99) %, by weight, of the total protein in a sample. Contaminant components of its natural environment are materials that would typically interfere with diagnostic or therapeutic uses for the polypeptide, and may include enzymes, hormones, and other proteinaceous or non-proteinaceous solutes. In embodiments, the polypeptide may be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the polypeptide natural environment will not be present. In embodiments, isolated polypeptide may be prepared by at least one purification step.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions.

"Active" or "activity" for the purposes herein refers to form(s) of a polypeptide, which retain a biological and/or an immunological activity of native or naturally-occurring form of that polypeptide, where "biological" activity refers to a biological function (either inhibitory or stimulatory) caused by a native or naturally-occurring polypeptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

COMPOSITION

In an aspect is provided a polymer having the formula: $R^1$-[M(O)]$_n$—$R^2$ wherein, n is an integer from 2 to 1000; M is a polymerized monomer; O is independently a polypeptide (a polypeptide moiety) covalently attached (e.g., bonded) to M through a covalent linker; and $R^1$ and $R^2$ are independently terminal polymer moieties.

In an aspect is provided a block copolymer having the formula: $R^1$-[M(O)]$_n$-[M(P)]$_m$—$R^2$ or $R^1$-[M(P)]$_m$-[M(O)]$_n$—$R^2$ wherein, n is an integer from 2 to 1000; m is an integer from 2 to 1000; M is a polymerized monomer; O is independently a polypeptide (a polypeptide moiety) covalently attached(e.g., bonded) to M through a covalent linker (a polypeptide moiety); P is independently a non-polypeptide moiety; and $R^1$ and $R^2$ are independently terminal polymer moieties.

In an aspect is provided a blend copolymer having the formula: $R^1$-([M(O)]$_n$-[M(P)]$_m$)$_z$—$R^2$ or $R^1$-([M(P)]$_m$-[M(O)]$_n$)$_z$—$R^2$ wherein, n is an integer from 2 to 1000; m is an integer from 2 to 1000; M is a polymerized monomer; O is independently a polypeptide (a polypeptide moiety) covalently attached (e.g., bonded) to M through a covalent linker; P is independently a non-polypeptide moiety; z is an integer from 2 to 100; and $R^1$ and $R^2$ are independently terminal polymer moieties.

In embodiments, O is covalently bonded to M (polymerizable monomer or polymerized monomer) through a covalent linker. In embodiments, O is covalently bonded to M through a covalent bond. O may also be referred to herein as $R^3$ as described herein. In embodiments, O is an -$L^1$-$R^4$ moiety as described herein. In embodiments, O is an -$L^1$-$R^4$ moiety wherein $L^1$ is a covalent bond.

In embodiments, the polymer or copolymer includes a linear backbone comprising a polymer of M units (the polymerized monomers). In embodiments, the linear backbone is a polynorbornyl chain (composed of norbornyl polymerized monomers as described herein). In embodiments, the linear backbone is a polynorbornyl derivative chain. In embodiments, the linear backbone is a poly-substituted norbornyl chain. In embodiments, the linear backbone is a substituted polynorbornene. In embodiments, the linear backbone is a polynorbornene. In embodiments, the linear backbone is a polynorbornene substituted with oligonucleotides at each norbornene monomer. In embodiments, the linear backbone is a polynorbornene substituted with a polypeptide, non-polypeptide, detectable moiety, therapeutic moiety, functional moiety, therapeutic polypeptide hydrophobic moiety, substituted or unsubstituted alkyl, substituted or unsubstituted heteroalkyl, substituted or unsubstituted cycloalkyl, substituted or unsubstituted heterocycloalkyl, substituted or unsubstituted aryl substituted or unsubstituted heteroaryl, or a combination thereof. In embodiments, the linear backbone (e.g., polyM) is polymerized from monomers of:

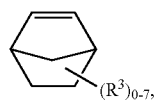 (IA)

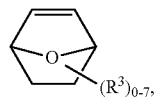 (IB)

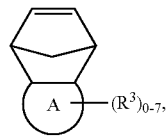 (IC)

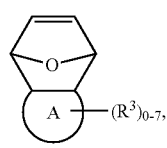 (ID)

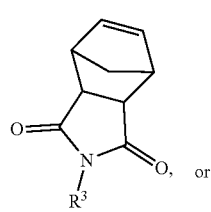 (IE)

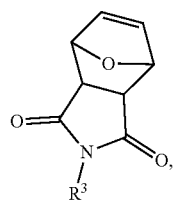 (IF)

wherein Ring A, n and $R^3$ (O or P) are as set forth herein. In embodiments, the linker backbone is polymerized from monomers of:

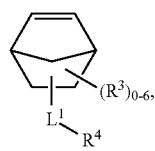 (IIA)

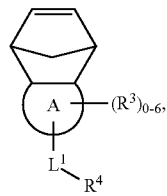 (IIB)

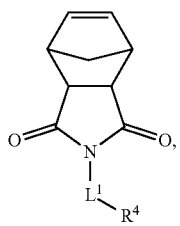 (IIC)

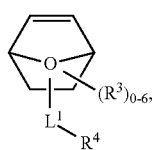 (IID)

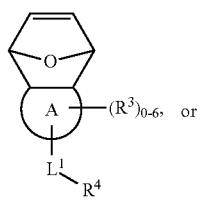 (IIE)

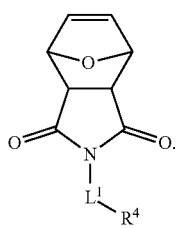 (IIF)

In formula (IIA)-(IIF), Ring A, $R^3$ (O or P), $R^4$, and $L^1$ are as set forth herein. In embodiments, the linker backbone is polymerized from monomers of:

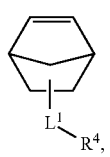 (IIIA)

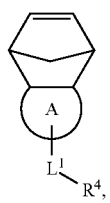 (IIIB)

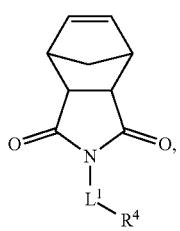 (IIIC)

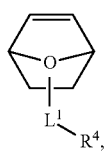
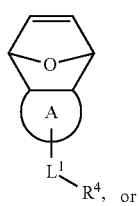
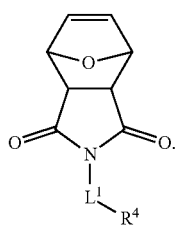
(IIIF). In formula (IIIA)-(IIIF), Ring A, L¹ and R4 is as defined herein. In embodiments, M(O) is
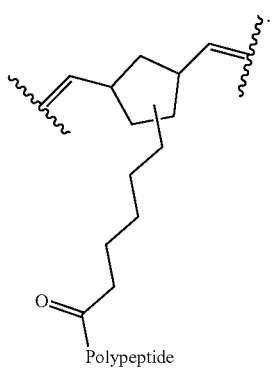
In embodiments, M(O) is
In embodiments, M(O) is
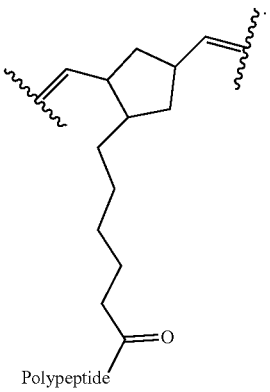
In embodiments, M(O) is
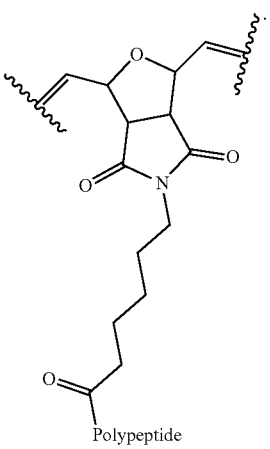
In embodiments, M(O) is
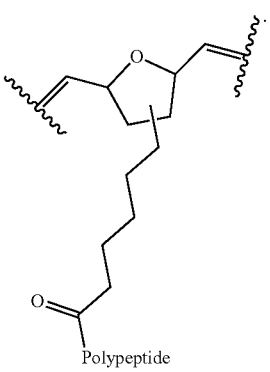

In embodiments, M(O) is

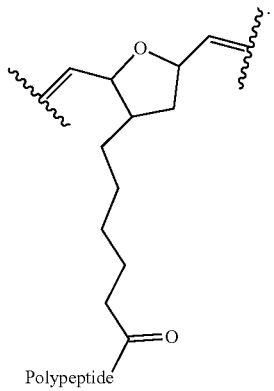

In the M(O) monomers immediately above, the polypeptide is bonded to the C(O) through the peptide backbone nitrogen when the polypeptide include naturally occurring amino acids (e.g., 20 natural amino acids). In embodiments, each polypeptide (O, and alternatively referred to herein as $R^3$) in the polymer is optionally different. In embodiments, each polypeptide (e.g. O; $R^3$ or $R^4$) in the polymer is identical. In embodiments, the polymer includes blocks of polypeptide (e.g. O; $R^3$ or $R^4$) wherein the polypeptides in each block are identical and the polypeptide (e.g. O; $R^3$ or $R^4$) in different blocks are optionally different. In embodiments, the polymer includes blocks of polypeptide (e.g. O; $R^3$ or $R^4$) wherein the polypeptides in each block are identical and the polypeptide (e.g. O; $R^3$ or $R^4$) in different blocks are different.

In embodiments, Ring A is independently substituted or unsubstituted cycloalkyl, substituted or unsubstituted heterocycloalkyl, substituted or unsubstituted aryl, or substituted or unsubstituted heteroaryl; $R^3$ is independently a polypeptide, non-polypeptide, detectable moiety, therapeutic moiety, functional moiety, therapeutic polypeptide hydrophobic moiety, hydrogen, halogen, oxo, —C(halo)$_3$, —CH(halo)$_2$, —CH$_2$(halo), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^3$ is independently a polypeptide. In embodiments, at least one $R^3$ is independently a polypeptide. In embodiments, $R^3$ is independently a halogen, oxo, —C(halo)$_3$, —CH(halo)$_2$, —CH$_2$(halo), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, at least one $R^3$ is independently a polypeptide. In embodiments, $R^3$ is independently a hydrogen, halogen, oxo, —C(halo)$_3$, —CH(halo)$_2$, —CH$_2$(halo), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $L^1$ is independently a bond, —O—, —NH—, —COO—, —S—, —SO$_2$—, —SO$_3$—, —SO$_4$—, —SO$_2$NH—, —NHC(O)—, —C(O)NH—, —NHC(O)O—, —NHC(O)NH—, —C(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^1$ is independently a bond, —C(O)O—, —C(O)NH—, —C(O)NHCH$_2$CH$_2$NH—, —CH$_2$—, —CH$_2$CH$_2$O—, —CH$_2$CH$_2$—, —CH$_2$NHC(O)—, —CH$_2$CH$_2$NHC(O)—, —CH$_2$CH$_2$NH—, —CH$_2$O—, —CH$_2$CH$_2$N(CH$_3$)2CH$_2$—, —CH$_2$C(O)—, or —CH$_2$CH$_2$C(O)—. In embodiments, $L^1$ is independently —C(O)O—, —C(O)NH—, —C(O)NHCH$_2$CH$_2$NH—, —CH$_2$—, —CH$_2$CH$_2$O—, —CH$_2$CH$_2$—, —CH$_2$NHC(O)—, —CH$_2$CH$_2$NHC(O)—, —CH$_2$CH$_2$NH—, —CH$_2$O—, —CH$_2$CH$_2$N(CH$_3$)$_2$CH$_2$—, —CH$_2$C(O)—, or —CH$_2$CH$_2$C(O)—. In embodiments, $L^1$ is independently —CH$_2$CH$_2$CH$_2$CH$_2$CH$_2$C(O)—. In embodiments, $L^1$ is independently —CH$_2$CH$_2$CH$_2$CH$_2$CH$_2$C(O)NH—. In embodiments, $L^1$ is a cleavable linker. In embodiments, $L^1$ is cleaved upon entering a cell. In embodiments, $L^1$ is cleaved by the environment inside a cell but not outside the cell. In embodiments, $L^1$ is cleaved by a change in pH. In embodiments, $L^1$ is cleaved by acidic pH. In embodiments, $L^1$ is cleaved by the pH of a lysosome. In embodiments, $L^1$ is cleaved by reducing conditions. In embodiments, $L^1$ is an enzyme substrate and is cleaved by the enzyme. In embodiments, $L^1$ is cleavable by radiation. In embodiments, $L^1$ is light. In embodiments, $L^1$ includes a prodrug cleavable linkage.

In embodiments, $R^4$ is independently a polypeptide, non-polypeptide moiety, detectable moiety, therapeutic moiety, functional moiety, therapeutic polypeptide hydrophobic moiety, hydrogen, halogen, oxo, —C(halo)$_3$, —CH(halo)$_2$, —CH$_2$(halo), —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OC(halo)$_3$, —OCH(halo)$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ may independently be an amino acid or polypeptide as described herein. $R^4$ may be a polypeptide as described herein. $R^4$ may be an amino acid as described herein.

In embodiments, the polymerized monomer is N-substituted-5-norbornene-2,3-dicarboximide, wherein the substitution comprises the therapeutic polypeptide. In embodiments, M(O) is

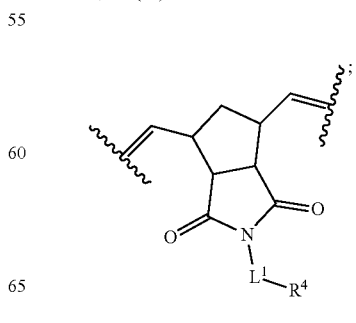

L¹ is independently a bond, —O—, —NH—, —COO—, —S—, —SO₂—, —SO₃—, —SO₄—, —SO₂NH—, —NHC(O)—, —C(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^4$ is a therapeutic polypeptide. In embodiments, M(O) is

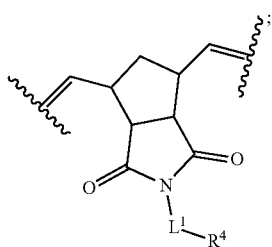

L¹ is independently a bond, —O—, —NH—, —COO—, —S—, —SO₂—, —SO₃—, —SO₄—, —SO₂NH—, —NHC(O)—, —C(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^4$ is a polypeptide.

In embodiments, n is an integer from 2 to 2000. In embodiments, n is an integer from 2 to 1000. In embodiments, n is an integer from 2 to 900. In embodiments, n is an integer from 2 to 800. In embodiments, n is an integer from 2 to 700. In embodiments, n is an integer from 2 to 600. In embodiments, n is an integer from 2 to 500. In embodiments, n is an integer from 2 to 400. In embodiments, n is an integer from 2 to 300. In embodiments, n is an integer from 2 to 200. In embodiments, n is an integer from 2 to 100. In embodiments, n is an integer from 2 to 50. In embodiments, n is an integer from 2 to 49. In embodiments, n is an integer from 2 to 48. In embodiments, n is an integer from 2 to 47. In embodiments, n is an integer from 2 to 46. In embodiments, n is an integer from 2 to 45. In embodiments, n is an integer from 2 to 44. In embodiments, n is an integer from 2 to 43. In embodiments, n is an integer from 2 to 42. In embodiments, n is an integer from 2 to 41. In embodiments, n is an integer from 2 to 40. In embodiments, n is an integer from 2 to 39. In embodiments, n is an integer from 2 to 38. In embodiments, n is an integer from 2 to 37. In embodiments, n is an integer from 2 to 36. In embodiments, n is an integer from 2 to 35. In embodiments, n is an integer from 2 to 34. In embodiments, n is an integer from 2 to 33. In embodiments, n is an integer from 2 to 32. In embodiments, n is an integer from 2 to 31. In embodiments, n is an integer from 2 to 30. In embodiments, n is an integer from 2 to 29. In embodiments, n is an integer from 2 to 28. In embodiments, n is an integer from 2 to 27. In embodiments, n is an integer from 2 to 26. In embodiments, n is an integer from 2 to 25. In embodiments, n is an integer from 2 to 24. In embodiments, n is an integer from 2 to 23. In embodiments, n is an integer from 2 to 22. In embodiments, n is an integer from 2 to 21. In embodiments, n is an integer from 2 to 20. In embodiments, n is an integer from 2 to 19. In embodiments, n is an integer from 2 to 18. In embodiments, n is an integer from 2 to 17. In embodiments, n is an integer from 2 to 16. In embodiments, n is an integer from 2 to 15. In embodiments, n is an integer from 2 to 14. In embodiments, n is an integer from 2 to 13. In embodiments, n is an integer from 2 to 12. In embodiments, n is an integer from 2 to 11. In embodiments, n is an integer from 2 to 10. In embodiments, n is an integer from 2 to 9. In embodiments, n is an integer from 2 to 8. In embodiments, n is an integer from 2 to 7. In embodiments, n is an integer from 2 to 6. In embodiments, n is an integer from 2 to 5. In embodiments, n is an integer from 2 to 4. In embodiments, n is an integer from 2 to 3. In embodiments, n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000.

In an embodiment the polypeptide is a therapeutic polypeptide. Non-limiting examples of a therapeutic polypeptide include: a cell growth or proliferation inhibitory peptide, an anti-inflammatory peptide, an anti-tumor or anti-cancer peptide, an anti-apoptotic peptide, anti-diabetic, anti-obesity, anti-infective, anti-bacterial, anti-viral, peptides for promoting cell growth and differentiation, peptides for preventing pain, and peptides for preventing or treating neural degeneration and/or peptides for promoting neurogenesis.

In embodiments, the polymer includes at least 5 polypeptide (e.g. O; $R^3$ or $R^4$) branches. In embodiments, the polymer includes at least 10 polypeptide (e.g. O; $R^3$ or $R^4$) branches. In embodiments, the polymer includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 polypeptide (e.g. O, $R^3$ or $R^4$) branches.

In embodiments, the polypeptide (e.g. O; $R^3$ or $R^4$) is from 5 to 2000 amino acids long. In embodiments, the polypeptide (e.g. O; $R^3$ or $R^4$) is from 5 to 1000 amino acids long. In embodiments, the polypeptide is from 5 to 900 amino acids long. In embodiments, the polypeptide is from 5 to 800 amino acids long. In embodiments, the polypeptide is from 5 to 700 amino acids long. In embodiments, the polypeptide is from 5 to 600 amino acids long. In embodiments, the polypeptide is from 5 to 500 amino acids long. In embodiments, the polypeptide is from 5 to 400 amino acids long. In embodiments, the polypeptide is from 5 to 300 amino acids long. In embodiments, the polypeptide is from 5 to 200 amino acids long. In embodiments, the polypeptide is from 5 to 100 amino acids long. In embodiments, the polypeptide is from 5 to 50 amino acids long. In embodiments, the polypeptide is from 5 to 49 amino acids long. In embodiments, the polypeptide is from 5 to 48 amino acids long. In embodiments, the polypeptide is from 5 to 47 amino acids long. In embodiments, the polypeptide is from 5 to 46 amino acids long. In embodiments, the polypeptide is from 5 to 45 amino acids long. In embodiments, the polypeptide is from 5 to 44 amino acids long. In embodiments, the polypeptide is from 5 to 43 amino acids long. In embodiments, the polypeptide is from 5 to 42 amino acids long. In embodiments, the polypeptide is from 5 to 41 amino acids long. In embodiments, the polypeptide is from 5 to 40 amino acids long. In embodiments, the polypeptide is from 5 to 39 amino acids long. In embodiments, the polypeptide is from 5 to 38 amino acids long. In embodiments, the polypeptide is from 5 to 37 amino acids long. In embodiments, the polypeptide is from 5 to 36 amino acids long. In embodiments, the polypeptide is from 5 to 35 amino acids long. In embodiments, the polypeptide is from 5 to 34 amino acids long. In embodiments, the polypeptide is from 5 to 33 amino acids long. In embodiments, the polypeptide is from 5 to 32 amino acids long. In embodiments, the polypeptide is from 5 to 31 amino acids long. In embodiments, the polypeptide is from 5 to 30 amino acids long. In embodiments, the polypeptide is from 5 to 29 amino acids long. In embodiments, the polypeptide is from 5 to 28 amino acids long. In embodiments, the polypeptide is from 5 to 27 amino acids long. In embodiments, the polypeptide is from 5 to 26 amino acids long. In embodiments, the polypeptide is from 5 to 25 amino acids long. In embodiments, the polypeptide is from 5 to 24 amino acids long. In embodiments, the polypeptide is from 5 to 23 amino acids long. In embodiments, the polypeptide is from 5 to 22 amino acids long. In embodiments, the polypeptide is from 5 to 21 amino acids long. In embodiments, the polypeptide is from 5 to 20 amino acids long. In embodiments, the polypeptide is from 5 to 19 amino acids long. In embodiments, the polypeptide is from 5 to 18 amino acids long. In embodiments, the polypeptide is from 5 to 17 amino acids long. In embodiments, the polypeptide is from 5 to 16 amino acids long. In embodiments, the polypeptide is from 5 to 15 amino acids long. In embodiments, the polypeptide is from 5 to 14 amino acids long. In embodiments, the polypeptide is from 5 to 13 amino acids long. In embodiments, the polypeptide is from 5 to 12 amino acids long. In embodiments, the polypeptide is from 5 to 11 amino acids long. In embodiments, the polypeptide is from 5 to 10 amino acids long. In embodiments, the polypeptide is from 5 to 9 amino acids long. In embodiments, the polypeptide is from 5 to 8 amino acids long. In embodiments, the polypeptide is from 5 to 7 amino acids long. In embodiments, the polypeptide is from 5 to 6 amino acids long. In embodiments, the polypeptide is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 amino acids long.

In embodiments, the polypeptide includes one (e.g. no more than one) arginine amino acid. In embodiments, the polypeptide includes two (e.g. no more than two) arginine amino acids. In embodiments, the polypeptide includes three (e.g. no more than three) arginine amino acids. In embodiments, the polypeptide includes four (e.g. no more than four) arginine amino acids. In embodiments, the polypeptide includes five (e.g. no more than five) arginine amino acids. In embodiments, the polypeptide includes six (e.g. no more than six) arginine amino acids. In embodiments, the polypeptide includes from 1 to 6 arginine amino acids. In embodiments, the polypeptide includes from 1 to 5 arginine amino acids. In embodiments, the polypeptide includes from 1 to 4 arginine amino acids. In embodiments, the polypeptide includes from 1 to 3 arginine amino acids. In embodiments, the polypeptide includes from 1 to 2 arginine amino acids. In embodiments, the polypeptide includes from 2 to 5 arginine amino acids. In embodiments, the polypeptide includes from 2 to 4 arginine amino acids. In embodiments, the polypeptide includes from 2 to 3 arginine amino acids. In embodiments, the polypeptide includes from 3 to 6 arginine amino acids. In embodiments, the polypeptide includes from 3 to 5 arginine amino acids. In embodiments, the polypeptide includes from 3 to 4 arginine amino acids. In embodiments, the polypeptide includes from 4 to 6 arginine amino acids. In embodiments, the polypeptide includes from 4 to 5 arginine amino acids. In embodiments, the polypeptide includes from 5 to 6 arginine amino acids.

In embodiments, the polypeptide includes one (e.g. no more than one) lysine amino acid. In embodiments, the polypeptide includes two (e.g. no more than two) lysine amino acids. In embodiments, the polypeptide includes three (e.g. no more than three) lysine amino acids. In embodiments, the polypeptide includes four (e.g. no more than four) lysine amino acids. In embodiments, the polypeptide includes five (e.g. no more than five) lysine amino acids. In embodiments, the polypeptide includes six (e.g. no more than six) lysine amino acids. In embodiments, the polypeptide includes from 1 to 6 lysine amino acids. In embodiments, the polypeptide includes from 1 to 5 lysine amino acids. In embodiments, the polypeptide includes from 1 to 4 lysine amino acids. In embodiments, the polypeptide includes from 1 to 3 lysine amino acids. In embodiments, the polypeptide includes from 1 to 2 lysine amino acids. In embodiments, the polypeptide includes from 2 to 5 lysine amino acids. In embodiments, the polypeptide includes from 2 to 4 lysine amino acids. In embodiments, the polypeptide includes from 2 to 3 lysine amino acids. In embodiments, the polypeptide includes from 3 to 6 lysine amino acids. In embodiments, the polypeptide includes from 3 to 5 lysine amino acids. In embodiments, the polypeptide includes from 3 to 4 lysine amino acids. In embodiments, the polypeptide includes from 4 to 6 lysine amino acids. In embodiments, the polypeptide includes from 4 to 5 lysine amino acids. In embodiments, the polypeptide includes from 5 to 6 lysine amino acids.

In embodiments, the polypeptide includes one (e.g. no more than one) Guanidinium group. In embodiments, the polypeptide includes two (e.g. no more than two) Guanidinium groups. In embodiments, the polypeptide includes three (e.g. no more than three) Guanidinium groups. In embodiments, the polypeptide includes four (e.g. no more than four) Guanidinium groups. In embodiments, the polypeptide includes five (e.g. no more than five) Guanidinium groups. In embodiments, the polypeptide includes six (e.g. no more than six) Guanidinium groups. In embodiments, the polypeptide includes from 1 to 6 Guanidinium groups. In embodiments, the polypeptide includes from 1 to 5 Guanidinium groups. In embodiments, the polypeptide includes from 1 to 4 Guanidinium groups. In embodiments, the polypeptide includes from 1 to 3 Guanidinium groups. In embodiments, the polypeptide includes from 1 to 2 Guanidinium groups. In embodiments, the polypeptide includes from 2 to 5 Guanidinium groups. In embodiments, the polypeptide includes from 2 to 4 Guanidinium groups. In embodiments, the polypeptide includes from 2 to 3 Guanidinium groups. In embodiments, the polypeptide includes from 3 to 6 Guanidinium groups. In embodiments, the polypeptide includes from 3 to 5 Guanidinium groups. In embodiments, the polypeptide includes from 3 to 4 Guanidinium groups. In embodiments, the polypeptide includes from 4 to 6 Guanidinium groups. In embodiments, the polypeptide includes from 4 to 5 Guanidinium groups. In embodiments, the polypeptide includes from 5 to 6 Guanidinium groups.

In embodiments, the polypeptide includes one (e.g. no more than one) positive charge. In embodiments, the polypeptide includes two (e.g. no more than two) positive charges. In embodiments, the polypeptide includes three (e.g. no more than three) positive charges. In embodiments, the polypeptide includes four (e.g. no more than four) positive charges. In embodiments, the polypeptide includes five (e.g. no more than five) positive charges. In embodiments, the polypeptide includes six (e.g. no more than six) positive charges. In embodiments, the polypeptide includes from 1 to 6 positive charges. In embodiments, the polypeptide includes from 1 to 5 positive charges. In embodiments, the polypeptide includes from 1 to 4 positive charges. In embodiments, the polypeptide includes from 1 to 3 positive charges. In embodiments, the polypeptide includes from 1 to 2 positive charges. In embodiments, the polypeptide includes from 2 to 5 positive charges. In embodiments, the polypeptide includes from 2 to 4 positive charges. In embodiments, the polypeptide includes from 2 to 3 positive charges. In embodiments, the polypeptide includes from 3 to 6 positive charges. In embodiments, the polypeptide includes from 3 to 5 positive charges. In embodiments, the polypeptide includes from 3 to 4 positive charges. In embodiments, the polypeptide includes from 4 to 6 positive charges. In embodiments, the polypeptide includes from 4 to 5 positive charges. In embodiments, the polypeptide includes from 5 to 6 positive charges.

In embodiments, the one or more arginine amino acids are at the carboxy terminus of the polypeptide. In embodiments, the one or more lysine amino acids are at the carboxy terminus of the polypeptide. In embodiments, the one or more guanidinium groups are at the carboxy terminus of the polypeptide. In embodiments, the one or more positive charges are at the carboxy terminus of the polypeptide. In embodiments, the two or more arginine amino acids are at the carboxy terminus of the polypeptide. In embodiments, the two or more lysine amino acids are at the carboxy terminus of the polypeptide. In embodiments, the two or more guanidinium groups are at the carboxy terminus of the polypeptide. In embodiments, the two or more positive charges are at the carboxy terminus of the polypeptide. In embodiments wherein one or more amino acid or charge (e.g., Arg, Lys, guanidinium, positive charge) at the carboxy terminus, the one or more amino acids or charges are the amino acids or units/monomeric units (e.g., positively charged or guanidinium containing units or monomeric units) that are the carboxy terminus (i.e., there are no additional amino acids or units/monomeric units in the polymer that are carboxy terminal to those amino acids or units/monomeric units). In embodiments, the one or more arginine amino acids are one residue from the carboxy terminus of the polypeptide. In embodiments, the one or more lysine amino acids are one residue from the carboxy terminus of the polypeptide. In embodiments, the one or more guanidinium groups are one residue from the carboxy terminus of the polypeptide. In embodiments, the one or more positive charges are one polymer unit (residue/amino acid) from the carboxy terminus of the polypeptide. In embodiments, the two or more arginine amino acids are together one residue from the carboxy terminus of the polypeptide. In embodiments, the two or more lysine amino acids are together one residue from the carboxy terminus of the polypeptide. In embodiments, the two or more guanidinium groups are together one residue or unit from the carboxy terminus of the polypeptide. In embodiments, the two or more positive charges are together one unit or residue from the carboxy terminus of the polypeptide.

In embodiments, the one or more arginine amino acids are in the interior of the polypeptide. In embodiments, the one or more lysine amino acids are in the interior of the polypeptide. In embodiments, the one or more guanidinium groups are in the interior of the polypeptide. In embodiments, the one or more positive charges are in the interior of the polypeptide. In embodiments, the two or more arginine amino acids are in the interior of the polypeptide. In embodiments, the two or more lysine amino acids are in the interior of the polypeptide. In embodiments, the two or more guanidinium groups are in the interior of the polypeptide. In embodiments, the two or more positive charges are in the interior of the polypeptide.

In embodiments, the one or more arginine amino acids are at the amino terminus of the polypeptide. In embodiments, the one or more lysine amino acids are at the amino terminus of the polypeptide. In embodiments, the one or more guanidinium groups are at the amino terminus of the polypeptide. In embodiments, the one or more positive charges are at the amino terminus of the polypeptide. In embodiments, the two or more arginine amino acids are at the amino terminus of the polypeptide. In embodiments, the two or more lysine amino acids are at the amino terminus of the polypeptide. In embodiments, the two or more guanidinium groups are at the amino terminus of the polypeptide. In embodiments, the two or more positive charges are at the amino terminus of the polypeptide.

In embodiments, the polypeptide includes from 2 to 6 arginine residues. In embodiments, the polypeptide includes 2 arginine residues. In embodiments, the arginine residues are the carboxyl terminal residues of the polypeptide. In embodiments, the polypeptide does not include a carboxy terminal lysine residue. In embodiments, the polypeptide is resistant to proteolysis relative to the unpolymerized polypeptide.

In embodiments, the polypeptide is resistant to proteolysis. In embodiments, the polypeptide in the polymer is resistant to proteolysis relative to the free polypeptide. In embodiments, the polymer polypeptide is 10, 20, 30, 40, 50, 60, 70, 80, 90, or 100% more resistant to proteolysis than the free polypeptide under the same conditions. In embodiments, the polymer polypeptide is 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 10000, 100000-fold more stable than the free polypeptide under the same conditions (e.g., after systemic administration, oral administration, injection). Resistance to proteolysis may be measured by catalytic efficiency, initial rate of proteolysis, kcat/Km (specificity constant), time to proteolyze a fixed amount of polypeptide, degree of proteolysis after a fixed time, among other well-known methods. In embodiments, the polymer polypeptide remains intact In embodiments, the polypeptide (e.g. O; $R^3$ or $R^4$) includes amino acids with alternate backbones from the naturally occurring protein backbone (e.g., peptoids, β-peptides, D-peptides.

In embodiments, the polypeptide includes a peptide tag. In embodiments, the polypeptide includes a protein tag. In embodiments, the polypeptide contacts (e.g., is bonded to) a $^{32}P$ fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("USPIO") nanoparticles, USPIO nanoparticle aggregate, superparamagnetic iron oxide ("SPIO") nanoparticle, SPIO nanoparticle aggregate, monochrystalline SPIO, monochrystalline SPIO aggregate, monochrystalline iron oxide nanoparticle, monochrystalline iron oxide, other nanoparticle contrast agent, liposome or other delivery vehicle containing Gadolinium chelate ("Gd-chelate") molecule, Gadolinium, radioisotope, radionuclide (e.g. carbon-11, nitrogen-13, oxygen-15, fluorine-18, rubidium-82), fluorodeoxyglucose (e.g. fluorine-18 labeled), any gamma ray emitting radionuclids, positron-emitting radionuclide, radiolabeled glucose, radiolabeled water, radiolabeled ammonia, biocolloids, microbubble (e.g. including microbubble shell including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agent (e.g. iohexol, iodixanol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, or hapten. In embodiments, the polypeptide includes poly-histidine (poly(His)), chitin binding protein, maltose binding protein, glutathione-S-transferase (GST), FLAG-tag, AviTag, Calmodulin-tag, polyglutamate tag, E-tag, HA-tag, Myc-tag, S-tag, SBP-tag, Softtag 1, Softtag 3, Strep-tag, TC tag, V5 tag, VSV tag, Xpress tag, Isopeptag, SpyTag, Biotin Carboxyl Carrier Protein (BCCP) tag, Halo-tag, thioredoxin-tag, or Fc-tag. In embodiments, the polymer includes a detectable moiety.

In embodiments, the polypeptide includes a therapeutic polypeptide (e.g., KLA polypeptide). In embodiments, the polypeptide is a therapeutic polypeptide.

In embodiments, the polypeptide includes Nesiritide, Ceruletide, Bentiromide, Exenatide, Gonadorelin, Enfuvirtide, Vancomycin, Icatibant, Secretin, Leuprolide, Glucagon recombinant, Oxytocin, Bivalirudin, Sermorelin, Gramicidin D, Insulin recombinant, Capreomycin, Salmon Calcitonin, Vasopressin, Cosyntropin, Bacitracin, Octreotide, Abarelix, Vapreotide, Thymalfasin, Insulin recombinant, Mecasermin, Cetrorelix, Teriparatide, Corticotropin, or Pramlintide. In embodiments, the polypeptide is Nesiritide, Ceruletide, Bentiromide, Exenatide, Gonadorelin, Enfuvirtide, Vancomycin, Icatibant, Secretin, Leuprolide, Glucagon recombinant, Oxytocin, Bivalirudin, Sermorelin, Gramicidin D, Insulin recombinant, Capreomycin, Salmon Calcitonin, Vasopressin, Cosyntropin, Bacitracin, Octreotide, Abarelix, Vapreotide, Thymalfasin, Insulin recombinant, Mecasermin, Cetrorelix, Teriparatide, Corticotropin, or Pramlintide. In embodiments, the polypeptide includes Tirofiban, captopril, eptifibatide, ziconotide, teriparatide, liraglutide, lanreotide, pramlintide, enfuvirtide, icatibant, ecallantide, tesamorelin, degarelix, mifamurtide, nesiritide, buserelin, gonadorelin, goserelin, histrelin, leuprolide, nafarelin, triptorelin, abarelix, cetrorelix, or ganirelix. In embodiments, the polypeptide is Tirofiban, captopril, eptifibatide, ziconotide, teriparatide, liraglutide, lanreotide, pramlintide, enfuvirtide, icatibant, ecallantide, tesamorelin, degarelix, mifamurtide, nesiritide, buserelin, gonadorelin, goserelin, histrelin, leuprolide, nafarelin, triptorelin, abarelix, cetrorelix, or ganirelix.

In embodiments, the polypeptide includes Tat (YGRKKRRQRRR, SEQ ID NO:2). In embodiments, the polypeptide includes Arg8 (RRRRRRRR, SEQ ID NO:3). In embodiments, the polypeptide is Tat (YGRKKRRQRRR, SEQ ID NO:2). In embodiments, the polypeptide is Arg8 (RRRRRRRR, SEQ ID NO:3).

In embodiments, $R^1$ includes a solid support (and optionally a covalent linker to the solid support). In embodiments, $R^1$ includes a nanoparticle (and optionally a covalent linker to the solid support). In embodiments, $R^1$ includes a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^1$ includes a functional moiety. In embodiments, $R^1$ includes a detectable moiety. In embodiments, $R^1$ includes a peptide tag, protein tag, $^{32}P$, fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("USPIO") nanoparticles, USPIO nanoparticle aggregate, superparamagnetic iron oxide ("SPIO") nanoparticle, SPIO nanoparticle aggregate, monochrystalline SPIO, monochrystalline SPIO aggregate, monochrystalline iron oxide nanoparticle, monochrystalline iron oxide, other nanoparticle contrast agent, liposome or other delivery vehicle containing Gadolinium chelate ("Gd-chelate") molecule, Gadolinium, radioisotope, radionuclide (e.g. carbon-11, nitrogen-13, oxygen-15, fluorine-18, rubidium-82), fluorodeoxyglucose (e.g. fluorine-18 labeled), any gamma ray emitting radionuclids, positron-emitting radionuclide, radiolabeled glucose, radiolabeled water, radiolabeled ammonia, biocolloids, microbubble (e.g. including microbubble shell including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agent (e.g. iohexol, iodixanol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, hapten, polyhistidine (poly(His)), chitin binding protein, maltose binding protein, glutathione-S-transferase (GST), FLAG-tag, Avi-Tag, Calmodulin-tag, polyglutamate tag, E-tag, HA-tag, Myc-tag, S-tag, SBP-tag, Softtag 1, Softtag 3, Strep-tag, TC tag, V5 tag, VSV tag, Xpress tag, Isopeptag, SpyTag, Biotin Carboxyl Carrier Protein (BCCP) tag, Halo-tag, thioredoxin-tag, or Fc-tag. In embodiments, $R^1$ includes a polymerization product of an ethyl vinyl ether. In embodiments, $R^1$ is the polymerization product of an alkene containing substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^1$ is the polymerization product of an alkene bonded to a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^1$ is the polymerization product of an alkene containing compound (e.g., also including a function group, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, therapeutic moiety, or detectable moiety). In embodiments, $R^1$ is selected from:

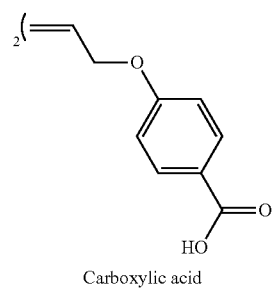

Carboxylic acid

35

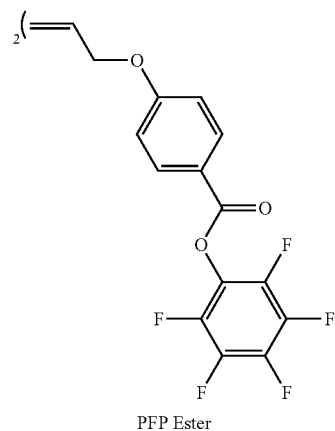

PFP Ester

36

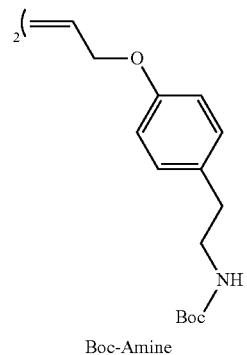

Boc-Amine

37

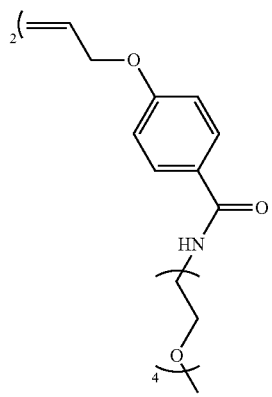

PEG

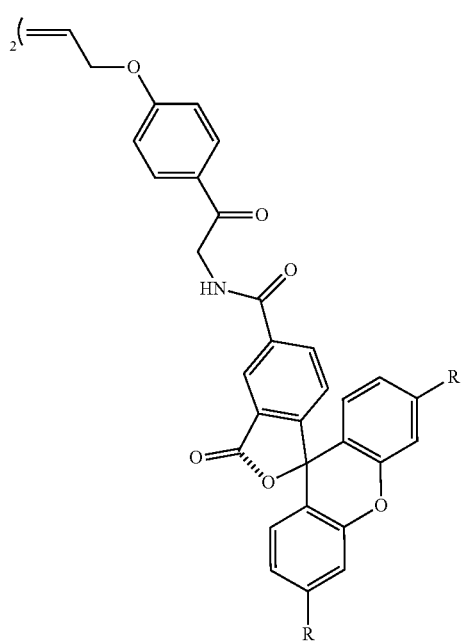

39) Fluorescein - R = OPiv
40) Rhodamine - R = N(Me)₂

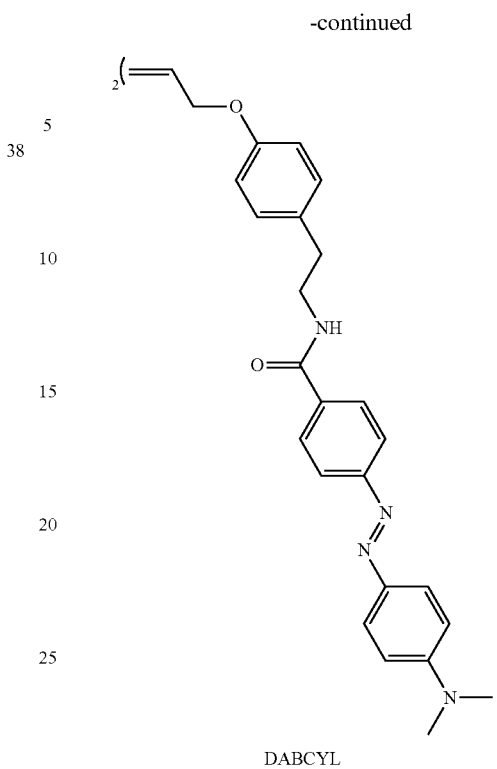

DABCYL

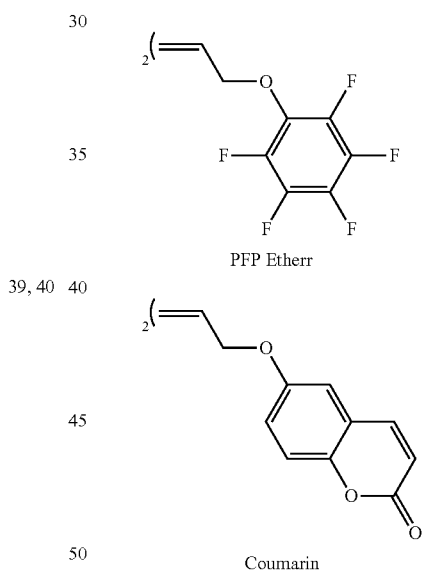

PFP Etherr

Coumarin

In embodiments, $R^2$ includes a solid support (and optionally a covalent linker to the solid support). In embodiments, $R^2$ includes a nanoparticle (and optionally a covalent linker to the solid support). In embodiments, $R^2$ includes a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^2$ includes a functional moiety. In embodiments, $R^2$ includes a therapeutic moiety. In embodiments, $R^2$ includes a detectable moiety. In embodiments, $R^2$ includes a peptide tag, protein tag, $^{32}P$, fluorescent dye, electron-dense reagent, enzyme (e.g., as commonly used in an ELISA), biotin, digoxigenin, paramagnetic molecule, paramagnetic nanoparticle, ultrasmall superparamagnetic iron oxide ("USPIO") nanoparticles, USPIO nanoparticle aggregate, superparamagnetic iron oxide ("SPIO") nanoparticle, SPIO nanoparticle aggregate, monochrystalline SPIO, monochrystalline SPIO aggregate, monochrystalline iron oxide nanoparticle, monochrystalline iron oxide, other nanoparticle contrast agent, liposome or other delivery vehicle containing Gadolinium chelate ("Gd-chelate") molecule, Gadolinium, radioisotope, radionuclide (e.g. carbon-11, nitrogen-13, oxygen-15, fluorine-18, rubidium-82), fluorodeoxyglucose (e.g. fluorine-18 labeled), any gamma ray emitting radionuclids, positron-emitting radionuclide, radiolabeled glucose, radiolabeled water, radiolabeled ammonia, biocolloids, microbubble (e.g. including microbubble shell including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agent (e.g. iohexol, iodixanol, ioversol, iopamidol, ioxilan, iopromide, diatrizoate, metrizoate, ioxaglate), barium sulfate, thorium dioxide, gold, gold nanoparticle, gold nanoparticle aggregate, fluorophore, two-photon fluorophore, hapten, polyhistidine (poly(His)), chitin binding protein, maltose binding protein, glutathione-S-transferase (GST), FLAG-tag, Avi-Tag, Calmodulin-tag, polyglutamate tag, E-tag, HA-tag, Myc-tag, S-tag, SBP-tag, Softtag 1, Softtag 3, Strep-tag, TC tag, V5 tag, VSV tag, Xpress tag, Isopeptag, SpyTag, Biotin Carboxyl Carrier Protein (BCCP) tag, Halo-tag, thioredoxin-tag, or Fc-tag. In embodiments, $R^2$ includes a polymerization product of an ethyl vinyl ether. In embodiments, $R^2$ is the polymerization product of an alkene containing substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^2$ is the polymerization product of an alkene bonded to a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^2$ is the polymerization product of an alkene containing compound (e.g., also including a function group, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, therapeutic moiety, or detectable moiety). In embodiments, $R^2$ is selected from:

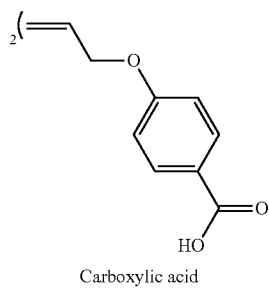

35

Carboxylic acid

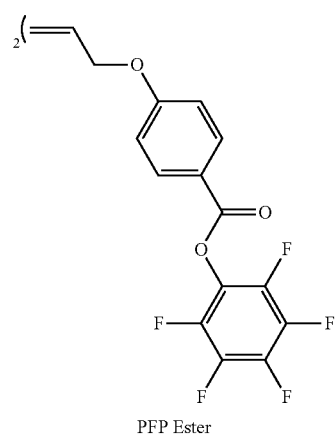

36

PFP Ester

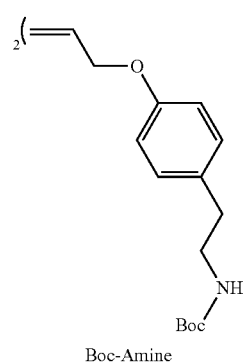

37

Boc-Amine

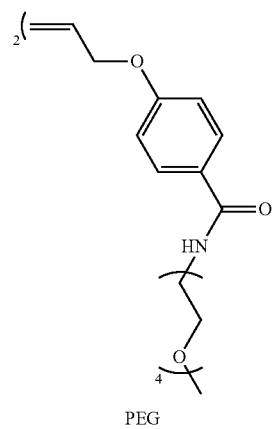

38

PEG

-continued

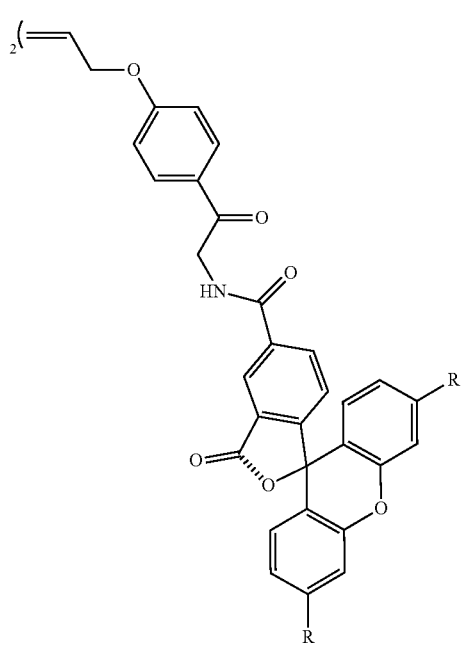

39) Fluorescein - R = OPiv
40) Rhodamine - R = N(Me)₂

41

DABCYL

42

PFP Etherr

-continued

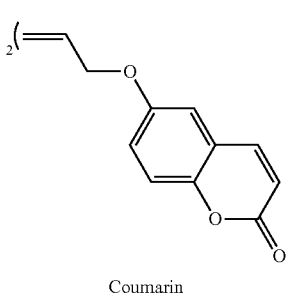

Coumarin

In embodiments, $R^1$ includes a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^2$ includes a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

A "non-polypeptide monomer" is a polymerizable monomer or polymerized monomer that does not include a polypeptide. A "non-polypeptide moiety" is the moiety covalently attached to a polymerizable monomer or polymerized monomer that does not include a polypeptide. A non-polypeptide monomer may be a polymerizable monomer or polymerized monomer covalently bound to a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, a non-polypeptide monomer or polymerized monomer is a hydrophobic monomer. In embodiments, each non-polypeptide monomer or polymerized monomer in the polymer is optionally different. In embodiments, each non-polypeptide monomer (polymerized monomer) in the polymer is identical. In embodiments, the polymer includes blocks of non-polypeptide monomers (polymerized monomers) wherein the non-polypeptide moiety in each block are identical and the non-polypeptide moiety in different blocks are optionally different. In embodiments, the polymer includes blocks of non-polypeptide monomers (polymerized monomers) wherein the non-polypeptide moieties in each block are identical and the non-polypeptide moieties in different blocks are different. In embodiments, the non-polypeptide polymerizable monomer is selected from:

1

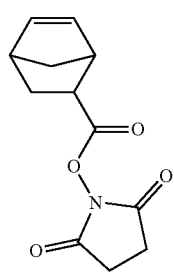

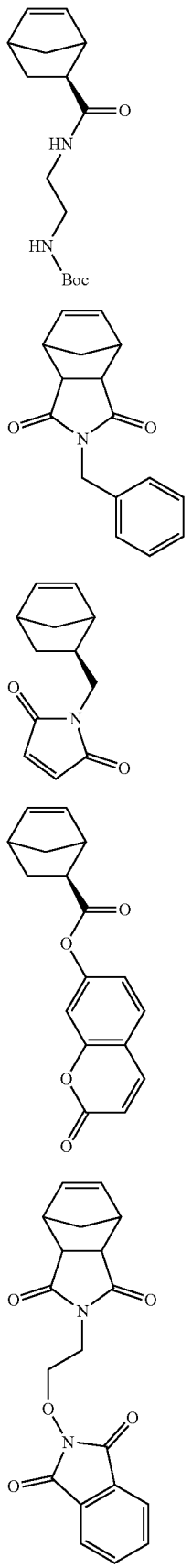
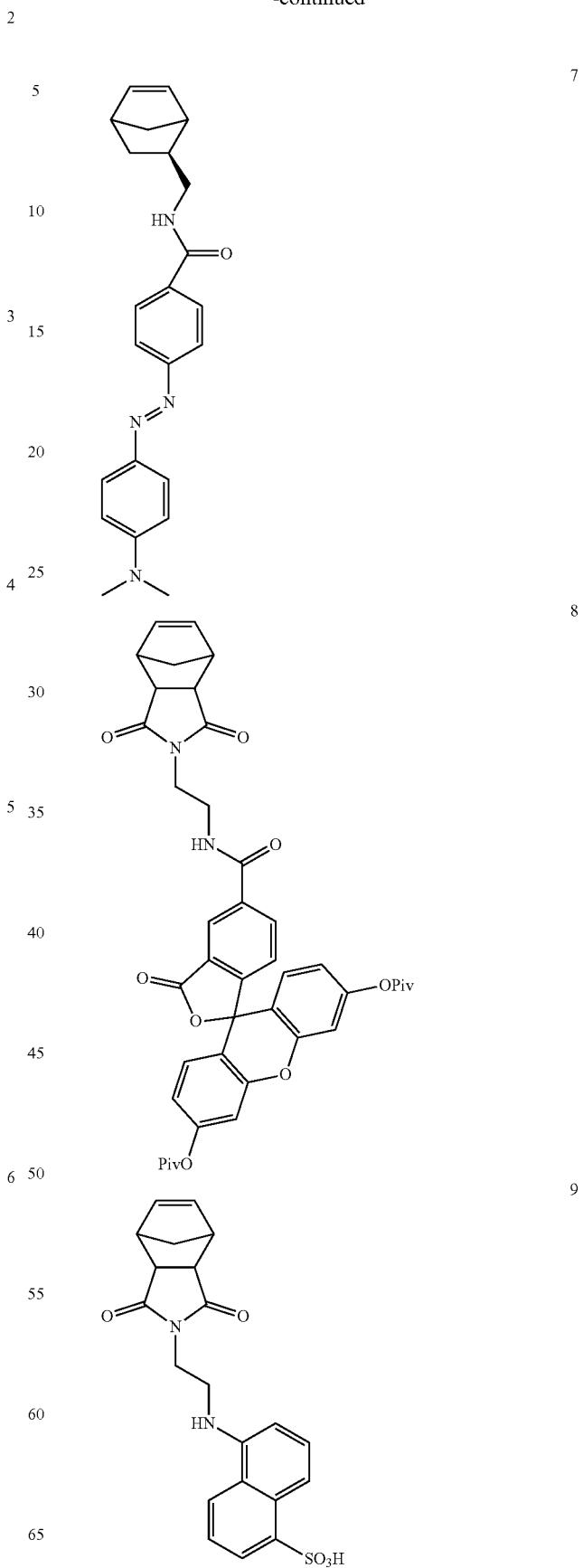

-continued

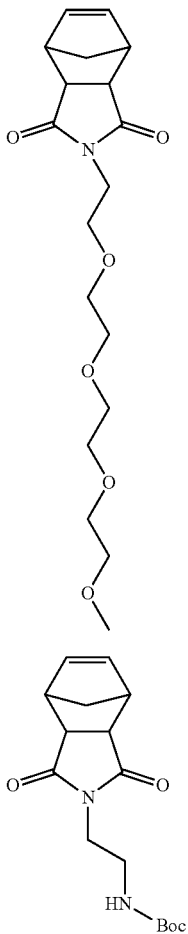

The above referenced non-polypeptide polymerizable monomer form polymerized monomers upon incorporation into the polymers described herein. In embodiments, a non-polypeptide moiety is a hydrophobic moiety. In embodiments, a non-polypeptide moiety does not include an oligonucleotide. In embodiments, a non-polypeptide moiety does not include a nucleotide. In embodiments, a non-polypeptide moiety does not include a nucleobase (e.g., A, T, C, G, U). In embodiments, the non-polypeptide moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl and wherein said non-polypeptide moiety does not comprise a nucleotide. In embodiments, the non-polypeptide moiety is a hydrophobic moiety. In embodiments, the non-polypeptide moiety does not include an oligonucleotide. In embodiments, the non-polypeptide moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the non-polypeptide moiety does not include a nucleotide. In embodiments, the non-polypeptide moiety does not include a polypeptide. In embodiments, the non-polypeptide moiety does not include an amino acid. In embodiments, the non-polypeptide moiety does not include an oligonucleotide. In embodiments, M(P) is

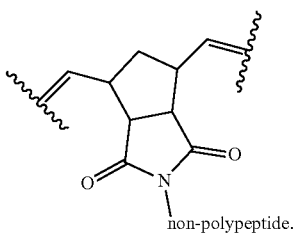

In embodiments, M(P) is

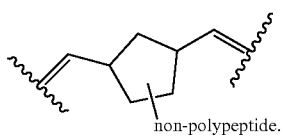

In embodiments, M(P) is

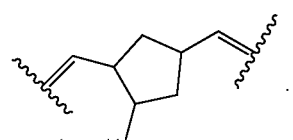

In embodiments, M(P) is

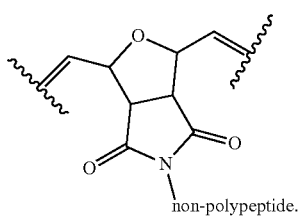

In embodiments, M(P) is

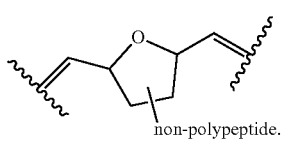

In embodiments, M(P) is

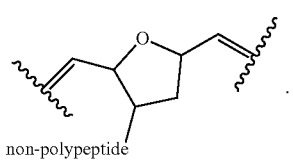

In embodiments, the hydrophobic moiety is sufficiently hydrophobic and of sufficient size such that the block polymer is capable of forming a micelle in an aqueous-based solvent. In embodiments, the hydrophobic moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, the hydrophobic moiety is an unsubstituted benzyl.

In embodiments, M(P) is

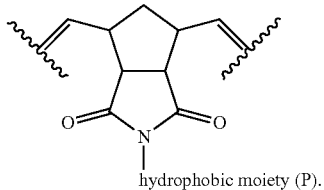
hydrophobic moiety (P).

In embodiments, M(P) is

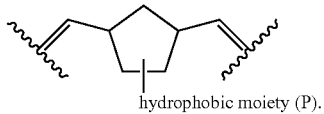
hydrophobic moiety (P).

In embodiments, M(P) is

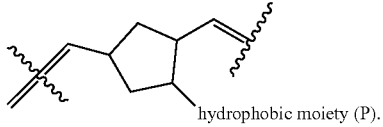
hydrophobic moiety (P).

In embodiments, M(P) is

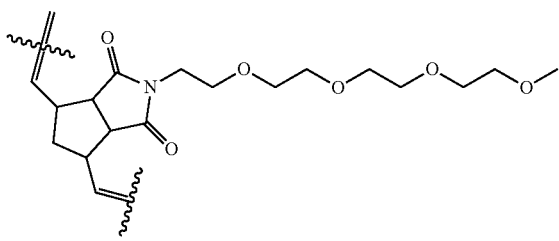

In embodiments, M(P) is

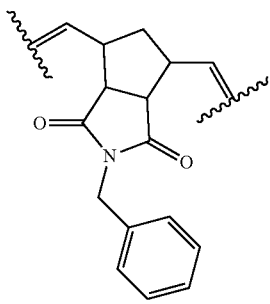

In embodiments, M(P) is

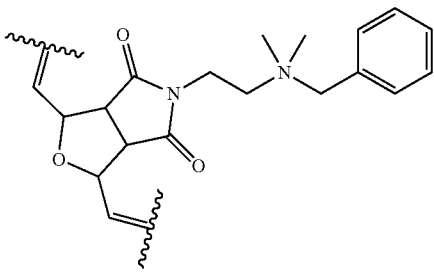

In embodiments, M(P) is

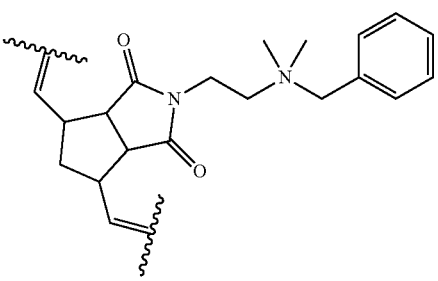

In embodiments, each hydrophobic moiety in the copolymer is optionally different. In embodiments, each hydrophobic moiety in the copolymer is identical. In embodiments, the copolymer includes blocks of hydrophobic moieties wherein the hydrophobic moieties in each block are identical and the hydrophobic moieties in different blocks are optionally different. In embodiments, the copolymer includes blocks of hydrophobic moieties wherein the hydrophobic moieties in each block are identical and the hydrophobic moieties in different blocks are different.

In embodiments, m is an integer from 2 to 900. In embodiments, m is an integer from 2 to 800. In embodiments, m is an integer from 2 to 700. In embodiments, m is an integer from 2 to 600. In embodiments, m is an integer from 2 to 500. In embodiments, m is an integer from 2 to 400. In embodiments, m is an integer from 2 to 300. In embodiments, m is an integer from 2 to 200. In embodiments, m is an integer from 2 to 100. In embodiments, m is an integer from 2 to 50. In embodiments, m is an integer from 2 to 49. In embodiments, m is an integer from 2 to 48. In embodiments, m is an integer from 2 to 47. In embodiments, m is an integer from 2 to 46. In embodiments, m is an integer from 2 to 45. In embodiments, m is an integer from 2 to 44. In embodiments, m is an integer from 2 to 43. In embodiments, m is an integer from 2 to 42. In embodiments, m is an integer from 2 to 41. In embodiments, m is an integer from 2 to 40. In embodiments, m is an integer from 2 to 39. In embodiments, m is an integer from 2 to 38. In embodiments, m is an integer from 2 to 37. In embodiments, m is an integer from 2 to 36. In embodiments, m is an integer from 2 to 35. In embodiments, m is an integer from 2 to 34. In embodiments, m is an integer from 2 to 33. In embodiments, m is an integer from 2 to 32. In embodiments, m is an integer from 2 to 31. In embodiments, m is an integer from 2 to 30. In embodiments, m is an integer from 2 to 29. In embodiments, m is an integer from 2 to 28. In embodiments, m is an integer from 2 to 27. In embodiments, m is an integer from 2 to 26. In embodiments, m is an integer from 2 to 25. In embodiments, m is an integer from 2 to 24. In embodiments, m is an integer from 2 to 23. In embodiments, m is an integer from 2 to 22. In embodiments, m is an integer from 2 to 21. In embodiments, m is an integer from 2 to 20. In embodiments, m is an integer from 2 to 19. In embodiments, m is an integer from 2 to 18. In embodiments, m is an integer from 2 to 17. In embodiments, m is an integer from 2 to 16. In embodiments, m is an integer from 2 to 15. In embodiments, m is an integer from 2 to 14. In embodiments, m is an integer from 2 to 13. In embodiments, m is an integer from 2 to 12. In embodiments, m is an integer from 2 to 11. In embodiments, m is an integer from 2 to 10. In embodiments, m is an integer from 2 to 9. In embodiments, m is an integer from 2 to 8. In embodiments, m is an integer from 2 to 7. In embodiments, m is an integer from 2 to 6. In embodiments, m is an integer from 2 to 5. In embodiments, m is an integer from 2 to 4. In embodiments, m is an integer from 2 to 3. In embodiments, m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000.

In embodiments of the blend copolymer described herein, the plurality of polypeptide branches and plurality of non-polypeptide side chains may be randomly mixed together through the length of the polymer. In embodiments, the plurality of polypeptide branches and plurality of non-polypeptide side chains are mixed in a repetitive pattern. For example, the polymer may include a repeated pattern of n polypeptide monomers followed by m non-polypeptide monomers, with this pattern repeated z times.

The linear backbone, polypeptides (e.g. O; $R^3$ or $R^4$), polypeptide moieties, non-polypeptide moieties, graft-through polymerization, and polymerizable or polymerized monomer, are as described herein, including in aspects (e.g., above), embodiments (e.g., above), examples, figures, tables, schemes, and claims.

In embodiments, z is an integer from 2 to 2000. In embodiments, z is an integer from 2 to 1000. In embodiments, z is an integer from 2 to 900. In embodiments, z is an integer from 2 to 800. In embodiments, z is an integer from 2 to 700. In embodiments, z is an integer from 2 to 600. In embodiments, z is an integer from 2 to 500. In embodiments, z is an integer from 2 to 400. In embodiments, z is an integer from 2 to 300. In embodiments, z is an integer from 2 to 200. In embodiments, z is an integer from 2 to 100. In embodiments, z is an integer from 2 to 50. In embodiments, z is an integer from 2 to 49. In embodiments, z is an integer from 2 to 48. In embodiments, z is an integer from 2 to 47. In embodiments, z is an integer from 2 to 46. In embodiments, z is an integer from 2 to 45. In embodiments, z is an integer from 2 to 44. In embodiments, z is an integer from 2 to 43. In embodiments, z is an integer from 2 to 42. In embodiments, z is an integer from 2 to 41. In embodiments, z is an integer from 2 to 40. In embodiments, z is an integer from 2 to 39. In embodiments, z is an integer from 2 to 38. In embodiments, z is an integer from 2 to 37. In embodiments, z is an integer from 2 to 36. In embodiments, z is an integer from 2 to 35. In embodiments, z is an integer from 2 to 34. In embodiments, z is an integer from 2 to 33. In embodiments, z is an integer from 2 to 32. In embodiments, z is an integer from 2 to 31. In embodiments, z is an integer from 2 to 30. In embodiments, z is an integer from 2 to 29. In embodiments, z is an integer from 2 to 28. In embodiments, z is an integer from 2 to 27. In embodiments, z is an integer from 2 to 26. In embodiments, z is an integer from 2 to 25. In embodiments, z is an integer from 2 to 24. In embodiments, z is an integer from 2 to 23. In embodiments, z is an integer from 2 to 22. In embodiments, z is an integer from 2 to 21. In embodiments, z is an integer from 2 to 20. In embodiments, z is an integer from 2 to 19. In embodiments, z is an integer from 2 to 18. In embodiments, z is an integer from 2 to 17. In embodiments, z is an integer from 2 to 16. In embodiments, z is an integer from 2 to 15. In embodiments, z is an integer from 2 to 14. In embodiments, z is an integer from 2 to 13. In embodiments, z is an integer from 2 to 12. In embodiments, z is an integer from 2 to 11. In embodiments, z is an integer from 2 to 10. In embodiments, z is an integer from 2 to 9. In embodiments, z is an integer from 2 to 8. In embodiments, z is an integer from 2 to 7. In embodiments, z is an integer from 2 to 6. In embodiments, z is an integer from 2 to 5. In embodiments, z is an integer from 2 to 4. In embodiments, z is an integer from 2 to 3. In embodiments, z is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000.

In embodiments of the blend copolymer, n is an integer from 2 to 100. In embodiments, n is an integer from 2 to 50. In embodiments, n is an integer from 2 to 49. In embodiments, n is an integer from 2 to 48. In embodiments, n is an integer from 2 to 47. In embodiments, n is an integer from 2 to 46. In embodiments, n is an integer from 2 to 45. In embodiments, n is an integer from 2 to 44. In embodiments, n is an integer from 2 to 43. In embodiments, n is an integer from 2 to 42. In embodiments, n is an integer from 2 to 41. In embodiments, n is an integer from 2 to 40. In embodiments, n is an integer from 2 to 39. In embodiments, n is an integer from 2 to 38. In embodiments, n is an integer from 2 to 37. In embodiments, n is an integer from 2 to 36. In embodiments, n is an integer from 2 to 35. In embodiments, n is an integer from 2 to 34. In embodiments, n is an integer from 2 to 33. In embodiments, n is an integer from 2 to 32. In embodiments, n is an integer from 2 to 31. In embodiments, n is an integer from 2 to 30. In embodiments, n is an integer from 2 to 29. In embodiments, n is an integer from 2 to 28. In embodiments, n is an integer from 2 to 27. In embodiments, n is an integer from 2 to 26. In embodiments, n is an integer from 2 to 25. In embodiments, n is an integer from 2 to 24. In embodiments, n is an integer from 2 to 23. In embodiments, n is an integer from 2 to 22. In embodiments, n is an integer from 2 to 21. In embodiments, n is an integer from 2 to 20. In embodiments, n is an integer from 2 to 19. In embodiments, n is an integer from 2 to 18. In embodiments, n is an integer from 2 to 17. In embodiments, n is an integer from 2 to 16. In embodiments, n is an integer from 2 to 15. In embodiments, n is an integer from 2 to 14. In embodiments, n is an integer from 2 to 13. In embodiments, n is an integer from 2 to 12. In embodiments, n is an integer from 2 to 11. In embodiments, n is an integer from 2 to 10. In embodiments, n is an integer from 2 to 9. In embodiments, n is an integer from 2 to 8. In embodiments, n is an integer from 2 to 7. In embodiments, n is an integer from 2 to 6. In embodiments, n is an integer from 2 to 5. In embodiments, n is an integer from 2 to 4. In embodiments, n is an integer from 2 to 3. In embodiments, n is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200.

In embodiments of the blend copolymer, m is an integer from 2 to 100. In embodiments, m is an integer from 2 to 50. In embodiments, m is an integer from 2 to 49. In embodiments, m is an integer from 2 to 48. In embodiments, m is an integer from 2 to 47. In embodiments, m is an integer from 2 to 46. In embodiments, m is an integer from 2 to 45. In embodiments, m is an integer from 2 to 44. In embodiments, m is an integer from 2 to 43. In embodiments, m is an integer from 2 to 42. In embodiments, m is an integer from 2 to 41. In embodiments, m is an integer from 2 to 40. In embodiments, m is an integer from 2 to 39. In embodiments, m is an integer from 2 to 38. In embodiments, m is an integer from 2 to 37. In embodiments, m is an integer from 2 to 36. In embodiments, m is an integer from 2 to 35. In embodiments, m is an integer from 2 to 34. In embodiments, m is an integer from 2 to 33. In embodiments, m is an integer from 2 to 32. In embodiments, m is an integer from 2 to 31. In embodiments, m is an integer from 2 to 30. In embodiments, m is an integer from 2 to 29. In embodiments, m is an integer from 2 to 28. In embodiments, m is an integer from 2 to 27. In embodiments, m is an integer from 2 to 26. In embodiments, m is an integer from 2 to 25. In embodiments, m is an integer from 2 to 24. In embodiments, m is an integer from 2 to 23. In embodiments, m is an integer from 2 to 22. In embodiments, m is an integer from 2 to 21. In embodiments, m is an integer from 2 to 20. In embodiments, m is an integer from 2 to 19. In embodiments, m is an integer from 2 to 18. In embodiments, m is an integer from 2 to 17. In embodiments, m is an integer from 2 to 16. In embodiments, m is an integer from 2 to 15. In embodiments, m is an integer from 2 to 14. In embodiments, m is an integer from 2 to 13. In embodiments, m is an integer from 2 to 12. In embodiments, m is an integer from 2 to 11. In embodiments, m is an integer from 2 to 10. In embodiments, m is an integer from 2 to 9. In embodiments, m is an integer from 2 to 8. In embodiments, m is an integer from 2 to 7. In embodiments, m is an integer from 2 to 6. In embodiments, m is an integer from 2 to 5. In embodiments, m is an integer from 2 to 4. In embodiments, m is an integer from 2 to 3. In embodiments, m is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200.

In embodiments, the polymer may be a block copolymer wherein each block is a blend copolymer.

In embodiments, the ratio of polypeptide monomers to non-polypeptide monomers in the polymer is about 1:10000, 1:1000, 1:100, 1:10, 1:1, 10:1, 100:1, 1000:1, or 10000:1. In embodiments, the ratio of polypeptide monomers to non-polypeptide monomers in the polymer is 1:10000, 1:1000, 1:100, 1:10, 1:1, 10:1, 100:1, 1000:1, or 10000:1.

In an aspect is provided a micelle including a polymer (e.g., copolymer) described herein.

In embodiments, the micelle has a longest dimension (e.g. diameter) of between about 1 and about 1000 nm. In embodiments, the micelle has a longest dimension (e.g. diameter) of between about 5 and about 100 nm. In embodiments, the micelle has a longest dimension (e.g. diameter) of between about 10 and about 50 nm. In embodiments, the micelle has a longest dimension (e.g. diameter) of between 1 and 1000 nm. In embodiments, the micelle has a longest dimension (e.g. diameter) of between 5 and 100 nm. In embodiments, the micelle has a longest dimension (e.g. diameter) of between 10 and 50 nm.

In embodiments, the micelle has a longest dimension (e.g. diameter) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm. In embodiments, the micelle has a diameter of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm.

In embodiments, the micelle longest dimension (e.g. diameter) is a hydrodynamic longest dimension (e.g. diameter). In embodiments, the longest dimension (e.g. diameter) is an average longest dimension (e.g. diameter) of a sample.

In an aspect is provided a nanoparticle including a polymer (e.g., copolymer) described herein.

In embodiments, the nanoparticle is a approximately spherical nanoparticle.

In embodiments, the nanoparticle has a longest dimension (e.g. diameter) of between about 1 and about 1000 nm. In embodiments, the nanoparticle has a longest dimension (e.g. diameter) of between about 5 and about 100 nm. In embodiments, the nanoparticle has a longest dimension (e.g. diameter) of between about 10 and about 50 nm. In embodiments, the nanoparticle has a longest dimension (e.g. diameter) of between 1 and 1000 nm. In embodiments, the nanoparticle has a longest dimension (e.g. diameter) of between 5 and 100 nm. In embodiments, the nanoparticle has a longest dimension (e.g. diameter) of between 10 and 50 nm.

In embodiments, the nanoparticle has a longest dimension (e.g. diameter) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm.

In embodiments, the nanoparticle has a longest dimension (e.g. diameter) of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm.

In embodiments, the nanoparticle longest dimension (e.g. diameter) is a hydrodynamic longest dimension (e.g. diameter). In embodiments, the longest dimension (e.g. diameter) is an average longest dimension (e.g. diameter) of a sample.

In embodiments, the polymer is capable of programmed self-assembly. In embodiments, the programmed self-assembly results in a nanoparticle (e.g., as described herein).

In embodiments, the polymer is a capable of cellular internalization.

In an aspect is provided a polymer including a linear backbone covalently bound to a plurality of polypeptide branches. The polymer (graft polymer) is assembled by graft-through polymerization of a plurality of polypeptide monomers including a polymerizable monomer covalently bound to an polypeptide. The polypeptide thereby forming each of the plurality of polypeptide branches.

In embodiments, the graft-through polymerization employs ring-opening metathesis polymerization (ROMP). In embodiments, the graft-through polymerization includes ring-opening metathesis polymerization (ROMP). In embodiments, the graft-through polymerization employs radical polymerization, controlled radical polymerization, reversible addition-fragmentation chain transfer (RAFT) polymerization, atom transfer radical polymerization (ATRP), ring-opening metathesis polymerization (ROMP), anionic polymerization, cationic polymerization, free radical living polymerization, acyclic diene metathesis polymerization, radiation-induced polymerization, ring-opening olefin metathesis polymerization, polycondensation reactions, or iniferter-induced polymerization.

In an aspect is provided a block copolymer including a linear backbone covalently bound to a plurality of polypeptide (e.g. O; $R^3$ or $R^4$) moiety branches and a plurality of non-polypeptide moiety side chains, wherein: the plurality of polypeptide moiety branches form a first block portion of the copolymer and the non-polypeptide moiety side chains form a second block portion of the copolymer; the copolymer is assembled by graft-through polymerization of a plurality of polypeptide moiety monomers and a plurality of non-polypeptide moiety monomers, wherein each of the plurality of polypeptide moiety monomers includes a polymerizable monomer covalently bound to an polypeptide moiety, the polypeptide moiety thereby forming each of the plurality of polypeptide moiety branches; and each of the plurality of non-polypeptide moiety monomers includes the polymerizable monomer covalently bound to a non-polypeptide moiety, the non-polypeptide moiety thereby forming each of the plurality of non-polypeptide moiety side chains.

In an aspect is provided an amphiphilic block copolymer including a linear backbone covalently bound to a plurality of polypeptide (e.g. O; $R^3$ or $R^4$) moiety branches and a plurality of hydrophobic moiety side chains, wherein: the plurality of polypeptide moiety branches form a hydrophilic block portion of the amphiphilic copolymer and the hydrophobic moiety side chains form a hydrophobic block portion of the amphiphilic copolymer; the copolymer is assembled by graft-through polymerization of a plurality of polypeptide moiety monomers and a plurality of hydrophobic moiety monomers, wherein each of the plurality of polypeptide moiety monomers includes a polymerizable monomer covalently bound to a polypeptide moiety, the polypeptide moiety thereby forming each of the plurality of polypeptide moiety branches; and each of the plurality of hydrophobic moiety monomers includes the polymerizable monomer covalently bound to a hydrophobic moiety, the hydrophobic moiety thereby forming each of the plurality of hydrophobic moiety side chains.

The linear backbone, polypeptide (e.g. O; $R^3$ or $R^4$) moiety branches, polypeptide monomers, graft-through polymerization, polymerizable monomer, and polypeptide are as described herein, including in aspects (e.g., above), embodiments (e.g., above), examples, figures, tables, schemes, and claims.

In embodiments, the amphiphilic block copolymer has the formula: $R^1\text{-}[M(O)]_n\text{-}[M(P)]_m\text{—}R^2$ or $R^1\text{-}[M(P)]_m\text{-}[M(O)]_n\text{—}R^2$ wherein, n is an integer from 2 to 1000; m is an integer from 2 to 1000; M is the polymerized monomer; O is independently apolypeptide; P is independently ahydrophobic moiety; and $R^1$ and $R^2$ are independently terminal polymer moieties.

$R^1$, M, O, n, and $R^2$ are as described herein, including in aspects (e.g., above), embodiments (e.g., above), examples, figures, tables, schemes, and claims.

In an aspect is provided a micelle including an amphiphilic block copolymer described herein, including in an aspect, embodiment, example, figures, table, scheme, or claim.

In an aspect is provided a nanoparticle including an amphiphilic block copolymer described herein, including in an aspect, embodiment, example, figure, table, scheme, or claim.

In an aspect is provided a blend copolymer including a linear backbone covalently bound to a plurality of polypeptide (e.g. O; $R^3$ or $R^4$) moiety branches and a plurality of non-polypeptide moiety side chains, wherein the plurality of polypeptide moiety branches and plurality of non-polypeptide moiety side chains are mixed.

In embodiments, the polymer, micelle, amphiphilic block copolymer, blend copolymer, or nanoparticle is as described herein, including in an aspect, embodiment, example, figure, table, scheme, and claim.

In one aspect the present disclosure provides a cell penetrating high density brush peptide polymer composition and/or delivery vehicle for delivering cell penetrating high density brush peptide polymer and drugs. In the composition and/or the delivery vehicle of the present disclosure the peptide is active on the polymer or may be released at a given place and time via a cleavable linkage.

In one aspect the present disclosure provides a composition including a high density brush peptide polymer, where the peptide is pendant to polymerized norbornene moieties. In one aspect, the present disclosure includes a drug delivery vehicle including a high density brush peptide polymer, where the peptide is pendant to polymerized norbornene moieties (polymerized moieties).

The norbornene may be a cis-5-norbornene-exo-2,3-dicarboxylic anhydride. In embodiments, the norbornene moieties are N-(hexanoic acid)-cis-5-norbornene-exo-dicarboximide (NorAha) moieties or N-(glycine)-cis-5-norbornene-exo-dicarboximide (NorGly) moieties.

In embodiments, blend co-polymers are prepared with in various ratios of block polymers. For example, 9:1 ratio blend co-polymer with the peptide monomer (m=1) at the end or in the middle of the polymer can be prepared, or an intermediate 5:5 ratio blend co-polymer can be prepared, shown below.

polymerization of the homopolymer is 8, 10, 15, 20, 25, 30, 35, 40, 45, 50, 55, 60, 65, 70, or any intervening digit.

In embodiments, the non-peptidic moieties is oligoethylene glycol (OEG), poly(ethylene glycol) 5000 (PEG 5000), or poly(ethylene glycol) 2000 (PEG 2000).

In embodiments, the norbornene moieties are linked to the polypeptide or non-polypeptide moiety with a linker. In embodiments, the linker is a carbon linker. In embodiments, the linker is a substituted or unsubstituted $C_1$-$C_{20}$ alkylene. The linker is a carboxylic acid of a substituted or unsubstituted $C_1$-$C_{20}$ alkylene. In embodiments, the linker is hexanoic acid of methane, ethane, propane, butane, pentane, hexane, heptane, octane, nonane, or decane.

In embodiments, the polypetide moiety includes peptides with arginine or lysine residues at the N- or at the C-terminus. In embodiments, the polymer includes peptide with arginine or lysine residues at the C-terminus. In embodiments, the polymer includes peptide with one or two arginine or lysine residues at the C-terminus. In embodiments, the polymer includes peptide with two arginine residues at the C-terminus. The C-terminus faces the solution. In embodiments, the polymer includes peptides with two arginine residues at the C-terminus. In embodiments, the polymer includes a therapeutic polypeptide. Non-limiting examples of the therapeutic polypeptide includes: a cell growth or proliferation inhibitory peptide, an anti-inflammatory peptide, an anti-tumor or anti-cancer peptide, an anti-apoptotic peptide, anti-diabetic, anti-obesity, anti-infective, anti-bacterial, anti-viral, peptides for promoting cell growth and differentiation, peptides for preventing pain, and peptides for preventing or treating neural degeneration and/or peptides for promoting neurogenesis.

In embodiments, the present disclosure includes a cell penetrating high density brush peptide polymer composition including: Nesiritide, Ceruletide, Bentiromide, Exenatide, Gonadorelin, Enfuvirtide, Vancomycin, Icatibant, Secretin, Leuprolide, Glucagon recombinant, Oxytocin, Bivalirudin, Sermorelin, Gramicidin D, Insulin recombinant, Capreomycin, Salmon Calcitonin, Vasopressin, Cosyntropin, Bacitracin, Octreotide, Abarelix, Vapreotide, Thymalfasin, Insulin recombinant, Mecasermin, Cetrorelix, Teriparatide, Corticotropin, or Pramlintide.

In embodiments, the peptide in the polymer is resistant to proteolytic degradation.

In embodiments, the high density brush peptide polymer forms spherical micelles of about 10-50 nm diameter (re-

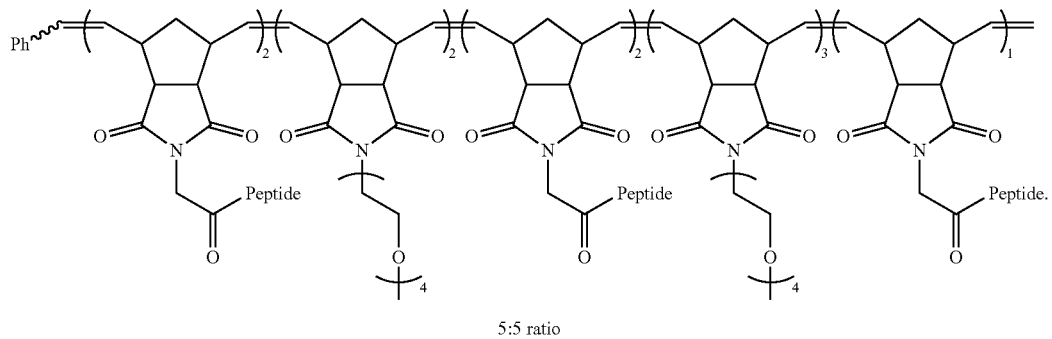

5:5 ratio

In embodiments, the present disclosure includes the high density brush peptide homopolymer or a block copolymer. In embodiments, the degree of polymerization of the homopolymer may be 8-70. In embodiments, the degree of phrase). In embodiments, a side chain protecting group—Pbf—is attached to the peptide during peptide synthesis.

In embodiments, the present disclosure includes norbornene monomers and polymerized high density peptide polymers prepared by ROMP. The high density peptide brush polymers of the present disclosure are less susceptible to proteolytic degradation compared to linear peptide sequences. In embodiments, the high density brush polymers are resistant to proteolysis and efficiently penetrate and carry a cargo into the cell.

In embodiments, the peptide brush polymers of the present disclosure forms ~10-50 nm diameter spherical micellar assemblies and penetrates cells efficiently. In embodiments, both polymer and particle formulations of the peptide brush polymers are cell penetrating peptides that are resistant to proteolysis under conditions that readily degrade the non-polymerized In embodiments, the polymer includes a longer linker between the norbornyl polymer backbone and the peptide in order to separate the peptide from the polymer backbone, thereby making the peptides more flexible and sterically accessible. In embodiments, the linkers are cleavable under appropriate biological conditions or by exogenous sources. Appropriate pH- or UV-sensitive linkers may be included in the polymers. Polymer-drug conjugates improve drug solubility, circulation time (through the properties of the polymer carrier), and drug targeting (via the use of appropriate linkers that can respond to changes in physiological conditions such as temperature, pH, and the presence of enzymes). In this type of polymer conjugate, multiple copies of bioactive agents, ranging from small molecule drugs to larger compounds like Pharmaceutical Compositions In another aspect is provided a pharmaceutical composition including a pharmaceutically acceptable excipient and a polymer (e.g., polypeptide polymer, copolymer, block copolymer, blend copolymer), micelle, or nanoparticle (e.g., each as described herein) as described herein.

In embodiments of the pharmaceutical compositions, the polymer (e.g., polypeptide polymer, copolymer, block copolymer, blend copolymer), micelle, or nanoparticle (e.g., each as described herein), is included in a therapeutically effective amount.

In embodiments of the pharmaceutical compositions, the pharmaceutical composition includes a second polymer (e.g., polypeptide polymer, copolymer, block copolymer, blend copolymer), micelle, or nanoparticle (e.g., each as described herein). In embodiments of the pharmaceutical compositions, the pharmaceutical composition includes a second polymer (e.g., polypeptide polymer, copolymer, block copolymer, blend copolymer), micelle, or nanoparticle (e.g., each as described herein) in a therapeutically effective amount.

Methods of Using Polymers

In an aspect is provided a method of administering a polypeptide to the interior of a cell including contacting the cell with a polymer (e.g., polypeptide polymer, copolymer, block copolymer, blend copolymer), micelle, or nanoparticle (e.g., each as described herein).

In embodiments, the cell is in a subject. In embodiments, the polymer, micelle, or nanoparticle is administered systemically to the subject.

In an aspect is provided a method of internalizing polypeptides (e.g., polypeptides copolymers, block copolymers, blend copolymers) into a cell including contacting the cell with a polymer. In embodiments, the polymer is described herein, including in an aspect, embodiment, example, figure, table, scheme, or claim. In embodiments, the polypeptide is a polypeptide as described herein.

In embodiments, the polymer is a polymer described herein (including in an aspect, embodiment, example, figure, table, claim, or scheme). In embodiments, the polymer is a brush polymer. In embodiments, the polymer is a block copolymer. In embodiments, the polymer is a block copolymer described herein, including in an aspect, embodiment, example, figure, table, scheme, or claim. In embodiments, the polymer is a blend copolymer (e.g., described herein).

In one aspect, the present disclosure provides a method of delivering a peptide, by the delivery device of the present disclosure.

Methods of Treatment

In an aspect is provided a method of treating a disease in a subject, including administering to the subject an effective amount of a polymer described herein (e.g., polypeptide polymer, copolymer, block copolymer, blend copolymer), micelle, or nanoparticle (e.g., each as described herein).

In embodiments, the subject is human. In embodiments, the polymer, micelle, or nanoparticle is administered systemically to the subject.

In an aspect is provided a method of internalizing polypeptides (e.g., polypeptides copolymers, block copolymers, blend copolymers) into a cell including contacting the cell with a polymer. In embodiments, the polymer is described herein, including in an aspect, embodiment, example, figure, table, scheme, or claim. In embodiments, the polypeptide is a polypeptide as described herein.

In embodiments, the polymer is a polymer described herein (including in an aspect,

ADDITIONAL EMBODIMENTS

1a. A composition comprising a cell penetrating high density brush peptide polymer, wherein the peptide polymer comprises peptides with arginine or lysine residues appended at the N- or at the C-terminus, and the peptide is pendant to polymerized norbornene moieties.

2a. A drug delivery vehicle for delivering a therapeutic agent into a cell, comprising a cell penetrating high density brush peptide polymer, wherein the peptide polymer comprises peptides with arginine or lysine residues appended at the N- or at the C-terminus, and peptide is pendant to polymerized norbornene moieties.

3a. The composition of any previous embodiment or the drug delivery vehicle of any previous embodiment, wherein the high density brush peptide polymer is linked to a small molecule pharmaceutically active agent or an oligonucleotide 4a. The composition or the drug delivery vehicle of one of above embodiments, wherein the polymer comprises peptide with arginine or lysine residues at the C-terminus.

5a. The composition or the drug delivery vehicle of one of above embodiments, wherein the polymer comprises peptide with one or two arginine or lysine residues at the C-terminus.

6a. The composition or the drug delivery vehicle of one of above embodiments, wherein the polymer comprises peptide with two arginine residues at the C-terminus.

7a. The composition of any previous embodiment or the drug delivery vehicle of any previous embodiment, wherein the high density brush peptide polymer is a homopolymer or a block copolymer.

8a. The composition or the drug delivery vehicle of any previous embodiment, wherein the degree of polymerization of the homopolymer is 8-70.

9a. The composition or the drug delivery vehicle of any previous embodiment, wherein the degree of polymerization of the homopolymer is 8, 15, 30, or 60.

10a. The composition or the drug delivery vehicle of any previous embodiment, wherein the block copolymer comprises a first block polymer comprising a peptide pendant to polymerized norbornene moieties, and a second block polymer comprising a peptidic or non-peptidic moiety pendant to norbornene moieties, wherein the degree of polymerization of the first block is 8-70, and the degree of polymerization of the second block is 10-30.

11a. The composition or the drug delivery vehicle of one of above embodiments, wherein the norbornene moieties are linked to the peptide or the non-peptidic moiety with a linker.

12a. The composition or the drug delivery vehicle of any previous embodiment, wherein the linker is a carbon linker.

13a. The composition or the drug delivery vehicle any previous embodiment, wherein the carbon linker is a substituted or unsubstituted $C_1$-$C_{20}$ alkane.

14a. The composition or the drug delivery vehicle of any previous embodiment, wherein the linker comprises a carboxylic acid of a substituted or unsubstituted $C_1$-$C_{20}$ alkane.

15a. The composition or the drug delivery vehicle of any previous embodiment wherein the linker is hexanoic acid of methane, ethane, propane, butane, pentane, hexane, heptane, octane, nonane, or decane.

16a. The composition or the drug delivery vehicle of one of above embodiments, wherein the norbornene moieties are 5-norbornene-exo-dicarboximide moieties.

17a. The composition or the drug delivery vehicle of embodiment 18, wherein the norbornene moieties are N-(hexanoic acid)-cis-5-norbornene-exo-dicarboximide (NorAha) moieties or N-(glycine)-cis-5-norbornene-exo-dicarboximide (NorGly) moieties.

18a. The composition or the drug delivery vehicle of embodiment 11, wherein the non-peptidic moiety is oligoethylene glycol (OEG), poly(ethylene glycol) 5000 (PEG 5000), or poly(ethylene glycol) 2000 (PEG 2000).

29a. The composition or the drug delivery vehicle of one of above embodiments, wherein the polymer comprises a therapeutic peptide.

20a. The composition or the drug delivery vehicle of one of above embodiments, wherein the peptide in the polymer is resistant to proteolytic degradation.

21a. The composition or the drug delivery vehicle of one of above embodiments, forming a spherical micellar assembly.

22a. The composition or the drug delivery vehicle of one of above embodiments, comprising a side chain protecting group.

23a. The composition or the drug delivery vehicle of one of above embodiments, comprising a detectable moiety.

24a. The composition or the drug delivery vehicle of one of above embodiments, wherein the detectable moiety is a poly-histidine (poly(His)), chitin binding protein, maltose binding protein, glutathione-S-transferase (GST), FLAG-tag, AviTag, Calmodulin-tag, polyglutamate tag, E-tag, HA-tag, Myc-tag, S-tag, SBP-tag, Softtag 1, Softtag 3, Strep-tag, TC tag, V5 tag, VSV tag, Xpress tag, Isopeptag, SpyTag, Biotin Carboxyl Carrier Protein (BCCP) tag, Halo-tag, thioredoxin-tag, or Fc-tag, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety.

25a. A method of preparing a cell penetrating high density brush peptide polymer, wherein the peptide polymer comprises peptides with an arginine or a lysine residue appended to the N- or at the C-terminus, and is pendant to a polymerized norbornene moieties, comprising combining a plurality of the peptide monomer with a ruthenium catalyst into a mixture for ring opening metathesis polymerization (ROMP).

26a. The method of any previous embodiment, wherein the polymer is a homopolymer or a block copolymer.

27a. The method of any previous embodiment, wherein the block copolymer is prepared by first polymerizing the peptide monomer to completion prior to adding and polymerizing the non-peptidic mononmer.

28a. A method of delivering a peptide, pharmaceutically active agent, or an oligonucleotide into a cell by the drug delivery vehicle of any previous embodiment.

As used herein, the term "Drug delivery vehicle or system" is used in accordance with its common meaning in the chemical sciences and refers to high density brush peptide polymers disclosed herein, that used for the targeted delivery and/or controlled release of therapeutic agents into an interior of a cell. In embodiments, the drug delivery vehicles of the present disclosure including an active therapeutic agent are administered as pharmaceutical compositions.

1. A polymer having the formula: $R^1$-$[M(O)]_n$—$R^2$ wherein, n is an integer from 2 to 1000; M is a polymerized monomer; O is independently a therapeutic polypeptide (a therapeutic polypeptide moiety) covalently attached to M through a covalent linker; and $R^1$ and $R^2$ are independently terminal polymer moieties.

2. A block copolymer having the formula: $R^1$-$[M(O)]_n$-$[M(P)]_m$—$R^2$ or $R^1$-$[M(P)]_m$-$[M(O)]_n$—$R^2$ wherein, n is an integer from 2 to 1000; m is an integer from 2 to 1000; M is a polymerized monomer; O is independently a polypeptide (a polypeptide moiety) covalently attached to M through a covalent linker; P is independently a non-polypeptide moiety; and $R^1$ and $R^2$ are independently terminal polymer moieties.

3. A blend copolymer having the formula: $R^1$-$([M(O)]_n$-$[M(P)]_m)_z$—$R^2$ or $R^1$-$([M(P)]_m$-$[M(O)]_n)_z$—$R^2$ wherein, n is an integer from 2 to 1000; m is an integer from 2 to 1000; M is a polymerized monomer; O is independently a polypeptide (a polypeptide moiety) covalently attached to M through a covalent linker; P is independently a non-polypeptide moiety; z is an integer from 2 to 100; and $R^1$ and $R^2$ are independently terminal polymer moieties.

4. The copolymer, wherein said non-polypeptide moiety is independently a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl and wherein said non-polypeptide moiety does not comprise a nucleotide.

5. The copolymer, wherein said polypeptide is independently a therapeutic polypeptide.
6. The copolymer, wherein said non-polypeptide moiety is independently a hydrophobic moiety.
7. The polymer, wherein the substitution independently comprises the therapeutic polypeptide.
8. The polymer, wherein M(O) is

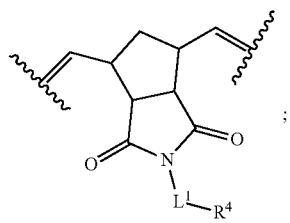

$L^1$ is independently a bond, —O—, —NH—, —COO—, —S—, —SO$_2$—, —SO$_3$—, —SO$_4$—, —SO$_2$NH—, —NHC(O)—, —C(O)NH—, —NHC(O)O—, NHC(O)NH—, C(O), substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^4$ is independently a therapeutic polypeptide.

9. The polymer, wherein the polypeptide comprises from 2 to 6 arginine residues.
10. The polymer, wherein the polypeptide comprises 2 arginine residues.
11. The polymer, wherein the arginine residues are the carboxyl terminal residues of the polypeptide.
12. The polymer, wherein the polypeptide does not comprise a carboxy terminal lysine residue.
13. The polymer, wherein the polypeptide is resistant to proteolysis relative to the unpolymerized polypeptide.
14. The polymer, wherein $R^1$ independently comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.
15. The polymer, wherein $R^2$ independently comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.
16. The polymer, wherein the polymer comprises a detectable moiety.
17. A micelle comprising the copolymer.
18. The micelle, having a longest dimension (e.g., diameter) of between about 1 and about 1000 nm.
19. The micelle, having a longest dimension (e.g., diameter) of between about 5 and about 100 nm.
20. The micelle, having a longest dimension (e.g., diameter) of between about 10 and about 50 nm.
21. A nanoparticle comprising the copolymer.
22. The nanoparticle, wherein said nanoparticle is a spherical nanoparticle.
23. The nanoparticle, having a longest dimension (e.g., diameter) of between about 1 and about 1000 nm.
24. The nanoparticle, having a longest dimension (e.g., diameter) of between about 5 and about 100 nm.
25. The nanoparticle, having a longest dimension (e.g., diameter) of between about 10 and about 50 nm.
26. A method of administering a polypeptide to the interior of a cell comprising contacting said cell with the polymer; the micelle; or the nanoparticle.
27. The method, wherein said cell is in a subject.
28. The method, wherein said polymer, micelle, or nanoparticle is administered systemically to said subject.
29. A method of treating a disease in a subject, comprising administering to said subject a polymer; the micelle; or the nanoparticle.

Examples

Example 1: Polymerization of Cell Penetrating Peptides

Materials

The following materials were used to generate the data described herein. Amino acids used in SPPS were purchased from Aapptec and NovaBiochem. All other materials were obtained from Sigma-Aldrich and used without further purification unless otherwise noted. Initiator 1 ((H$_2$IMES)(pyr)$_2$-(Cl)$_2$Ru=CHPh) was prepared. Analytical scale RP-HPLC was performed with a Jupiter Proteo90A Phenomenex column (150×4.60 mm) using a Hitachi-Elite LaChrom L2130 pump with a UV-vis detector (Hitachi-Elite LaChrome L-2420) monitoring at 214 nm. Peptides were purified with a Jupiter Proteo90A Phenomenex column (2050×25.0 mm) on a Waters DeltaPrep 300 System. For all RP-HPLC assays, gradient solvent systems were used in which Buffer A was 0.1% TFA in water and Buffer B was 0.1% TFA in acetonitrile. Polymer dispersities and molecular weights were determined by size-exclusion chromatography (Phenomenex Phenogel 5 u 10, 1-75 K, 300×7.80 mm in series with a Phenomenex Phenogel 5 u 10, 10-1000 K, 300×7.80 mm with 0.05 M LiBr in DMF as the running buffer at a flow rate of 0.75 mL/min) using a Shimadzu pump equipped with a multiangle light scattering detector (DAWN-HELIO, Wyatt Technology) and a refractive index detector (HITACHI L2490 or a Wyatt Optilab T-rEX detector) normalized to a 30 K MW polystyrene standard. For SEC-MALS chromatograms in which a multimodal distribution is observed by light scattering but not in the RI chromatogram, only the peak width that has an associated RI component was analyzed. DLS measurements were performed on a DynaPro NanoStar (Wyatt Tech). TEM images were obtained by depositing samples on carbon-formavar-coated copper grids (Ted Paella, Inc.), which were then stained with 1% w/w uranyl acetate and then imaged on a Techanai G2 Sphera operating at an accelerating voltage of 200 kV. All concentrations of fluorescent materials were obtained by measuring UV absorbance of the fluorophore on a Thermo-Scientific Nanodrop 2000c and the data was fit to the standard curves. Fluorescent data was recorded on a fluorescence plate reader, PerkinElmer HTS 7000 Plus Bio Assay Reader (excitation: 340 nm; emission: 465 nm), or on a Photon Technology International fluorescence reader. 1H (400 MHz) and 13C (100 MHz) NMR spectra were recorded on a Varian Mercury Plus spectrometer. Chemical shifts are reported in ppm relative to the DMF-d7 or CDCl3 residual peaks.

SEC-MALS chromatograms was obtained for GSGSG (SEQ ID NO:1) polymers at a peptide m of ~60 in DMF with 0.05 M LiBr. In some traces, a multimodal distribution is seen by LS, but only a monomodal distribution is observed at t>15 m in the RI component. In these scenarios, only the peak width with an associated RI component is used to calculate values. Note that the GSGSGK (SEQ ID NO:16) monomer with side chain protecting groups formed a gel upon polymerization, which made it difficult to run these samples on the SEC column. A saturated solution of LiBr was added to break up the gel to achieve the traces shown. The deprotected polymer did not aggregate in DPBS and showed no signal by dynamic light scattering, suggesting that no larger aggregates were present. SEC-MALS chromatograms were obtained for R control polymer at a peptide m of ~60 in DMF with 0.05 M LiBr. SEC-MALS chromatograms were obtained for RGSGSG (SEQ ID NO:12) polymer at a peptide m of ~60 in DMF with 0.05 M LiBr. SEC-MALS chromatograms were obtained for RRGSGSG (SEQ ID NO:13) polymer at a peptide m of ~60 in DMF with 0.05 M LiBr. SEC-MALS chromatograms were obtained for RGSGSG (SEQ ID NO:12) polymer at a peptide m of ~60 in DMF with 0.05 M LiBr. SEC-MALS chromatograms were obtained for GSGSGRR (SEQ ID NO:15) polymer at a peptide m of ~60 in DMF with 0.05 M LiBr. SEC-MALS chromatograms were obtained for GSGSGK (SEQ ID NO:16) polymer at a peptide m of ~60 in DMF with 0.05 M LiBr.

RP-HPLC chromatatograms were obtained for: Norgly-E(EDANS)RPAHLRDSGK(dabcyl)GSGSG-NH$_2$ (SEQ ID NO:6) gradient at 0-67% Buffer B; NorGly-K(dabcyl)RPAHLRDSGE(EDANS)GSGSG-NH$_2$ (SEQ ID NO:8), gradient at 0-67% Buffer B; NorGly-GSGSGE(EDANS)RPAHLRDSGK(dabcyl)NH$_2$ (SEQ ID NO:10), gradient at 10-67% Buffer B; the C-terminal fragment H-RPAHL-RDSGK(dabcyl)GSGSG-NH$_2$ (SEQ ID NO:76), gradient at 0-67% Buffer B; and the N-terminal fragment NorGly-E(EDNAS)RPAH-H (SEQ ID NO:77), gradient at 10-30% Buffer B. Other enzymes used herein cleave the substrate at different locations. The C- and N-terminal chromatograms were used to generate standard curves for all kinetic assays.

A spectrum monitoring the polymerization by $^1$HNMR of NorGly-E(EDANS)RPAHLRDSGK(dabcyl)GSGSG-NH$_2$ (SEQ ID NO:6) was obtained. The absence of the olefenic proton from the monomer (seen at δ 6.32 ppm in the spectrum of the monomer) after 3 hours of polymerization and the corresponding appearance of two broad peaks from approximately δ 5.4-6 ppm signify the cis- and trans-olefin protons of the norbornyl polymer backbone. A spectrum monitoring the polymerization by $^1$HNMR of NorGly-K(dabcyl)RPAHLRDSGE(EDANS)GSGSG-NH$_2$ (SEQ ID NO:8) was obtained. The absence of the olefenic proton from the monomer (seen at δ 6.32 ppm in the spectrum of the monomer) after 3 hours of polymerization and the corresponding appearance of two broad peaks from approximately δ 5.4-6 ppm signify the cis- and trans-olefin protons of the norbornyl polymer backbone. A spectrum monitoring the polymerization by $^1$HNMR of NorGly-GSGSGE(EDANS)RPAHLRDSGK(dabcyl)NH$_2$ (SEQ ID NO:10) was obtained. The absence of the olefenic proton from the monomer (seen at δ 6.32 ppm in the spectrum of the monomer) after 3 hours of polymerization and the corresponding appearance of two broad peaks from approximately δ 5.4-6 ppm signify the cis- and trans-olefin protons of the norbornyl polymer backbone.

Validation of the proteolytic resistance and bioactivity of polymerized CPPs (canonical cell-penetrating peptides) required preparation of well-defined brush polymers with low dispersity via a living polymerization method. High-density brush polymers of known cell-penetrating peptides, Tat and Arg8, together with appropriate control polymers, were prepared via living ROMP (ring opening metathesis polymerization) by an initiator, ((H$_2$IMES)-(pyr)$_2$(Cl)$_2$Ru=CHPh) (FIG. 1A). ROMP by this initiator was selected for preparation of these materials for a variety of reasons. First, the initiator exhibits fast initiation and slower propagation kinetics, which typically afford polymers with exceptionally narrow molecular weight distributions. Second, it is highly functional group tolerant, enabling the incorporation of a wide range of chemical functionality via polymerization of groups pendant to a norbornene moiety, including fluorophores, drugs, sugars, oligonucleotides, and peptides. Very few polymerization techniques have been shown to incorporate peptides directly by graft-through polymerization from a peptide-containing monomer. Reports on graft-through polymerization of peptides by reversible addition-fragmentation chain transfer (RAFT) or free-radical polymerizations describe only blend polymers with less than 50% incorporation of peptides. Additionally, the polymers produced by these methods generally have broader molecular weight distributions than those typically afforded by ROMP. Furthermore, a high degree of functionality and complexity can be readily generated on a single polymer via ROMP by preparing multiblock copolymers of appropriately functionalized norbornene monomers or via the use of chain transfer agents to end-label a polymer through a single cross metathesis event upon complete consumption of monomers.

Guanidinium Monomer Synthesis Methods

A 10 mL round-bottom flask equipped with a stir bar was charged with an amine-terminated norbornene (2-(2-amino-ethyl)-3a,4,7,7a-tetrahydro-1H-4,7-methanoi-soindole-1,3-(2H)-dione) (70 mg, 0.24 mmol, 1 equiv), which was prepared and dissolved in 4.5 mL of dry DMF under N$_2$ (g). To this was added N,N-bis(boc)-1-guanylpyrazole (105 mg, 0.34 mmol, 1 equiv) and diisopropylethylamine (120 µL, 0.68 mmol, 2 equiv). The reaction mixture was stirred at room temperature for 12 h. The solution was concentrated to dryness and re-suspended in 25 mL of CH$_2$C$_2$, then washed with water (×3) and then brine. The CH$_2$C$_2$ layer was collected, dried over Na$_2$SO$_4$ (s) and concentrated to dryness. The material was then purified by flash column chromatography on silica gel (33% EtOAC in hexanes) to yield a white powder in 92% yield (140 mg, 0.31 mmol) R$_f$ 0.37 (33% EtOAc in hexanes): $^1$H NMR (400 MHz, CDCl$_3$, 298 K) δ 11.43 ppm (1H, b), 8.45 (1H, b), 6.27 (2H, t, J=1.5 Hz), 3.71 (2H, dd, J=7.0, 4.4), 3.64 (2H, m), 3.25 (2H, d, J=1.5 Hz), 2.7 (2H, m), 1.51 (1H, d, J=1.1 Hz), 1.48 (9H, s), 1.47 (9H, s), 1.25 (1H, d, J=1.8 Hz); $^{13}$C NMR (100 MHz, CDCl$_3$, 298 K) δ 178.1, 157.0, 156.6, 153.0, 137.9, 137.7, 83.3, 79.5, 48.0, 45.0, 43.1, 40.0, 38.0, 28.3, 28.1; High-resolution MS analysis (ESI-TOFMS) m/z calculated 449.2395, found 449.2394.

Peptide Synthesis Methods

Peptides were synthesized using standard Solid Phase Peptide Synthesis (SPPS) procedures on an AAPPTec Focus XC automated synthesizer. The Arg8 peptide was synthesized with the Pbf protecting group left on the side chains by the use of highly acid-sensitive Sieber Amide resin. Most peptide monomers were synthesized to contain amino acid side chain protecting groups by the use of the highly acid-sensitive Sieber Amide resin, which allows for cleavage of the peptide from the resin without removal of the protecting groups. All other peptides were prepared protecting group-free via the use of Rink Amide MBHA resin.

A typical SPPS procedure involved FMOC deprotection with 20% methyl-piperidine in DMF (one 5 min deprotection followed by one 15 min deprotection), and 45 min amide couplings using 3.75 equiv of the FMOC-protected, and side chain-protected amino acid, 4 equiv of HBTU and 8 equiv of DIPEA. Peptide couplings that were incomplete by Kaiser Test were drained and then subjected to fresh reagents. Monomers were prepared by amide coupling to N-(hexanoic acid)-cis-5-norbornene-exo-dicarboximide or to N-(glycine)-cis-5-norbornene-exo-dicarboximide for the fluorogenic substrates at the N-terminus of the peptide.

The "R control" was prepared by conjugating Arg to N-(glycine)-cis-5-norbornene-exo-dicarboximide. The N-glycine derivative was used to produce a shorter linker between the Arg residue and the norbornene unit to provide as little flexibility as possible. Data from this control is, thus, taken to reflect the maximum theoretical uptake that should be achieved by a peptide containing a single Arg.

Fluorescein-labeled peptides were assembled by addition of Boc-Lys(FMOC)—OH to the N-terminus of the peptide, followed by removal of the FMOC protecting group and amide coupling to 5/6-carboxy fluorescein. Following completion of the synthesis, peptides were cleaved from the resin. Following completion of the synthesis, peptides were cleaved from the resin. All side-chain protected peptide monomers were cleaved from the Sieber amide resin by five consecutive rinses with 2% TFA in DCM for two minutes each. All other peptides were cleaved from Rink MBHA resin and deprotected by treatment with TFA/H2O/TIPS in a 9.5:2.5:2.5 ratio for 2 hrs. The peptides were then precipitated in cold ether and purified by RP-HPLC. The purity of each peptide was verified by analytical RP-HPLC, where a single peak in the chromatogram of a newly purified peptide was taken as an indication of a pure material. The identity of each peptide was confirmed by ESI MS (Table 1 and Table 2). The side-chain protected Arg8 peptide was cleaved from the Sieber amide resin by five 2 min rinses with 2% TFA in DCM. A chromatogram showing the purity of the NorAhaR (Pbf)GS(OtBu)GS(OtBu)G-NH$_2$ (SEQ ID NO:44) peptide at 30-50% Buffer B was obtained. The identity of the peak was confirmed using ESI MS shown in Table 1. A chromatogram showing the purity of the NorAhaR(Pbf)R(Pbf)GS(OtBu)GS(OtBu)G-NH$_2$ (SEQ ID NO:45) peptide at 40-60% Buffer B was obtained. The identity of the peak was confirmed using ESI MS shown in Table 1. A chromatogram showing the purity of the NorAhaGS(OtBu)GS(OtBu)GR(Pbf)-NH$_2$ (SEQ ID NO:46) peptide at 30-50% Buffer B was obtained. The identity of the peak was confirmed using ESI MS shown in Table 1. A chromatogram showing the purity of the NorAhaGS(OtBu)GS(OtBu)GR(Pbf)R(Pbf)-NH$_2$ (SEQ ID NO:47) peptide at 40-60% Buffer B was obtained. The identity of the peak was confirmed using ESI MS shown in Table 1. A chromatogram showing the purity of the NorAhaGS(OtBu)GS(OtBu)GK(Boc)-NH$_2$ (SEQ ID NO:48) peptide at 30-90% Buffer B was obtained. The identity of the peak was confirmed using ESI MS shown in Table 1. A chromatogram showing the purity of the NorAhaGSGSGKK-NH$_2$ (SEQ ID NO:49) peptide at 10-50% Buffer B was obtained. The identity of the peak was confirmed using ESI MS shown in Table 1. A chromatogram showing the purity of the NorGlyR-NH$_2$ peptide at 30-75% Buffer B was obtained. The identity of the peak was confirmed using ESI MS shown in Table 1. An RP-HPLC chromatogram confirming the purity of) NorAhaKLAK-LAKKLAKLAK-NH$_2$ (full length KLA, SEQ ID NO:50) at 0-50% Buffer B was obtained. NorAha=N-(hexanoic acid)-cis-5-norbornene-exo-dicarboximide; The identity of each peak was confirmed by ESI MS as shown in Table 1. An RP-HPLC chromatogram confirming the purity NorAhaK-LAKLAK-NH$_2$ (fragment KLA, SEQ ID NO:51) at 10-40% Buffer B was obtained. NorGly=N-(glycine)-cis-5-norbornene-exo-dicarboximide. Note that some peptides were synthesized with protecting groups on the amino acid side chains. The identity of each peak was confirmed by ESI MS as shown in Table 1. An RP-HPLC chromatogram confirming the purity of K(Flu)RGSGSG (SEQ ID NO:52) was obtained. The peptide was purified using a gradient of 0-67% Buffer B. The identity of each peak was confirmed by ESI MS as shown in Table 2. Flu represents 5/6-carboxyfluorescein, which is conjugated to the F amino group of the N-terminal Lys on each peptide. An RP-HPLC chromatogram confirming the purity of K(Flu)RRGSGSG (SEQ ID NO:53) was obtained. The peptide was purified using a gradient of 0-67% Buffer B. The identity of each peak was confirmed by ESI MS as shown in Table 2. An RP-HPLC chromatogram confirming the purity of K(Flu)GSGSGR (SEQ ID NO:54) was obtained. The peptide was purified using a gradient of 0-67% Buffer B. The identity of each peak was confirmed by ESI MS as shown in Table 2. An RP-HPLC chromatogram confirming the purity of K(Flu)GSGSGRR (SEQ ID NO:55) was obtained. The peptide was purified using a gradient of 0-67% Buffer B. The identity of each peak was confirmed by ESI MS as shown in Table 2. An RP-HPLC chromatogram confirming the purity of K(Flu)GSGSGK (SEQ ID NO:56) was obtained. The peptide was purified using a gradient of 0-67% Buffer B. The identity of each peak was confirmed by ESI MS as shown in Table 2. An RP-HPLC chromatogram confirming the purity of K(Flu)GSGSGKK (SEQ ID NO:57) was obtained. The peptide was purified using a gradient of 0-67% Buffer B. The identity of each peak was confirmed by ESI MS as shown in Table 2. An RP-HPLC chromatogram confirming the purity of K(Flu)KLAKLAKKLAKLAK (SEQ ID NO:58) was obtained. The peptide was purified using a gradient of 0-67% Buffer B. The identity of each peak was confirmed by ESI MS as shown in Table 2.

Figure 21A:
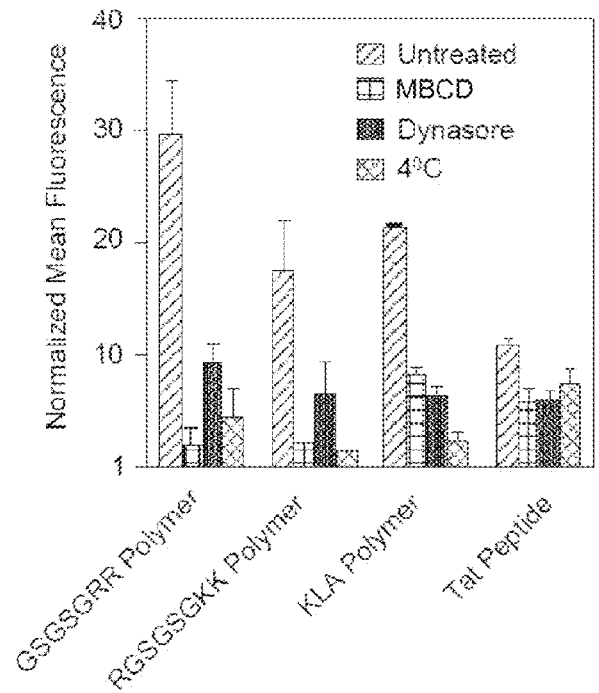
FIG. 21A is a histogram bar graph showing flow cytometry data describing pharmacological inhibition of dynamin-mediated endocytosis by dynasore, membrane fluidity by methyl-β-cyclodextrin (M-βCD) or membrane trafficking by a reduction in incubation temperature. Data is normalized to DPBS at a value of 1. Each bin of the histogram (left to right): untreated, MBCD, Dynbasore, 4° C.
Figure 21B:
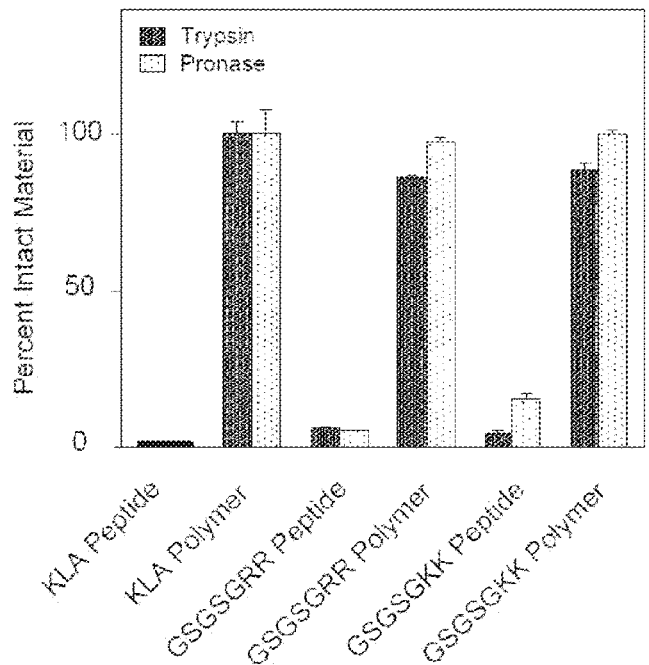
FIG. 21B is a bar graph showing RP-HPLC chromatograms of the material before and after treatment with trypsin or the protease cocktail Pronase that was used to determine proteolytic susceptibility.

A standard curve, correlating peak area on RP-HPLC chromatograms with concentration on an 18 µL injection for the determination of the concentration of intact KLA peptide remaining after proteolytic cleavage was obtained. Percent proteolytic cleavage is given in FIG. 21B. The concentration is with respect to the peptide content. A standard curve, correlating peak area on RP-HPLC chromatograms with concentration on an 18 µL injection for the determination of the concentration of intact KLA polymer (DP~10) remaining after proteolytic cleavage was obtained. Percent proteolytic cleavage is given in FIG. 21B. The concentration is with respect to the peptide content. A standard curve, correlating peak area on RP-HPLC chromatograms with concentration on an 18 µL injection for the determination of the concentration of intact GSGSGRR (SEQ ID NO:15) peptide remaining after proteolytic cleavage. Percent proteolytic cleavage is given in FIG. 21B. The concentration is with respect to the peptide content. A standard curve, correlating peak area on RP-HPLC chromatograms with concentration on an 18 µL injection for the determination of the concentration of intact GSGSGRR (SEQ ID NO:15) polymer (DP-60) remaining after proteolytic cleavage was obtained. Percent proteolytic cleavage is given in FIG. 21B. The concentration is with respect to the peptide content. A standard curve, correlating peak area on RP-HPLC chromatograms with concentration on an 18 µL injection for the determination of the concentration of intact GSGSGKK (SEQ ID NO:17) peptide remaining after proteolytic cleavage was obtained. Percent proteolytic cleavage is given in FIG. 21B. The concentration is with respect to the peptide content. A standard curve, correlating peak area on RP-HPLC chromatograms with concentration on an 18 μL injection for the determination of the concentration of intact GSGSGKK (SEQ ID NO:17) polymer (DP~60) remaining after proteolytic cleavage was obtained. Percent proteolytic cleavage is given in FIG. 21B. The concentration is with respect to the peptide content.

A trace of a RP-HPLC assay for the proteolytic cleavage of the K(Flu)GSGSGRR (SEQ ID NO:55) peptide with no pronase was obtained. Similarly, a trace of a RP-HPLC assay for the proteolytic cleavage of the GSGSGR (SEQ ID NO:14) polymer (m~60) with no pronase was obtained. Similarly, a trace of a RP-HPLC assay for the proteolytic cleavage of the K(Flu)GSGSGRR (SEQ ID NO:55) peptide with trypsin was obtained. The peptide (50 M) was incubated with trypsin (1 μM) for 3 hours in DPBS. The identity of the major peptide fragments were determined by ESI MS. Similarly, a trace of a RP-HPLC assay for the proteolytic cleavage of the GSGSGRR (SEQ ID NO:15) polymer (m~60) with trypsin was obtained. The peptide (50 μM) was incubated with trypsin (1 μM) for 3 hours in DPBS. The identity of the major peptide fragments were determined by ESI MS. Similarly, a trace of a RP-HPLC assay for the proteolytic cleavage of the K(Flu)GSGSGRR (SEQ ID NO:55) peptide with a pronase (cocktail) was obtained. The peptide (50 μM) was incubated with the pronase cocktail (1 μM) for 3 hours in DPBS. The identity of the major peptide fragments were determined by ESI MS. Similarly, a trace of a RP-HPLC assay for the proteolytic cleavage of the GSGSGRR (SEQ ID NO:15) polymer (m~60) with a pronase (cocktail) was obtained. The peptide (50 M) was incubated with the pronase cocktail (1 μM) for 3 hours in DPBS. The identity of the major peptide fragments were determined by ESI MS. Similarly, a trace of a RP-HPLC assay for the proteolytic cleavage of the K(Flu)GSGSGKK (SEQ ID NO:57) peptide with no pronase was obtained. Similarly, a trace of a RP-HPLC assay for the proteolytic cleavage of the GSGSGKK (SEQ ID NO:17) polymer (m~60) with no pronase was obtained. Similarly, a trace of a RP-HPLC assay for the proteolytic cleavage of the K(Flu) GSGSGKK (SEQ ID NO:57) peptide with trypsin was obtained. The peptide (50 M) was incubated with trypsin (1 μM) for 3 hours in DPBS. The identity of the major peptide fragments were determined by ESI MS. Similarly, a trace of a RP-HPLC assay for the proteolytic cleavage of the GSGSGKK (SEQ ID NO:17) polymer (m~60) with trypsin was obtained. The peptide (50 M) was incubated with trypsin (1 μM) for 3 hours in DPBS. The identity of the major peptide fragments were determined by ESI MS. Similarly, a trace of a RP-HPLC assay for the proteolytic cleavage of the K(Flu) GSGSGKK (SEQ ID NO:57) peptide with a pronase (cocktail) was obtained. The peptide (50 μM) was incubated with the pronase cocktail (1 μM) for 3 hours in DPBS. The identity of the major peptide fragments were determined by ESI MS. Similarly, a trace of a RP-HPLC assay for the proteolytic cleavage of the GSGSGKK (SEQ ID NO:17) polymer (m~60) with a pronase (cocktail) was obtained. The peptide (50 μM) was incubated with the pronase cocktail (1 μM) for 3 hours in DPBS. The identity of the major peptide fragments were determined by ESI MS. Similarly, a trace of a RP-HPLC assay for the proteolytic cleavage of the K(Flu) KLAKLAKKLAKLAK (SEQ ID NO:58) peptide with no pronase was obtained. Similarly, a trace of a RP-HPLC assay for the proteolytic cleavage of the KLAKLAKKLAKLAK (SEQ ID NO:18) polymer (m~10) with no pronase. Similarly, a trace of a RP-HPLC assay for the proteolytic cleavage of the K(Flu) KLAKLAKKLAKLAK (SEQ ID NO:58) peptide with trypsin was obtained. The peptide (50 M) was incubated with trypsin (1 μM) for 3 hours in DPBS. The identity of the major peptide fragments were determined by ESI MS. Similarly, a trace of a RP-HPLC assay for the proteolytic cleavage of the KLAKLAKKLAKLAK (SEQ ID NO:18) (m~10) polymer with trypsin was obtained. The peptide (50 μM) was incubated with trypsin (1 μM) for 3 hours in DPBS. The identity of the major peptide fragments were determined by ESI MS. Similarly, a trace of a RP-HPLC assay for the proteolytic cleavage of the K(Flu) KLAKLAKKLAKLAK (SEQ ID NO:58) peptide with a pronase (cocktail) was obtained. The peptide (50 μM) was incubated with the pronase cocktail (1 μM) for 3 hours in DPBS. The identity of the major peptide fragments were determined by ESI MS. Similarly, a trace of a RP-HPLC assay for the proteolytic cleavage of the KLAKLAKKLAKLAK (SEQ ID NO:18) (m~10) polymer with a pronase (cocktail) was obtained. The peptide (50 μM) was incubated with the pronase cocktail (1 μM) for 3 hours in DPBS. The identity of the major peptide fragments were determined by ESI MS.

TABLE 1

Molecular masses obtained for each peptide monomer.

| Peptide Monomer | Calculated Mass | Obtained Mass (ESI) |
|---|---|---|
| NorAhaR(Pbf)GS(OtBu)GS(OtBu)G-NH$_2$ (SEQ ID NO: 44) | 1142 | 1143 |
| NorAhaR(Pbf)R(Pbf)GS(OtBu)GS(OtBu)G-NH$_2$ (SEQ ID NO: 45) | 1550 | 1552 |
| NorAhaGS(OtBu)GS(OtBu)GR(Pbf)-NH$_2$ (SEQ ID NO: 46) | 1142 | 1143 |
| NorAhaGS(OtBu)GS(OtBu)GR(Pbf)R(Pbf)-NH$_2$ (SEQ ID NO: 47) | 1550 | 1552 |
| NorAhaGS(OtBu)GS(OtBu)GK(Boc)-NH$_2$ (SEQ ID NO: 48) | 964 | 963 |
| NorAhaGSGSGKK-NH$_2$ (SEQ ID NO: 49) | 879 | 878 |
| NorAhaKLAKLAKKLAKLAK-NH$_2$ (full length) (SEQ ID NO: 50) | 1781 | 1782 |
| NorAhaKLAKLAK-NH$_2$ (fragment) (SEQ ID NO: 51) | 1029 | 1027 |
| NorGlyR(Pbf)-NH$_2$ | 628 | 627 |

Note that several sequences were synthesized with protecting groups on the amino acid side chains. Masses were obtained by ESI MS and confirm the identity of each monomer.

TABLE 2

Molecular masses obtained for each fluorescently-labeled peptide control.

| Peptide Control | Calculated Mass | Obtained Mass (ESI) |
|---|---|---|
| K(Flu)RGSGSG-NH$_2$ (SEQ ID NO: 52) | 1005 | 1004 |
| K(Flu)RRGSGSG-NH$_2$ (SEQ ID NO: 53) | 1161 | 1160 |
| K(Flu)GSGSGR-NH$_2$ (SEQ ID NO: 54) | 1005 | 1004 |
| K(Flu)GSGSGRR-NH$_2$ (SEQ ID NO: 55) | 1161 | 1160 |
| K(Flu)GSGSGK-NH$_2$ (SEQ ID NO: 56) | 977 | 978 |

TABLE 2-continued

Molecular masses obtained for each fluorescently-labeled peptide control.

| Peptide Control | Calculated Mass | Obtained Mass (ESI) |
|---|---|---|
| K(Flu)GSGSGKK-NH$_2$ (SEQ ID NO: 57) | 1106 | 1105 |
| K(Flu)KLAKLAKKLAKLAK-NH$_2$ (SEQ ID NO: 58) | 2011 | 2010 |

All sequences are prepared with an N-terminal Lys that is conjugated to 5/6-carboxyfluorescein via the -amino group. Masses were obtained by ESI MS and confirm the identity of each monomer.

TABLE 3

Calculated and obtained molecular weight values of peptides prepared for cell penetration studies. Sequence legend (in order of appearance): SEQ ID NO: 59-64, respectively.

| Peptide | Sequence | Mass Calculated | Mass Obtained |
|---|---|---|---|
| Flu-Tat Peptide | K(5/6-Flu)YGRKKRRQRRR-NH$_2$ | 2045.4 | 2044.8 |
| Flu-Arg8 Peptide | K(5/6-Flu)RRRRRRRR-NH$_2$ | 1753.02 | 1752.1 |
| Flu-GSGSG Peptide | K(5/6-Flu)GSGSG-NH$_2$ | 848.82 | 849.1 |
| NorAha-TAT Monomer | NorAha-YGRKKRRQRRR-NH$_2$ | 1818.9 | 1818.5 |
| NorAha-Arg8 Monomer | NorAha-R(Pbf)R(Pbf)R(Pbf)R(Pbf)R(Pbf)R(Pbf)R(Pbf)R(Pbf)-NH$_2$ | 3541.6 | 3542.4 |
| NorAha-GSGSG Monomer | NorAha-GSGSG-NH$_2$ | 622.3 | 623.3 |

Tat and Arg8 masses were obtained via MALDI-TOF MS and GSGSG (SEQ ID NO:1) masses were taken on ESI (+) MS.

TABLE 4

Characterization data for each homopolymer containing the thrombin peptide substrate as determined by batch mode SLS (static light scattering) in a cuvette.

| Polymer | $M_n$ | DP |
|---|---|---|
| Thrombin Homopolymer (10 mer) | 16,800 | 11 (10) |
| Thrombin Homopolymer (20 mer) | 33,300 | 23 (20) |
| Thrombin Homopolymer (30 mer) | 43,900 | 30 (30) |

TABLE 5

Amino acid sequences and molecular weights calculated and obtained for fluorogenic monomers and authentic products. Molecular weights were obtained by ESI (+) MS. Sequence legend (order of appearance): SEQ ID NOs: 6, 8, 10, 65 and 66, respectively.

| Peptide | Sequence | Mass Calculated | Mass Obtained |
|---|---|---|---|
| Fluorogenic monomer | NorGly-E(EDANS)RPAHLRDSGK(dabcyl)GSGSG-NH$_2$ | 2311.03 | 2312.9 |
| Reversed Fluorogenic Monomer | NorGly-K(dabcyl)RPAHLRDSGE(EDANS)GSGSG-NH$_2$ | 2311.03 | 2312.8 |
| Fluorogenic Monomer with linker | NorGly-GSGSGE(EDANS)RPAHLRDSGK(dabcyl)-NH$_2$ | 2311.03 | 2313.7 |
| N-terminal Fragment | NorGly-E(EDANS)RPAH-H | 1059.42 | 1060.6 |
| C-terminal Fragment | H-LRDSGK(dabcyl)GSGSG-NH$_2$ | 1269.5 | 1270.6 |

TABLE 6

Theoretical and experimentally determined $M_n$ values for fluorogenic homopolymers. $M_n$ is obtained by batch mode SLS with a cuvette.

| Polymer | Theoretical $M_n$ | $M_n$ | DP |
|---|---|---|---|
| Fluorogenic Homopolymer | 46,000 | 43,000 | 19 |
| Reversed Fluorogenic Homopolymer | 46,000 | 43,000 | 19 |
| Fluorogenic Homopolymer with Linker | 46,000 | 45,000 | 20 |

Polymerizations Methods

Polymerizations were carried out in a glovebox under $N_2$ (g). A typical protocol used to generate a polymer with DP=10 involved mixing the monomer (0.0125 mmol, 10 equiv, 25 mM) with the catalyst (0.00125 mmol, 1 equiv, 2.5 mM) in dry DMF (0.5 mL). Homopolymerizations were performed in DMF-d7 and followed by 1H NMR to confirm complete consumption of the monomer and to determine the time period required to reach completion. Polymers for cell penetration studies were end-labeled with a copy of fluorescein using a chain transfer agent (1.5 equiv) for 2 h, followed by termination with ethyl vinyl ether (10 equiv) for 1 h at room temperature. Block copolymers were prepared by polymerizing the first monomer (either phenyl or PEG) to completion and then adding the second monomer (a peptide or the guanidinium group), followed by end labeling with the fluorescein chain transfer agent and finally termination with ethyl vinyl ether. Fluorescein-labeled polymers were treated with NH$_4$OH (aq) for 20 min to remove the pivolate protecting group. The resulting polymers were directly characterized by SEC-MALS.

The sidechain protected Arg8 polymer was precipitated with cold ether and collected by centrifugation. The resulting powder was dissolved in 2 mL of a mixture of TFA/H2O/TIPS (95:2.5:2.5) and stirred for 4 h at room temperature. The product was precipitated with cold ether, collected by centrifugation and dried. In preparation for in vitro studies, all polymers were washed (×3) with cold ether (to remove the Ru catalyst) and then dissolved in PBS and dialyzed in an effort to remove any residual monomer or catalyst. The Tat and GSGSG (SEQ ID NO: 1) particles were generated by dissolving the amphiphilic polymers in DMF, and then diluting with an equivalent volume of PBS over 1 hand finally dialyzing this solution into PBS over 48 h with 3 buffer changes using dialysis cups of MWCO 3500 (Thermo Scientific, cat. #69552).

Figure 12:
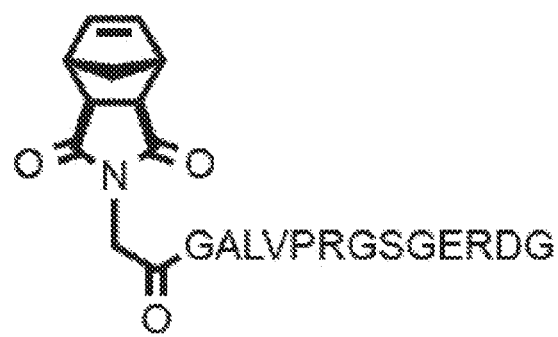
FIG. 12 is a chemical structure of thrombin substrate monomer.

Peptides used to generate ROMP monomers were prepared by solid phase peptide synthesis (SPPS) using standard fluorenylmethyloxycarbonyl (FMOC) chemistry. Peptide monomers were prepared by coupling a carboxylic acid-modified norbornene to the N-terminus of the desired peptide sequence on resin. Peptide monomers with side chain protecting groups and a five-carbon linker between the peptide and the norbornene unit generally polymerize at faster rates than those with shorter linkers or those that possess no protecting groups. Therefore, all peptide monomers were prepared with this linker and used an Arg8 monomer with side chains protected. However, efforts to prepare and polymerize the protected Tat peptide were thwarted by poor solubility of the protected material in solvents compatible with the ROMP initiator. Therefore, the Tat peptide monomer was prepared without protecting groups (FIG. 12 for chemical structures of monomers). All peptides that were incorporated into polymers were also separately prepared (without norbornyl-groups) as fluorescein-labeled peptides via conjugation of 5/6-carboxyfluorescein to the F-amino group of an N-terminal lysine, for use as controls to evaluate the cellular uptake efficiency of the peptides alone versus polymerized materials. (Table 3)

HPLC chromatogram of purified peptide monomer NorAha-RRRRRRRR—NH$_2$ (NorAha-Arg8, SEQ ID NO:67) at 80-100% B gradient was obtained, demonstrating a single peak at about 26 min. HPLC chromatogram of purified peptide monomer NorAhaYGRKKRRQRRR-NH$_2$ (NorAha-Tat, SEQ ID NO:68) at 10-40% B gradient was obtained, demonstrating a major peak at about 17 min. HPLC chromatogram of purified peptide monomer NorAha-GSGSG-NH$_2$ (NorAha-GSGSG, SEQ ID NO:69) at 0-67% B gradient was obtained, demonstrating a major peak at about 18 min. HPLC chromatogram of purified peptide monomer K(Fluorescein)-RRRRRRRR—NH$_2$ (Flu-Arg8, SEQ ID NO:70) at 0-67% B gradient was obtain, demonstrating a major peak at about 20.5 min. HPLC chromatogram of purified peptide monomer K(Fluorescein)-YGRKKRRQRR-NH$_2$ (Flu-Tat, SEQ ID NO:71) at 0-67% B gradient was obtained, demonstrating a major peak at about 17 min. HPLC chromatogram of purified peptide K(Fluorescin)-GSGSG-NH$_2$ (Flu-GSGSG, SEQ ID NO:72) at 0-67% B gradient) was obtained, demonstrating a major peak at about 18.5 min. $^1$H NMR and $^{13}$C NMR spectra of a guanidinium monomer were obtained.

Characterization of Polymerized Peptides

Figure 1B:
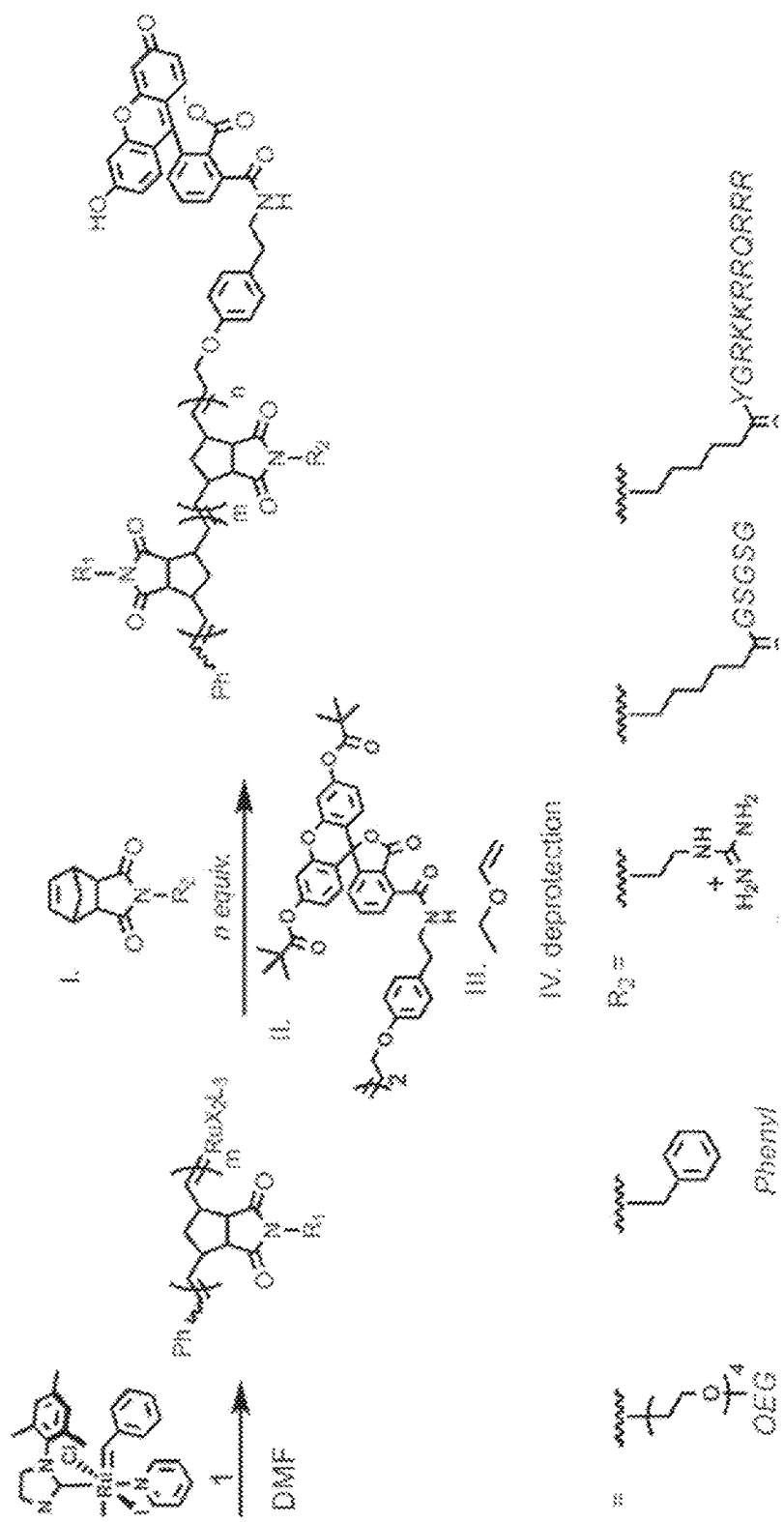
FIG. 1B is a schematic showing synthetic routes for the polymerization of cell penetrating polymers and controls, and routes to the preparation of block copolymers. Note that the guanidinium moiety and Arg8 peptide are polymerized with protecting groups and deprotected after polymerization by treatment of the polymers with a TFA solution. For each polymer, m and n are the degrees of polymerization (DPs).

Each peptide-based monomer was polymerized, and the resulting polymers were end-labeled with fluorescein to enable tracking of the uptake of the material and to serve as a model cargo (FIG. 1A). In addition to polymers containing the canonical Tat and Arg8 CPPs, several control polymers were prepared, including a polymer of an uncharged, non-peptide unit of oligoethylene glycol (OEG) and another consisting of a peptide side chain that did not contain any charged residues (GSGSG) (SEQ ID NO:1). For comparison, a polymer composed of monomers bearing a single guanidinium moiety was prepared as a graft-through analogue of polymers prepared via the graft-to technique employed in other studies. These graft-to guanidinium-containing polymers are the only other cell penetrating polymers prepared by ROMP techniques. The graft-to guanidinium polymer prepared displayed poor solubility as a homopolymer and was therefore prepared as a block copolymer with a water-solubilizing OEG monomer (FIG. 1B, where R$_1$=OEG and R$_2$=guanidinium). After polymerization, the polymers were characterized by size-exclusion chromatography with multiangle light scattering (SEC-MALS) to ascertain degree of polymerization (DP) and molecular weight distribution (dispersity or M$_w$/M$_n$) (Table 1). Good agreement between the obtained DP and the theoretical DP based on the initial monomer-to-initiator ratio ([M]$_0$/[I]$_0$) was observed. Further, all dispersities were less than 1.11, indicating the expected narrow molecular weight distributions.

A chromatogram showing characterization of OEG polymer by SEC-MALS (size exclusion chromatography, multi-angle static light scattering) was obtained, including SLS and Solid colored line indicates SLS, and black dotted line indicates the efractive index (RI). SLS data was only tabulated for peaks that have a corresponding RI signal. The chromatogram is noisy in the SLS component because the polymer runs coincident with the solvent front due to its low molecular weight (~3500). A chromatogram showing characterization of GSGSG (SEQ ID NO:1) polymer by SEC-MALS was obtained. A chromatogram showing characterization of Arg8 polymer by SEC-MALS was obtained. A chromatogram showing characterization of OEG-b-Guanidinium polymer, first "m" block (OEG) by SEC-MALS was obtained. A chromatogram showing characterization of OEG-b-Guanidinium polymer, second "n" block (guanidinium) by SEC-MALS was obtained. A chromatogram showing characterization of phenyl-b-GSGSG polymer, first "m" block (Phenyl) by SEC-MALS was obtained. A chromatogram showing characterization of phenyl-b-GSGSG polymer, second "n" block (GSGSG) (SEQ ID NO:1) by SEC-MALS was obtained. A chromatogram showing characterization pheyl-b-Tat polymer, first "m" block (Phenyl) by SEC-MALS was obtained. A chromatogram showing characterization phenyl-b-Tat polymer, second "n" block (Phenyl) by SEC-MALS was obtained. Solid colored line indicates SLS, and black dotted line indicates the refractive index (RI). Red traces represent homopolymers or the first block of a block copolymer while the second block of block polymers are shown in blue. SLS data is only tabulated for peaks that have a corresponding RI signal.

A plot showing side and forward scattering of the region gated for each flow cytometry experiment was obtained. The percentage given is the percentage of cells that fall within the gated region (10,000 events total). Experiment was performed in triplicate on separate cultures of HeLa cells, and the data for one recording is given.

A histogram showing fluorescence intensity of the gated region for the vehicle control was obtained. Y-axis is number of cells and x-axis is fluorescence. Experiment was performed in triplicate on separate cultures of HeLa cells, and the data for one recording is given.

Table 7. Characterization of cell penetrating polymer and controls[a]

TABLE 7

Characterization of cell penetrating polymer and controls[a]

| Polymer | Block m | | | Block n | | |
|---|---|---|---|---|---|---|
| | M$_n$[a] | M$_w$/M$_n$[b] | DP[c] | M$_n$[a] | M$_w$/M$_n$[b] | DP[d] |
| OEG (10 mer) | 3,600 | 1.03 | 10 (10) | — | — | — |
| OEG (25 mer) | 8,800 | 1.07 | 25 (25) | — | — | — |
| GSGSG | 5,700 | 1.05 | 10 (12) | — | — | — |
| Tat | 8,600 | n/a | 5 (6) | — | — | — |
| Arg8 | 36,000 | 1.08 | 8 (6) | — | — | — |
| PEG-Guanidium | 8,300 | 1.02 | 23 (15) | 12,000 | 1.07 | 8 (12) |

TABLE 7-continued

Characterization of cell penetrating polymer and controls[a]

| Polymer | Block m | | | Block n | | |
|---|---|---|---|---|---|---|
| | $M_n{}^a$ | $M_w/M_n{}^b$ | $DP^c$ | $M_n{}^a$ | $M_w/M_n{}^b$ | $DP^d$ |
| Phenyl-GSGSG | 14,000 | 1.02 | 54 (70) | 18,000 | 1.02 | 8 (12) |
| Phenyl-Tat | 13,000 | 1.01 | 52 (70) | 22,000 | 1.11 | 5 (6) |

*Block m and n refer to the first and second block to be polymerized as shown in FIGS. 1A-1B.
[7]Each polymer is named according to identity of the monomer polymerized as drawn in FIGS. 1A-1B. Block co-polymers are listed with block m first and block n second, separated by a hyphen. Further annotation is as follows:
[a]The number average molecular weight,
[b]the dispersity of each block with theoretical values based based on the amount of material used given in parentheses, c,
[d]degree of polymerization or m (c) and n (d) as denoted in FIG. 1B. All data were obtained by SEC-MALS, except for those describing the Tat polymer, which did not elute on the SEC column and was instead characterized in a cuvette by static light scattering. Without the SEC component, no information on the molecular weight distribution of this polymer was obtained. However, the amphipilic polymer that contains Tat eluted well on SEC and yielded close to the predicted DP in low dispersity.

*Block m and n refer to the first and second block to be polymerized as shown in FIGS. 1A-1B. [7]Each polymer is named according to identity of the monomer polymerized as drawn in FIGS. 1A-1B. Block co-polymers are listed with block m first and block n second, separated by a hyphen. Further annotation is as follows: a.) The number average molecular weight, b.) the dispersity of each block with theoretical values based based on the amount of material used given in parentheses, c, d.) degree of polymerization or m (c) and n (d) as denoted in FIG. 1B. All data were obtained by SEC-MALS, except for those describing the Tat polymer, which did not elute on the SEC column and was instead characterized in a cuvette by static light scattering. Without the SEC component, no information on the molecular weight distribution of this polymer was obtained. However, the amphipilic polymer that contains Tat eluted well on SEC and yielded close to the predicted DP in low dispersity.

The Tat peptide-containing homopolymer, lacking side-chain protecting groups, performed poorly on SEC-MALS, presumably due to unfavorable interactions of the peptide with the size exclusion column. Therefore, no information on the molecular weight distribution of these polymers was obtained, but a molecular weight determination was achieved by measuring the bulk light scattering of the solution in a cuvette (without the size exclusion column); and complete consumption of the Tat monomer after polymerization was verified by $^1$H NMR. An $^1$H NMR spectrum of NorAha-GSGSG polymerization of monomers. Initial spectrum was taken prior to addition of the initiator. Resonance at δ 6.32 ppm corresponds to the norbornene olefin protons of the monomer. Subsequent spectrum was recorded at the end of the polymerization (t=3 hr) and verifies complete consumption of the monomer (no resonance at δ6.32 ppm). The new resonance at ~δ 5.5-6 ppm corresponds to the cis-trans olefin protons of the polymerized material. An $^1$H NMR spectrum NorGuanidinium polymerization of monomers was obtained. Initial spectrum was taken prior to addition of the initiator. Resonance at δ 6.32 ppm corresponds to the norbornene olefin protons of the monomer. Subseuqent spectrum was recorded at the end of the polymerization (t=3 hr) and verifies complete consumption of the monomer (no resonance at δ 6.32 ppm). The new resonance at ~δ 5.5-6 ppm corresponds to the cis-trans olefin protons of the polymerized material. An $^1$H NMR spectrum of NorAha-Tat polymerization of monomers was obtained. Initial spectrum was taken prior to addition of the initiator. Resonance at δ 6.32 ppm corresponds to the norbornene olefin protons of the monomer. Subsequent spectrum was recorded at the end of the polymerization (t=3 hr) and verifies complete consumption of the monomer (no resonance at δ 6.32 ppm). The new resonance at ~δ 5.5-6 ppm corresponds to the cis-trans olefin protons of the polymerized material.

Given the complexity of the Tat and Arg8 peptide-containing polymers (i.e., multiple charged and nucleophilic side chains), it was investigated whether ROMP of these materials proceeds in a living fashion, in order to ensure that well-defined and well-ordered structures, devoid of cross-metathesis or premature termination, could regularly be accessed by this strategy. Confirming the living nature of the polymerization, a plot of $M_n$ (obtained by SEC-MALS) vs $[M]_0/[I]_0$ for the Arg8 monomer yields a linear fit for $[M]_0/[I]_0$ less than 9 (Table 2). At larger $[M]_0/[I]_0$ ratios, propagation ceased, presumably due to steric hindrance encountered from assembling multiple copies of the long, side-chain protected peptide sequence, whose molecular weight as a monomer is 3.5 kDa. A similar plot was obtained from data gathered for polymerization of the Tat polymer, collected by static light scattering (SLS) in a cuvette (and Table 2). Therefore, both CPP monomers were polymerized in a living fashion to a DP of <9, despite the complexity and functionality of their side chains, making this an exceptionally convenient strategy for predictably generating polymeric architectures from peptide monomers.

Plots correlating the number-average molecular weight (Mn) with the initial monomer-to-catalyst ratio ($[M_0/I_0]$ for the polymerization of the Arg8 monomer were calculated. Linear fits are indicative of a living polymerization. Propagation ceased after the polymerization of ~9 monomers.

Plots correlating the number-average molecular weight (Mn) with the initial monomer-to-catalyst ratio ($[M_0/I_0]$ for the polymerization of the Tat monomer were calculated. Linear fits are indicative of a living polymerization. Propagation ceased after the polymerization of ~9 monomers.

TABLE 8

Characterization of the polymerization of the Tat and Arg8 monomers at multiple initial monomer-to-catalyst ratios

| Arg8 Polymerization | | | | Tat Polymerization | | | |
|---|---|---|---|---|---|---|---|
| $[M]_0:[I]_0{}^a$ | $M_n{}^b$ | $DP^c$ | $M_w/M_n{}^d$ | $[M]_0:[I]_0{}^a$ | $M_n{}^b$ | $DP^c$ | $M_w/M_n{}^d$ |
| 5 | 11000 | 3 | 1.05 | 5 | 6400 | 4 | n/a |
| 10 | 20000 | 6 | 1.05 | 10 | 9600 | 5 | n/a |
| 15 | 30000 | 9 | 1.03 | 15 | 15000 | 8 | n/a |
| 20 | 27000 | 8 | 1.05 | 20 | 14000 | 8 | n/a |
| 40 | 31000 | 9 | 1.07 | 40 | 16000 | 9 | n/a |
| 60 | 23000 | 6 | 1.08 | 60 | 15000 | 8 | n/a |

*The polymers listed are all homopolymers as shown in FIG. 1A. Annotation is described as:
[a]the initial monomer-to-catalyst ratio used,
[b]the number average molecular weight obtained,
[c]the degree of polymerization obtained
[d]the dispersity of the polymerization. All data for the Arg8 monomer polymerization were collected by SEC-MALS. Data for the Tat monomer polymerization were obtained in a cuvette via static light scattering, so no information on the dispersity of the Tat polymers was obtained.

* The polymers listed are all homopolymers as shown in FIG. 1A. Annotation is described as: a.) the initial monomer-to-catalyst ratio used, b.) the number average molecular weight obtained, c.) the degree of polymerization obtained d.) the dispersity of the polymerization. All data for the Arg8 monomer polymerization were collected by SEC-MALS. Data for the Tat monomer polymerization were obtained in a cuvette via static light scattering, so no information on the dispersity of the Tat polymers was obtained.

Figure 2A:
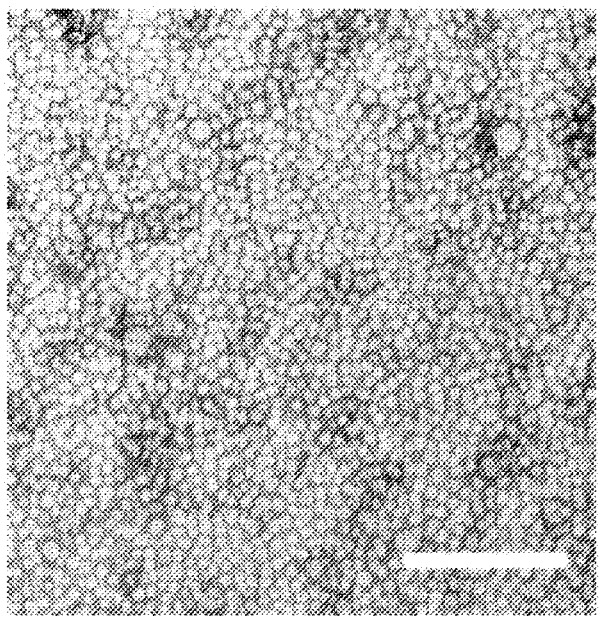
FIG. 2A is a TEM (transmission electron microscopy) image for the Tat particle. Scale bar is 200 nm
Figure 2B:
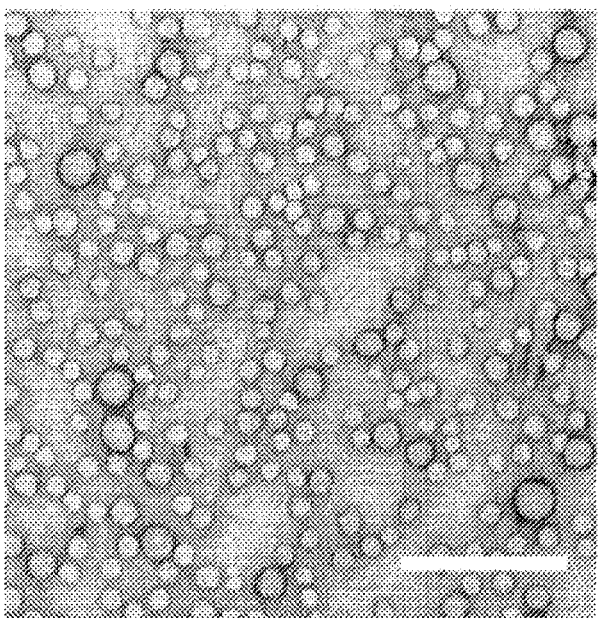
FIG. 2B is a TEM image for the GSGSG (SEQ ID NO:1) particle. Scale bar is 200 nm.

Proteolytic Resistance and Bioactivity of Large Assemblies of Peptide-Containing Polymers In addition to exploring the activity of a single polymer chain, the proteolytic resistance and bioactivity of large assemblies of peptide-containing polymers were examined. Although it was predicted that nanoscale assemblies of multiple peptide-polymers would be large enough to avoid renal clearance thresholds in future applications that might otherwise prevent long circulation times of peptides or lower molecular weight polymers, it was unclear whether these large assemblies would resist proteolysis, or enter cells. To generate nano-particles, amphiphilic polymers of two peptides were prepared: Tat and a GSGSG (SEQ ID NO:1) control peptide (FIG. 1B). The design of these amphiphiles was such that the phenyl-modified norbornene monomers operated as hydrophobic moieties to drive self-assembly of the amphiphiles into micellar nano-particles containing many copies of polymers. To prepare these amphiphiles, a hydrophobic monomer was polymerized to completion prior to addition of the peptide monomer to the living polymer (FIG. 1B, where $R_1$ is phenyl and $R_2$ is GSGSG (SEQ ID NO:1) or Tat). Self-assembly of these amphiphilic polymers into a nanoscale structure was then accomplished by slow dialysis of the material from an organic co-solvent, in which the amphiphile was completely dissolved (DMF), into a selective solvent, in which only the peptide brush is soluble (aqueous phosphate-buffered saline, PBS). The amphiphilic polymers of Tat and GSGSG (SEQ ID NO:1) were found, by DLS and TEM, to form spherical micelles of ~10-50 nm diameter (FIGS. 2A and 2B). DLS data for the Tat and GSGSG (SEQ ID NO:1) particles indicate maximum intensity at about 80 nm radius.

Example 2: Cellular Uptake in HeLa Cells by Flow Cytometry and Live-Cell Confocal Microscopy Cell Culture Assay Methods HeLa cells were purchased from ATCC (CCL-2). Cells were cultured at 37° C. under 5% $CO_2$ in phenol red-containing Dulbecco's Modified Eagle Medium (DMEM; Gibco Life Tech., cat. #11960-044) supplemented with 10% fetal bovine serum (Omega Scientific, cat. #FB02) and with 1× concentrations of nonessential amino acids (Gibco Life Tech., cat. #11140-050) sodium pyruvate (Gibco Life Tech., cat. #11360-070), L-glutamine (Gibco Life Tech., cat. #35050-061), and the antibiotics penicillin/streptomycin (Corning Cellgro, cat. #30-002-C1). Cells were grown in T75 culture flasks and subcultured at ~75-80% confluency (every ~3-4 days). An image showing the live-cell confocal microscopy images of the GSGSGKK (SEQ ID NO:17) polymer (DP ~60) was obtained. All images are the average intensity from six consecutive 1 µm Z-slices using a 40× objective. Cells were treated with 2.5 µM of the material (with respect to fluorophore). GSGSGKK (SEQ ID NO:17) polymer has a peptide m of ~60 and the KLA polymer is m ~10. Each polymer that contains Lys or Arg shows a mixture of diffuse and punctate fluorescence, indicating that the material resides in the cytosol and in cellular compartments, respectively. An image showing the live-cell confocal microscopy images of the GSGSGRR (SEQ ID NO:15) polymer (DP ~60) was obtained. All images are the average intensity from six consecutive 1 µm Z-slices using a 40× objective. Cells were treated with 2.5 µM of the material (with respect to fluorophore). GSGSGRR (SEQ ID NO:15) polymer has a peptide m of ~60 and the KLA polymer is m~10. An image showing the live-cell confocal microscopy images of the KLA polymer (DP ~10) was obtained. All images are the average intensity from six consecutive 1 µm Z-slices using a 40× objective. Cells were treated with 2.5 µM of the material (with respect to fluorophore). KLA polymer has a peptide m of ~10 and the KLA polymer is m~10.

Flow Cytometry Methods

HeLa cells were plated at a density of 90,000 cells per well of a 24-well plate 18 h prior to treatment. Materials dissolved in Dulbecco's Phosphate Buffered Saline (DPBS without $Ca^{2+}$ or $Mg^{2+}$; Corning Cellgro, cat. #21-031-CM) at 10× the desired concentration were added to the wells, and the plates were incubated for 30 min at 37° C. The medium was then removed, and the cells were washed twice with DPBS and then incubated three times for 5 min with heparin (0.5 mg/mL in DPBS; Affymetrix, cat. #16920), and finally rinsed again with DPBS. The cells were then trypsinized (0.25% trypsin; Gibco Life Tech., cat. #15090-046) for 10 min, cold medium was added, and the cells were transferred to Eppendorfs, centrifuged to pellets and then resuspended in a minimal amount of cold DPBS. Fluorescence activated cell sorting data (10000 events on three separate cultures) was acquired on an Accuri C6 flow cytometer set to default "3 blue 1 red" configuration with standard optics and slow fluidics (14 µL/min). For proteolysis studies, the indicated concentration of Tat peptide, homopolymer or particle was pretreated with 1 µM of trypsin, chymotrypsin or Pronase for 20 min in DPBS, after which the protease was heat denatured for 15 min at 65° C. The cells were then incubated, prepared and analyzed by flow cytometry as described above. For mechanistic studies, cells were preincubated with the indicated compound for 30 min at 37° C. prior to addition of the cell-penetrating material. The following concentrations were used: 80 µM dynasore (Enzo Life Sciences, cat. #270-502-M005) and 9.5 mM MJ3CD (Fischer Scientific, cat. #AC377110050). For studies at reduced temperature, cells were incubated at 4° C. for 30 min prior to and during the incubation with the compound of interest. All subsequent washes and manipulations were also done with ice-cooled media and other materials. Data is reported as the normalized mean fluorescence, which are the mean fluorescence yielded by the material/the mean fluorescence from the vehicle control.

Live-Cell Confocal Microscopy Methods

HeLa cells were seeded on glass-bottom 24-well plates at a cell density of 90,000 cells per well 18 h prior to treatment. The medium was removed and then replaced with medium lacking phenol red (Gibco Life Tech., cat #31053-028) to minimize background fluorescence. Materials dissolved in DPBS (at 10× the desired concentration) were added to the wells and the plates were incubated for 30 min at 37° C. The washing procedure used in the flow cytometry experiments (2×DPBS, 3× heparin for 5 min, 1×DPBS) was followed here. Following removal of the final DPBS rinsate, fresh media (phenol red-free) was added to each well. Live cells were imaged on an Olympus FV1000 confocal microscope. For proteolysis studies, the indicated concentration of Tat peptide, homopolymer and particle were pretreated with 1 µM of trypsin, chymotrypsin or Pronase for 20 min in DPBS, after which the protease was heat denatured for 15 min at 65° C. The cells were then incubated, prepared and analyzed by confocal microscopy as described above.

Cellular Uptake of Peptide Controls, Polymer and Nanoparticles

Fluorescence-based in vitro assays were performed in HeLa cells to compare the cellular uptake of the peptide controls, polymers, and nanoparticles. The goal was to determine whether polymerization of the CPPs had an impact on their ability to facilitate cellular entry or on their mechanisms of cellular uptake. In these studies, flow cytometry was used to quantify the amount of cellular uptake, and live-cell confocal microscopy was used to verify internalization and examine the localization of the internalized material.

Figure 3:
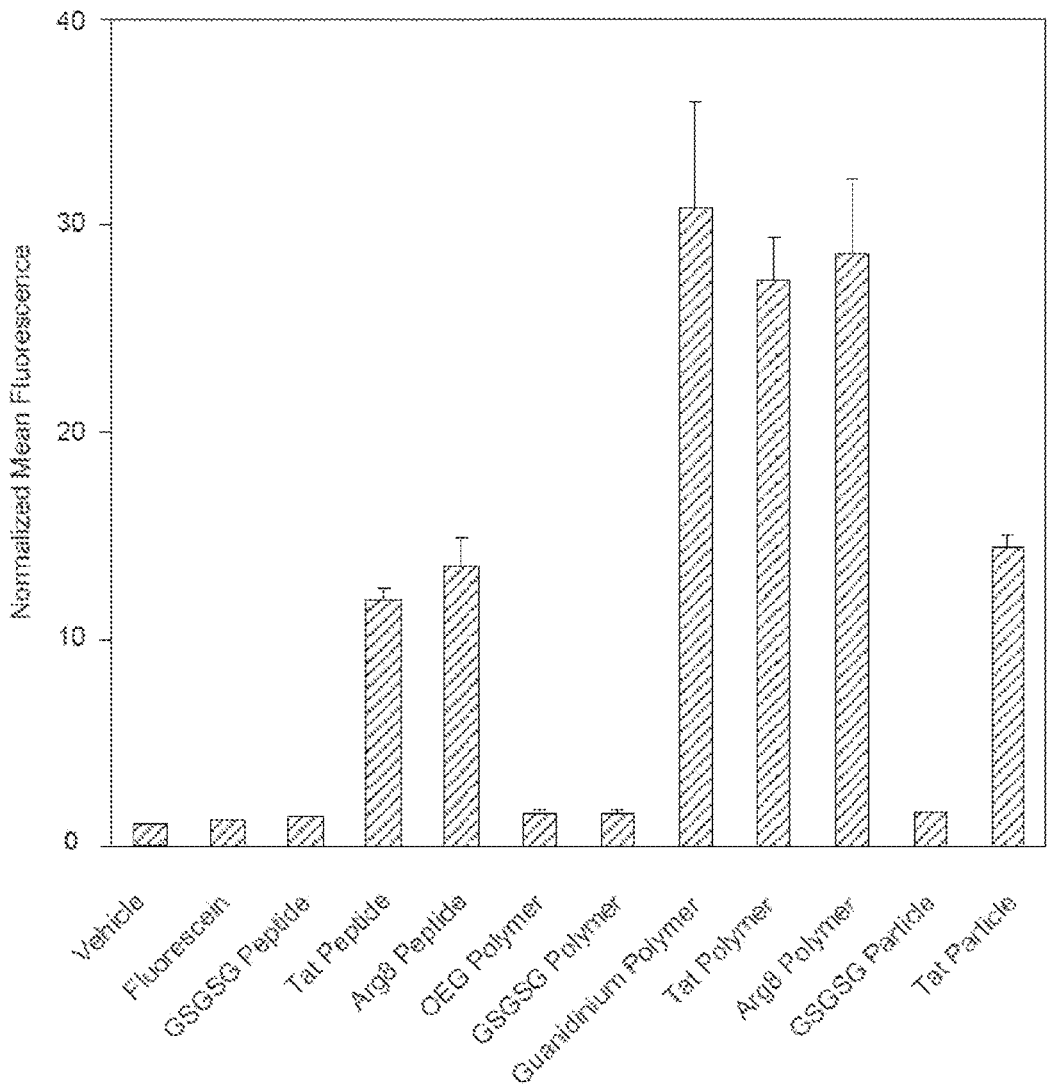
FIG. 3 is a bar graph showing the quantitative comparison of cellular uptake of peptides, polymers and particles at 2.5 µM after 30 min incubation with HeLa cells by flow cytometry. On the y-axis, normalized mean fluorescence refers to the mean fluorescence counts detected for the material divided by the mean fluorescence counts exhibited by the vehicle control (PBS).
Figure 4:
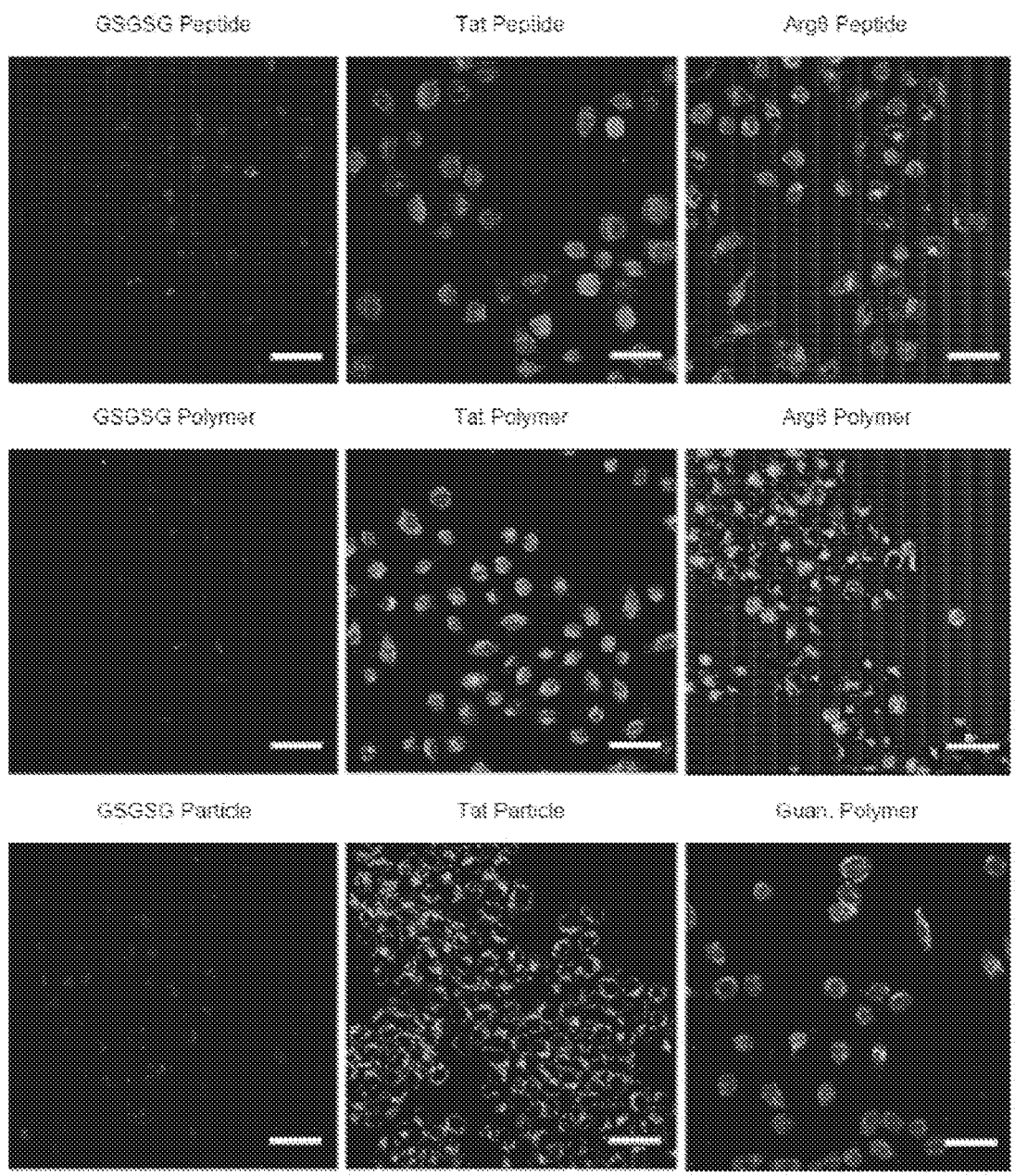
FIG. 4 are images showing live-cell confocal images of peptides, polymers and nanoparticles labeled with fluorescein. Images are the average maximum intensity from six consecutive 1 µm slices. Scale bars are 50 µm.
Figure 5A:
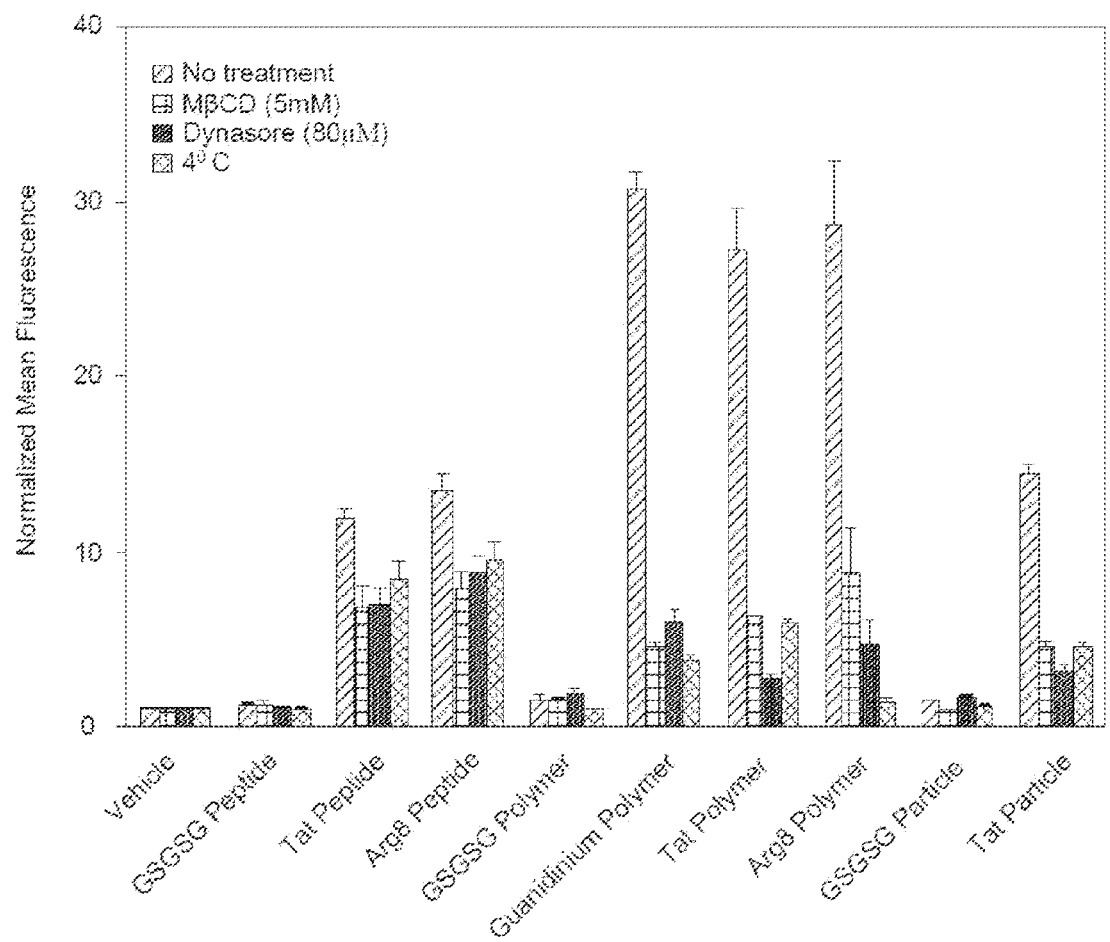
FIG. 5A is a histogram bar graph showing the pharmacological and thermal probes of cellular uptake mechanisms. HeLa cells were pretreated with MβCD (9.5 mM) or dynasore (80 M) for 30 min prior to incubation with the material of interest or preincubated at 4° C. For each bin of the histogram, treatments were (left to right): No treatment, MβCD (5 mM), Dynasore (80 µM), and 4° C.
Figure 5B:
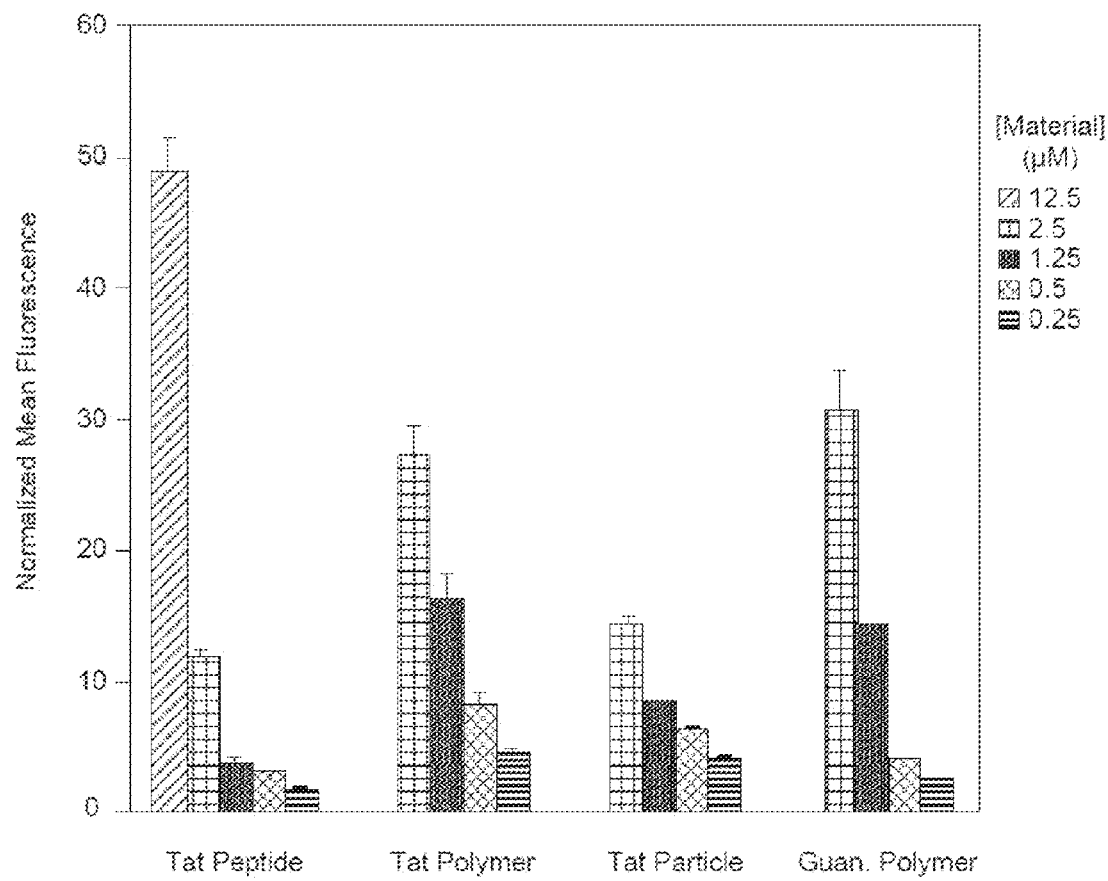
FIG. 5B is a histogram bar graph showing the concentration dependence of the cellular uptake of key materials. All reported flow cytometry data are described as a fold-shift relative to the vehicle control. All experiments described here were performed in DMEM with 10% FBS. For each bin of the histogram, concentrations (µM) were (left to right): 12.5, 2.5, 1.25, 0.5, and 0.25.

In flow cytometry experiments, relative to the vehicle control (PBS), all CPP-containing peptide polymers and particles gave robust fluorescent counts, approximately 2-fold higher than those of the peptides alone (FIG. 3 and FIGS. 5A-5B). These data verify that CPPs maintain or have enhanced function when incorporated into brush polymers or larger polymeric assemblies. The Tat and Arg8 polymers gave responses similar to those of the guanidinium polymer, which is an analogue of the only other cell-penetrating ROMP polymer reported to date. A graph depicting flow cytometry data for fluorescein was obtained; recordings were gated to the vehicle control (PBS). A graph depicting flow cytometry data for the OEG polymer was obtained; recordings were gated to the vehicle control (PBS). A histogram showing any shifts in fluorescence of fluorescein (in green) relative to the vehicle control was obtained. A histogram showing any shifts in fluorescence of the OEG polymer relative to the vehicle control was obtained. A graph depicting flow cytometry data for the GSGSG (SEQ ID NO: 1) peptide was obtained; recordings were gated to the vehicle control (PBS). The observed percentage (50.2) refers to the cells within the gated region for each sample (10,000 events total). A graph depicting flow cytometry data for the GSGSG (SEQ ID NO: 1) polymer was obtained; recordings were gated to the vehicle control (PBS). The observed percentage (35.9) refers to the cells within the gated region for each sample (10,000 events total). A graph depicting flow cytometry data for the GSGSG (SEQ ID NO: 1) particle was obtained; recordings were gated to the vehicle control (PBS). The observed percentage (37.7) refers to the cells within the gated region for each sample (10,000 events total). A histogram showing any shifts in fluorescence of GSGSG (SEQ ID NO: 1) peptide relative to the vehicle control was constructed. A histogram showing any shifts in fluorescence of the GSGSG (SEQ ID NO: 1) polymer relative to the vehicle control was constructed. A histogram showing any shifts in fluorescence of the GSGSG (SEQ ID NO: 1) particle relative to the vehicle control was constructed. A graph depicting flow cytometry data for the Tat Peptide was obtained; recordings were gated to the vehicle control (PBS). The observed percentage (58.2) refers to the cells within the gated region for each sample (10,000 events total). A graph depicting flow cytometry data for the Tat Polymer was obtained; recordings were gated to the vehicle control (PBS). The observed percentage (41.2) refers to the cells within the gated region for each sample (10,000 events total). A graph depicting flow cytometry data for the Tat Particle was obtained; recordings were gated to the vehicle control (PBS). The observed percentage (47.9) refers to the cells within the gated region for each sample (10,000 events total). A histogram showing any shifts in fluorescence of the Tat Peptide relative to the vehicle control was constructed. A histogram showing any shifts in fluorescence of the Tat Polymer relative to the vehicle control was constructed. A histogram showing any shifts in fluorescence of the Tat Particle relative to the vehicle control was constructed. A graph depicting flow cytometry data for the Arg8 Peptide was obtained; recordings were gated to the vehicle control (PBS). The observed percentage (71.8) refers to the cells within the gated region for each sample (10,000 events total). A graph depicting flow cytometry data for the Arg8 Polymer was obtained; recordings were gated to the vehicle control (PBS). The observed percentage (32.7) refers to the cells within the gated region for each sample (10,000 events total). A graph depicting flow cytometry data for the Guanidinium Polymer was obtained; recordings were gated to the vehicle control (PBS). The observed percentage (76.2) refers to the cells within the gated region for each sample (10,000 events total). A histogram showing any shifts in fluorescence of the Arg8 Peptide relative to the vehicle control was constructed. A histogram showing any shifts in fluorescence of the Arg8 Polymer relative to the vehicle control was constructed. A histogram showing any shifts in fluorescence of the Guanidinium Polymer relative to the vehicle control was constructed.

To probe whether the cellular uptake of the polymerized materials was due to the peptide amino acid sequence and not the polymer backbone itself, or the result of the arrangement of any peptide into a brush polymer, the uptake of polymeric materials containing an OEG brush and a GSGSG (SEQ ID NO:1) brush were investigated, both of which do not enter cells as their monomer units. The control materials showed negligible fluorescence signals (less than a 2-fold increase in fluorescence relative to vehicle), similar to the small molecule fluorescein tag itself. Therefore, these data indicate that the amino acid sequences of Tat and Arg8 drive the internalization of the polymers.

Compartmentalization of Fluorescence within Cytoplasm

To confirm that the fluorescence observed in the initial studies resided within the cytoplasm, rather than on the cell's external surface. To this end, live-cell confocal microscopy was performed, because fixation of cells by formaldehyde, methanol or other agents, can cause artifacts due to the release of fluorescently labeled materials entrapped in endosomes. In particular, Z-stack analyses was performed at 1 μm step sizes on live cells treated with each peptide-based material. Across multiple Z-slices for cells treated with all Tat-, Arg8- and guanidinium-containing materials, at the same concentration used in flow cytometry experiments, a combination of punctate and diffuse fluorescence was observed, indicative of compartmentalized and cytosolic localization, respectively. By contrast, no fluorescence was seen for any of the negative controls (GSGSG (SEQ ID NO:1) and OEG polymers), which did not contain cationic moieties and did not penetrate cells in any detectable manner. Images showing the consecutive Z-stack slices that were averaged together to yield the averaged image of the Tat peptide were obtained. Slices were acquired every 1p m. Punctate and diffuse fluorescence are seen in each slice, indicating that the Tat peptide has permeated the cell and does not just reside at the cell membrane.

Polymerization Toxicity to Cells

Figure 11:
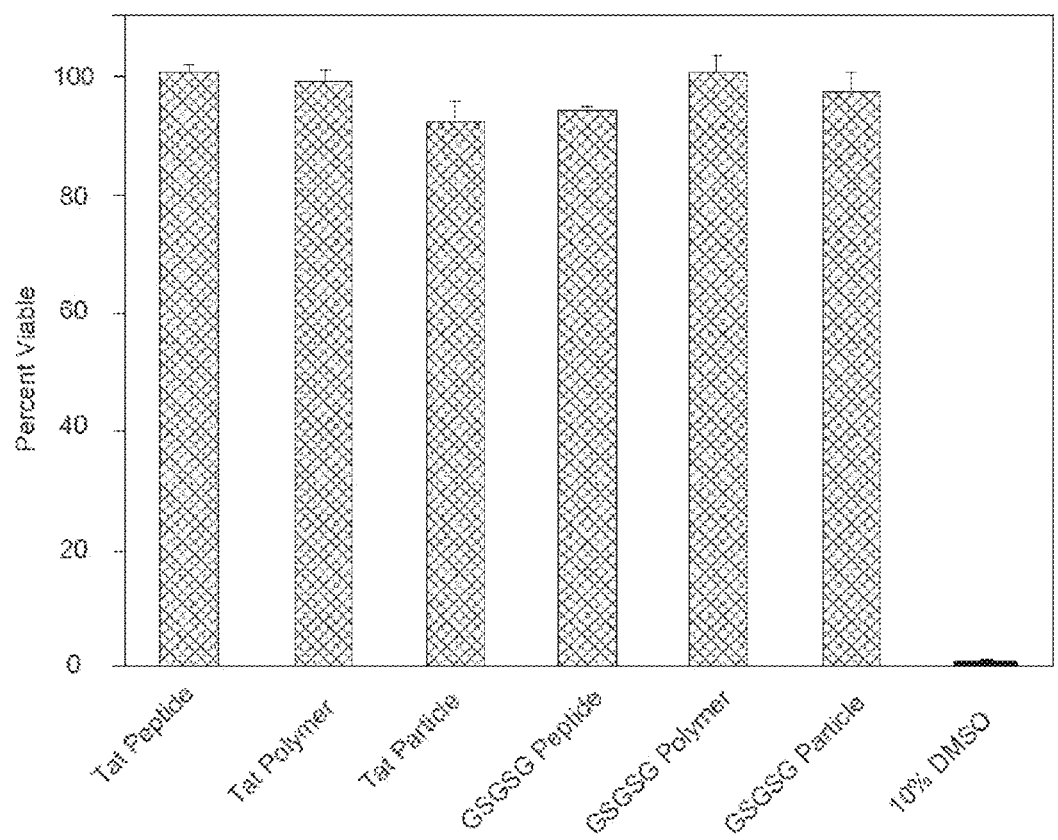
FIG. 11 is a bar graph showing cell cytotoxicity studies using the CellTiter Blue Assay. Percentages are relative to vehicle control. Cells were treated for 48 hours with the Tat and GSGSG (SEQ ID NO:1) peptide, polymer and particle at 5 μM. The positive control is 10% DMSO. Cells treated with any peptide-based material remained at least 92% viable.

Polymerization did not render the peptides toxic to cells. The viability of cells treated with the Tat and GSGSG (SEQ ID NO: 1) peptide, polymer and nanoparticles was assayed via the CellTiter-Blue assay. When compared to the vehicle control, HeLa cells treated with all formulations of the materials at 5 μM, twice the concentration used in the uptake studies described above, remained >92% viable for 48 h (FIG. 11).

Example 3: The Mechanism of Cellular Uptake

Cell Viability Assay Methods

The CellTiter-Blue assay (Promega, cat. #G8081) measures the reduction of resazurin to resorufin via fluorescence.

HeLa cells were plated at a density of 4,000 cells per well of a 96-well plate 18 h prior to treatment. Materials dissolved in DPBS at 5 μM were added to the wells along with a 10% DMSO positive control. Cells were incubated for 48 h at 37° C. The medium was removed and 80 μL of fresh media lacking phenol red was added. To this was added 20 μL of the CellTiter-Blue reagent and the cells were then incubated for 2 h prior to measuring fluorescence in a plate reader using 560 nm excitation and 590 nm emission. The fluorescence measurements were corrected for background fluorescence from the CellTiter-Blue reagent by subtracting the fluorescence reading of wells treated with the reagent in the absence of cells. Fluorescence values were then referenced as a percentage of the value obtained for the PBS vehicle control.

Internalization Routes of CPPs Via Thermal Inhibition and Pharmacological Compounds Much debate in the literature resides over the mechanism of entry of CPPs. However, it is generally agreed that the cellular uptake of these materials requires association with anionic species at the cell membrane (i.e., sulfated proteoglycans or phospholipid polar headgroups) followed by internalization via endocytosis or membrane disruption. To investigate whether the monomeric, polymeric, and nanoparticle formulations of the CPPs follow similar internalization routes, cells were subjected to thermal inhibition and common pharmacological compounds that disrupt different aspects of membrane trafficking and endocytosis.

First, membrane trafficking was arrested by reducing the incubation temperature to 4° C. This resulted in a dramatic decrease in the fluorescent signals for the Tat, Arg8, and guanidinium polymers and nanoparticles by flow cytometry, but had no influence on the values from the GSGSG (SEQ ID NO:1) controls (FIG. 5A). Similar effects were seen with an inhibitor of dynamin-dependent endocytosis (dynasore) and also with methyl-β-cyclodextrin (MβCD), an agent known to remove membrane cholesterol, and thereby alters the fluidity of the membrane. Each condition resulted in no change in the fluorescence values obtained for the GSGSG (SEQ ID NO:1) controls, which was consistent with the notion that these uncharged materials do not internalize. The polymers containing guanidinium, Tat and Arg8 side chains all showed uptake, as was expected for these modes of inhibition. Note that, in all cases, pharmacological and thermal inhibition exhibited only a small effect on the flow cytometry readings of the Tat and Arg8 peptides. Together, these results indicate that cell penetration of the peptides (individual CPPs) is due, in part; to membrane disruption or endocytotic processes and that these mechanisms of entry are maintained or enhanced upon polymerization.

Effect of Fetal Bovine Serum (FBS) Components on Cellular Entry

To verify that the wide range of components found in fetal bovine serum (FBS) did not play a role in facilitating or inhibiting cellular entry of the materials, experiments were also performed in FBS-free media. No significant difference in mean fluorescence from any material was observed by flow cytometry in the presence or absence of FBS, indicating that FBS components, such as growth factors, lipids, hormones, etc., did not influence uptake of these materials.

A bar graph showing flow cytometry data for materials incubated with and without fetal bovine serum was obtained. No significant differences in values were obtained, indicating that serum components do not affect cellular uptake of the materials. A standard curve used to determine concentration of fluorescein-containing materials was obtained. Data was recorded and fit for the small molecule 5/6-carboxyfluorescein and confirmed for use with the fluorescein-Tat polymers and particles. Absorbance was at 492 nm. A standard curve for peak area of untreated Tat peptide-99 μL injections was obtained. A standard curve for peak area of untreated Tat peptide-20 μL injections was obtained. A standard curve for peak area of untreated Tat polymer-99 μL injections was obtained. A standard curve for peak area of untreated Tat particle-15 μL injections was obtained. A chromatogram showing Tat peptide at 2.5 μM with chymotrypsin before and after (dotted black line) treatment with 1 μM protease was obtained. A chromatogram showing Tat peptide at 2.5 μM with trypsin before and after treatment with 1 μM protease was obtained. A chromatogram showing Tat peptide at 2.5 μM with pronase before and after treatment with 1 μM protease was obtained. A chromatogram showing Tat peptide at 12.5 μM with chymotrypsin before and after treatment with 1 μM protease was obtained. A chromatogram showing Tat peptide at 12.5 μM with trypsin before and after treatment with 1 μM protease was obtained. A chromatogram showing Tat peptide at 12.5 μM with pronase before and after treatment with 1 μM protease was obtained. A chromatogram showing Tat polymer at 2.5 μM with chymotrypsin before and after treatment with 1 μM protease was obtained. A chromatogram showing Tat polymer at 2.5 μM with trypsin before and after treatment with 1 μM protease was obtained. A chromatogram showing Tat polymer at 2.5 μM with pronase before and after treatment with 1 μM protease was obtained. A chromatogram showing Tat particle at 2.5 μM with chymotrypsin before and after treatment with 1 μM protease was obtained. A chromatogram showing Tat particle at 2.5 μM with trypsin before and after treatment with 1 μM protease was obtained. A chromatogram showing Tat particle at 2.5 μM with pronase before and after treatment with 1 μM protease was obtained. A bar graph showing the time course of the treatment of the TAT polymer (2.5 μM) with chymotrypsin (1 μM) was obtained. The peptide was cleaved to less than 10% of the starting concentration of material after 20 minutes of incubation with chymotrypsin. The functional impact of proteolytic treatment is measured by flow cytometry while the percentage of intact peptide remaining after incubation was assayed by RP-HPLC.

An $^1$H NMR time course spectra for the polymerization of R control was obtained. Polymers were polymerized to a DP (m) of ~ 10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone. An $^1$H NMR time course spectra for the polymerization of GSGSGR (SEQ ID NO:14) was obtained. Polymers were polymerized to a DP (m) of ~10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone. An $^1$H NMR time course spectra for the polymerization of GSGSGR (SEQ ID NO:14) was obtained. Polymers are polymerized to a DP (m) of ~10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone. An $^1$H NMR time course spectra for the polymerization of RRGSGSG (SEQ ID NO:13) was obtained. Polymers are polymerized to a DP (m) of ~10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone. An $^1$H NMR time course spectra for the polymerization of GSGSGRR (SEQ ID NO:15) was obtained. Polymers were polymerized to a DP (m) of ~10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone. An $^1$H NMR time course spectra for the polymerization of GSGSGK (SEQ ID NO:16) was obtained. Polymers were polymerized to a DP (m) of ~10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone. An $^1$H NMR time course spectra for the polymerization of GSGSGKK (SEQ ID NO:17) was obtained. Polymers were polymerized to a DP (m) of ~10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone. An $^1$H NMR time course spectra for the polymerization of KLA (full length) was obtained. Polymers were polymerized to a DP (m) of ~10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone. An $^1$H NMR time course spectra for the polymerization of KLA (fragment) was obtained. Polymers were polymerized to a DP (m) of 10. Initial spectra were taken at t=0 and subsequent spectra were taken at t=3 hr. A disappearance was observed of the resonance at δ=6.32 ppm corresponding to the olefin protons of the monomer and the coincident appearance of resonances at δ=5.5-6 ppm, which correspond to the cis and trans olefin protons of the polymer backbone.

Effect of Peptide Concentration on Cellular Uptake

To examine how the concentration of the Tat peptide-containing materials impacted their cellular uptake, flow cytometry experiments were performed at several concentrations of material. The concentration in these experiments was with respect to the fluorophore, where there was one fluorophore per peptide or polymer, but many copies of fluorophore per particle. In general, the peptide was less competent in cell penetration than the polymer or particle formulations, with cellular uptake of the peptide nearly abolished at 1.25 µM. This is in contrast to the polymer and nanoparticles that were still taken up by cells at concentrations as low as 0.5 µM (FIG. 5B).

Effect on Number of Guanidiniums for Cell Penetration

Studies on linear peptides have shown that 8-16 guanidiniums are optimal for cell penetration, with activity dramatically decreasing when over 16 guanidiniums were used. Likewise, polynorbornyl polymers bearing guanidi-nium moieties showed decreased internalization when 25 guanidiniums were incorporated, compared to when 10 were employed. Efficient penetration for the Tat side chain 5-mer homopolymer and nanoparticle, which contains at least 30 guanindinium units (FIG. 5B) was observed. In fact, the polymer penetrated cells as efficiently (within a factor of 2 fluorescence counts) as the relevant peptide analogue, even in scenarios in which 5-fold fewer fluorophores were present to achieve the same effective concentration of peptide (such as 2.5 M Tat polymer and 12.5 M Tat peptide). These data indicate that the arrangement of the brush polymer may aid in the cellular uptake mechanism, which could require assembly of multiple CPPs for proper transport across the membrane. Indeed, oligomerization of CPPs into "carpet" bundles and direct transportation of these bundles across the membrane has been proposed for many years as the so-called "carpet mechanism". Alternatively, efficient cellular entry could be due to tangled pendant peptide chains presenting a lower effective number of charged residues to the cell membrane.

Example 4: Evaluation of Proteolysis of Cell Penetrating Peptides, Polymers and Nanoparticles RP-HPLC Analysis of CPP Proteolysis Methods The extent of proteolytic degradation of the Tat peptide, polymer and particle by trypsin (Gibco Life Tech., cat. #15090-046), a-chymotrypsin (Fisher Scientific, cat. #ICN1522722) and Pronase (Roche, cat. #10165921001) was assessed by comparison of chromatograms in RP-HPLC. I n these experiments, the material at the indicated concentration was incubated with each protease (at 1 µM) for 20 min, and then the enzymes were heat denatured at 65° C. for 15 min, and the solution was immediately injected onto an analytical RP-HPLC. Given that treatment with each protease gives multiple fragments of the Tat sequence, a standard curve for each starting material was prepared to assess the percentage of intact material remaining after proteolytic digestion. Note that the standard curves for the polymer and particle will be biased due to the fact that after cleavage, the polymer backbone and fluorophore should remain intact, and will comprise part of the measured peak area. Nevertheless, no new peaks were seen in the chromatograms of the polymer or particle post enzyme treatment, suggesting that these materials are not susceptible to cleavage by the proteases.

Resistance to Proteolysis in Cell-Penetrating Materials

The resistance to proteolysis was assessed in the cell-penetrating materials. The proteolytic cleavage of materials containing the Tat peptide was emphasized, given that it had a more diverse amino acid sequence than the Arg8 peptide and would therefore have more unique cleavage sites.

Tat-containing materials, at the same concentration used in flow cytometery and confocal microscopy studies described above (2.5 M), were challenged for 20 min with various proteases at high enzyme concentration (~1 M) prior to determining the extent of proteolytic cleavage and residual bioactivity. Such activity was assayed by three separate methods: reverse-phase high-performance liquid chromatography (RP-HPLC), flow cytometry, and confocal microscopy. In these assays, RP-HPLC was used to determine the degree to which proteolytic treatment degrades the integrity of the peptide as a monomer or as part of a polymeric formulation. The bioactivity of enzymatically digested materials was then assessed in cellular assays by both flow cytometry and confocal microscopy. To determine whether the location of the peptide cleavage site(s) affects the sensitivity of the peptide to enzymatic cleavage, several different proteases were tested: trypsin (7 predicted cleavage sites), chymotrypsin (2 predicted cleavage sites), and the protease cocktail Pronase, which had the potential to digest the peptide backbone at every amino acid position.

Figure 6A:
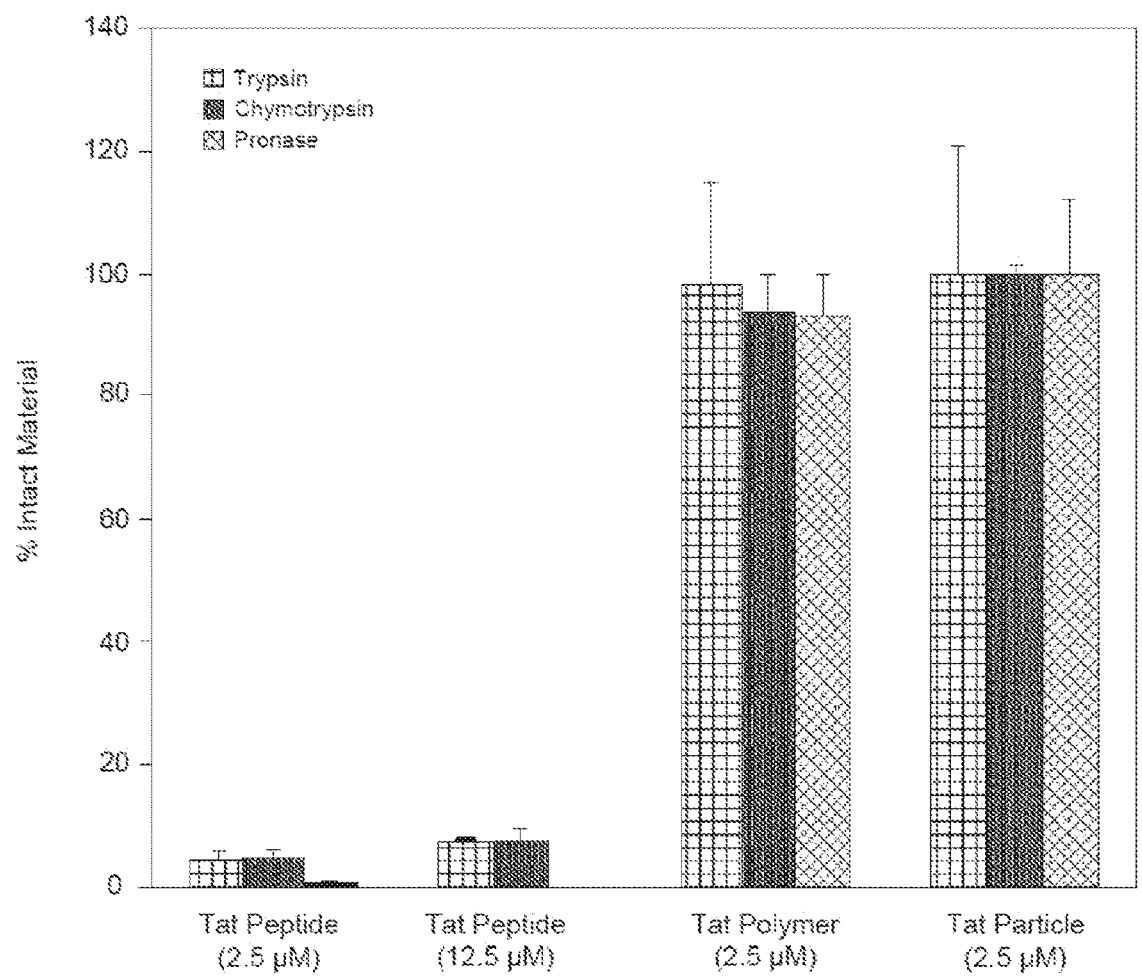
FIG. 6A is a histogram bar graph showing RP-HPLC (reverse-phase high pressure liquid chromatography) of the quantity of remaining material postenzymatic treatment. For each bin of the histogram, protein component was (left to right): trypsin, chymotrypsin, and pronase.
Figure 7A:
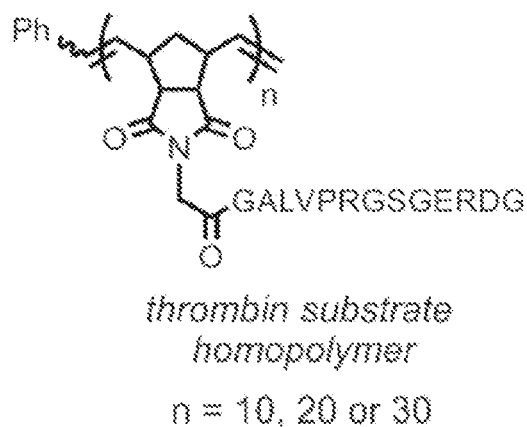
FIG. 7A is the chemical structure of a set of homopolymers containing a thrombin peptide substrate. Sequence legend: GALVPRGSGERDG (SEQ ID NO:4).
Figure 7B:
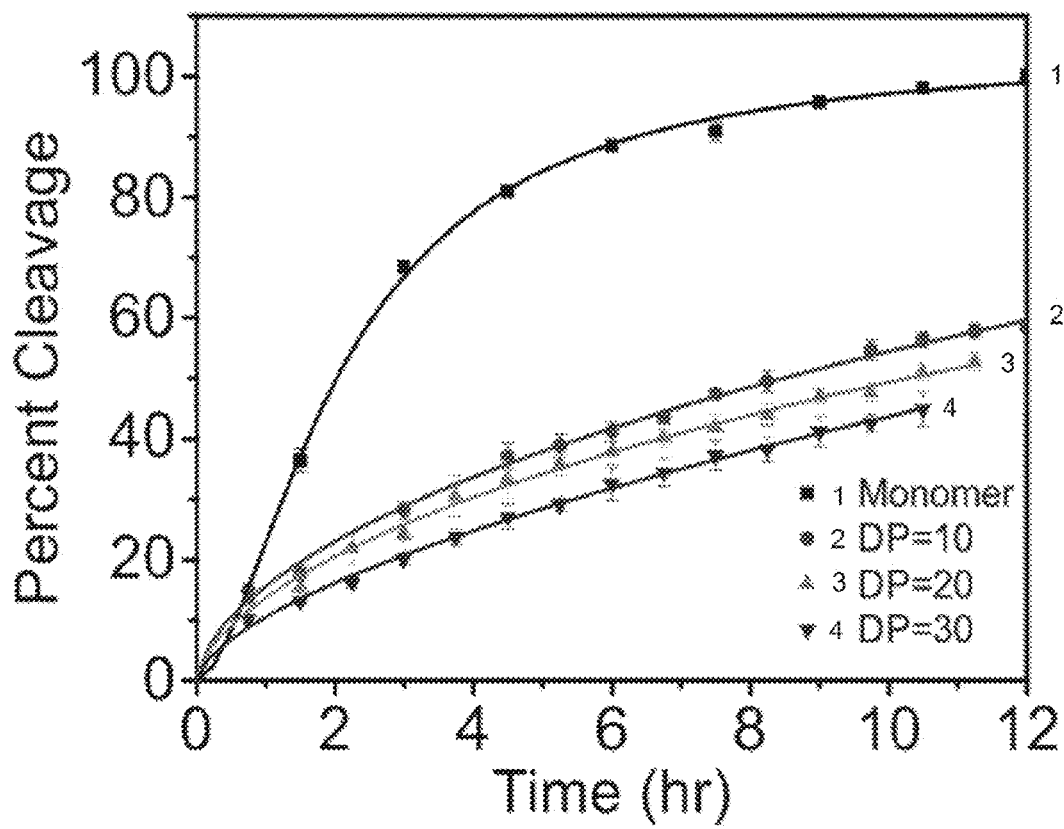
FIG. 7B is a graph showing the cleavage kinetics of thrombin-sensitive monomers and homopolymers at DP (degree of polymerization)=10, 20 and 30.

RP-HPLC was used to assess the percent of intact material following enzymatic digestion (FIG. 6A). Standard curves were generated that compared peak areas of the uncleaved Tat peptide, polymer, or nanoparticle at an appropriate concentration range, such that the concentration of material remaining after incubation with enzyme could be estimated. The absorbance measurements of the intact polymer were affected by the norbornyl polymer backbone, the phenyl coblock, and the fluorescein end-label, which were still present after proteolytic digestion. In these assays, no differences in the peak area or retention time of the polymer or particle were observed after treatment with any of the proteases tested and the RP-HPLC chromatograms were identical with and without enzyme treatment (i.e. no new peaks formed in the chromatogram), indicating that the Tat polymers and particles were resistant to proteolysis. By contrast, complete consumption of the Tat peptide was detected, along with the appearance of new peaks in the RP-HPLC chromatograms. Correspondingly, the mean fluorescence counts of the polymer or particle measured by flow cytometry were largely unaffected by protease treatment (presumably since the peptide chains have not been digested). However, proteolytic digestion of the Tat peptide diminished the intensity of the fluorescence signal to less than 10% of the value obtained prior to enzymatic digestion (FIG. 7B). The same trends were observed by both RP-HPLC and flow cytometry when the peptide concentration was kept uniform (12.5 M peptide, 2.5 M polymer) to normalize the number of potential cleavage events. This difference was substantial given that the peptides had 5 times the number of fluorescein (1 per peptide) equivalents per peptide than the polymer (1 per 5 peptides). Furthermore, a time-course plot of RP-HPLC and flow cytometry data revealed that the Tat polymer was stable to chymotrypsin treatment over 14 h and the material retained the ability to enter cells after incubation with the enzyme.

Figure 7C:
FIG. 7C is a chemical structure of the fluorogenic substrate homopolymer. Sequence legend: E(EDANS)RPAHLRDSGK(DABCYL)GSGSG (SEQ ID NO:5).

Confocal microscopy was used to verify trends observed by RP-HPLC and flow cytometry. In these experiments, the Tat peptide, Tat polymer, and Tat nanoparticle were pretreated with chymotrypsin (under identical conditions as used in the flow cytometry and RP-HPLC assays) prior to incubation with HeLa cells. These cells were then imaged by live-cell confocal microscopy alongside cells incubated with the same materials that had not been subjected to the enzyme pretreatment. A dramatic comparison emerged in which cells treated with protease-digested Tat peptides showed minimal fluorescence relative to those treated with undigested peptides (FIG. 7C). In contrast, the Tat polymer and particles gave identical fluorescence images with or without enzyme treatment.

Example 5: Assessment of Approach Utilizing Two Additional Protease Substrates

Polymerization of Thrombin Substrate Methods

Polymerizations were carried out in a glovebox under a $N_2$ (g) atmosphere. To generate the polymers containing the thrombin peptide sequence, the monomer (0.007 mmol, 10 equiv, 23 mM for DP=10; 0.013 mmol, 20 equiv, 45 mM for DP=20; 0.021 mmol, 30 equiv, 70 mM for DP=30) was mixed with the catalyst (0.0007 mmol, 1 equiv, 2.3 mM) in DMF-d7 (0.3 mL) and monitored by $^1$H NMR to confirm complete consumption of the monomer and to determine the time period required to reach completion. Upon completion, the polymers were quenched with ethyl vinyl ether for 10 min, and then precipitated with cold ether and dried under a vacuum. The resulting polymers were directly characterized by SEC-MALS.

RP-HPLC Analysis of Thrombin Proteolysis Methods

The extent of proteolytic degradation of the thrombin peptide polymers by thrombin (Sigma, cat. #T6884-100UN) was assessed by comparison of chromatograms in reverse-phase HPLC. In these experiments, the monomer and polymers were dissolved in PBS buffer (2.2 mM with respect to peptide). Thrombin (10 units) was added to each sample and an HPLC trace was immediately obtained followed by subsequent HPLC injections every 45 min. A standard curve of the authentic C-terminal fragment was generated to convert the peak area to percent cleavage.

Fluorogenic Peptide Studies Methods

The fluorogenic peptide NorG-E(EDANS)RPAHL-RDSGK(dabcyl)GSGSG (SEQ ID NO:6) was prepared by SPPS as described above where the EDANS was added as a modified Glu (FMOC-Glu(EDANS)—OH; AAPTec, cat. #AFE150) while dabcyl (Anaspec, cat #81800) was conjugated to the e-amino group of a lysine. This monomer was polymerized into a homopolymer with DP=20, determined by bulk light scattering. Note that the fluorogenic peptide sequence did not run as a polymer on the SEC column needed for SEC-MALS. Blend copolymers with a PEG monomer were prepared by first assessing the rate of polymerization of the two monomers. At the concentration of monomer studied, the PEG monomer was quick to polymerize (complete within 15 min), while the fluorogenic substrate polymerized at a rate of 1.78 monomers per hr. To ensure reasonable interdigitation of the two monomers in the random blend copolymer, the PEG monomer was added via syringe pump at appropriate rates to prepare peptide: PEG polymers at a ratio of 1:19, 5:15, 10:10, 15:5 and 19:1 as described in Table 9. Cleavage of the homopolymer monomer and blend copolymers (40 µM) by the noted protease in (at 25 nM) in reaction buffer (50 mM Tris (pH 7.4), 1 mM $ZnCl_2$, 150 mM NaCl, 5 mM $CaCl_2$)) was monitored by measurement of fluorescence in a plate reader or fluorimeter. The proteases, MT1-MMP (catalytic domain; Calbiochem, cat. #476935), MMP-9 (catalytic domain; Enzo Life Sciences cat. #BML-AW360-0010), thermolysin (Promega, cat. #V4001), trypsin (Gibco Life Tech., cat. #15090-046) and Pronase (Roche, cat. #10165921001) were purchased from commercial sources.

Graphs showing the determination of concentration of fluorogenic materials in water at 340 nm (EDANS absorbance) and at 378 (dabcyl absorbance) were obtained. The concentrations used in proteolysis studies are the average concentration obtained at the two wavelengths. A spectra showing the excitation and emission for authentic products on a fluorimeter were obtained. Max excitation and emission were determined to be at 340 nm and 495 nm, respectively. A standard curve was obtained on a fluorimeter (used for monitoring cleavage kinetics of homopolymers and all cleavage reactions by MMP-9 due to higher sensitivity than the plate reader). A plot showing a standard curve on a plate reader (used for assessing cleavage kinetics of monomers for enzymes other than MMP-9) was obtained.

TABLE 9

Tabulated values for the preparation of reasonably interdigitated random copolymers.

| OEG:Peptide Ratio (m:n) | Peptide Volume (µL) | OEG Solution Volume (µL) | Initiator Solution Volume (µL) | Total Reaction Volume (µL) | Calculated Reaction Time (hr) | Rate of OEG Addition (µL/hr) | Theoretical $M_n$ | $M_n$ |
|---|---|---|---|---|---|---|---|---|
| 0:20 | 368.4 | 0 | 20 | 388.4 | 11.2 | — | 46,200 | 43,000 |
| 5:15 | 276.3 | 92.1 | 20 | 388.4 | 8.4 | 10.9 | 36,500 | 36,000 |
| 10:10 | 184.2 | 184.2 | 20 | 388.4 | 5.6 | 32.8 | 26,700 | 26,000 |
| 15:5 | 92.1 | 276.3 | 20 | 388.4 | 2.8 | 98.4 | 16,900 | 16,300 |
| 19:1 | 18.4 | 350 | 20 | 388.4 | 0.56 | — | 8,670 | 8,700 |

Given that OEG monomer is fast to polymerize (at the concentration used, the OEG monomer polymerizes to DP=20 in less than 15'), this monomer is doped into a stirring solution of the substrate monomer and the initiator via a syringe pump in a glove box. For the 19:1 blend copolymer, the OEG monomer was added in one portion to the reaction vessel after ~2 hr. The initial concentration of the OEG monomer, substrate monomer and catalyst were 0.012 M, 0.012M and 0.6 mM, respectively. The bulk $M_n$ obtained for the homopolymer was 43,000 (DP=19). Given that the monomers and imitators were taken from the same pots, it is assumed that the ratios of m:n are as indicated. Nevertheless, $M_n$ values obtained by batch mode SLS are listed and are in good agreement with the theoretical values calculated from the intended m:n ratios.

Evaluation of Two Additional Polymerized Peptide Substrates

To test whether the strategy could be extended to different proteases and to peptide sequences other than the highly charged Tat and Arg8 sequences, two additional peptide substrates were polymerized. Importantly, the two peptides each had a more extensive sampling of amino acid side chains compared to the CPP sequences and were optimized substrates for degradation by two different enzymes: a serine protease and a metalloprotease.

Figure 13:
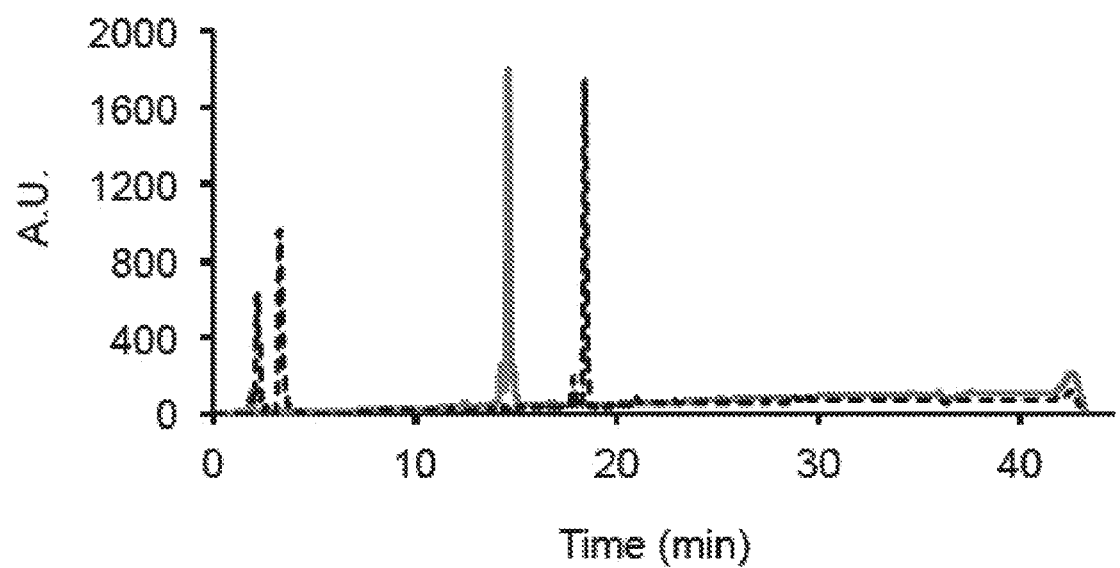
FIG. 13 is a chromatogram showing proteolytic digestion of the monomer at t=12 hours. The chromatogram of the polymer at t=0 is purple and the reaction at t=12 is black with gradient at 0-80% Buffer B.
Figure 14:
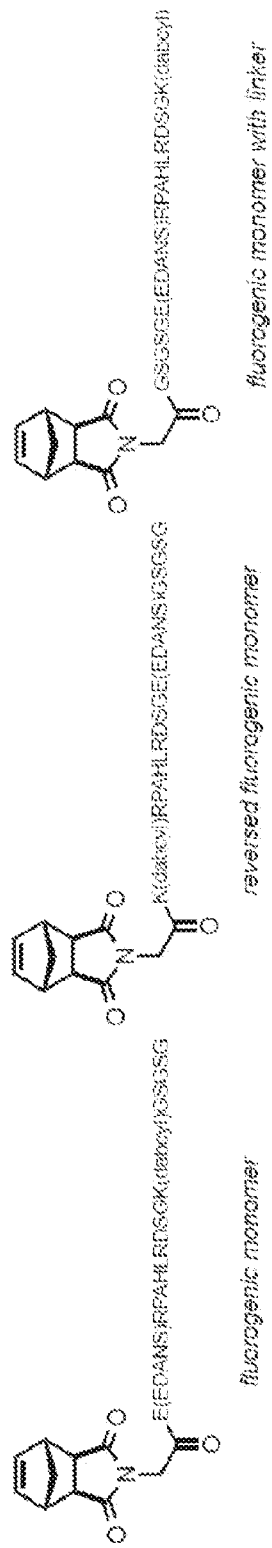
FIG. 14 are chemical structures of fluorogenic monomers prepared. Sequence legend: E(EDANS)RPAHLRDSGK(DABCYL)GSGSG (SEQ ID NO:5); K(DABCYL)RPAHLRDSGE(EDANS)GSGSG (SEQ ID NO:7); GSGSGE(EDANS)RPAHLRDSGK(DABCYL) (SEQ ID NO:9)).
Figure 15A:
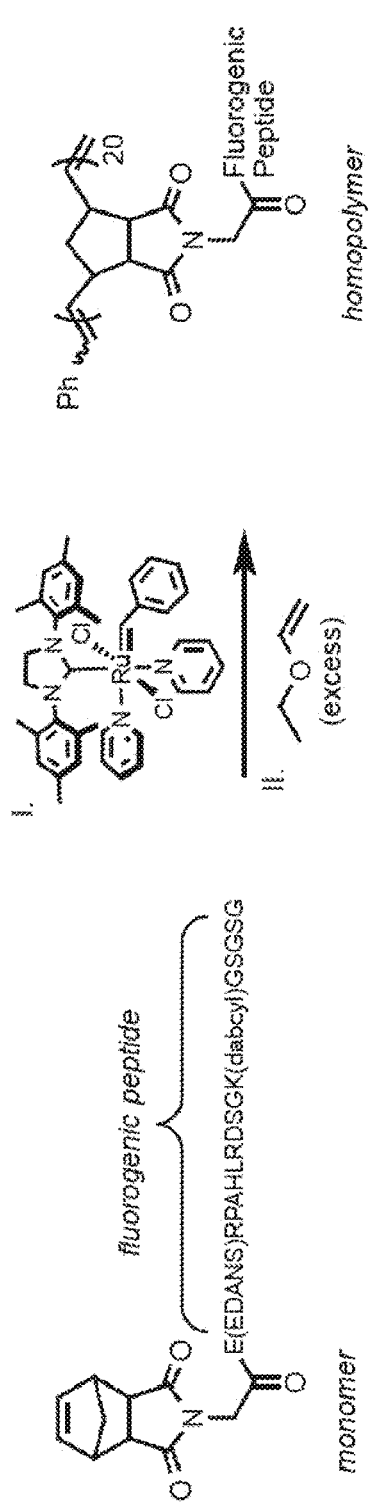
FIG. 15A is a schematic showing polymerization of fluorogenic monomer into a homopolymer.
Figure 15B:
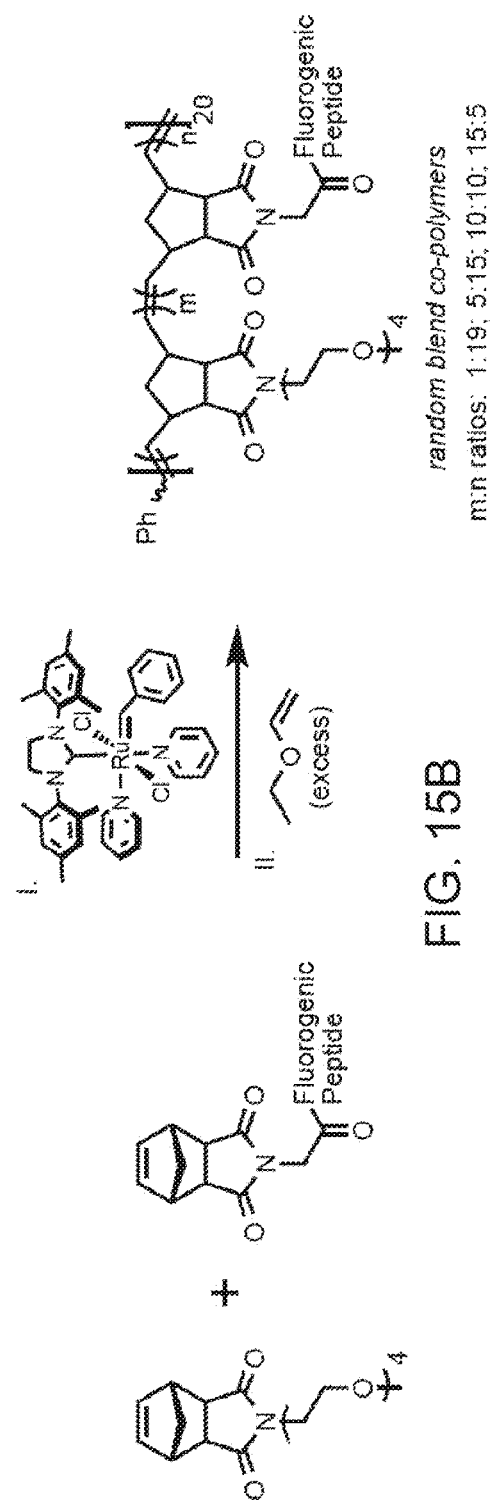
FIG. 15B is a schematic showing polymerization of fluorogenic monomer into a random blend co-polymer with an OEG monomer.
Figure 16:
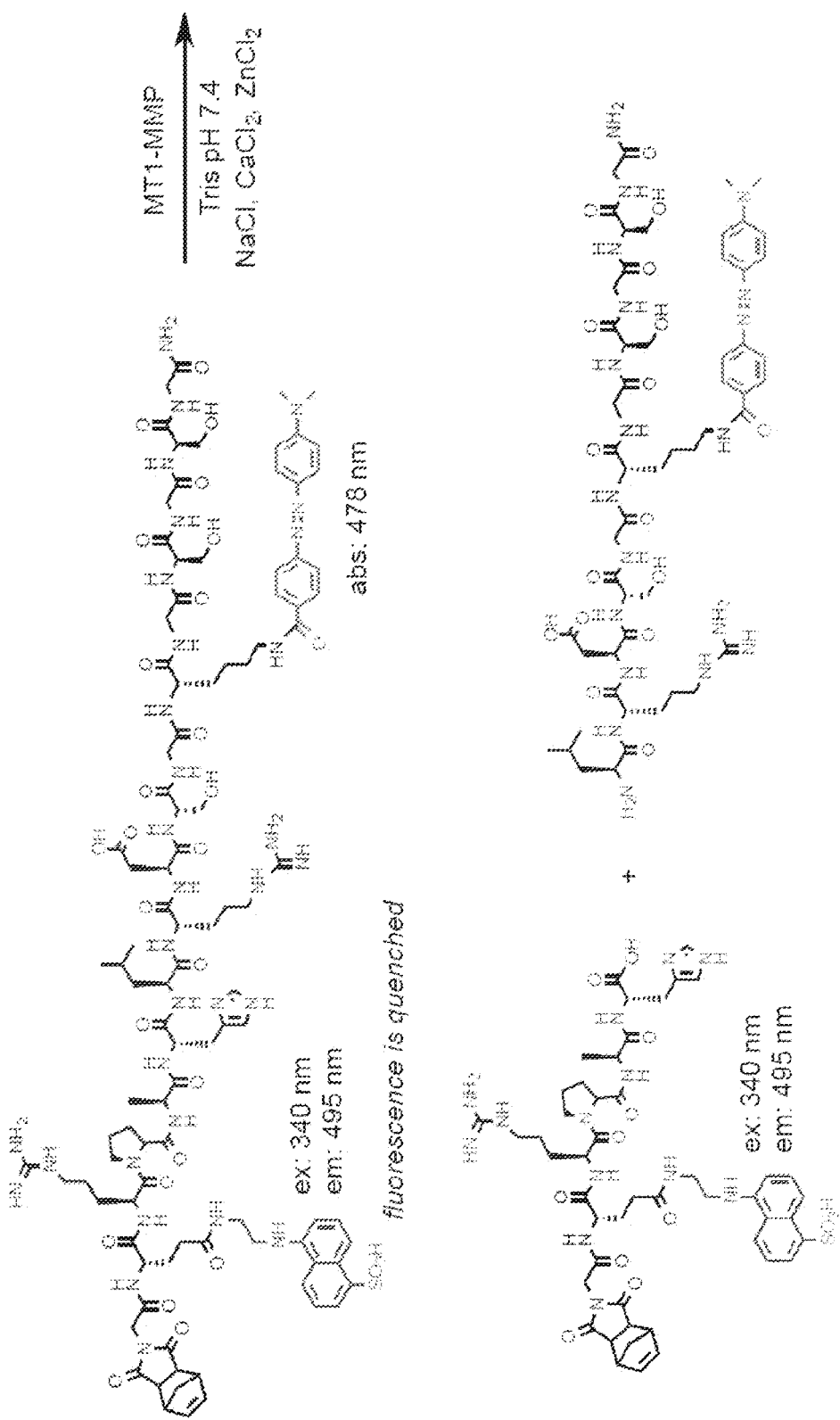
FIG. 16 is a schematic showing the fluorescent assay used to detect cleavage of the fluorogenic substrate by MT1-MMP. In the intact monomer (NorGly-E(EDANS)-RPAHLRDSGK(dabcyl)GSGSG-NH$_2$) (SEQ ID NO:11), the fluorescence of the donor, EDANS is quenched by the acceptor, DABCYL until cleavage of the substrate by the protease. Note that the other proteases used in this study will cleave at other locations along the peptide substrate, but scission at any amide bond of the substrate sequence will result in liberation of the quencher and the onset of fluorescence.

The generality of the approach was examined by preparing a peptide substrate for thrombin, a coagulation factor protease. A monomer bearing the thrombin substrate sequence (GALVPRGS, SEQ ID NO:73) was readily prepared via SPPS with a short, water-solubilizing peptide sequence (GERDG, SEQ ID NO:74) at the C-terminus (FIG. 12), and was polymerized by ROMP to several degrees of polymerization (characterization data for polymers are given in Table 4). The monomer peptide and homopolymers were treated with thrombin, and the resulting product mixture was analyzed by RP-HPLC (FIG. 13). These analyses indicate that the monomeric peptide was readily degraded by thrombin, as evidenced by the disappearance of the monomer peak and corresponding appearance of product peaks, however, homopolymers at several degrees of polymerization were resistant to cleavage relative to the monomer, albeit not completely shut off from proteolysis, confirming the generality of the approach (FIGS. 7A and 7B).

A chromatogram showing RP-HPLC characterization of the purified monomer at a gradient of 15-30% buffer B was obtained. ESI-MS (electrospray ionization mass spectrometry) confirmed the identity-calculated: 1473.5 m/z, obtained: 1471.6 m/z. A spectra showing polymerization of thrombin substrate monomer as determined by $^1$H NMR was obtained. A chromatogram showing authentic product resulting from a cleavage reaction (GSGERDG-NH$_2$) was obtained with gradient of 0-20% Buffer B. ESI-MS confirms the identity-calculated: 675.7 m z, obtained: 674.4 m/z. A standard curve used to determine the concentration of products, which compares the concentration of the authentic product to the corresponding peak area in RP-HPLC chromatograms with gradient 0-80% Buffer B, was obtained.

An optimized peptide substrate sequence for a cancer-associated membrane-bound matrix metallopro-tease (MMP) was examined. Here, the N-terminal Cys residue was omitted from the optimized peptide sequence, CRPAHLRDSG (SEQ ID NO:75), because free thiols (lacking protecting groups) are difficult to polymerize by ROMP, due to coordination to the initiators. Since this peptide was not expected to function in an orthogonal bioactivity assay, as for the CPP studies above, the sequence was prepared as a fluorogenic substrate, to readily and rapidly quantify cleavage events at low concentrations of material to obtain detailed kinetic information.

Kinetic and Enzymatic Assays

Figure 7D:
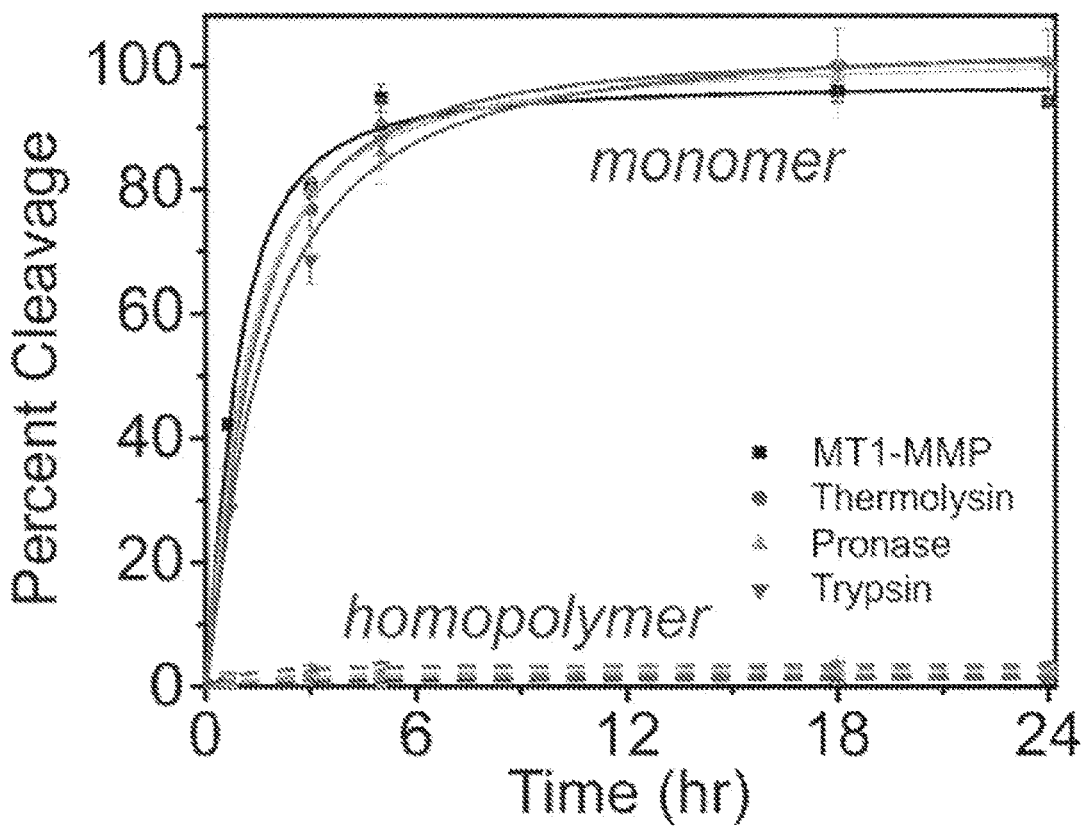
FIG. 7D is a graph showing the cleavage kinetics of the fluorogenic homopolymer relative to the monomer, by multiple proteases in addition to the protease for which the substrate is optimized, MT1-MMP (matrix metalloprotease).
Figure 17:
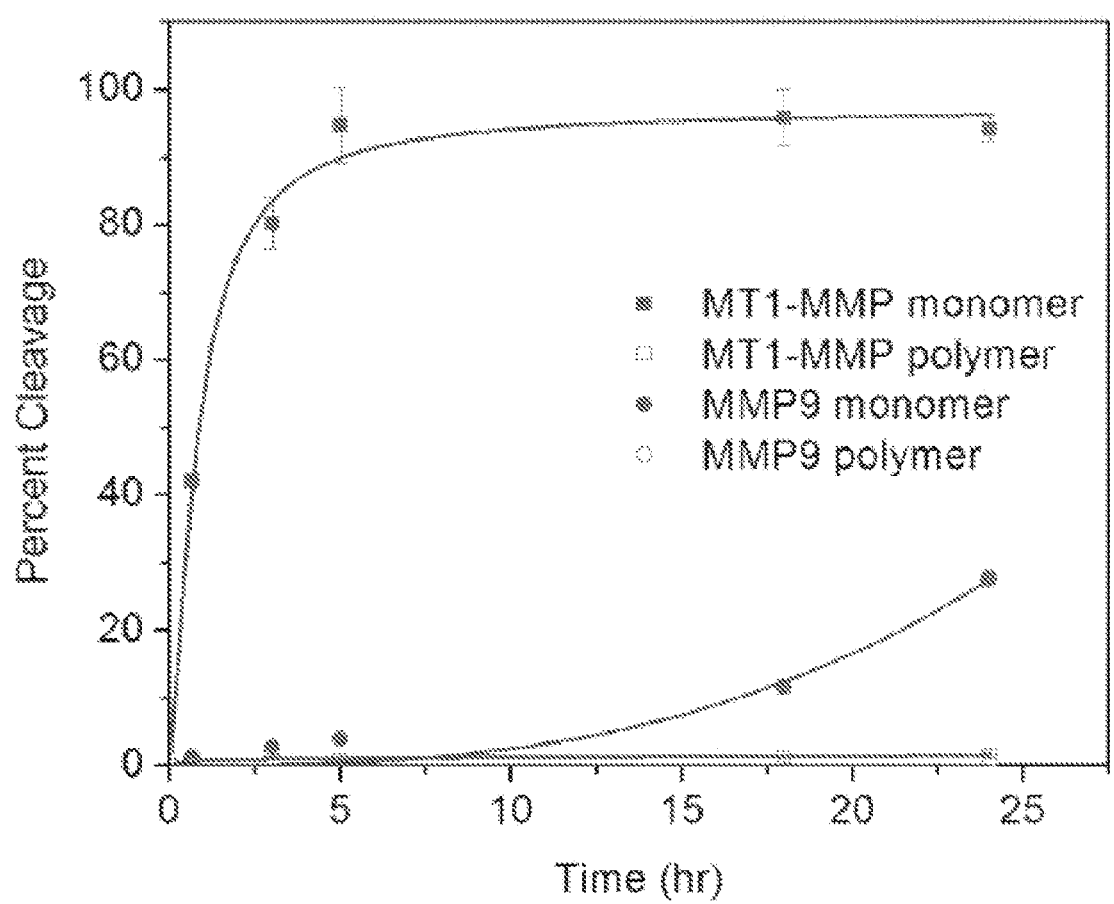
FIG. 17 is a graph showing the time course of the proteolysis of the fluorogenic monomer and homopolymer by MT1-MMP and MMP-9 (for which the amino acid sequence should not be a substrate). While the monomer is cleaved readily by MT1-MMP, MMP-9 shows little activity. Neither enzyme was able to proteolytically digest the homopolymer.
Figure 18:
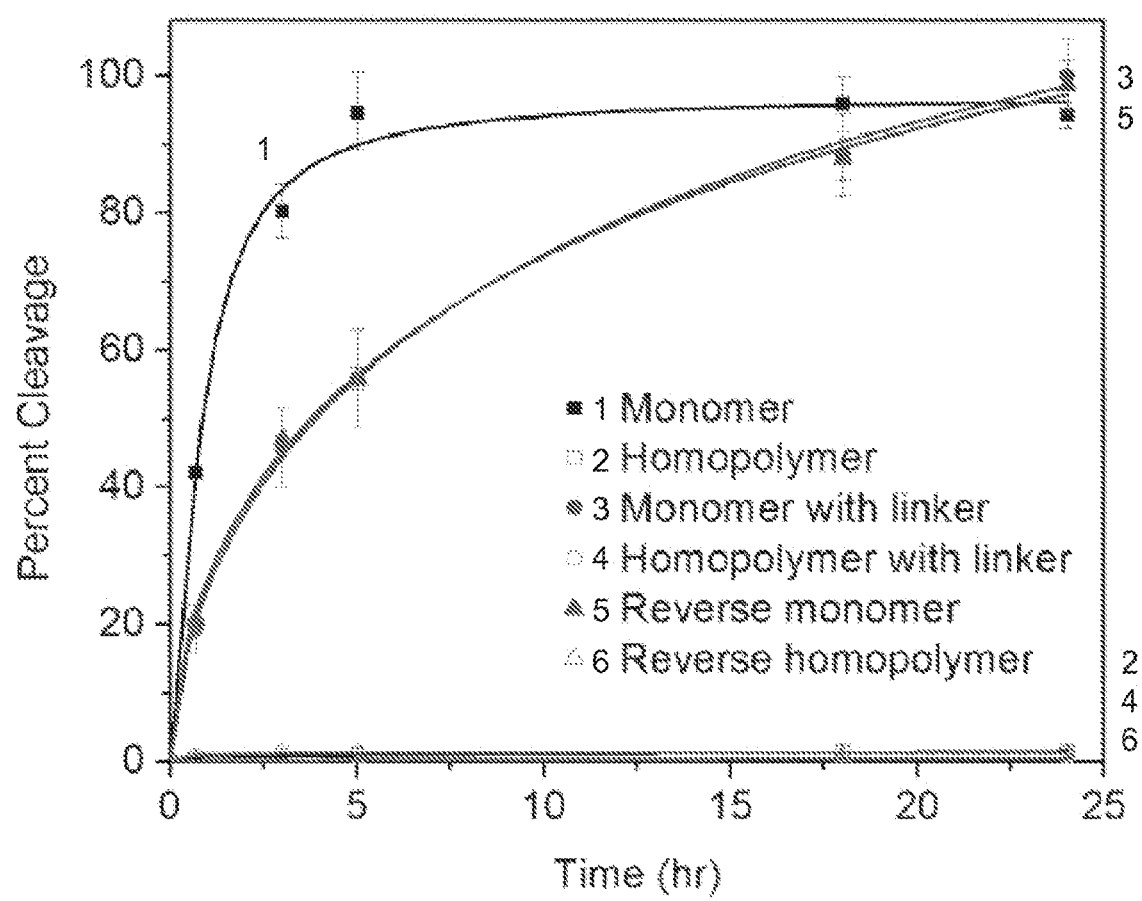
FIG. 18 is a graph showing the time course of proteolysis of fluorogenic homopolymers and their monomer building blocks (40 μM) by MT1-MMP (25 nM). Chemical structures are shown in FIG. 14. Little proteolysis of the homopolymers was observed regardless of the location of the quencher or donor or whether a five-amino acid linker (GSGSG) (SEQ ID NO:1) was used to space the substrate from the polymer backbone.

In kinetic assays, the fluorogenic monomer was readily cleaved by an assortment of proteases (FIGS. 7C and 7D), but not by MMP-9 for which it is not a substrate (FIG. 17). In contrast, the homopolymer (DP=20) exhibited very little cleavage upon treatment with multiple proteases, as seen in the 24-h time course plots (FIG. 7B). Initial enzymatic reaction rates ($V_0$), obtained by monitoring each reaction for the first 40 min (less than 25% cleavage seen for all materials), indicated that the monomer was cleaved 17- to 95-fold faster than the homopolymer at comparable peptide concentrations (Table 10). Michaelis-Menten plots were obtained for the cleavage of the monomer by MT1-MMP, yielding a specificity constant (kcat/Km) of $0.52 \pm \mu M^- 1 min^{-1}$ and a Km of 11 µM. A Michaelis-Menten plot of the homopolymer time-course data revealed that saturation kinetics had not been reached at ~7 times the calculated Km of the monomer, as suggested by the near linear fit to the data obtained. Note that the fluorescence observed in assays of the homopolymer approached the lower limit of detection, resulting in large standard errors in the data. Moreover, solubility limits of the homopolymer prevented a full Michaelis-Menten plot from being generated. Nevertheless, these data clearly indicated that the protease exhibited lower affinity for and activity on the peptide substrate when it was incorporated into a brush polymer.

A graph showing the time course of the fluorogenic substrate monomer as monitored by $^1$HNMR was obtained. At each time point, integration of the olefinic proton of the monomer δ 6.32 is tabulated and normalized relative to a time point at which the reaction is complete (final spectrum; t=12 hr). This value is converted into a number of monomers consumed by assuming that the integration value at t=12 represents the consumption of 20 monomers and the value at t=0 hrs represents that of no monomers consumed. The strategy for preparing random blend copolymers of the fluorogenic substrate is shown. A plot showing the number of monomers consumed as calculated in A vs. time was obtained. The slope of the line is the rate of monomers consumed per hour.

TABLE 10

Initial velocities ($V_0$) for the proteolysis of fluorogenic monomer and homopolymer by assorted proteases

| Protease | Monomer $V_0$ (µM min$^{-1}$) | Homopolymer $V_0$ (µM min$^{-1}$) |
|---|---|---|
| MT1-MMP | 0.11 ± 0.01 | 0.0066 ± 0.002 |
| Thermolysin | 0.27 ± 0.03 | 0.0055 ± 0.001 |
| Trypsin | 0.18 ± 0.01 | 0.002 ± 0.001 |
| Pronase | 0.2 ± 0.01 | 0.0021 ± 0.001 |
| MMP-9 | 0.005 ± 0.0002 | |

$^a$The terms monomer and homopolymer correspond to the fluorogenic homopolymer and polymers. The fluorogenic peptide is optimized so that it is not a substrate for MMP-9. No fluorescence was detected during treatment of the homopolymer with MMP-9.

Example 6: Proteolytic Susceptibility of Peptide-Containing Brush Polymers

The origin of proteolytic resistance was studied, and it was also recognized that, in certain circumstances, it might be disadvantageous to render a peptide entirely refractory to proteolysis, for example, in the case of a peptide sensor for a protease, or when designing a device that targets tissue or releases a drug in response to proteolytic digestion. Therefore, the proteolytic susceptibility of the fluorogenic substrate for MT1-MMP described above was evaluated. The proteolytic resistance of homopolymers may result from packing or other stabilizing peptide-peptide interactions, leading to steric protection against enzymatic cleavage. This picture led to the notion that proteolytic susceptibility would be restored by spacing the peptides out along the polymer backbone.

Figure 8A:
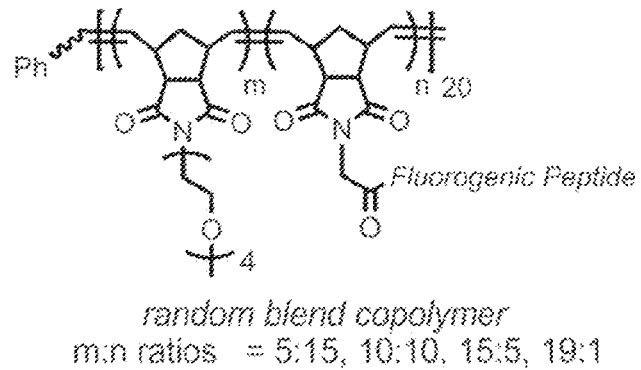
FIG. 8A is a chemical structure of a series of random blend copolymers of the fluorogenic peptide substrate monomer and an OEG (oligoethylene glycol) monomer.
Figure 8B:
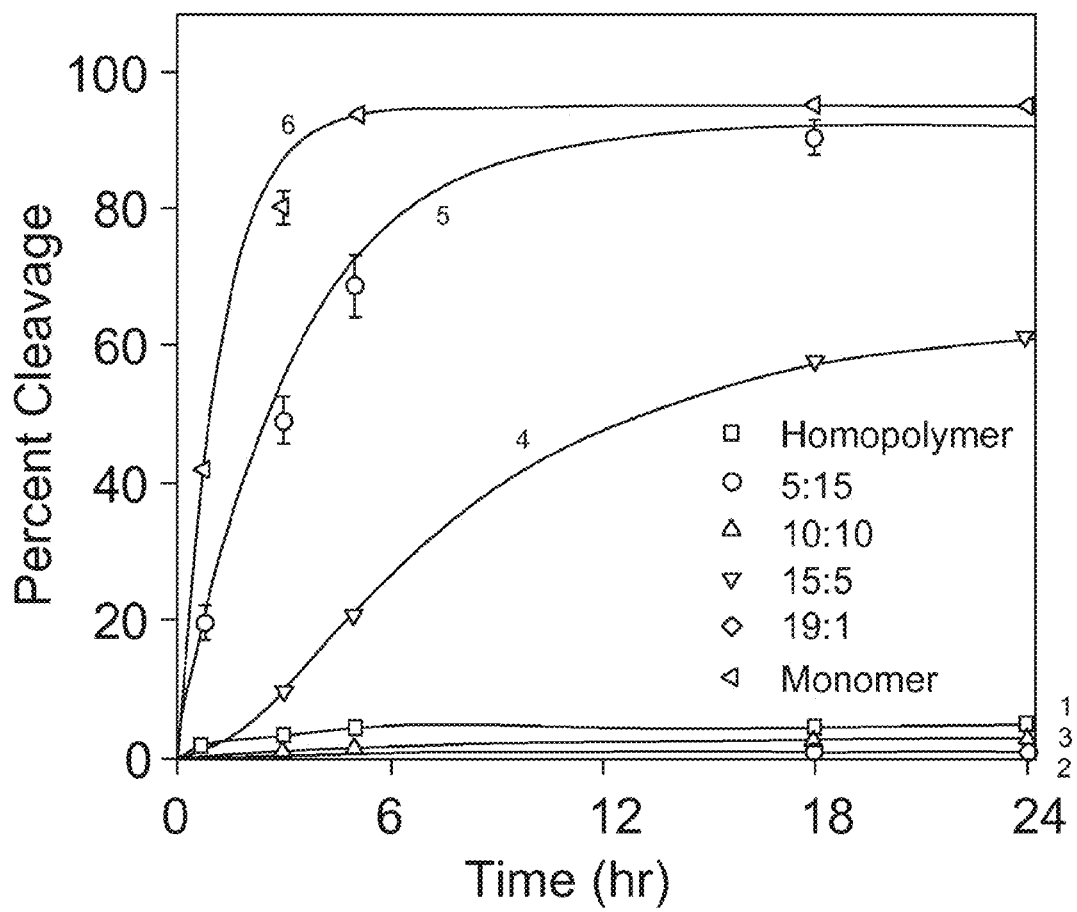
FIG. 8B is a graph showing the comparison of the cleavage kinetics of the fluorogenic random blend copolymers, (ratio is m:n as shown in A, overall DP=20) homopolymer (DP=20) and monomer.

Spacing was accomplished by preparation of random blend copolymers that incorporated a monomer "spacer" or "diluent" at varying blend ratios (FIG. 8A). The spacer chosen was a water-soluble OEG monomer, which is inert to proteolytic enzymes. Random blend copolymers (total DP=20) were prepared at substrate to OEG ratios of 1:19, 5:15, 10:10, and 15:5 (FIG. 8A). A general trend emerged in which proteolytic activity of MT1-MMP was greatest when more spacers were incorporated. Indeed, the 1:19 blend polymer proved to be as susceptible to proteolytic degradation as the substrate monomer (FIG. 8B). These data indicated that the protection from proteolysis observed in the systems did not result simply from the attachment of the peptide to a high molecular weight polymer, but rather from its arrangement into a high-density peptide brush.

Example 7: Molecular Dynamics Simulations

Computational Methods

Figure 9A:
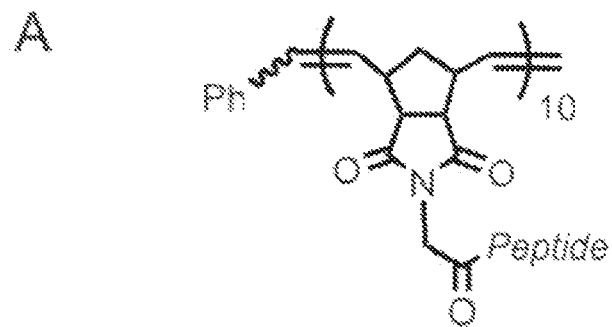
FIG. 9A is a chemical structure of the homopolymer with ten fluorogenic peptides; Monomer=NorG-E(EDANS)RPAHLRDSGK(DABCYL)GSGSG) (SEQ ID NO:6), MW=23.2 kDa; N=200.
Figure 9B:
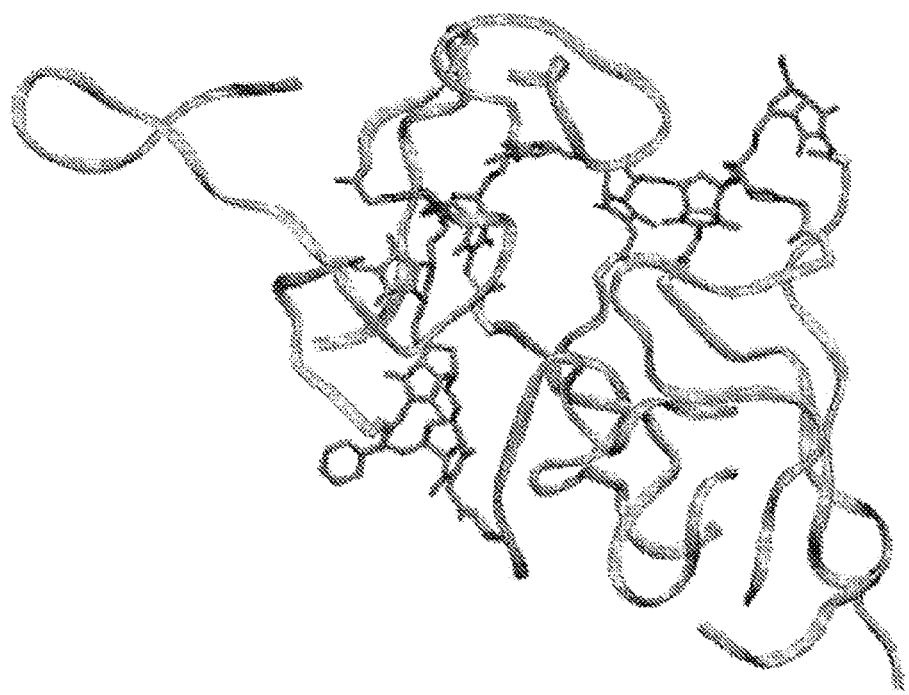
FIG. 9B is a representative conformation and surface-accessibility data for in silico models of the homopolymer.
Figure 9C:
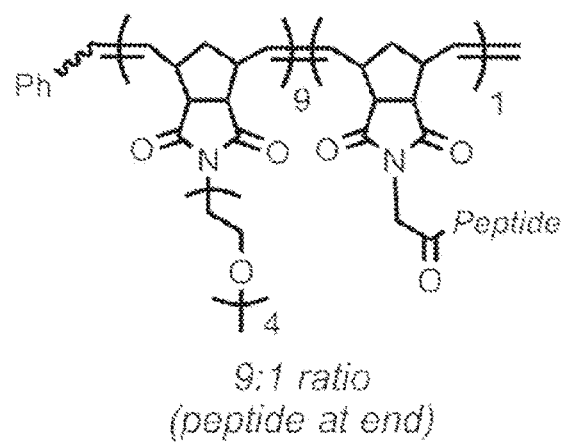
FIG. 9C is a chemical structure of the 9:1 ratio blend copolymer with the peptide at the end of the polymer where nine of the norbornene moites are linked to OEG-4 and the tenth, at position 10 of the norbornene chain, is linked to the fluorogenic peptide, MW=5.6 kDa, N=65. Simulated polymer without dye components (same chemical structure); MW=5.11 kDa, N=63.
Figure 9D:
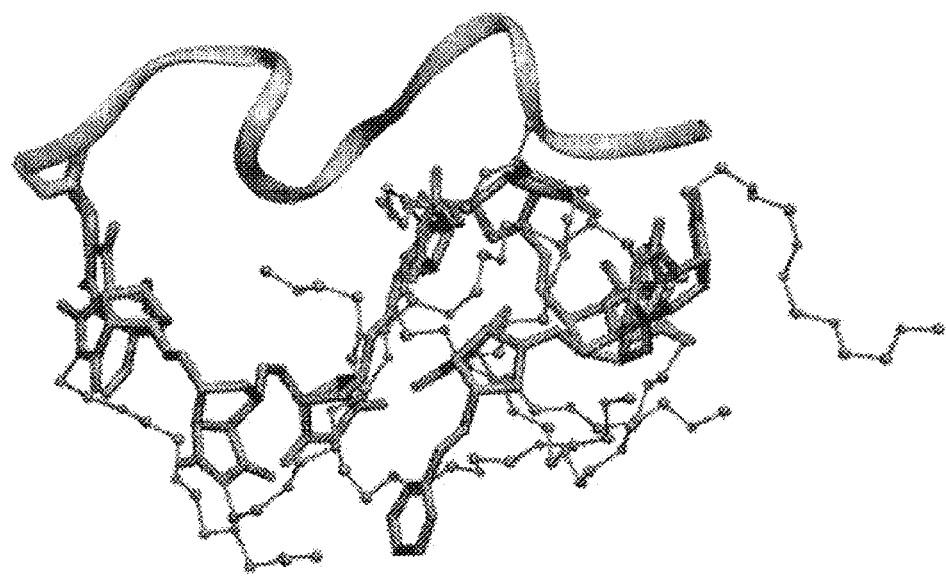
FIG. 9D is a representative conformation and surface-accessibility data for in silico models of the peptide at the end of the polymer.
Figure 9E:
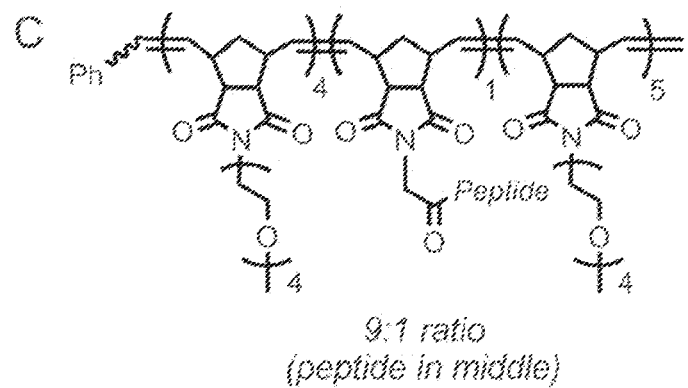
FIG. 9E is a chemical structure of the 9:1 ratio blend with the peptide in the middle (i.e., position 5), blend polymer where the peptide is linked to the fifth norbornene of the chain, MW=5.6 kDa, N=65. Simulated polymer without dye components (same chemical structure); MW=5.11 kDa, N=63.
Figure 9F:
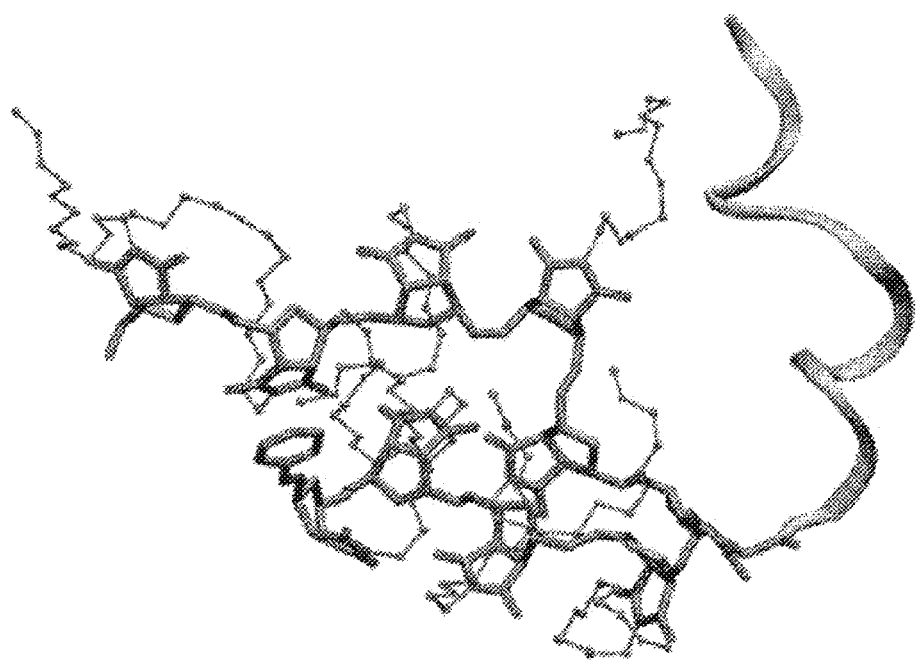
FIG. 9F is a representative conformation and surface-accessibility data for in silico models of the peptide at the end of the polymer.
Figure 9G:
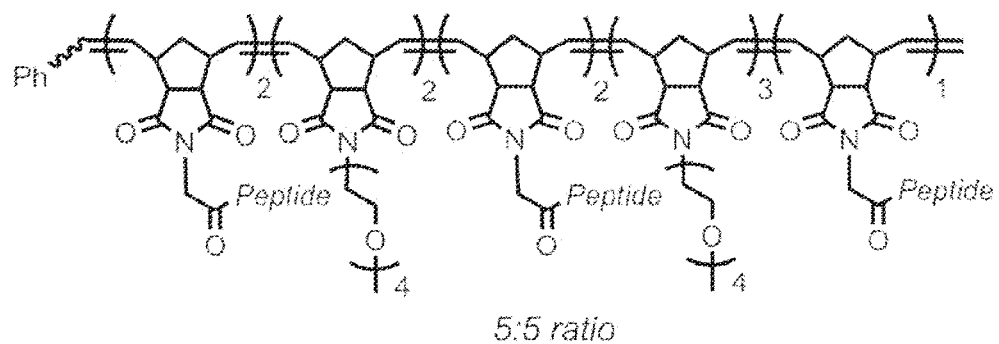
FIG. 9G is a chemical structure of the intermediate 5:5 ratio blend copolymer, where five norbornene moieties are linked to the fluorogenic peptide and the other five are linked to OEG-4; MW=13.4 kDa, N=125.
Figure 9H:
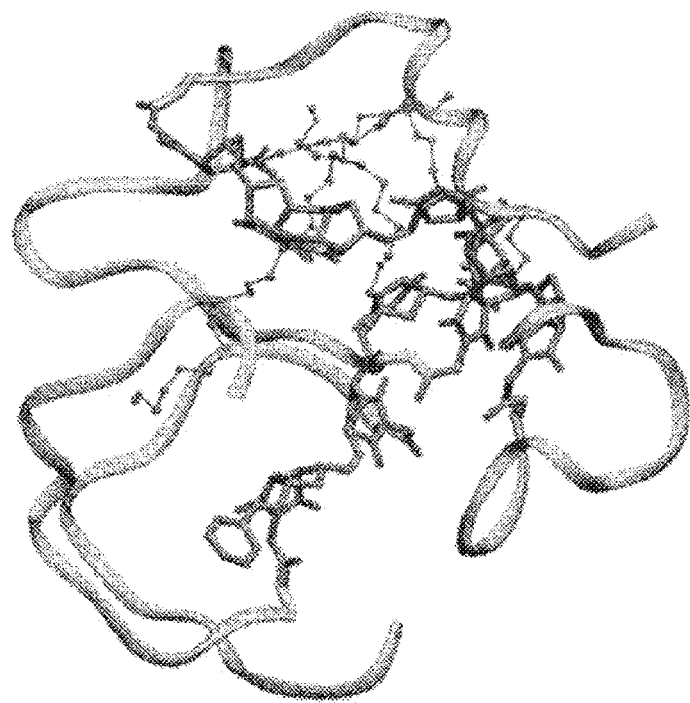
FIG. 9H is a representative conformation and surface-accessibility data for in silico models of the intermediate 5:5 ratio blend copolymer.

Details of the polymer constructs that were simulated are as follows. In all cases, the polymer backbone was composed of 10 norbornene units, flexibly linked by olefin bonds, with a 1:1 mix of cis and trans units. In the homopolymer, each norbornene residue was linked to the N-terminus of the fluorogenic peptide NorGlyE(EDANS)RPAHL-RDSGK(DABCYL)GSGSG) (SEQ ID NO:6) (FIG. 9A), where the EDANS and DABCYL fluorophores are linked to E and K residues, respectively. The C-terminus of each peptide was amide capped. In the 5:5 blend copolymer, five of these peptide-dye chains were linked to norbornenes 1, 2, 5, 6, and 10 (counting from the end of the phenyl ring); and five OEG chains, each with four ethylene glycol units, were linked to the remaining norbornenes (FIGS. 9G and 9H). In the 9:1 blend copolymers, all positions are occupied by OEGs except that the tenth or fifth norbornene (FIGS. 9C and 9D or 9E and 9F) is occupied by the fluorogenic peptide.

All-atom molecular dynamics simulations were performed to study the conformations of the simulated polymers, using the explicit water model TIP3P91 and the Gromacs 4.6 software package. All bonded and Lennard-Jones terms of the polymer backbone and dye moieties were assigned by the General Amber Force Field (GAFF) and partial atomic charges were assigned using AM1-BCC. Parameters from the Amber ff99SB-ILDN force field were assigned to the peptide components. All simulations started from extended polymer backbone and peptide configuration and were performed using periodic boundary conditions. Each polymer construct was solvated in a cubic simulation box with edge lengths set to the longest dimension of the molecule plus 2 nm. This led to box sizes with edge lengths of 10-15 nm. The systems were first energy minimized with the steepest-descent algorithm, and then equilibrated for 10 ns under constant volume and temperature conditions and then another 10 ns under constant temperature and pressure conditions. The Particle-Mesh-Ewald (PME) method was used for electrostatic interactions, and the cutoff distance of the Lennard-Jones (LJ) interactions was 10 Å. In some simulations, a heat-cool cycle was used immediately after the equilibration phase to boost the systems out of local energy minima and search for additional stable conformational states. Here, the temperature was increased from 300 to 500 K linearly over 2 ns; the simulation was run for 1 ns at 500 K; and the temperature was then reduced back to 300 K linearly over 2 ns, and kept at 300 K for 95 ns of production dynamics. For comparison, regular MD simulations at constant 300 K were also performed for 100 ns following the same equilibration phase. The two 9:1 blend copolymers without the dye components were stimulated, to verify that the dye molecules do not influence the major conclusions. For these simulated polymers, one Cl-counterion was added in order to neutralize the +1 charge.

Molecular Dynamic Simulation Methods

Here, MW is molecular weight (Da); and N, the number of constituent monomers, is computed as the number of norbornene monomers (10) plus the number of amino acid residues (number of peptides ×17) plus the number of ethylene oxide units (number of OEG chains ×4) plus the number of dye moieties (either 2 or 0). Each simulation began with the molecule in an artificial extended conformation, with a straight norbornene chain and with straight peptides and OEGs arrayed at right angles to the norbornene chain. After an initial 20 ns equilibration phase at 300K, each simulation was split and continued in two ways. One simulation was simply continued for another 100 ns at 300K. The other was randomized further by briefly heating it to 500K, cooling it back to 300K, and then continuing it at 300 K for the rest of the 100 ns production simulation.

In every simulation, the initial extended structure collapsed quickly into a much more compact conformational ensemble. The collapse is evident from an rapid early drop in the radii of gyration, Rg. The values of Rg then changed little for the runs that continued at 300K (blue and green). For simulated polymers 1 and 2, which contain ten and five peptides, respectively, the heatcool cycle (red and orange) generated a spike in Rg, followed by a further reduction in Rg below the value seen for the standard 300K runs. Thus, for these two molecules, the heat-cool cycle allows the polymer construct to anneal into an even more compact conformation. For simulated polymers 3-6, which have one peptide and nine PEGs, the heat-cool cycle changed Rg but did not consistently lead to a lower value. Thus, the heat-cool cycle did not seem to lead to greater compaction of these one-peptide constructs.

Radii of Gyration (Rg) Methods

The values of Rg observed here may be put into context by comparing them with the values associated with folded proteins having a similar number of residues or molecular weight. Thus, simulated polymer 1, with 200 monomers and molecular weight of 23.2 kDa, has final Rg values of 1.8-2.0 nm. For comparison, folded proteins with 151-200 residues have Rg values ranging approximately from 1.6-1.8 nm, and the proteins ribonuclease and chymotrypsinogen alpha, with molecular weights of 17 and 38 kDa, have Rg values of 1.5 and 1.8 nm, respectively. Although simulated polymers 3-6, have molecular weights about four times smaller (5-6 kDa), their Rg values of ~1.2 nm are not even two-fold smaller, suggesting that these single-peptide constructs do not compact as tightly as the more peptide-rich 1 and 2.

Conformational fluctuations of the simulated molecules were quantified by using overall rotations and translations to optimize the overlay of each MD snapshot on the final snapshot (120 ns) of the corresponding MD trajectory, and computing the root-mean-square deviations (RMSDs) of the overlaid snapshots relative to the final snapshots, as a function of time. The RMSD values in all cases remained less than 1.5 nm in the final 100 ns of each simulation, and in many cases, they remained below 1.0 or even 0.4 nm, particularly for the trajectories which include the heat-cool cycle. Presumably, the heat-cool cycle in these cases allowed the structures to find a particularly stable conformational state. The structural fluctuations observed here are larger than those typically observed in similar MD simulations of stably folded, naturally occurring proteins, but the lower end of the present range is commensurate. It should be noted that the final conformations generated from the simple 300K simulations and from the corresponding heat-cool simulations are quite different from each other: for simulated polymers 1 and 2, the RMSDs between these conformer are 1.35 and 1.32 nm respectively.

the 1:9 copolymers, 3 and 4, are visible as relatively isolated components at the surface of these peptide-polymer constructs. Salt-bridges and occasional segments of alpha-helix were observed.

Molecular Dynamic Simulations with the Random Blend Copolymers

To further examine the proteolytic susceptibility trends observed with the random blend copolymers of the fluorogenic substrate and OEG moiety, a series of molecular dynamics simulations were performed, examining analogous blend copolymers with discrete structures and no dispersity (i.e., a single molecular entity was modeled for each structural analogue). For computational simplicity, all polymers were constructed in silico to have a DP of 10, instead of 20, in four key arrangements meant to best simulate idealized scenarios: a homopolymer of ten repeated fluorogenic substrates (FIGS. 9A and 9B); two blend copolymers with an OEG:peptide ratio of 9:1, one having the peptide at one end of the polymer (FIGS. 9C and 9D), and the other having the peptide at position five (FIGS. 9E and 9F); and one with an intermediate peptide:OEG ratio of 5:5 (FIGS. 9G and 9H).

Simulations were performed on each structure, starting with the molecule in an artificial, extended conformation with a straight norbornyl backbone, extended peptides, and OEG brushes arrayed at right angles to the polymer backbone. In the simulations, each structure was equilibrated for an initial 20 ns at 300 K, after which each simulation was split and continued in two ways: one simulation for each molecule was continued for 100 ns at 300 K and the other was further randomized by a single heating (500 K) and cooling (300 K) cycle before continuing at 300 K for remainder of the 100 ns simulation.

In every simulation, the initial extended structure of each molecule collapsed quickly into a more compact conformational ensemble. Representative conformations of each construct were obtained by applying a root-mean-square deviation (RMSD)-based clustering algorithm to the last 40 ns of the respective heat-cool simulations. In these structures, the homopolymer and 5:5 copolymer collapsed into an elongated globule, with their peptide chains tangled around the polymer backbone. In contrast, the single peptide chain in the 9:1 copolymers, were visible as relatively isolated com-

TABLE 11 hydrogen bond counts of simulated polymers 1-6, averaged over the last 40 ns of the heat-cool trajectories.

|  | Polymer 1 | Polymer 2 | Polymer 3 | Polymer 4 | Polymer 5 | Polymer 6 |
| --- | --- | --- | --- | --- | --- | --- |
| AA-AA | 88 | 33 | 7 | 6 | 8 | 5 |
| EDANS-AA | 24 | 9 | 0 | 1 | — | — |
| DABCYL-AA | 7 | 3 | 0 | 0 | — | — |
| Peptide-peptide | 119 | 45 | 7 | 7 | 8 | 5 |
| PEG-AA | 0 | 2 | 1 | 1 | 2 | 0 |
| NOR-AA | 2 | 1 | 2 | 0 | 0 | 2 |
| EDANS-OEG | 0 | 0 | 0 | 0 | 0 | 0 |
| DABCYL-OEG | 0 | 0 | 0 | 0 | 0 | 0 |
| EDNAS-NOR | 1 | 1 | 0 | 0 | 0 | 0 |
| DABCYL-NOR | 0 | 0 | 0 | 0 | 0 | 0 |
| Peptide-nonpeptide | 3 | 4 | 3 | 1 | 2 | 2 |

Representative conformations of simulated polymers 1-4 were obtained by applying an RMSD-based clustering algorithm to the last 40 ns of the respective heat-cool simulations. Homopolymer 1 and the 5:5 copolymer 2 collapsed into an elongated globule, with their peptide chains tangled around the polymer backbone. The single peptide chains in ponents at the surface of the constructs. A detailed analysis of differences in radius of gyration of each structure and also on conformational fluctuations in the structures as quantified by RMSDs was determined. A graph showing radii of gyration (Rg) of simulated polymer 1 under constant temperature condition (300K) and using simulated annealing procedure was constructed. A graph showing Rg of simulated polymer 2 under constant temperature condition (300K) and using simulated annealing procedure was constructed. A graph showing Rg of simulated polymer 3 under constant temperature condition (300K) and using simulated annealing procedure was constructed. A graph showing Rg of simulated polymer 4 under constant temperature condition (300K) and using simulated annealing procedure was constructed. A graph showing Rg of simulated polymer 5 under constant temperature condition (300K) and using simulated annealing procedure was constructed. A graph showing Rg of simulated polymer 6 under constant temperature condition (300K) and using simulated annealing procedure was constructed. A graph of RMSD (root-mean square deviation) of simulated polymer 1 was obtained. RMSD values were calculated with respect to the structure in the last frame in each run. The program g_rms in Gromacs3 was used to generate the rotational and translational overlays and compute RMSD values. Similarly, a graph of RMSD of simulated polymer 2 was constructed. a graph of RMSD of simulated polymer 3 was constructed. Similarly, k a graph of RMSD of simulated polymer 4 was constructed. Similarly, a graph of RMSD of simulated polymer 5 was constructed. Similarly, a graph of RMSD of simulated polymer 6 was constructed. A representative conformation of simulated polymer 1 was generated. Similarly, a representative conformation of simulated polymer 2 was constructed. A representative conformation of simulated polymer 3 was constructed. A representative conformation of simulated polymer 4 was constructed.

Role of Hydrogen Bonding to Facilitate Compression or Tangling of the Peptide-Containing Structures The role of hydrogen bonding in facilitating the compression or tangling of the peptide-containing structures by computing the numbers of intrasolute hydrogen bonds during the last 40 ns of each heat-cool trajectory (Table 11) was examined. The homopolymer averaged 0.5 amino acid-amino acid peptide bonds per residue (88 interactions over 17 residues per monomer), which was about half the ratio typically of a folded protein. The three copolymers averaged fewer (0.4) hydrogen bonds per residue, with very few hydrogen bonds to the OEG moieties (less than four in all cases). Overall, these hydrogen bond counts were consistent view that although the polymers collapsed, they were not as well structured as typical globular proteins and the inclusion of OEG units lead to a decrease in hydrogen bonding. Thus, the addition of OEG units effectively "diluted" the density of the peptide-brush by reducing the overall degree of hydrogen bonding in the polymer structure. Moreover, the OEG moieties blocked what would otherwise be stabilizing interactions among the peptides brushes without compensating with new OEG-peptide interactions.

Accessibility of Peptide Components to Large and Small Molecules

Figure 9I:
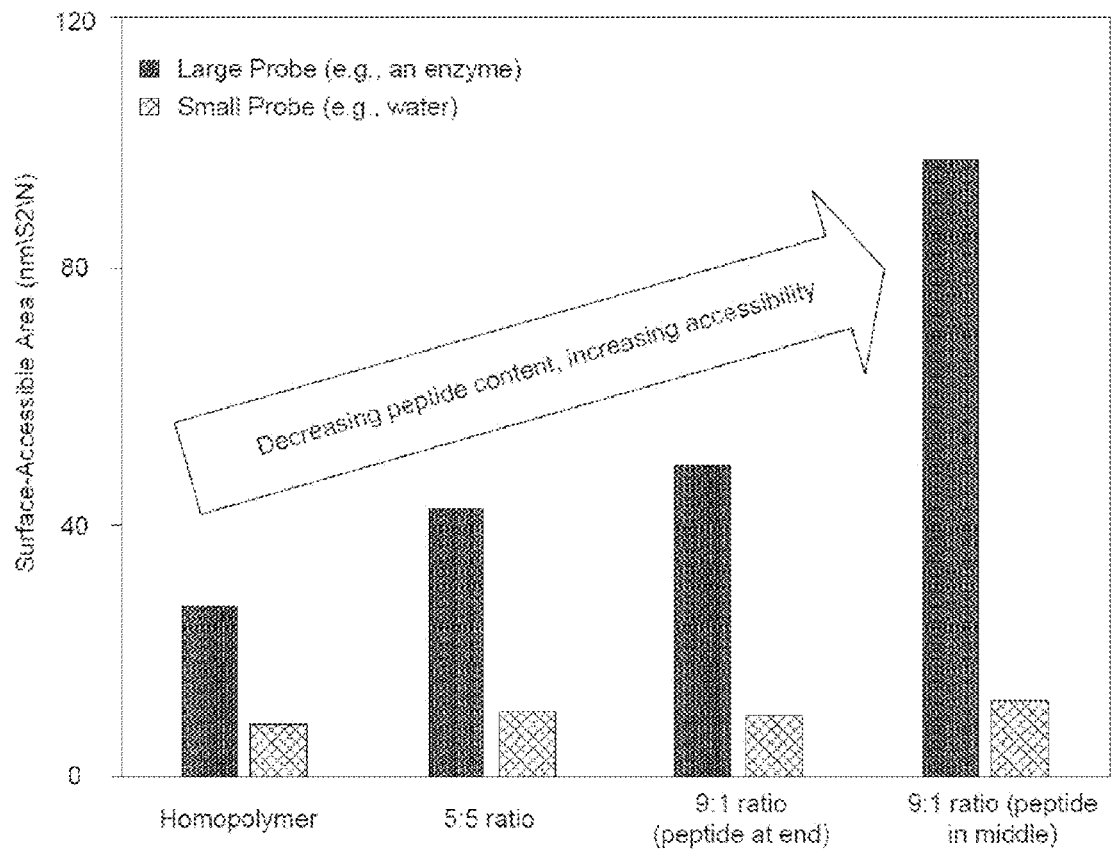
FIG. 9I is a plot showing the probe-accessible surface area of the four structures (11A-11H), averaged over the last 40 ns of each heat-cool cycle. Blue bars represent the surface area accessible per peptide to a spherical probe with a radius of 3.14 nm (size on the order of a typical protease) and the gray bars represent the same measurement using a probe radius of 0.14 nm (approximately the size of a water molecule).
Figure 10:
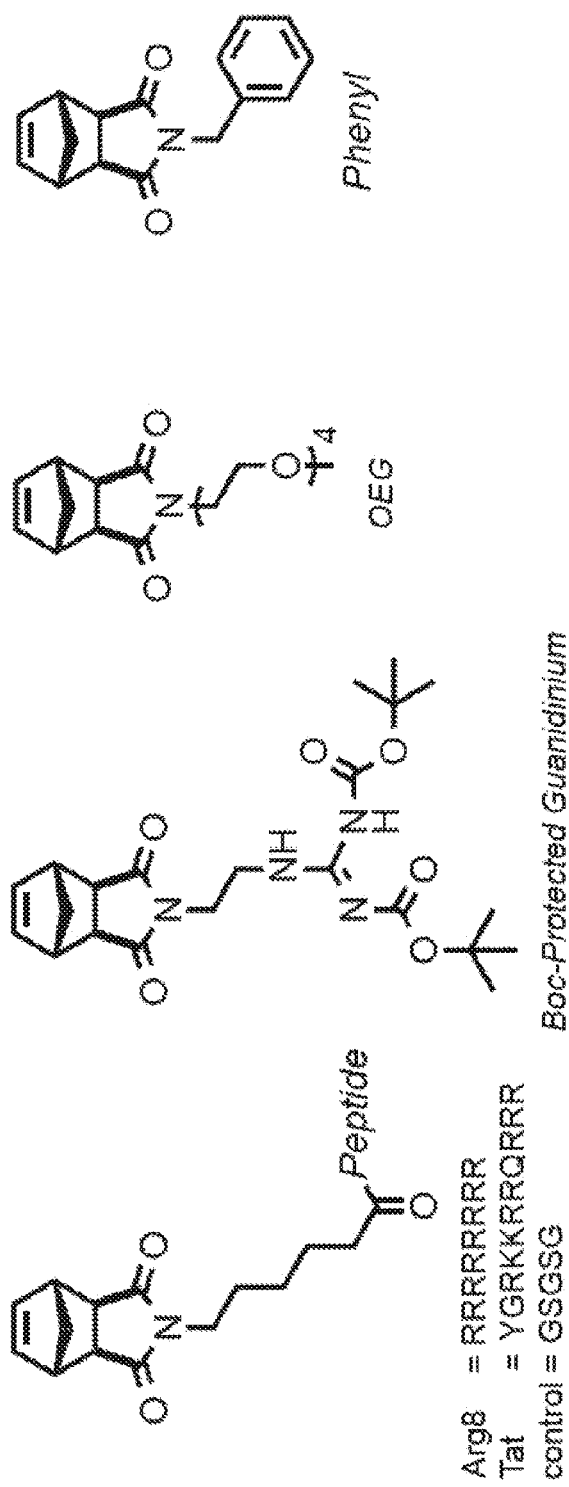
FIG. 10 are chemical structures of monomers used in cell penetration studies. The side-chains on the arg8 monomer are protected with a Pbf (2,2,4,6,7-pentamethyldihydrobenzofuran-5-sulfonyl chloride) group.

The accessibility of the peptide components of the various constructs to large and small molecules was examined by computing their time-averaged probe-accessible surface area (SA), using a large (3.14 nm) probe sphere whose size is similar to that of a protein, and a small (0.14 nm) water-sized probe sphere (FIG. 9I). A general trend was seen with the large probe, where larger surface accessibility was seen as the peptide content decreased. The greatest accessibility was observed for the 9:1 copolymer with the peptide at position 5. This was the closest representation to the experimental 19:1 random blend copolymer (based on the polymerization method, Table 9), which was nearly as susceptible to proteolytic degradation as the peptide monomer in vitro. In contrast, the probe-accessible surface areas obtained with the water-sized probe were relatively uniform across all constructs. These results indicated that the peptides in all five constructs maintained similar accessibility to small molecules, like water, but that the tighter packing of the more peptide-rich constructs reduced accessibility to protein-size molecules, such as the proteases examined experimentally. Moreover, these data indicate that peptides whose function depends on interaction with a small molecule or a receptor with a relatively accessible binding site exhibited ample binding to the peptide substrates in any of the constructs considered, including the homopolymer. The implication is that the bioactivity of many peptides will be maintained after polymerization of the sequence into a high-density brush. For peptides whose function depends on interaction with proteins or macromolecules with tight or cramped binding pockets (such as a protease), polymerization into a high-density brush polymer may impede function, as is consistent with the data presented herein.

The simulation results indicated that all of the constructs studied collapsed into fairly compact globular conformations, and that a higher peptide content lead to formation of more stabilizing intramolecular hydrogen bonds and reduced accessibility of the peptides to proteins in solution. This picture was qualitatively consistent with the experimental observation that constructs with high peptide content are better protected from enzymatic degradation. Although the simulations are subject to error due to their limited duration and uncertainties in the force field, they yield a detailed representation of the systems under study and offer a plausible explanation for the key experimental results.

Example 8: Activating Peptides for Cellular Uptake Via Polymerization into High Density Brushes Materials All amino acids used to prepare peptides by solid phase peptide synthesis (SPPS) were obtained from AAPPTec and NovaBiochem. Unless otherwise noted, all other compounds and materials were purchased from Sigma Aldrich and used without further purification. The GSGSG (SEQ ID NO:1) monomer,[1] GSGSG (SEQ ID NO:1) peptide control, Tat peptide control, and OEG monomer were synthesized. The polymerization initiator, 51, (H2IMES)(pyr)2(Cl) 2Ru=CHPh was also prepared by a published protocol.[3] Analytical scale reverse-phase HPLC (RP-HPLC) was performed on a Jupiter Proteo90A Phenomenex column (150× 4.60 mm) equipped with a Hitachi-Elite LaChrom L2130 pump and a UV-Vis detector (Hitachi-Elite LaChrome L-2420) monitoring at 214 nm. Peptides were purified on a preparative-scale Jupiter Proteo90A Phenomenex column (2050×25.0 mm) using an Armen Spot Prep II System. In all cases, peptides were purified and analyzed for purity using a gradient buffer system in which Buffer A is 0.1% TFA in water and Buffer B is 0.1% TFA in acetonitrile. Polymer dispersities (Mw/Mn) and molecular weights (Mn) were determined by size-exclusion chromatography coupled with multiangle light scattering (SEC-MALS). To this end, SEC was performed on a Phenomenex Phenogel 5 u 10, 1K-75K, 300×7.80 mm column in series with a Phenomenex Phenogel 5 u 10, 10K-1000K, 300×7.80 mm column, which ran with 0.05 M LiBr in DMF as the running buffer (flow rate of 0.75 mL/min) using a Shimadzu pump. The instrument was also equipped with a MALS detector (DAWN-HELIO, Wyatt Technology) and a refractive index (RI) detector (Wyatt Optilab T-rEX detector). The entire SEC-MALS set-up was normalized to a 30K MW polystyrene standard.

All concentrations of fluorescein-labeled materials were obtained by measuring UV absorbance of the fluorophore (at 495 nm) on a ThermoScientific Nanodrop 2000c and fitting the data obtained to the standard curves. The emission profiles of all materials were equivalent at these concentrations (ex: 495 nm, em: 520 nm). Fluorescent data was recorded on a Perkin Elmer EnSpire Multimode Plate Reader. A Varian Mercury Plus spectrometer was used to obtain all 1H (400 MHz) NMR spectra. Chemical shifts are reported in ppm relative to the DMF-d7 residual proton peaks. Flow cytometry was performed on an Accuri C6 flow cytometer set to default "3 blue 1 red" configuration with standard optics and slow fluidics (14 µL/min).

Polymerizations Methods

Figure 23:
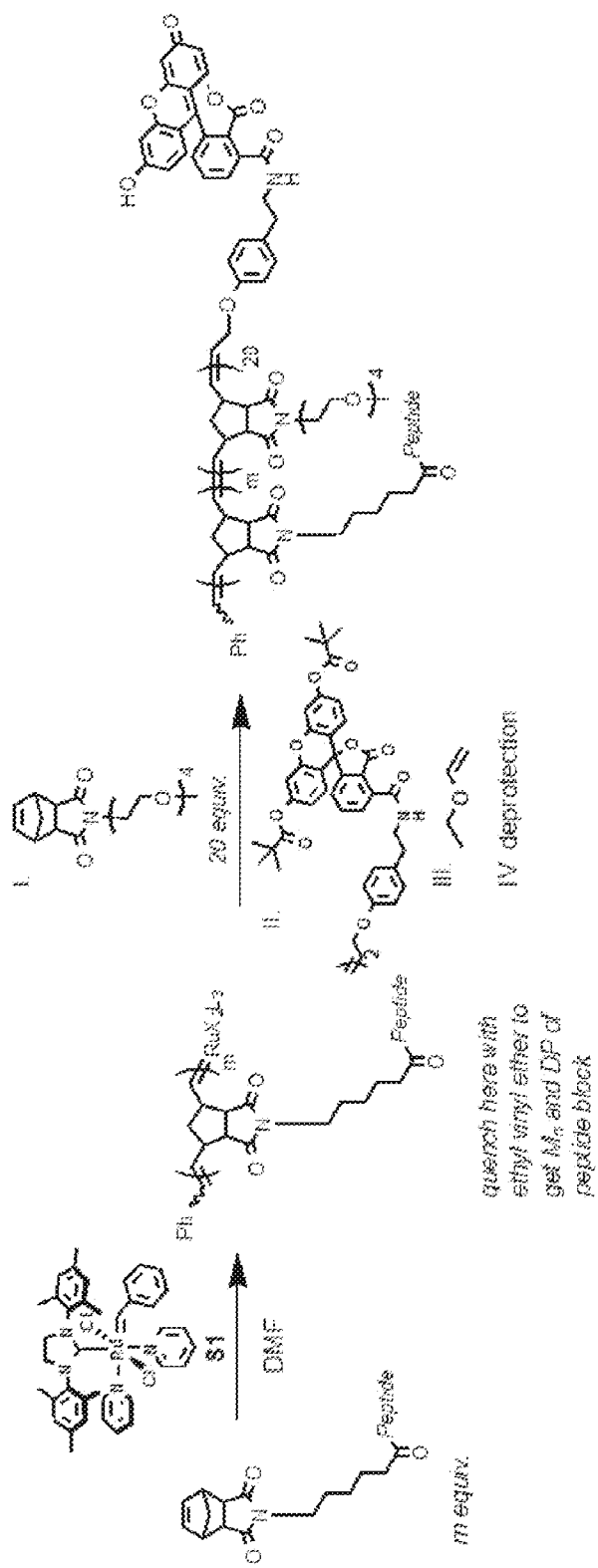
FIG. 23 is a schematic showing the polymerization scheme for the preparation of GSGSG (SEQ ID NO:1) peptide polymers and analogues. Peptide polymers for this series are prepared via ROMP as block copolymers with an accessory OEG block to ensure aqueous solubility of all GSGSG (SEQ ID NO:1) analogues. Each peptide block is polymerized to m~8, 15, 30, and 60. The OEG block is kept constant at a DP of ~20. The living polymer can be terminated with ethyl vinyl ether after completion of the peptide block to gain accurate molecular weights ($M_n$), dispersity ($M_w/M_n$) and degree of polymerization (DP). To monitor uptake of the materials, each polymer is end-labeled with fluorescein. Polymers used in all toxicity studies, were prepared without a fluorophore by terminating the polymerization with ethyl vinyl ether prior after addition of the second (OEG) block.
Figure 24:
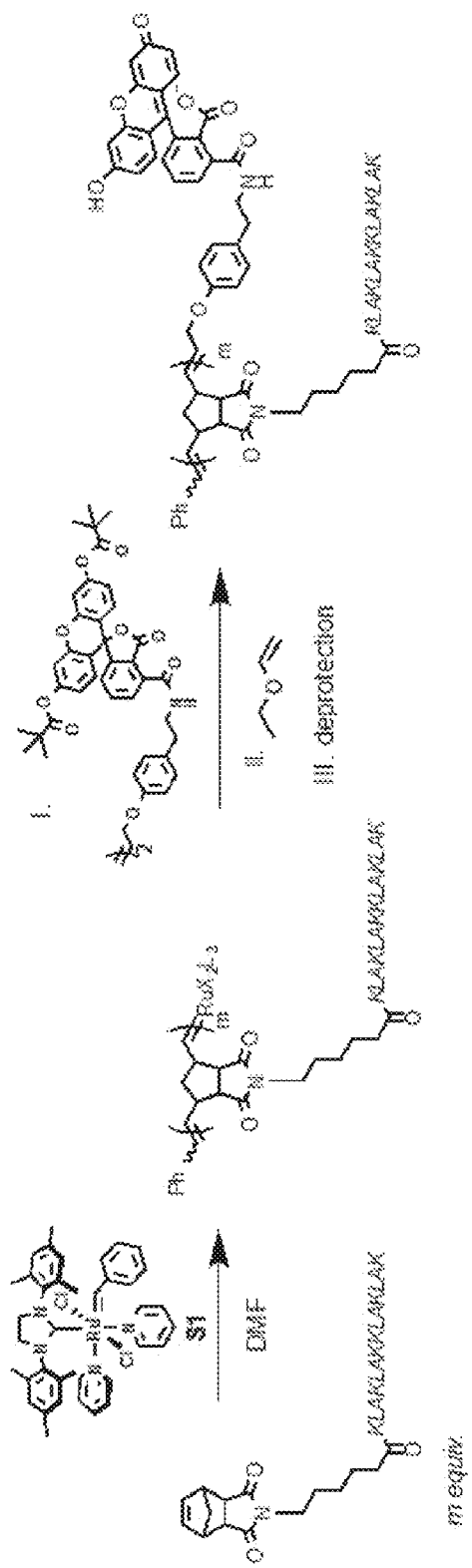
FIG. 24 is a schematic showing the polymerization scheme for the preparation of KLA homopolymers. KLA peptide polymers were prepared as homopolymers (m~5, 10, 15) via ROMP and end-labeled with fluorescein as with the block copolymers. Identical conditions were used to prepare the KLAKLAK (SEQ ID NO:24) (fragment) control polymer. Polymers used in all toxicity studies, were prepared without a fluorophore by terminating the polymerization with ethyl vinyl ether after the peptide has finished polymerizing. Sequence legend: KLAKLAKKLAKLAK (SEQ ID NO:18).

All polymerizations were carried out in a glove box under $N_2$ (g). A typical protocol (FIG. 23) used to generate a polymer with DP (or "m" in FIG. 19A)=8 involved mixing the monomer (0.0125 mmol, 8 equiv., 25 mM) with the catalyst initiator (FIG. 1A) (0.00156 mmol, 1 equiv., 3.1 mM) in dry DMF (0.5 mL). For each peptide monomer whose polymerization has not been reported previously in the literature, the time course of the polymerization in DMF-d7 by $^1$H NMR was followed to confirm complete consumption of the monomer and to determine the time period required to reach completion (FIG. 24). To track cellular uptake, each polymer was end-labeled with a copy of fluorescein by treatment with a chain transfer agent (1.5 equiv.) for 2 hrs, followed by termination with ethyl vinyl ether (10 equiv.) for 1 hr at room temperature. Block copolymers used in the GSGSG (SEQ ID NO:1) series were prepared by first polymerizing the peptide monomer to completion prior to adding and polymerizing the OEG monomer. The block copolymers were prepared in this manner to obtain an accurate estimation of the DP or m of the functional peptide block (using a dn/dc of 0.179 in DMF) since the peptide and OEG blocks have different dn/dc values in DMF. The accessory, water-solubilizing OEG block (dn/dc=0.11 in DMF) was then polymerized second and ratios of the dn/dc values of the two blocks were used to calculate values for this block (i.e., the dn/dc for m=8, 15, 30 and 60 was 0.131, 0.141, 0.151 and 0.161 based on the ratio of peptide:OEG used). Following completion of the second block, the resulting polymers were end-labeled with the fluorescein chain transfer agent and the active catalyst was then terminated with ethyl vinyl ether as described above. Fluorescein-labeled polymers were treated with $NH_4OH$ (aq) for 30 min to remove the pivolate protecting group. The resulting polymers were then directly characterized by SEC-MALS to obtain the polymer molecular weight ($M_n$), dispersity and degree of polymerization (DP).

All polymers were then precipitated with cold ether and collected by centrifugation. For the side-chain protected peptide monomers, the resulting powder was dissolved in 2 mL of a mixture of $TFA/H_2O/TIPS$ (95:2.5:2.5) and stirred for 4 hours at room temperature. The product was precipitated with cold ether, collected by centrifugation and dried. In preparation for in vitro studies, all polymers were washed (3×) with cold ether (to remove the Ru catalyst) and then dissolved in DPBS and dialyzed in dialysis cups with a molecular weight cut-off value of 3500 (Thermo Scientific, cat. #69552) in an effort to remove any residual monomer or catalyst.

Cell Culture Methods

HeLa cells were purchased from ATCC (CCL-2). Cells were cultured at 37° C. under 5% CO2 in Dulbecco's Modified Eagle Medium containing phenol red (DMEM; Gibco Life Tech., cat #11960-044) that was supplemented with 10% fetal bovine serum (Omega Scientific, cat #FB02) and with 1× concentrations of non-essential amino acids (Gibco Life Tech., cat #11140-050) sodium pyruvate (Gibco Life Tech., cat. #11360-070), L-Glutamine (Gibco Life Tech., cat. #35050-061), and the antibiotics penicillin/streptomycin (Corning Cellgro, cat. #30-002-C1). Cells were grown in T75 culture flasks and subcultured at ~75-80% confluency (every 3-4 days).

Flow Cytometry Methods

HeLa cells were plated at a density of 90,000 cells per well of a 24-well plate 18 hrs prior to treatment with the material of interest. Materials dissolved in Dulbecco's Phosphate Buffered Saline (DPBS without Ca2+ or Mg2+; Corning Cellgro, cat. #21-031-CM) at 10× the desired concentration (where concentration is with respect to fluorophore concentration to ensure propare comparison of each molecular transporter) were added to the wells and the plates were incubated for 30 min at 37° C. The medium was then removed and the cells were washed 2× with DPBS and then incubated 3× for five minutes each with heparin (0.5 mg/mL in DPBS; Affymetrix, cat. #16920) to remove any membrane-bound, non-internalized material, and finally rinsed again with DPBS. The cells were then trypsinized (0.25% trypsin in DPBS; Gibco Life Tech., cat. #15090-046) for 10 min, cold medium was added, and the cells were transferred to Eppendorfs. The suspended cells were centrifuged to pellets and then resuspended in a minimal amount of cold DPBS. Flow cytometry data (10,000 events on three separate cultures) was then acquired.

Live-Cell Confocal Microscopy Methods

HeLa cells were plated on glass-bottom 24-well plates at a cell density of 90,000 cells per well 18 hrs prior to treatment with the compound of interest. The medium was removed and then replaced with medium lacking phenol red (Gibco Life Tech., cat #31053-028) to minimize background fluorescence. Materials dissolved in DPBS (at 10× the desired concentration, 2.5 M, where concentration is with respect to fluorophore) were added to the wells and the plates were incubated for 30 min at 37° C. The medium was then removed and the cells were rinsed 2× with DPBS, and then fresh medium (phenol red-free) was added to each well. Live cells were imaged on an Olympus FV1000 confocal microscope with a chamber at 37° C. under 5% CO2 via a Z-stack analysis (set to 1 m slices) using identical instrument settings for each image and a 40× objective.

Cell Viability Assay Methods

The cytotoxicity of materials was assessed using the CellTiter-Blue® assay (Promega, cat #G8081), which measures the metabolic reduction of resazurin to resorufin via fluorescence. For these studies, HeLa cells were plated at a density of 3,500 cells per well of a 96-well plate 18 hrs prior to treatment. Materials dissolved in DPBS at 10× the desired concentrations were added to the wells along with a 10% DMSO positive control. Cells were incubated for 72 hrs at 37° C. Note that concentration for all toxicity measurements is with respect to peptide concentration to ensure that all peptides and polymers are fairly compared with respect to their therapeutic components. There was also no fluorophore present on the polymers or peptides used in these experiments to minimize potential background signals in the fluorescent measurements. The medium was removed and 80 µL of fresh medium lacking phenol red was added. To this was added 20 µL of the CellTiter-Blue® reagent and the cells were then incubated for 2 hrs prior to measuring fluorescence using 560 nm excitation and 590 nm emission. The fluorescence measurements were corrected for background fluorescence from the CellTiter-Blue® reagent by subtracting the fluorescence reading of wells treated with the reagent in the absence of cells. Fluorescence values were then referenced as a percentage of the value obtained for the DPBS vehicle control.

Circular Dichroism Methods

UV-Vis circular dichroism (CD) was used to evaluate whether the secondary structure of KLA, a mixture of random coil and alpha helix, is maintained upon polymerization. The peptide and polymer were dissolved in DPBS to a final concentration of 100 µM (with respect to peptide concentration). CD spectra were measured using an Aviv 215 spectrometer and each sample was measured from 190 to 260 nm with a slit width of 1 nm, scanning at 1 nm intervals with a 1s integration time. Measurements were taken 3× at 25° C. and then averaged to give the spectra in FIGS. 30A-30D.

JC-1 Mitochondrial Integrity Assay

The mitochondrial membrane potential was measured using the MitoProbe® JC-1 assay kit (Life Technologies, cat #M34152), which measures the membrane potential using the JC-1 dye. The JC-1 dye forms J aggregates in healthy mitochondria that are red fluorescent, but cannot form the J aggregates when the mitochondria are disrupted, leading to a decrease of red fluorescence and an increase of green fluorescent J monomers in the cytosol. HeLa cells were plated at a density of 90,000 cells per well of a 24-well plate 18 hrs prior to treatment. Materials dissolved in DPBS at 10× the desired concentrations (where concentration is with respect to peptide and no fluorophore is present) were added to the wells and incubated for 30 minutes. The materials were removed and the cells were washed with DPBS, then medium was added to the cells followed by incubation with 10 µL of a 200 µM solution of JC-1 dye to give a final concentration of 2 µM. To one set of wells, 2 µL of 50 mM carbonyl cyanide 3-chlorophenylhydrazone (CCCP) was added to give a final concentration of 50 µM. The small molecule CCCP is used as a positive control because it can associate with and depolarize mitochondrial membranes. The cells were incubated for 30 more minutes. The medium was then removed and the cells were washed 2× with DPBS and then incubated 3× for five minutes each with heparin (0.5 mg/mL in DPBS; Affymetrix, cat. #16920), and finally rinsed again with DPBS. The cells were then trypsinized (0.25% trypsin in DPBS; Gibco Life Tech., cat. #15090-046) for 10 min, cold medium was added, and the cells were transferred to Eppendorfs. The suspended cells were then centrifuged to pellets and then resuspended in a minimal amount of cold DPBS. Flow cytometry data (10,000 events on three separate cultures) was then acquired.

Apoptosis Assay Methods

The expression of caspase enzymes, markers of apoptotic cells, in the cells treated with KLA materials was assessed using the Apo-One® assay (Promega, cat #G7790), which measures the expression of caspase 3/7, a marker of apoptosis, using a fluorogenic substrate for those enzymes. HeLa cells were plated at a density of 5,000 cells per well of a 96-well plate 18 hrs prior to treatment. Materials dissolved in DPBS at 10× the desired concentration (10 PM, where concentration is with respect to peptide and no fluorophore is present) were added to the wells. Cells were incubated for 30 minutes at 37° C. The medium was removed the cells were washed 3× with DPBS. 100 µL of the Apo-One® reagent was added to the cells and to wells that contain no cells to get a baseline reading. The plate was mixed for 30 seconds using a shaker followed by incubation at 37° C. After 3 hrs of incubation, the fluorescence was measured using an excitation of 499 nm and emission at 521 nm. The baseline fluorescence was subtracted from the fluorescence values for the wells, and fluorescence values were then referenced as a percentage of the value obtained for the DPBS vehicle control.

Mechanistic Studies by Flow Cytometry

For mechanistic studies, cells were plated and treated as described in the previous flow cytometry experiments, except here cells were preincubated with the indicated compound for 30 minutes at 37° C. prior to addition of the cell-penetrating material. The following concentrations were used: 80 µM dynasore (Enzo Life Sciences, cat. #270-502-M005) and 9.5 mM MβCD (Fischer Scientific, cat #AC377110050). For studies at reduced temperature, cells were incubated at 4° C. for 30 min prior to and during incubation with the compound of interest. For the reduced temperature studies only, all subsequent washes and manipulations were also done with ice-cooled media and other materials. Data is reported as the normalized mean fluorescence, which is the mean fluorescence yielded by the material divided by the mean fluorescence from the vehicle control. Each measurement was preformed 3× on at least three separate subcultures.

RP-HPLC Analysis of Proteolytic Susceptibility

The percent of intact GSGSGKK (SEQ ID NO:17), GSGSGRR (SEQ ID NO:15) or KLA peptides and polymers after incubation with trypsin (Gibco Life Tech., cat. #15090-046) or Pronase (Roche, cat. #10165921001) was assessed by comparing RP-HPLC chromatograms. In these experiments, each peptide or polymer (50 µM, where concentration is with respect to peptide content to ensure fair comparison between the peptides and polymers) was incubated with each protease (at 1 µM) for 3 hrs. At this point, the proteases were heat denatured at 65° C. for 15 m and the resulting solution was immediately injected onto an analytical RP-HPLC. Given that treatment with each protease often yielded multiple peptide fragments, a standard curve for each starting material (rather than every potential product) was prepared to assess the percentage of intact material remaining after proteolytic digestion. Note that the standard curves for polymers will be biased because the polymer backbone, OEG coblock and fluorophore should remain intact after cleavage, and will therefore comprise part of the measured peak area. Nevertheless, no new peaks were seen in the chromatograms of any polymer post enzyme treatment, suggesting that these materials are not susceptible to cleavage by the proteases. Major fragments of the peptide controls were also identified by ESI MS. Consistent with the notion that the polymers are protected from proteolysis, no discernable peptide fragments were identified by MS in the polymer reaction mixtures.

Obstacles in Peptide-Based Therapeutic and Diagnostic Agents

The chemical diversity inherent to natural and unnatural amino acids enables the formulation of peptides that are selectively and precisely coded for interaction with target receptors and other biological surfaces. This ability has fostered the development and identification of unique natural, semi-synthetic and synthetic peptide sequences capable of diverse medicinal and diagnostic applications. Despite their promise, the clinical efficacy of many peptide-based therapeutic and diagnostic agents is severely hampered by three key obstacles: errant proteolysis, inefficiencies in cellular uptake, and size-dependent renal clearance. A strategy for protecting peptides from proteolysis in which peptides are packaged as high density brush polymers via graft-through ring opening metathesis polymerization (ROMP) of peptide-based monomers, generating structures that are resistant to proteolytic degradation was reported. This strategy does not require chemical modification of the primary amino acid sequence and is, therefore, a facile approach to access formulations of protease-resistant peptides that maintain their inherent function. Here it is demonstrated that when polymerized into a high density brush polymer, peptides bearing at least one Arg or Lys can efficiently penetrate cells.

The biological target of most therapeutic agents resides in the cytosol or nuclei of cells. Therefore, potential therapeutic peptides that cannot gain entry into the interior of a cell are generally ineffective. Conventional strategies for conferring cellular uptake typically involve appending the peptide of interest to a cell penetrating peptide (CPP). CPPs, such as Tat and Arg8, are most often highly charged sequences that contain multiple copies of arginine (Arg). CPPs of this type have been shown to deliver a wide variety of conjugated cargo into cells. However, materials linked to CPPs in a linear arrangement maintain their susceptibility to proteolytic digestion. Thus, the development of general strategies that provide the needed dual function of protecting peptides from proteolysis while facilitating cellular entry have the potential to change the way peptides are prepared and delivered.

Non-CPP Based Molecular Transporters

There are a number of non-CPP based molecular transporters capable of traversing cellular membranes with cargo in tow. These constructs are mostly comprised of a nanomaterial scaffold, such as a dendrimer, whose surface is decorated with several copies of guanidinium, the chemical moiety present on Arg side chains that endows CPPs with their cell penetrating properties. Near to the goal of cell penetration by peptide polymers, is a strategy developed by Kiessling and co-workers in which guanidinium units are appended via a graft-to approach to a preformed polymer prepared by ROMP. This system and close derivatives designed by Tew remain the only examples of membrane penetrating polynorbornyl polymers.

The strategy reported herein is inspired by these designs, but seeks a simpler, generalizable approach specific to peptide uptake. Incorporation of a single Arg residue into the amino acid sequence of a non-CPP, and subsequent polymerization of that peptide into a high density brush polymer, would enable cellular uptake of these materials. This strategy may provide a new route to the development of peptide-based therapeutics solving two major issues; 1) degradation by proteases and 2) inefficient cellular uptake; each of which have severely limited (if not negated) the success of many promising peptide-based drug candidates. Moreover, the strategy offers key advantages over traditional methods for conferring cellular uptake because the brush polymers produced have a much higher density (weight percentage) of the therapeutic agent and require few synthetic or purification steps.

Figure 19A:
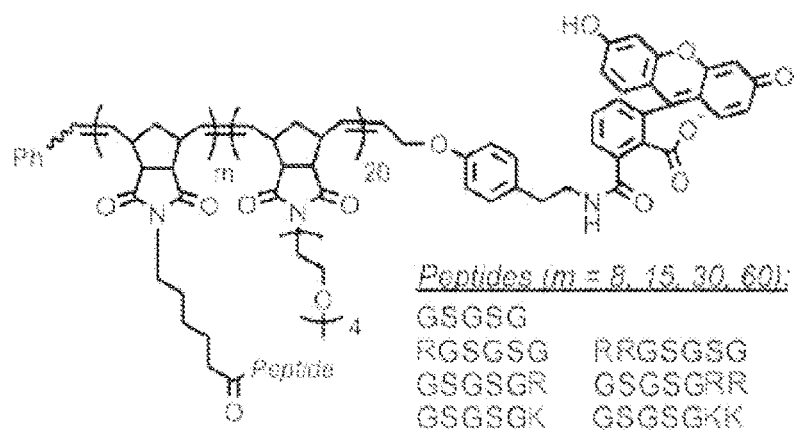
FIG. 19A is a chemical structure showing the peptide block copolymers. Sequence legend: GSGSG (SEQ ID NO:1); RGSGSG (SEQ ID NO:12); RRGSGSG (SEQ ID NO:13); GSGSGR (SEQ ID NO:14); GSGSGRR (SEQ ID NO:15); GSGSGK (SEQ ID NO:16); GSGSGKK (SEQ ID NO: 17).
Figure 19B:
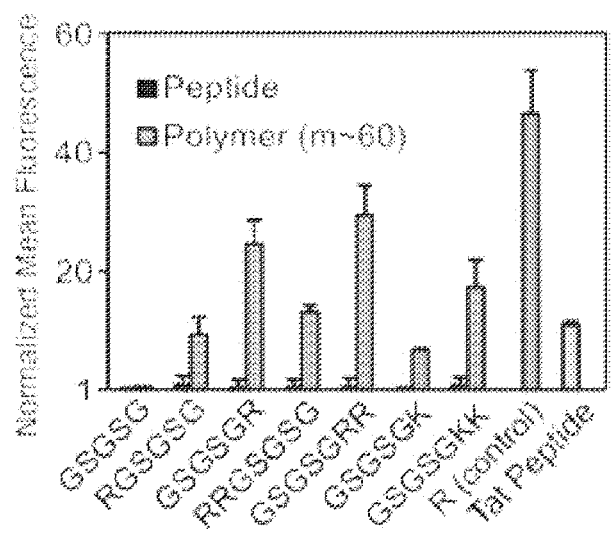
FIG. 19B is a bar graph showing flow cytometry data of fluorescent signatures of HeLa cells treated with the polymers (m~60) and their monomeric counterparts. All data are normalized to the vehicle (DPBS), which is assigned a value of 1. The R control is a block copolymer that contains a single Arg attached via a short linker at each polymer side chain of the first block (m~60). "Flu" is the fluorescein end-label shown in FIG. 19A
Figure 19B:
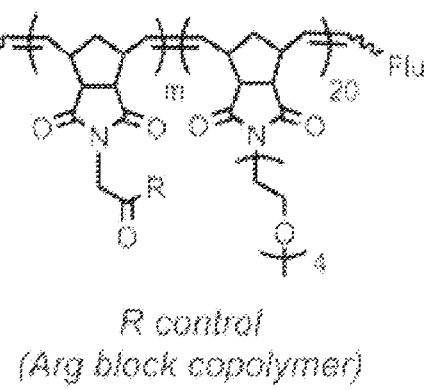
Figure 22:
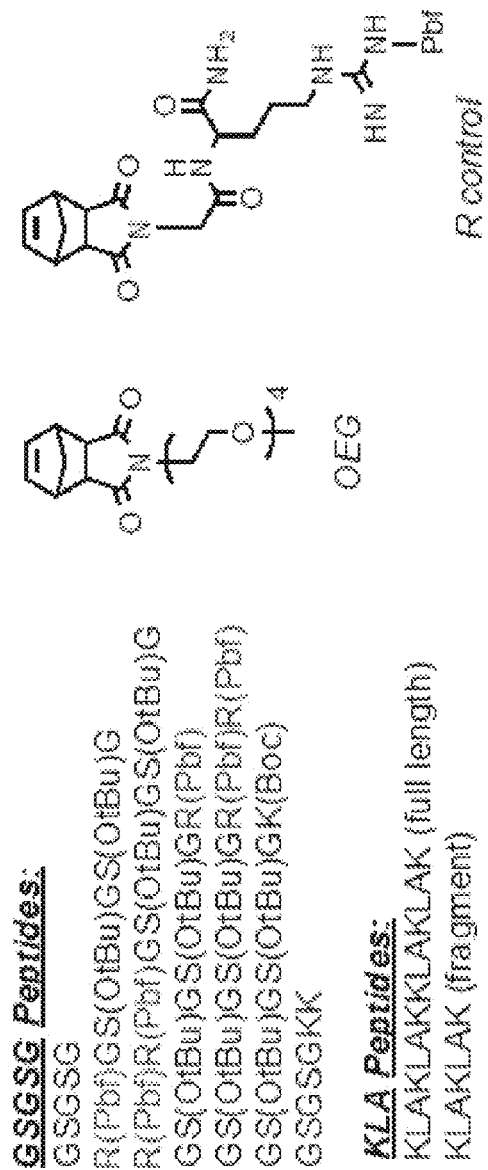
FIG. 22 is a chemical structure showing ROMP monomers. The GSGSGKK (SEQ ID NO:17) peptide and all KLA variants were prepared without protecting groups for enhanced solubility in DMF in preparation for polymerization. Sequence legend: GSGSG (SEQ ID NO:1); R(Pbf)GS(OtBu)GS(OtBu)G (SEQ ID NO:19); R(Pbf)R(Pbf)GS(OtBu)GS(OtBu)G (SEQ ID NO:20); GS(OtBu)GS(OtBu)GR(Pbf) (SEQ ID NO:21); GS(OtBu)GS(OtBu)GR(Pbf)R(Pbf) (SEQ ID NO:22); GS(OtBu)GS(OtBu)GK(Boc) (SEQ ID NO:23); GSGSGKK (SEQ ID NO:17); KLAKLAKKLAKLAK (SEQ ID NO:18); KLAKLAK (SEQ ID NO:24).

To test the strategy, a peptide sequence, GSGSG (SEQ ID NO:1) was synthesized, that does not penetrate cells and appended one or two Arg residues to the N or C terminus, reasoning that these locations would yield the highest likelihood of maintaining the inherent bioactivity of an otherwise intact peptide sequence (FIGS. 19A-19B, FIG. 22 and Tables 10 and 11). These peptides were prepared as fluorescein-labeled peptide controls and also as fluorescein-terminated brush polymers via the graft-through ROMP strategy (FIG. 19A). To ensure solubility, polymers were prepared as block copolymers with a second block containing an OEG (oligoethylene glycol) unit (degree of polymerization (DP) approx. 20), which does not penetrate cells alone (for polymer synthesis and characterization data, FIGS. 23-24 and Table 12). The relative extent of uptake of each material in HeLa cells was quantified by flow cytometry, where concentration in these studies is with respect to fluorophore (2.5 µM) to ensure direct comparison of each material's ability to transport itself and its cargo (fluorescein). In all cases, the monomeric peptide controls showed fluorescence signals that were indistinguishable from that of the vehicle control. However, peptides containing at least one Arg that were polymerized with a DP (or "m" in FIG. 1A) of approximately 60, penetrated cells as efficiently as a canonical CPP (Tat). Images from live-cell confocal microscopy supported this data, in which fluorscence signatures are observed across consecutive 1 µM Z-slices for only polymers containing cationic residues, indicating that these materials are internalized and not simply bound to the surface of the cell membrane. Live-cell confocal microscopy images were obtained showing the average intensities from six consecutive 1 um slices of HeLa cells treated with peptides and polymers (m ~60). In each study, the concentration of materials is 2.5 µM with respect to the fluorophore. A graph showing flow cytometry data for the vehicle control (DPBS) was obtained. Healthy populations (10,000 events each) were gated identically and referenced to vehicle (DPBS). Each measurement was repeated 3× on three separate cultures. The concentration for each material is 2.5 µM, where concentration is with respect to the fluorophore. A graph showing flow cytometry data for the GSGSGRR (SEQ ID NO:15) polymer (m~8) was obtained. Healthy populations (10,000 events each) were gated identically and referenced to vehicle (DPBS). Each measurement was repeated 3× on three separate cultures. The concentration for each material is 2.5 µM, where concentration is with respect to the fluorophore. A graph showing flow cytometry data for the GSGSGRR (SEQ ID NO:15) polymer (m~15) was obtained. Healthy populations (10,000 events each) were gated identically and referenced to vehicle (DPBS). Each measurement was repeated 3× on three separate cultures. The concentration for each material is 2.5 µM, where concentration is with respect to the fluorophore. A graph showing flow cytometry data for the GSGSGRR (SEQ ID NO:15) polymer (m~30) was obtained. Healthy populations (10,000 events each) were gated identically and referenced to vehicle (DPBS). Each measurement was repeated 3× on three separate cultures. The concentration for each material is 2.5 µM, where concentration is with respect to the fluorophore. A graph showing flow cytometry data for the GSGSGRR (SEQ ID NO:15) polymer (m~60) was obtained. Healthy populations (10,000 events each) were gated identically and referenced to vehicle (DPBS). Each measurement was repeated 3× on three separate cultures. The concentration for each material is 2.5 µM, where concentration is with respect to the fluorophore. A graph showing flow cytometry data for the GSGSGRR (SEQ ID NO:15) polymer (m~8-60) was obtained.

TABLE 12

GSGSG-derived block copolymers and KLA homopolymers

| Polymer Name in Text[a] | Polymer IUPAC[b] | First Block (Peptide Block) | | | Second Block (OEG Block) | | |
|---|---|---|---|---|---|---|---|
| | | $M_n$[c] | $M_w/M_n$[d] | DP[e] ("m") | $M_n$[c] | $M_w/M_n$[d] | DP[e] |
| GSGSG, m ~8 | GSGSG$_{11}$-b-OEG$_{18}$ | 6,560 | 1.012 | 11 (8) | 12,800 | 1.12 | 18 (20) |
| GSGSG, m ~15 | GSGSG$_{16}$-b-OEG$_{21}$ | 9,800 | 1.108 | 16 (15) | 17,000 | 1.054 | 21 (20) |
| GSGSG, m ~30 | GSGSG$_{28}$-b-OEG$_{16}$ | 17,700 | 1.125 | 28 (30) | 23,500 | 1.075 | 16 (20) |
| GSGSG, m ~60 | GSGSG$_{56}$-b-OEG$_{28}$ | 35,000 | 1.274 | 56 (60) | 45,100 | 1.052 | 28 (20) |
| R control, m ~8 | R$_{12}$-b-OEG$_{15}$ | 7700 | 1.17 | 12 (8) | 13,000 | 1.101 | 15 (20) |
| R control, m ~15 | R$_{18}$-b-OEG$_{27}$ | 11,700 | 1.009 | 19 (15) | 21,500 | 1.061 | 27 (20) |
| R control, m ~30 | R$_{26}$-b-OEG$_{20}$ | 16,800 | 1.027 | 27 (30) | 23,700 | 1.048 | 20 (20) |
| R control, m ~60 | R$_{52}$-b-OEG$_{20}$ | 33,900 | 1.036 | 54 (60) | 40,800 | 1.046 | 20 (20) |
| RGSGSG, m ~8 | RGSGSG$_{10}$-b-OEG$_{21}$ | 11,600 | 1.005 | 10 (8) | 19,300 | 1.015 | 21 (20) |
| RGSGSG, m ~15 | RGSGSG$_{15}$-b-OEG$_{16}$ | 16,500 | 1.09 | 15 (15) | 22,230 | 1.06 | 16 (20) |
| RGSGSG, m ~30 | RGSGSG$_{29}$-b-OEG$_{27}$ | 33,100 | 1.007 | 29 (30) | 42,800 | 1.014 | 27 (20) |
| RGSGSG, m ~60 | RGSGSG$_{68}$-b-OEG$_{26}$ | 78,000 | 1.143 | 68 (60) | 90,300 | 1.142 | 26 (20) |
| GSGSGR, m ~8 | GSGSGR$_{11}$-b-OEG$_{22}$ | 12,130 | 1.08 | 11 (8) | 20,000 | 1.034 | 22 (20) |
| GSGSGR, m ~15 | GSGSGR$_{18}$-b-OEG$_{18}$ | 20,000 | 1.034 | 18 (15) | 26,300 | 1.085 | 18 (20) |
| GSGSGR, m ~30 | GSGSGR$_{26}$-b-OEG$_{14}$ | 30,100 | 1.053 | 26 (30) | 35,000 | 1.025 | 14 (20) |
| GSGSGR, m ~60 | GSGSGR$_{71}$-b-OEG$_{26}$ | 81,100 | 1.151 | 71 (60) | 90,300 | 1.142 | 26 (20) |
| RRGSGSG, m ~8 | RRGSGSG$_9$-b-OEG$_{16}$ | 14,500 | 1.018 | 9 (8) | 20,000 | 1.018 | 16 (20) |
| RRGSGSG, m ~15 | RRGSGSG$_{15}$-b-OEG$_{28}$ | 23,800 | 1.018 | 15 (15) | 33,700 | 1.019 | 28 (20) |
| RRGSGSG, m ~30 | RRGSGSG$_{31}$-b-OEG$_{14}$ | 48,500 | 1.006 | 31 (30) | 53,400 | 1.007 | 14 (20) |
| RRGSGSG, m ~60 | RRGSGSG$_{52}$-b-OEG$_{29}$ | 80,700 | 1.001 | 52 (60) | 90,800 | 1.003 | 29 (20) |
| GSGSGRR, m ~8 | GSGSGRR$_8$-b-OEG$_{19}$ | 12,500 | 1.052 | 8 (8) | 19,200 | 1.014 | 19 (20) |
| GSGSGRR, m ~15 | GSGSGRR$_{18}$-b-OEG$_{23}$ | 28,500 | 1.056 | 18 (15) | 36700 | 1.078 | 23 (20) |
| GSGSGRR, m ~30 | GSGSGRR$_{30}$-b-OEG$_{19}$ | 47,000 | 1.27 | 30 (30) | 48,200 | 1.041 | 19 (20) |
| GSGSGRR, m ~60 | GSGSGRR$_{57}$-b-OEG$_{13}$ | 89,000 | 1.103 | 57 (60) | 93,600 | 1.053 | 13 (20) |
| GSGSGK, m ~8 | GSGSGK$_{10}$-b-OEG$_{23}$ | 9,650 | 1.047 | 10 (8) | 17,900 | 1.044 | 23 (20) |
| GSGSGK, m ~15 | GSGSGK$_{13}$-b-OEG$_{16}$ | 12,100 | 1.022 | 13 (15) | 17,800 | 1.16 | 16 (20) |
| GSGSGK, m ~30 | GSGSGK$_{26}$-b-OEG$_{17}$ | 24,800 | 1.056 | 26 (30) | 30,700 | 1.042 | 17 (20) |
| GSGSGK, m ~60 | GSGSGK$_{53}$-b-OEG$_{20}$ | 50,800 | 1.114 | 53 (60) | 57,900 | 1.165 | 20 (20) |
| GSGSGKK, m ~8 | GSGSGKK$_8$-b-OEG$_{22}$ | 7,170 | n.d. | 8 (8) | 14,900 | n.d. | 22 (20) |
| GSGSGKK, m ~15 | GSGSGKK$_{16}$-b-OEG$_{17}$ | 13,700 | n.d. | 16 (15) | 19,800 | n.d. | 17 (20) |
| GSGSGKK, m ~30 | GSGSGKK$_{33}$-b-OEG$_{19}$ | 29,000 | n.d. | 33 (30) | 35,600 | n.d. | 19 (20) |
| GSGSGKK, m ~60 | GSGSGKK$_{61}$-b-OEG$_{30}$ | 54,000 | n.d. | 61 (60) | 64,500 | n.d. | 30 (20) |
| KLA full length, m ~5 | KLA$_6$ | 10,300 | n.d. | 6 (5) | — | — | — |
| KLA full length, m ~10 | KLA$_{11}$ | 20,200 | n.d. | 11 (10) | — | — | — |

TABLE 12-continued

GSGSG-derived block copolymers and KLA homopolymers

| Polymer Name in Text[a] | Polymer IUPAC[b] | First Block (Peptide Block) | | | Second Block (OEG Block) | | |
|---|---|---|---|---|---|---|---|
| | | $M_n{}^c$ | $M_w/M_n{}^d$ | DP[e] ("m") | $M_n{}^c$ | $M_w/M_n{}^d$ | DP[e] |
| KLA full length, m ~15 | KLA$_{14}$ | 25,000 | n.d. | 14 (15) | — | — | — |
| KLA fragment, m ~10 | KLA(fragment)$_{11}$ | 11,200 | n.d. | 11 (10) | | | |

GSGSG-derived block copolymers and KLA homopolymers.
[a]The name of the polymer as referred to in the text. Note that the approximate degree of polymerization (DP) is given to best compare similarly sized polymers. Also note that the OEG coblock is omitted from the name.
[b]The IUPAC name of the polymer with the actual DPs of blocks in the block copolymer. All polymers are end-labeled with a copy of fluorescein.
[c]Number average molecular weight, except for GSGSGKK (SEQ ID NO: 17) and KLA polymers, which are weight average molecular weight ($M_w$)
[d]Dispersity of each block.
[e]Experimentally determined DPs with the theoretical DPs, based on the initial monomer-to-initiator ratio, given in parentheses. These values were obtained by SEC-MALS except for those describing the GSGSGKK (SEQ ID NO: 17) and KLA polymers, which did not elute on the SEC column. All values for these polymers were determined by batch-mode static light scattering without the SEC component. As such, no information on the dispersity of these polymers was obtained. The SEC-MALS chromatogram for all m~60 GSGSG (SEQ ID NO: 1) derivatives that do elute on the SEC column were obtained. All peptide values are calculated with a dn/dc of 0.179. The OEG block has a dn/dc of 0.11 and so a ratio (based on the initial monomer-to-OEG ratio) was used to calculate values for this block: the dn/dc from m ~8, 15, 30 and 60 were 0.131, 0.141, 0.151 and 0.161, respectively.

GSGSG-derived block copolymers and KLA homopolymers. [a]The name of the polymer as referred to in the text. Note that the approximate degree of polymerization (DP) is given to best compare similarly sized polymers. Also note that the OEG coblock is omitted from the name. [b]The IUPAC name of the polymer with the actual DPs of blocks in the block copolymer. All polymers are end-labeled with a copy of fluorescein. [c]Number average molecular weight, except for GSGSGKK (SEQ ID NO:17) and KLA polymers, which are weight average molecular weight ($M_w$) [d]Dispersity of each block. [e]Experimentally determined DPs with the theoretical DPs, based on the initial monomer-to-initiator ratio, given in parentheses. These values were obtained by SEC-MALS except for those describing the GSGSGKK (SEQ ID NO:17) and KLA polymers, which did not elute on the SEC column. All values for these polymers were determined by batch-mode static light scattering without the SEC component. As such, no information on the dispersity of these polymers was obtained. The SEC-MALS chromatogram for all m~60 GSGSG (SEQ ID NO:1) derivatives that do elute on the SEC column were obtained. All peptide values are calculated with a dn/dc of 0.179. The OEG block has a dn/dc of 0.11 and so a ratio (based on the initial monomer-to-OEG ratio) was used to calculate values for this block: the dn/dc from m~8, 15, 30 and 60 were 0.131, 0.141, 0.151 and 0.161, respectively.

Figure 25:
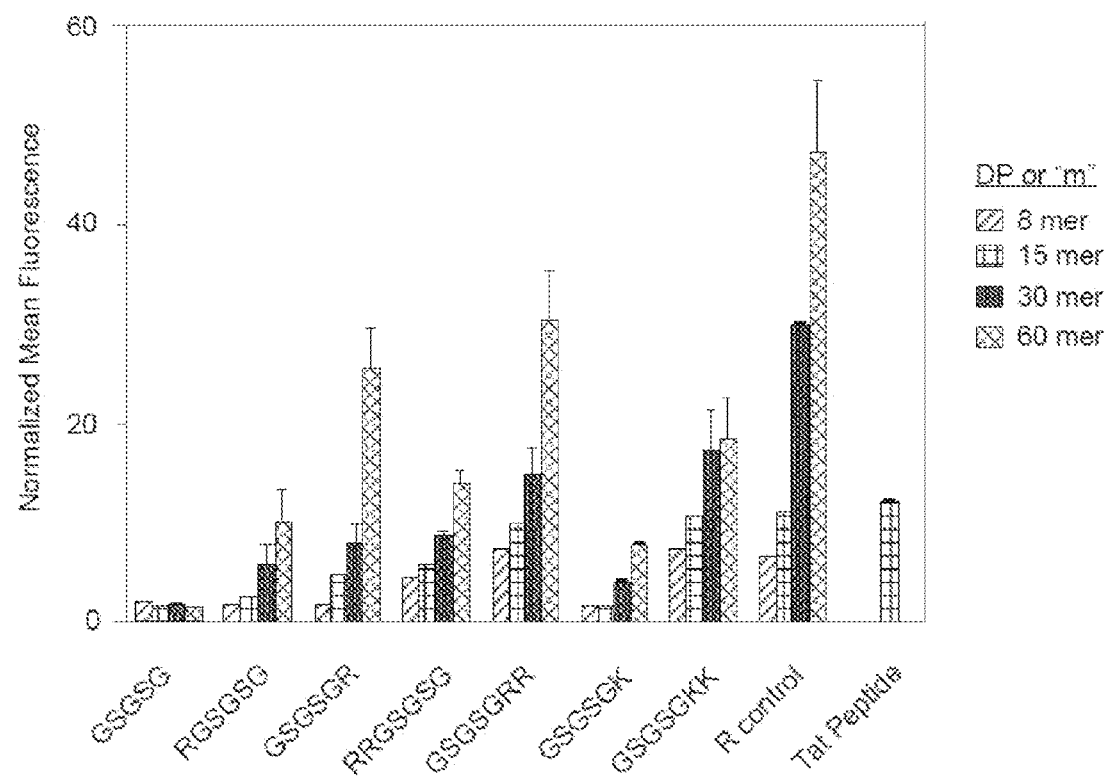
FIG. 25 is a histogram bar graph showing the influence of the degree of polymerization or "m" on cellular uptake as quantified by flow cytometry. All data are referenced to vehicle (DPBS), which gives a value of 1. The concentration for each material is 2.5 μM, where concentration is with respect to the fluorophore. For each histogram bin (left to right); 8-mer, 14-mer, 30-mer and 60-mer.
Figure 26:
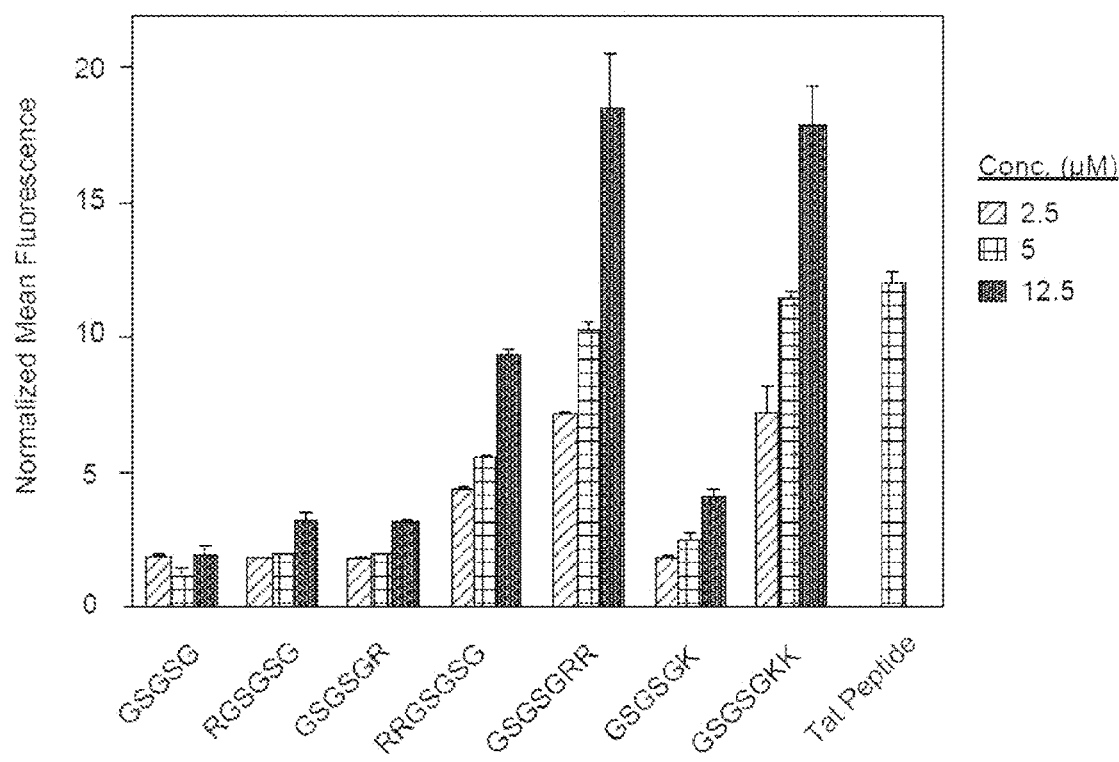
FIG. 26 is a histogram bar graph showing the concentration dependence of cellular uptake as quantified by flow cytometry. All data are referenced to vehicle (DPBS), which gives a value of 1. Concentration of all materials is with respect to the fluorophore. For each histogram bin (left to right): 2.5 μM, 5 μM, 12.5 μM.
Figure 27:
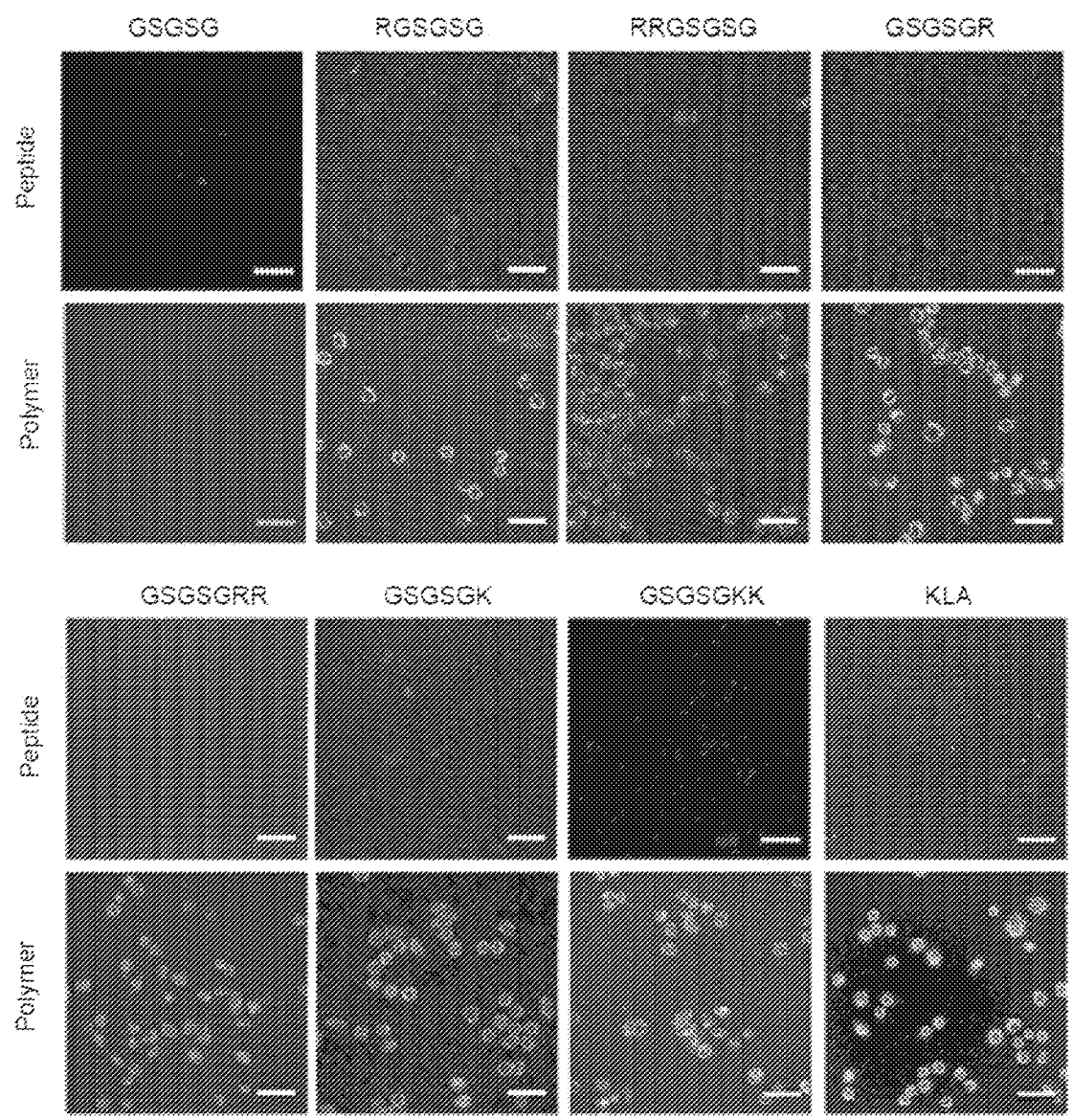
FIG. 27 are live cell confocal microscopy images of peptides and polymers. All images are the average intensity from six consecutive 1 μm Z-slices using a 40× objective. Cells were treated with 2.5 μM of the material (with respect to fluorophore). All GSGSG (SEQ ID NO:1) polymers and analogues have a peptide m of ~60 and the KLA polymer is m~10. Scale bars are 50 μm. Each polymer that contains Lys or Arg shows a mixture of diffuse and punctate fluorescence, indicating that the material resides in the cytosol and in cellular compartments, respectively.
Figure 28:
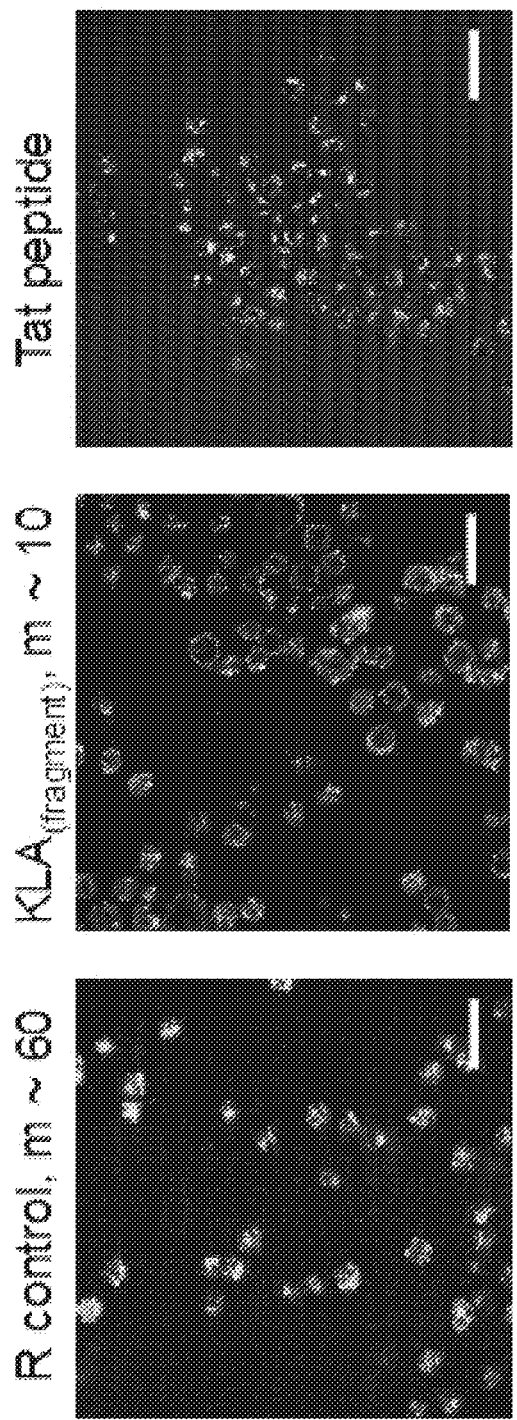
FIG. 28 are live-cell confocal microscopy images of R control (DP or m of ~60), KLAfragment (m~10) and Tat peptide. All images are the average intensity from six consecutive 1 μm Z-slices using a 40× objective. Scale bars are 50 μm. Each image shows a mixture of diffuse and punctate fluorescence, indicating that the material resides in the cytosol and in cellular compartments, respectively.
Figure 29:
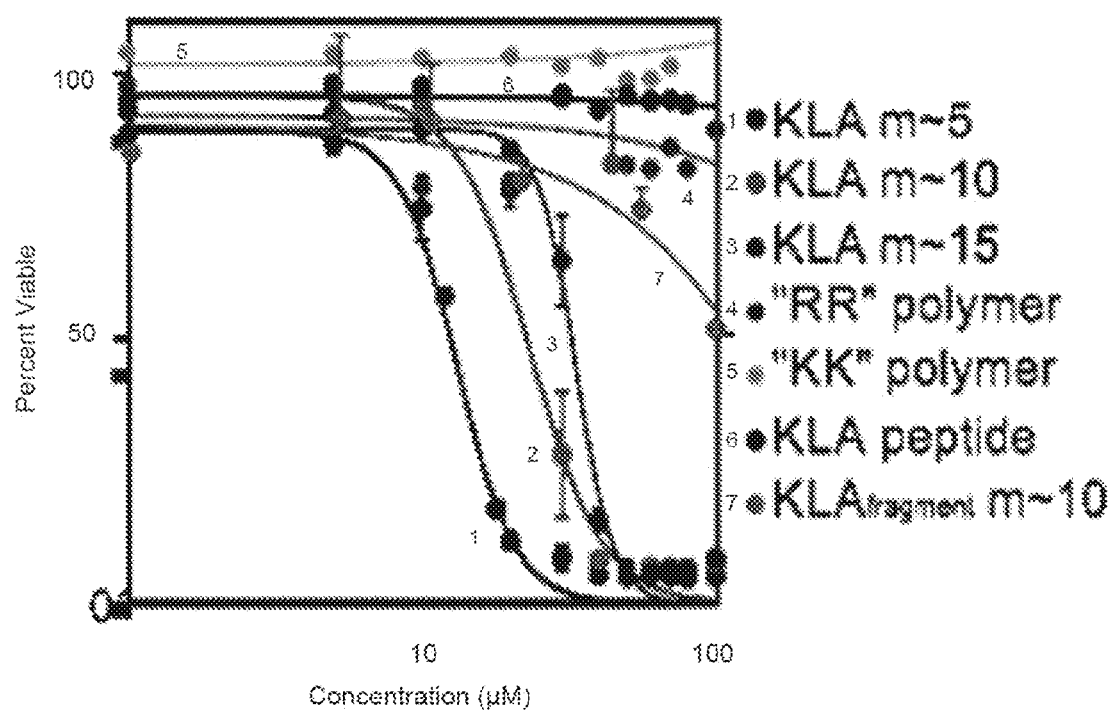
FIG. 29 is a graph showing a comparison of cytotoxicity curves for KLA materials and controls. This figure is identical to that of FIG. 20C, except it also contains the dose-response curves for the KLA (full length) polymers at m~10 and 15.
Figure 30A:
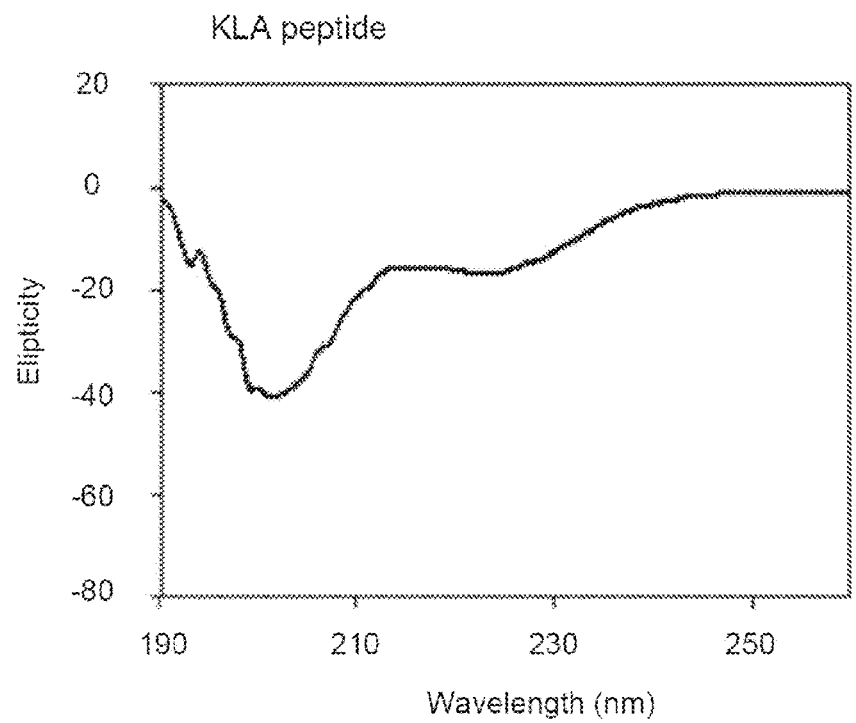
FIG. 30A is a spectra showing UV-Vis circular dichroism of the KLA peptide. Since spectra for the full length and polymer are nearly identical, polymerization of the KLA sequence does not perturb the secondary structure of the peptide.
Figure 30B:
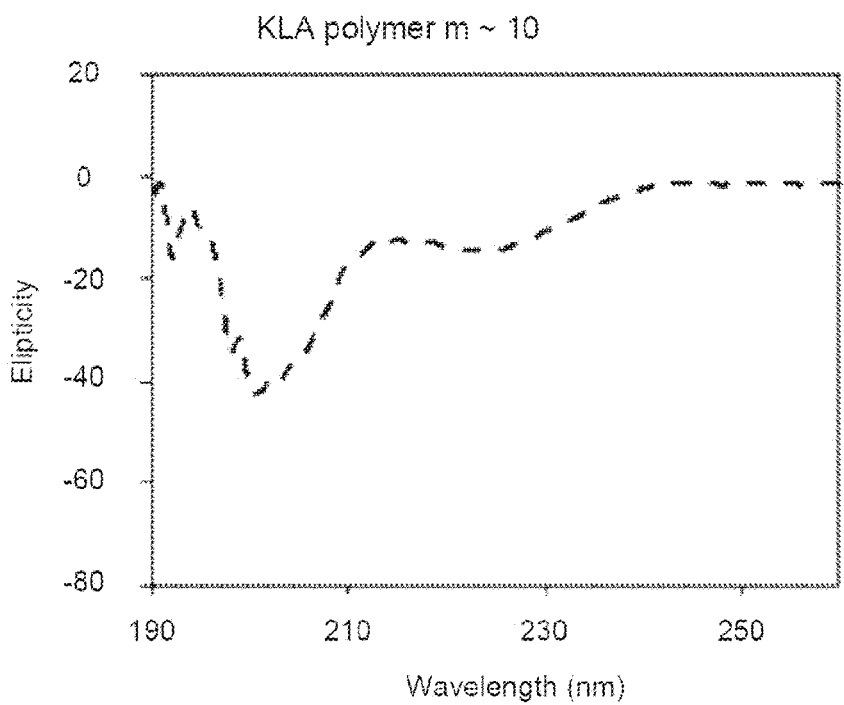
FIG. 30B is a spectra showing UV-Vis circular dichroism of the KLA homopolymer polymer (m~10).
Figure 30C:
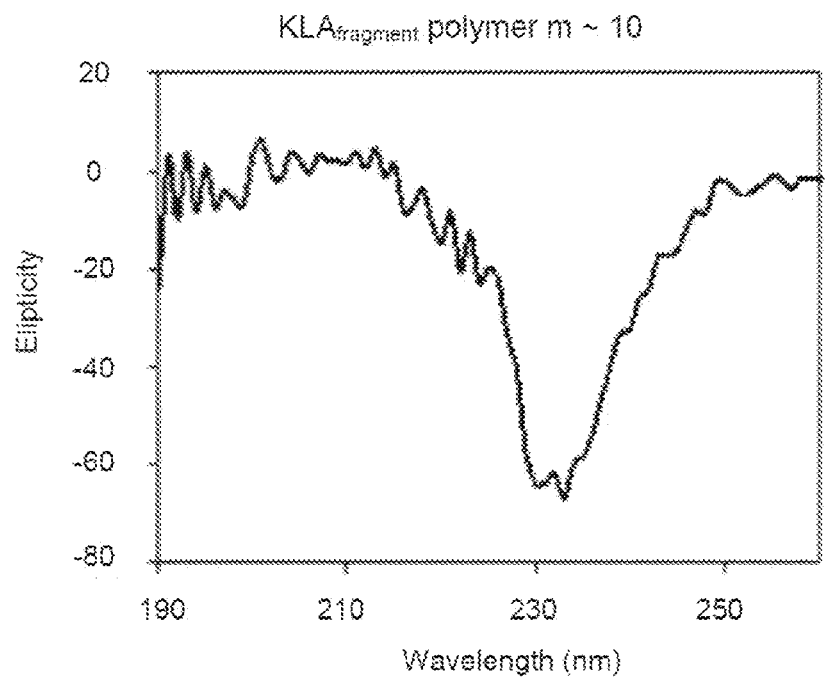
FIG. 30C is a spectra showing UV-Vis circular dichroism of the KLA fragment polymer with m~10. The spectra are different from the full length constructs, indicating that the secondary structure for this material is unique.
Figure 30D:
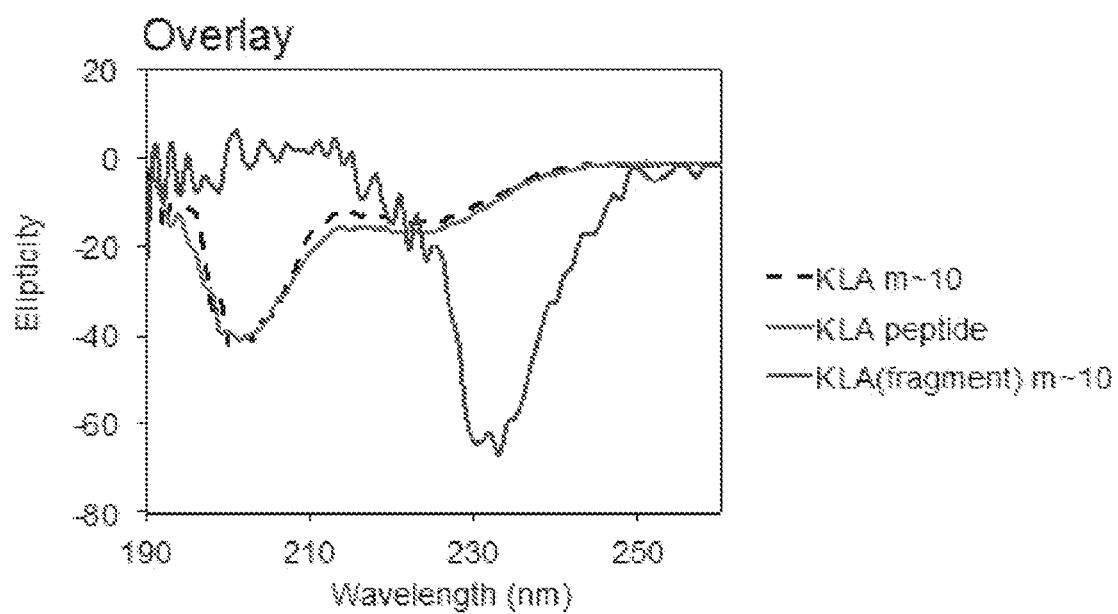
FIG. 30D is a spectra of an overlay of FIGS. 30A (KLA peptide), 30B (KLA homopolymer m~10) and 30C (KLA fragment polymer m~10).
Figure 31A:
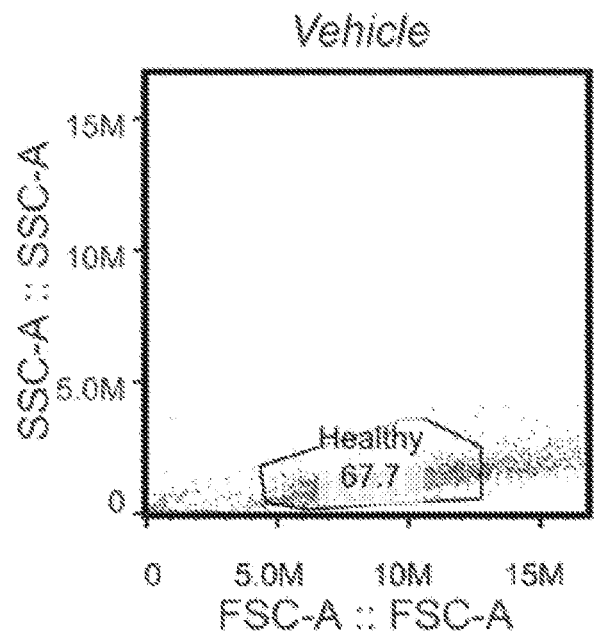
FIG. 31A is a graph showing flow cytometry data for the vehicle control (DPBS) in a JC-1 (mitochondrial dye) assay for mitochondrial integrity. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.
Figure 31B:
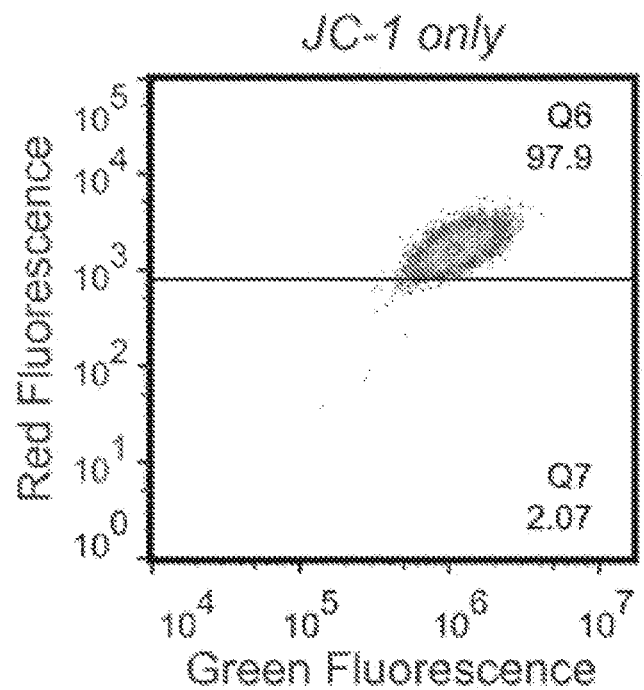
FIG. 31B is a graph showing flow cytometry data for JC-1 only. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.
Figure 31C:
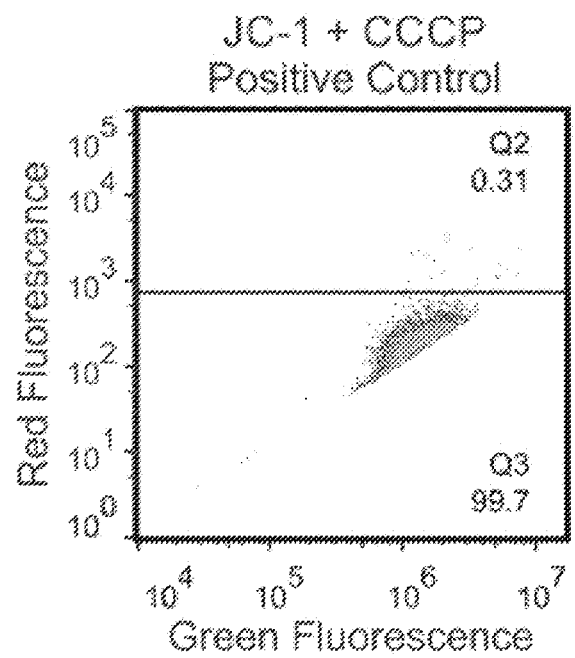
FIG. 31C is a graph showing flow cytometry data for the JC-1+CCCP (Carbonyl cyanide m-chlorophenyl hydrazone) in a JC-1 (mitochondrial dye) assay for mitochondrial integrity. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.
Figure 31D:
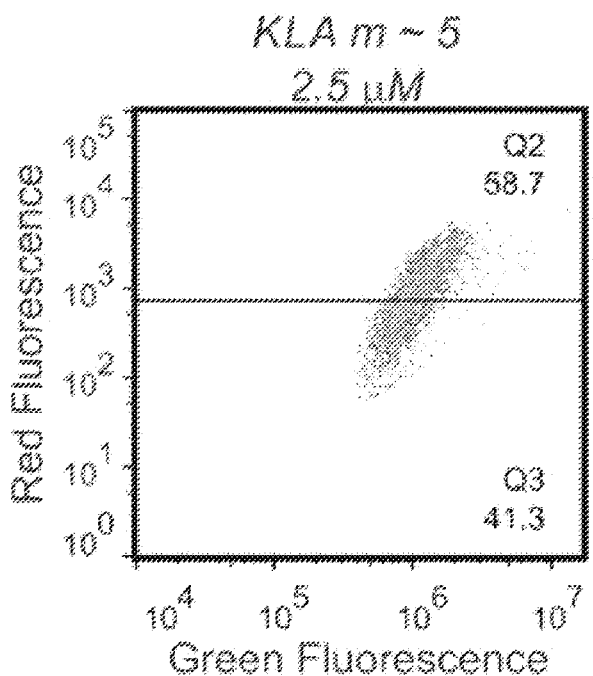
FIG. 31D is a graph showing flow cytometry data for KLA (m~5) in a JC-1 (mitochondrial dye) assay for mitochondrial integrity. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.
Figure 31E:
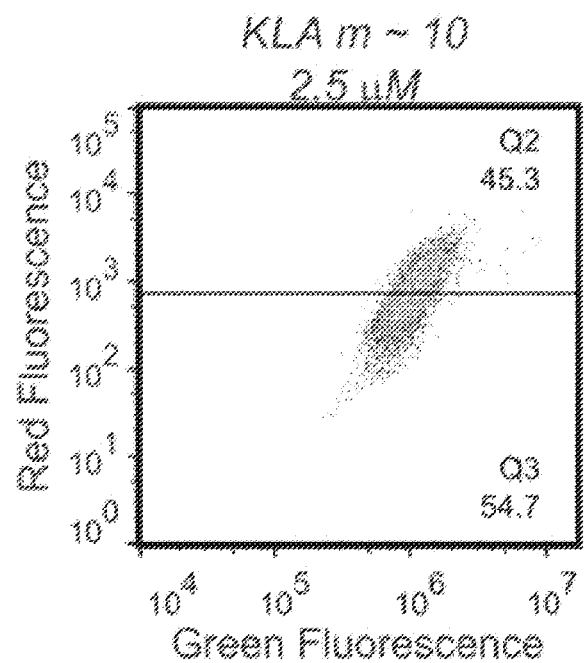
FIG. 31E is a graph showing flow cytometry data for KLA (m~10) in a JC-1 (mitochondrial dye) assay for mitochondrial integrity. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.
Figure 31F:
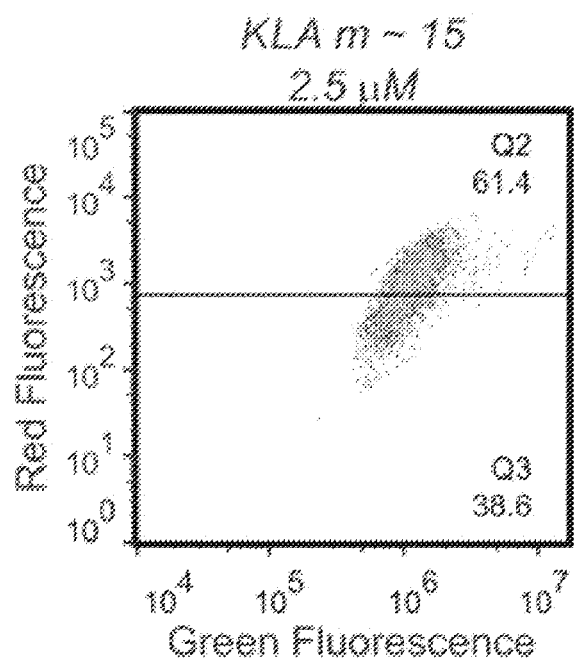
FIG. 31F is a graph showing flow cytometry data for KLA (m~15) in a JC-1 (mitochondrial dye) assay for mitochondrial integrity. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.
Figure 31G:
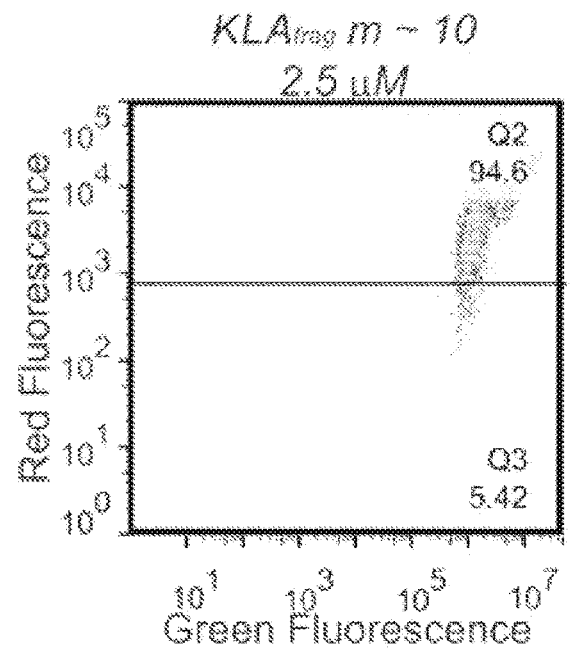
FIG. 31G is a graph showing flow cytometry data for KLA fragment (m~10) in a JC-1 (mitochondrial dye) assay for mitochondrial integrity. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.
Figure 31H:
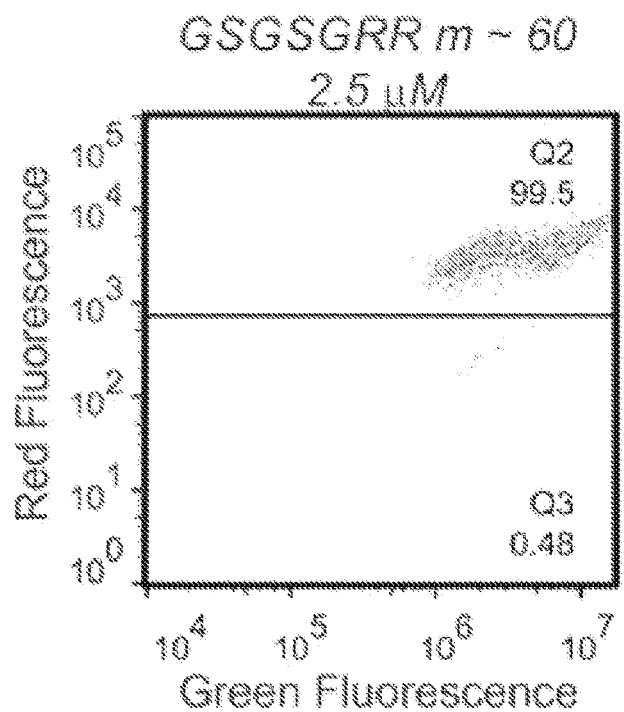
FIG. 31H is a graph showing flow cytometry data for GSGSGRR (SEQ ID NO:15) (m~60) in a JC-1 (mitochondrial dye) assay for mitochondrial integrity. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.
Figure 31I:
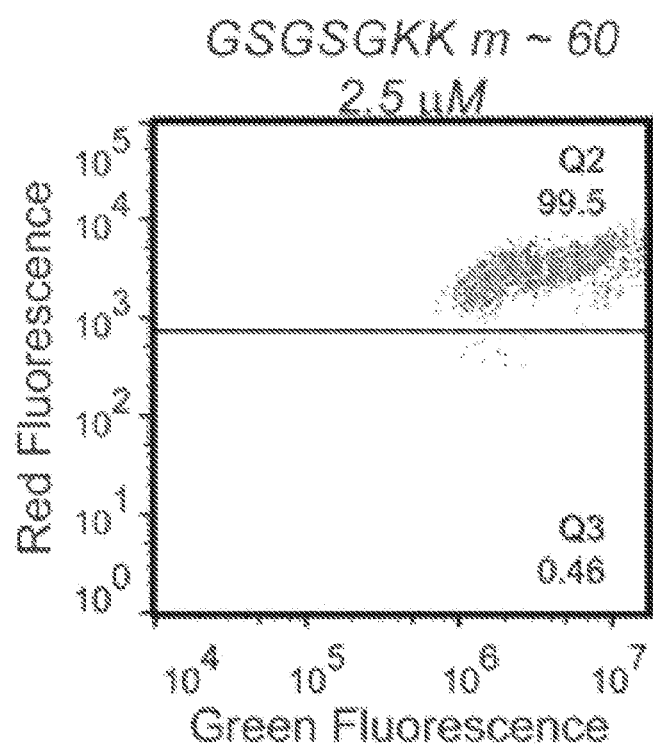
FIG. 31I is a graph showing flow cytometry data for GSGSGKK (SEQ ID NO:17) (m~60) in a JC-1 (mitochondrial dye) assay for mitochondrial integrity. The quadrants were chosen based on where cells treated with CCCP (Q3) and cells that were untreated reside (Q2), with the line drawn between these two regions. Q2 is the percent of cells with healthy mitochondria, and Q3 is the percent of cells with the unhealthy mitochondria.

In general, these data indicated that Arg residues appended to the C-terminus (GSGSGR, SEQ ID NO:14 or GSGSGRR, SEQ ID NO:15) exhibited better intracellular penetration than the internally buried N-terminal derivatives (RGSGSG, SEQ ID NO:12; RRGSGSG, SEQ ID NO:13) (FIG. 19B). Peptides containing two Arg residues showed more robust fluorescent signals when polymerized than those containing only one in the same position. Interestingly, in all cases, the Arg-containing peptide polymers gave slightly lower values than that of a polymer prepared by polymerizing a single Arg reside (R control polymer), which is the maximum theoretical signal that can result from a polymer containing one Arg per polymer side chain. In addition, peptides containing one or two lysine residues were taken up by cells when prepared as polymers (but not as peptides alone), indicating that the presence of primary amino or guandinium units was sufficient for uptake. Moreover, the extent of uptake of each polymer was shown to be dependent upon both the degree of polymerization (FIG. 25) and the concentration of material (FIG. 26), suggesting that uptake of these peptides can be improved by increasing either factor.

Many bioactive peptides already contain one or more cationic amino acids in their sequence. Therefore, it was demonstrated whether one such peptide could penetrate cells upon polymerization without the appendage of additional Arg or Lys residues. Moreover, it was determined if the peptide maintaine its intended biological function when incorporated into a polymer in this manner (FIGS. 20A-20D). For this purpose, a known therapeutic peptide, KLA was chosen (sequence: KLAKLAKKLAKLAK, SEQ ID NO:18), that does not penetrate cells at sub-millimolar concentrations despite having multiple Lys residues in its parent sequence. KLA was shown to function by lysing cellular mitochondria, resulting in apoptosis of the cell. However, because KLA does not inherently penetrate cells, to function it must be conjugated to a CPP, prepared as a multimer, or appended to a molecular transporter.

Cell Penetration of KLA

Figure 20A:
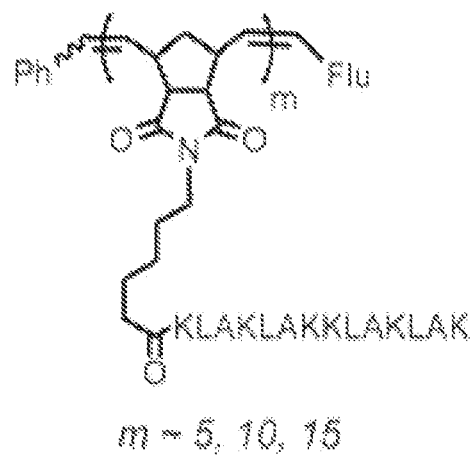
FIG. 20A is a chemical structure showing the homopolymers. "Flu" is the fluorescein-end label. Sequence legend: KLAKLAKKLAKLAK (SEQ ID NO:18).

To ascertain whether KLA could penetrate cells as a polymer brush, the peptide was polymerized to varying DPs (DP or "m" in FIG. 20A are approx. 5, 10 and 15). At each DP, the polymers gave strong fluorescence signals by flow cytometry, similar to the Tat peptide control (FIG. 20B), whereas the KLA peptide yielded fluorescence signals indistinguishable from that of the vehicle control. Live-cell confocal microscopy verified internalization of the homopolymers at each Z-slice depth. Live-cell confocal microscopy images were obtained showing average intensities from six consecutive 1 m slices of HeLa cells treated with the KLA peptide or polymer (m~10).

Biological Function of the KLA Peptide

Figure 20B:
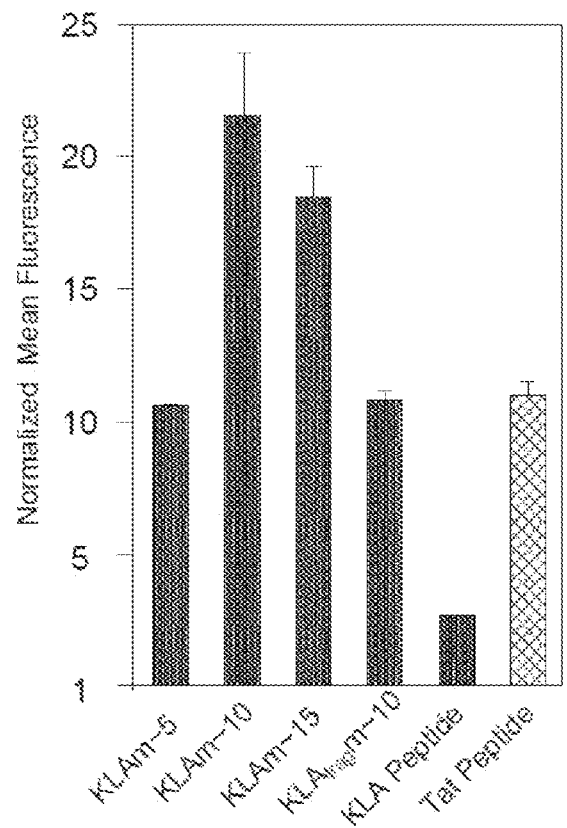
FIG. 20B is a bar graph showing flow cytometry data showing fluorescent signatures of HeLa cells treated with the KLA polymers and peptide. Data is normalized to DPBS at a value of 1.
Figure 20C:
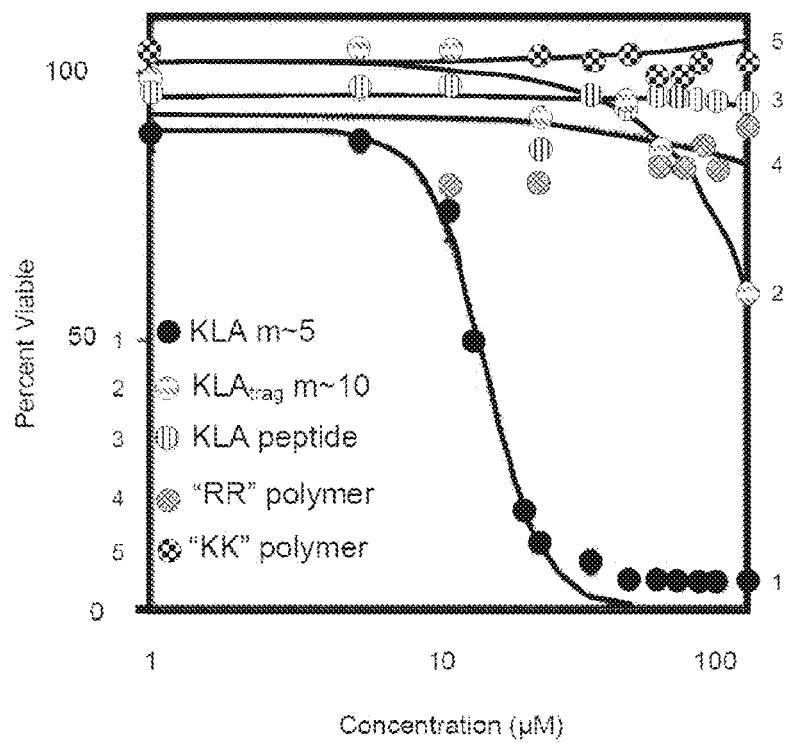
FIG. 20C is a graph showing Viability of cells treated with KLA polymers (m~5), GSGSGRR (SEQ ID NO:15) (m~60) polymer, GSGSGKK (SEQ ID NO:17) (m~60) polymer and the KLA peptide. LD$_{50}$ values for the KLA polymers, obtained by fitting data to the Hill equation, are 12.5, 25, and 30 μM for the m~5, 10 and 15 polymers, respectively. Note that the dose-response curves for the m~10 and 15 KLA polymers are provided in FIG. 29.
Figure 20D:
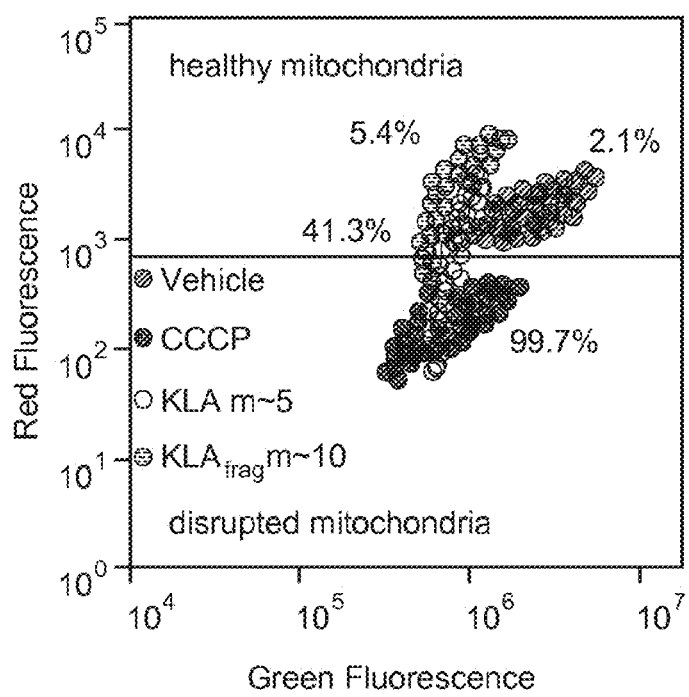
FIG. 20D is a graph showing mitochondrial membrane potential disruption assays. The percentages given describe the percent of signal for each material in the disrupted mitochondria region.

The reported biological function of the KLA peptide was determined, namely cytotoxicity by way of mitochondrial disruption, was not affected by polymerization. Validating this notion, KLA polymers demonstrated dose-dependent cytotoxicity in HeLa cells (where concentration for all cytotoxicity studies is with respect to peptide) with $LD_{50}$ values in the range of what is seen for KLA-CPP conjugates (FIG. 20C). Furthermore, no cytotoxicity was detected for the unmodified KLA peptide, presumably due to its inability to penetrate cells (FIGS. 19A-19B).

Cell Toxicity by Polymers not Caused by Polymer Scaffold

Figure 32:
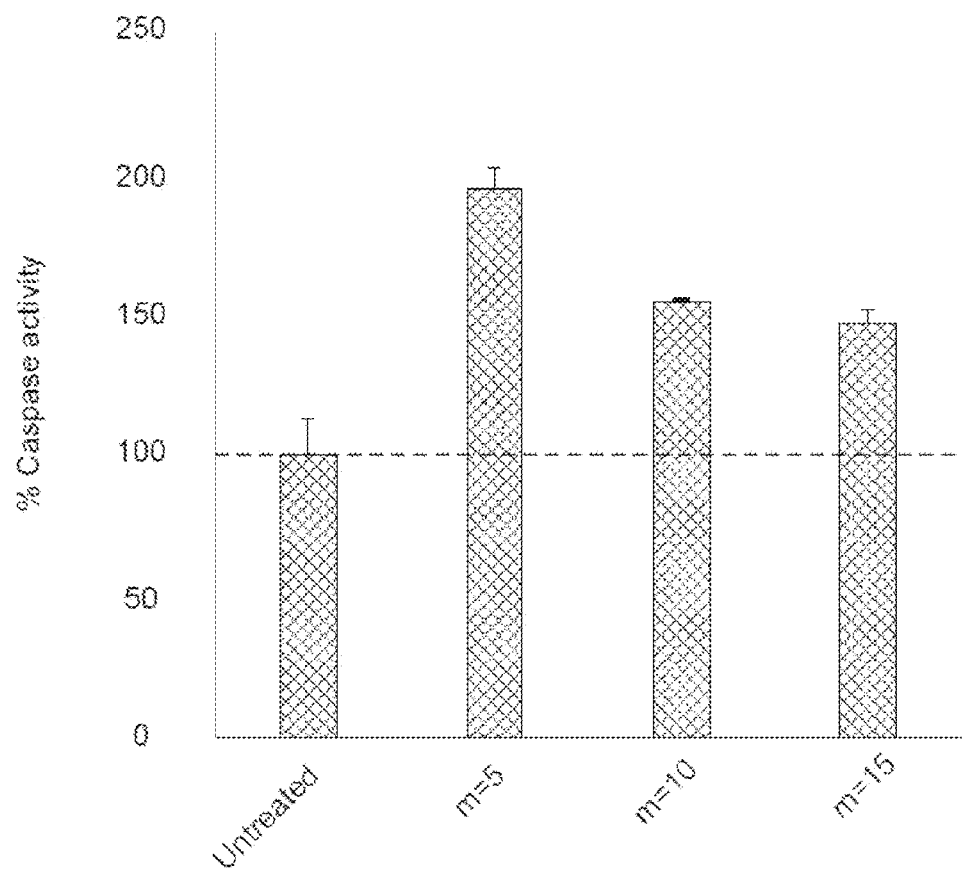
FIG. 32 is a bar graph showing the levels of Caspase 3/7 in untreated cells and cells treated with KLA polymers at varying DP. The baseline level of expression is taken as 100% in the untreated cells. Those treated with polymers show an increase in expression, which is indicative of apoptosis. Each measurement was performed 3-fold on at least two separate subcultures.

To confirm that the cell toxicity exhibited by the polymers was not caused by the polymer scaffold or by internalization of any cationic peptide polymer, performed the same assays with the GSGSG (SEQ ID NO:1), GSGSGKK (SEQ ID NO:17) and GSGSGRR (SEQ ID NO:15) polymers (each at m~60) were performed. No cytotoxicity was exhibited by any of these materials at concentrations up to 1 mM. In addition, polymers composed of an analogue of the KLA sequence (KLA$_{fragment}$) with fewer Lys-Leu-Ala repeats (i.e., KLAKLAK (SEQ ID NO:24), m~10), in which the total number of amino acids is identical to that of the full length KLA polymer at m~5, exhibited negligible toxicity, despite having the ability to enter cells (FIG. 20B). This is likely because the secondary structure of this peptide polymer, which is important for the toxicity of KLA, differed dramatically from that of the KLA peptide and its direct polymer analogue. Importantly, these data clearly indicate that the full-length KLA sequence was necessary for toxicity and not simply a high density display of sequences with multiple lysines. Complimentary experiments confirmed that the cytotoxicity of the KLA polymers was the result of a disruption of mitochondrial membrane potentials (FIG. 20D and FIGS. 31A-31I) leading to mitochondrial dependent apoptosis of HeLa cells (FIG. 32), much like their KLA-CPP or multimeric KLA analogues, further verifying that the key function of the peptide is not perturbed by polymerization.

Route of Cellular Entry

The route of cellular entry was determined by employing thermal and pharmacological inhibitors of known uptake pathways. In all cases, the uptake of the materials was similarly affected by the inhibitors tested. These data, especially the results from dynasore, an inhibitor of the key endocytosis player dynamin, indicate that polymers enter cells by endocytosis in a manner similar to the Tat peptide.

Resistance to Proteolytic Degradation of Peptides

Figure 6B:
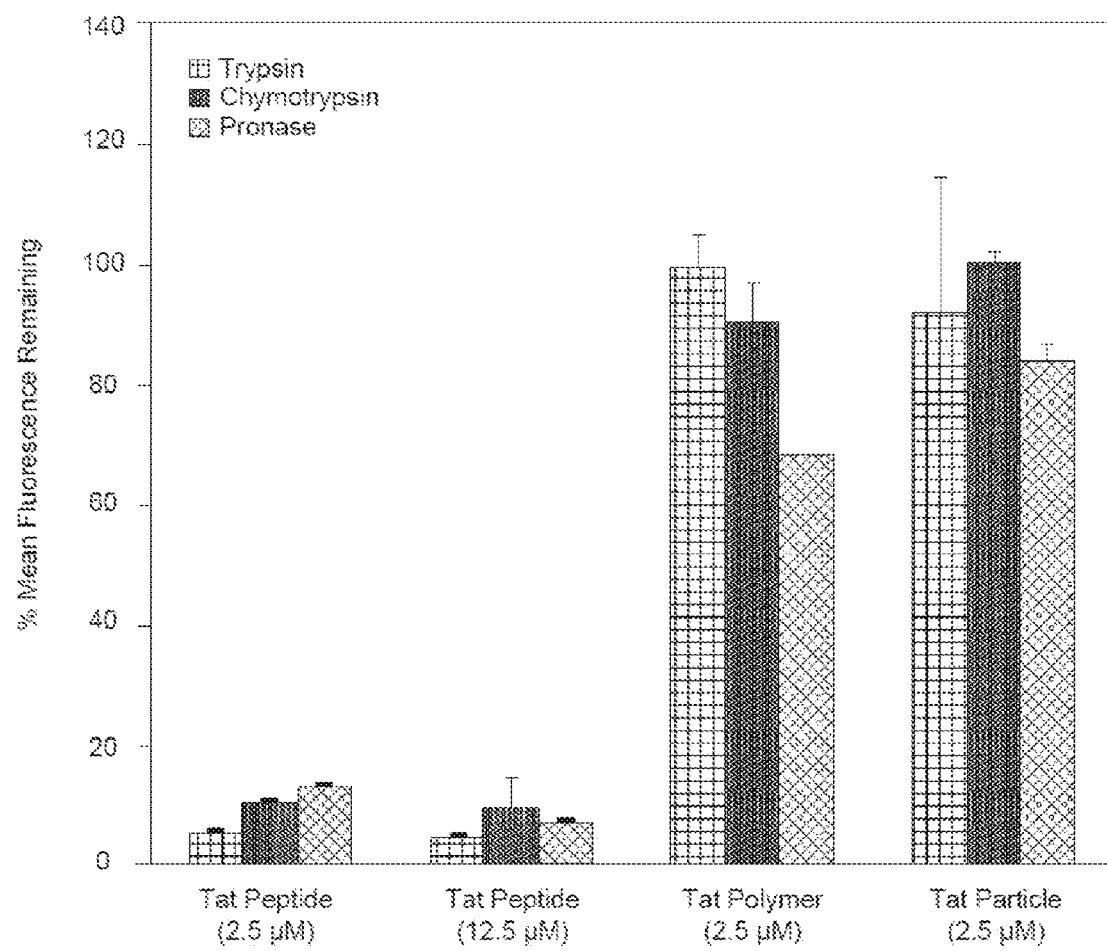
FIG. 6B is a histogram bar graph showing flow cytometry data of the materials after proteolytic digestion. Data is reported as the percentage of fluorescence seen after enzyme treatment relative to the value seen without treatment. For each bin of the histogram, concentrations (µM) were (left to right): 12.5, 2.5, 1.25, 0.5, and 0.25.
Figure 6C:
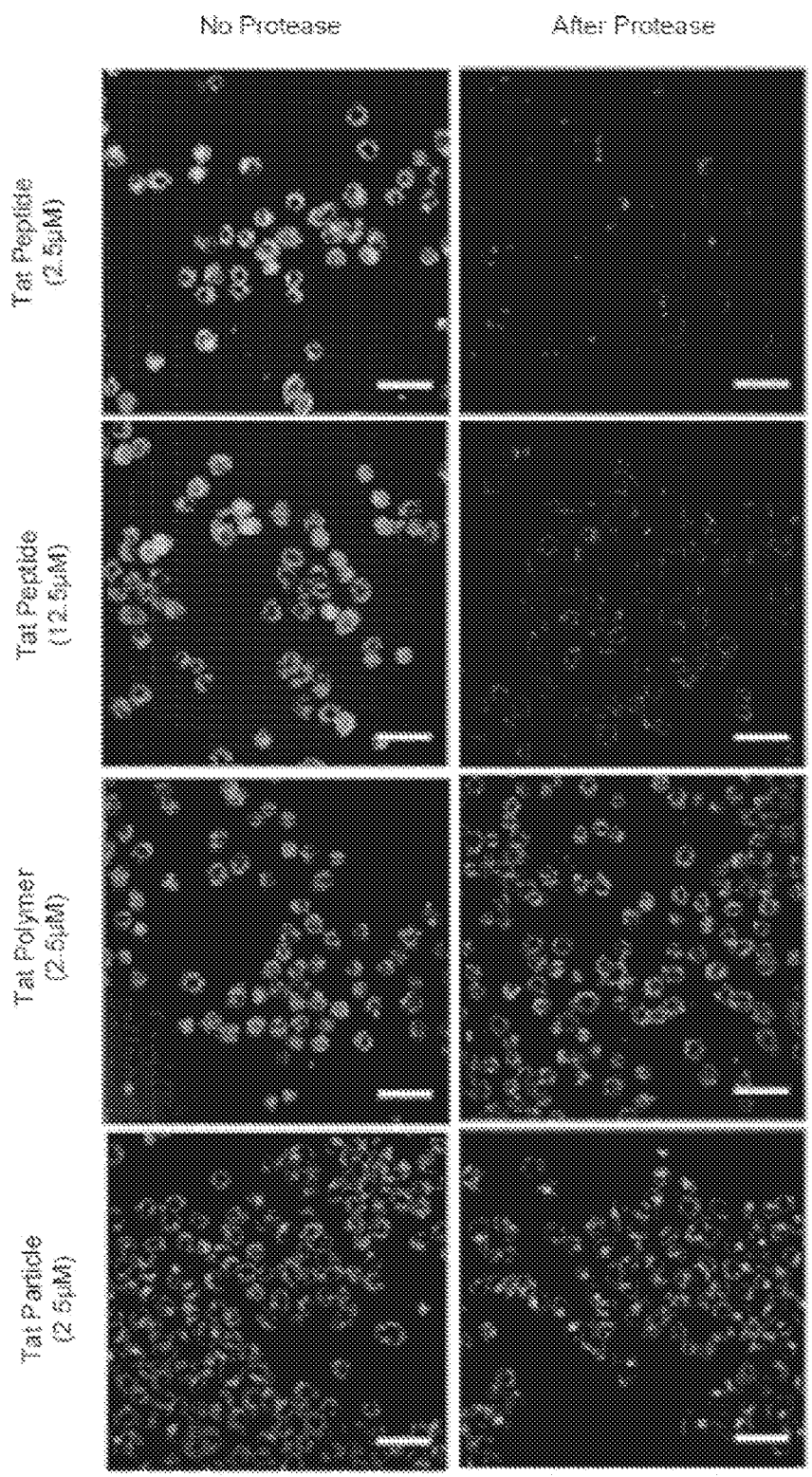
FIG. 6C depict confocal microscopy images comparing cells incubated with materials that have been pretreated with chymotrypsin alongside cells incubated with materials that have not received this pretreatment. Images are the maximum average intensity from six consecutive 1 µm slices. Scale bars are 50 m. In all cases Tat-containing materials at the indicated concentrations were treated with 1 µM of protease for 20 min at 37° C. Left column: no protease; right column: after protease.

Resistance of peptides to proteolytic degradation was confirmed. Analysis of reverse-phase HPLC (RP-HPLC) chromatograms before and after proteolytic digestion indicated that while the peptide controls were completely degraded into fragments, the peptide polymers showed little or no indication of proteolysis after incubation with multiple proteases (FIGS. 6A-6B).

In summary, a new method for rendering peptides cell penetrating by incorporating them into high density polymer brushes via graft-through ROMP was demonstrated. The only requirement for successful penetration is the presence of a single Arg or Lys in the peptide sequence, preferably at the solvent-facing C-terminal end of the peptide. A known therapeutic peptide is the KLA peptide, which cannot enter cells on its own, was shown to be cell penetrating by polymerization and, importantly, maintained its sequence-specific cytotoxic function as part of a polymer. This strategy offers the potential for the formulation of a therapeutic with an exceptionally high weight percentage of the active peptide (85% in the KLA homopolymer vs 50% for a Tat-KLA conjugate) that is also resistant to proteolysis. Thus, a simple, effective and broadly applicable alternative to existing strategies that enable cell penetration of peptides intended for medicinal or diagnostic purposes is described in this disclosure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A copolymer having the formula:

$$R^1\text{-}[M(O)]_n\text{-}[M(P)]_m\text{—}R^2$$

wherein, n and m are each an integer from 2 to 1000, provided that n is greater than m;

M is a polymerized ROMP polymerizable monomer;

O is independently a therapeutic polypeptide covalently attached to M through a covalent linker; wherein the therapeutic polypeptide is capable of treating a disease and is a cell growth or proliferation inhibitory peptide, an anti-inflammatory peptide, an anti-tumor or anti-cancer peptide, an anti-apoptotic peptide, anti-diabetic peptide, anti-obesity peptide, anti-infective peptide, anti-bacterial peptide, anti-viral peptide, a peptide for promoting cell growth and differentiation, a peptide for treating pain, a peptide for treating neural degeneration or peptides for promoting neurogenesis;

P is independently a non-polypeptide moiety; and $R^1$ and $R^2$ are independently terminal polymer moieties, wherein the polymerizable monomer is N-substituted-5-norbornene-2,3-dicarboximide, wherein the substitution comprises the therapeutic polypeptide, and wherein the therapeutic polypeptide comprises from 5 to 2000 amino acids.

2. The copolymer of claim 1, wherein the copolymer is a block copolymer.

3. The copolymer of claim 1, wherein the copolymer is a blend copolymer.

4. The copolymer of claim 1, wherein the therapeutic polypeptide comprises from 2 to 6 arginine residues.

5. The copolymer of claim 4, wherein the arginine residues are the carboxyl terminal residues of the therapeutic polypeptide.

6. The copolymer of claim 1, wherein $R^1$ comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

7. The copolymer of claim 1, wherein $R^2$ comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

8. The copolymer of claim 1, wherein said non-polypeptide moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl and wherein said non-polypeptide moiety does not comprise a nucleotide.

9. The copolymer of claim 1, wherein said non-polypeptide moiety is a hydrophobic moiety.

10. The copolymer of claim 1, wherein the therapeutic peptide is Nesiritide, Ceruletide, Bentiromide, Exenatide, Gonadorelin, Enfuvirtide, Vancomycin, Icatibant, Secretin, Leuprolide, Glucagon recombinant, Oxytocin, Bivalirudin, Sermorelin, Gramicidin D, Insulin recombinant, Capreomycin, Salmon Calcitonin, Vasopressin, Cosyntropin, Bacitracin, Octreotide, Abarelix, Vapreotide, Thymalfasin, Insulin recombinant, Mecasermin, Cetrorelix, Teriparatide, Corticotropin, or Pramlintide.

11. The copolymer of claim 1, wherein the therapeutic peptide is tirofiban, captopril, eptifibatide, ziconotide, teriparatide, liraglutide, lanreotide, pramlintide, enfuvirtide, icatibant, ecallantide, tesamorelin, degarelix, mifamurtide, nesiritide, buserelin, gonadorelin, goserelin, histrelin, leuprolide, nafarelin, triptorelin, abarelix, cetrorelix, or ganirelix.

12. The copolymer of claim 1, wherein the therapeutic polypeptide is an active therapeutic moiety when included in the copolymer.

13. The copolymer of claim 1, wherein the therapeutic polypeptide is an active therapeutic agent when released from the copolymer.

14. The copolymer of claim 1, the copolymer having the formula:

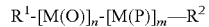

wherein, n and m are each an integer from 2 to 1000, provided that n is greater than m;

M is a polymerized ROMP polymerizable monomer;

O is independently a therapeutic polypeptide covalently attached to M through a covalent linker; wherein the therapeutic polypeptide is capable of treating a disease and is a cell growth or proliferation inhibitory peptide, an anti-inflammatory peptide, an anti-tumor or anti-cancer peptide, an anti-apoptotic peptide, anti-diabetic peptide, anti-obesity peptide, anti-infective peptide, anti-bacterial peptide, anti-viral peptide, a peptide for promoting cell growth and differentiation, a peptide for treating pain, a peptide for treating neural degeneration or peptides for promoting neurogenesis;

P is independently a non-polypeptide moiety; and $R^1$ and $R^2$ are independently terminal polymer moieties, wherein the polymerizable monomer is N-substituted-5-norbornene-2,3-dicarboximide, wherein the substitution comprises the therapeutic polypeptide, wherein the therapeutic polypeptide comprises from 5 to 2000 amino acids, and wherein M(O) is

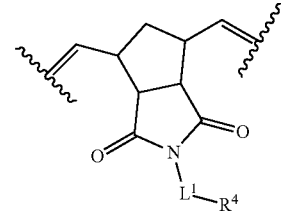

wherein, $L^1$ is independently a bond, —O—, —NH—, —COO—, —S—, —SO$_2$—, —SO$_3$—, —SO$_4$—, —SO$_2$NH—, —NHC(O)—, —C(O)NH—, —NHC(O)O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and $R^4$ is the therapeutic polypeptide.

15. The copolymer of claim 14, wherein $R^1$ comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

16. The copolymer of claim 15, wherein $R^2$ comprises a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

17. The copolymer of claim 16, wherein said non-polypeptide moiety is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl and wherein said non-polypeptide moiety does not comprise a nucleotide.

18. The copolymer of claim 16, wherein said non-polypeptide moiety is a hydrophobic moiety.

19. The copolymer of claim 16, wherein the therapeutic peptide is Nesiritide, Ceruletide, Bentiromide, Exenatide, Gonadorelin, Enfuvirtide, Vancomycin, Icatibant, Secretin, Leuprolide, Glucagon recombinant, Oxytocin, Bivalirudin, Sermorelin, Gramicidin D, Insulin recombinant, Capreomycin, Salmon Calcitonin, Vasopressin, Cosyntropin, Bacitracin, Octreotide, Abarelix, Vapreotide, Thymalfasin, Insulin recombinant, Mecasermin, Cetrorelix, Teriparatide, Corticotropin, or Pramlintide.

20. The copolymer of claim 16, wherein the therapeutic peptide is tirofiban, captopril, eptifibatide, ziconotide, teriparatide, liraglutide, lanreotide, pramlintide, enfuvirtide, icatibant, ecallantide, tesamorelin, degarelix, mifamurtide, nesiritide, buserelin, gonadorelin, goserelin, histrelin, leuprolide, nafarelin, triptorelin, abarelix, cetrorelix, or ganirelix.

21. A method of administering a polypeptide to the interior of a cell comprising contacting said cell with the copolymer of claim 1.

22. A method of treating a disease in a subject in need thereof, comprising administering to said subject the copolymer of claim 1, wherein the disease is treatable by the therapeutic peptide.

23. A pharmaceutical composition including a pharmaceutically acceptable excipient and the copolymer of claim 1.

24. A method of treating a disease in a subject in need thereof, comprising administering to said subject the pharmaceutical composition of claim 23, wherein the disease is treatable by the therapeutic peptide.

25. A method of administering a polypeptide to the interior of a cell comprising contacting said cell with the copolymer of claim 14.

26. A method of treating a disease in a subject in need thereof, comprising administering to said subject the copolymer of claim 14, wherein the disease is treatable by the therapeutic peptide.

27. A pharmaceutical composition including a pharmaceutically acceptable excipient and the copolymer of claim 14.

28. A method of treating a disease in a subject in need thereof, comprising administering to said subject the pharmaceutical composition of claim 27, wherein the disease is treatable by the therapeutic peptide.

* * * * *

SEQUENCE LISTING

<160> NUMBER OF SEQ ID NOS: 77

<210> SEQ ID NO 1
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 1

Gly Ser Gly Ser Gly
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 2

Tyr Gly Arg Lys Lys Arg Arg Gln Arg Arg Arg
1               5                   10

<210> SEQ ID NO 3
<211> LENGTH: 8

```
<212> TYPE: PRT
<213> ORGANISM: Artificial Sequence
<220> FEATURE:
<223> OTHER INFORMATION: Synthetic polypeptide

<400> SEQUENCE: 3

Arg Arg Arg Arg Arg Arg Arg Arg
1               5

<210> SEQ ID NO 4
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 4

Gly Ala Leu Val Pro Arg Gly Ser Gly Glu Arg Asp Gly
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with EDANS
<220> FEATURE:
<221> NAME/KEY: MISC_FEATURE
<222> LOCATION: (11)..(11)
<223> OTHER INFORMATION: Residue sidechain modified with DABCYL
<220> FEATURE:
<221> NAME/KEY: MOD_RES
<222> LOCATION: (16)..(16)
<223> OTHER INFORMATION: AMIDATION

<400> SEQUENCE: 5

Glu Arg Pro Ala His Leu Arg Asp Ser Gly Lys Gly Ser Gly Ser Gly
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue modified by NorGly
<220> FEATURE:
<221> NAME/KEY: MISC_FEATURE
<222> LOCATION: (1)..(1)
<223> OTHER INFORMATION: Residue sidechain modified with EDANS
<220> FEATURE:
<221> NAME/KEY: MISC_FEATURE
<222> LOCATION: (11)..(11)
<223> OTHER INFORMATION: Residue sidechain modified with DABCYL
<220> FEATURE:
<221> NAME/KEY: MOD_RES
<222> LOCATION: (16)..(16)
<223> OTHER INFORMATION: AMIDATION

<400> SEQUENCE: 6

Glu Arg Pro Ala His Leu Arg Asp Ser Gly Lys Gly Ser Gly Ser Gly
1               5                   10                  15

<210> SEQ ID NO 7
```

```
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with DABCYL
<220> FEATURE:
<221> NAME/KEY: MISC_FEATURE
<222> LOCATION: (11)..(11)
<223> OTHER INFORMATION: Residue sidechain modified with EDANS
<220> FEATURE:
<221> NAME/KEY: MOD_RES
<222> LOCATION: (16)..(16)
<223> OTHER INFORMATION: AMIDATION

<400> SEQUENCE: 7

Lys Arg Pro Ala His Leu Arg Asp Ser Gly Glu Gly Ser Gly Ser Gly
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorGly
<220> FEATURE:
<221> NAME/KEY: MISC_FEATURE
<222> LOCATION: (1)..(1)
<223> OTHER INFORMATION: Residue sidechain modified with DABCYL
<220> FEATURE:
<221> NAME/KEY: MISC_FEATURE
<222> LOCATION: (11)..(11)
<223> OTHER INFORMATION: Residue sidechain modified with EDANS
<220> FEATURE:
<221> NAME/KEY: MOD_RES
<222> LOCATION: (16)..(16)
<223> OTHER INFORMATION: AMIDATION

<400> SEQUENCE: 8

Lys Arg Pro Ala His Leu Arg Asp Ser Gly Glu Gly Ser Gly Ser Gly
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: Residue sidechain modified with EDANS
<220> FEATURE:
<221> NAME/KEY: MISC_FEATURE
<222> LOCATION: (16)..(16)
<223> OTHER INFORMATION: Residue sidechain modified with DABCYL
<220> FEATURE:
<221> NAME/KEY: MOD_RES
<222> LOCATION: (16)..(16)
<223> OTHER INFORMATION: AMIDATION

<400> SEQUENCE: 9

Gly Ser Gly Ser Gly Glu Arg Pro Ala His Leu Arg Asp Ser Gly Lys
1               5                   10                  15

<210> SEQ ID NO 10
```

```
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorGly
<220> FEATURE:
<221> NAME/KEY: MISC_FEATURE
<222> LOCATION: (6)..(6)
<223> OTHER INFORMATION: Residue sidechain modified with EDANS
<220> FEATURE:
<221> NAME/KEY: MISC_FEATURE
<222> LOCATION: (16)..(16)
<223> OTHER INFORMATION: Residue sidechain modified with DABCYL
<220> FEATURE:
<221> NAME/KEY: MOD_RES
<222> LOCATION: (16)..(16)
<223> OTHER INFORMATION: AMIDATION

<400> SEQUENCE: 10

Gly Ser Gly Ser Gly Glu Arg Pro Ala His Leu Arg Asp Ser Gly Lys
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorGly
<220> FEATURE:
<221> NAME/KEY: MISC_FEATURE
<222> LOCATION: (1)..(1)
<223> OTHER INFORMATION: Residue sidechain modified with EDANS
<220> FEATURE:
<221> NAME/KEY: MISC_FEATURE
<222> LOCATION: (11)..(11)
<223> OTHER INFORMATION: Residue sidechain modified with DABCYL
<220> FEATURE:
<221> NAME/KEY: MOD_RES
<222> LOCATION: (16)..(16)
<223> OTHER INFORMATION: AMIDATION

<400> SEQUENCE: 11

Glu Arg Pro Ala His Leu Arg Asp Ser Gly Lys Gly Ser Gly Ser Gly
1               5                   10                  15

<210> SEQ ID NO 12
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 12

Arg Gly Ser Gly Ser Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 13
```

Arg Arg Gly Ser Gly Ser Gly
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 14

Gly Ser Gly Ser Gly Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 15

Gly Ser Gly Ser Gly Arg Arg
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 16

Gly Ser Gly Ser Gly Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 17

Gly Ser Gly Ser Gly Lys Lys
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 18

Lys Leu Ala Lys Leu Ala Lys Lys Leu Ala Lys Leu Ala Lys
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Pbf

```
<220> FEATURE:
<221> NAME/KEY: MISC_FEATURE
<222> LOCATION: (3)..(3)
<223> OTHER INFORMATION: Residue sidechain modified with OtBu
<220> FEATURE:
<221> NAME/KEY: MISC_FEATURE
<222> LOCATION: (5)..(5)
<223> OTHER INFORMATION: Residue sidechain modified with OtBu

<400> SEQUENCE: 19

Arg Gly Ser Gly Ser Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Pbf
<220> FEATURE:
<221> NAME/KEY: MISC_FEATURE
<222> LOCATION: (2)..(2)
<223> OTHER INFORMATION: Residue sidechain modified with Pbf
<220> FEATURE:
<221> NAME/KEY: MISC_FEATURE
<222> LOCATION: (4)..(4)
<223> OTHER INFORMATION: Residue sidechain modified with OTBu
<220> FEATURE:
<221> NAME/KEY: MISC_FEATURE
<222> LOCATION: (6)..(6)
<223> OTHER INFORMATION: Residue sidechain modified with OTBu

<400> SEQUENCE: 20

Arg Arg Gly Ser Gly Ser Gly
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Residue sidechain modified with OtBu
<220> FEATURE:
<221> NAME/KEY: MISC_FEATURE
<222> LOCATION: (4)..(4)
<223> OTHER INFORMATION: Residue sidechain modified with OtBu
<220> FEATURE:
<221> NAME/KEY: MISC_FEATURE
<222> LOCATION: (6)..(6)
<223> OTHER INFORMATION: Residue sidechain modified with Pbf

<400> SEQUENCE: 21

Gly Ser Gly Ser Gly Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Residue sidechain modified with OtBu
```

```
<220> FEATURE:
<221> NAME/KEY: MISC_FEATURE
<222> LOCATION: (4)..(4)
<223> OTHER INFORMATION: Residue sidechain modified with OtBu
<220> FEATURE:
<221> NAME/KEY: MISC_FEATURE
<222> LOCATION: (6)..(6)
<223> OTHER INFORMATION: Residue sidechain modified with Pbf
<220> FEATURE:
<221> NAME/KEY: MISC_FEATURE
<222> LOCATION: (7)..(7)
<223> OTHER INFORMATION: Residue sidechain modified with Pbf

<400> SEQUENCE: 22

Gly Ser Gly Ser Gly Arg Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Residue sidechain modified with OtBu
<220> FEATURE:
<221> NAME/KEY: MISC_FEATURE
<222> LOCATION: (4)..(4)
<223> OTHER INFORMATION: Residue sidechain modified with OtBu
<220> FEATURE:
<221> NAME/KEY: MISC_FEATURE
<222> LOCATION: (6)..(6)
<223> OTHER INFORMATION: Residue sidechain modified with Boc

<400> SEQUENCE: 23

Gly Ser Gly Ser Gly Lys
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 24

Lys Leu Ala Lys Leu Ala Lys
1               5

<210> SEQ ID NO 25
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 25

Gly Leu Asn Asp Ile Phe Glu Ala Gln Lys Ile Glu Trp His Glu
1               5                   10                  15

<210> SEQ ID NO 26
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 26
```

```
Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25
```

<210> SEQ ID NO 27
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 27

```
Glu Glu Glu Glu Glu Glu
1               5
```

<210> SEQ ID NO 28
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 28

```
Gly Ala Pro Val Pro Tyr Pro Asp Pro Leu Glu Pro Arg
1               5                   10
```

<210> SEQ ID NO 29
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 29

```
Asp Tyr Lys Asp Asp Asp Asp Lys
1               5
```

<210> SEQ ID NO 30
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 30

```
Tyr Pro Tyr Asp Val Pro Asp Tyr Ala
1               5
```

<210> SEQ ID NO 31
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 31

```
His His His His His His
1               5
```

<210> SEQ ID NO 32
<211> LENGTH: 10
<212> TYPE: PRT
<213> ORGANISM: Artificial Sequence
<220> FEATURE:
<223> OTHER INFORMATION: Synthetic polypeptide

```
<400> SEQUENCE: 32

Glu Gln Lys Leu Ile Ser Glu Glu Asp Leu
1               5                   10

<210> SEQ ID NO 33
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 33

Lys Glu Thr Ala Ala Ala Lys Phe Glu Arg Gln His Met Asp Ser
1               5                   10                  15

<210> SEQ ID NO 34
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 34

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 35
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 35

Ser Leu Ala Glu Leu Leu Asn Ala Gly Leu Gly Gly Ser
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 36

Thr Gln Asp Pro Ser Arg Val Gly
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 37

Trp Ser His Pro Gln Phe Glu Lys
1               5

<210> SEQ ID NO 38
<211> LENGTH: 6
```

```
<212> TYPE: PRT
<213> ORGANISM: Artificial Sequence
<220> FEATURE:
<223> OTHER INFORMATION: Synthetic polypeptide

<400> SEQUENCE: 38

Cys Cys Pro Gly Cys Cys
1               5

<210> SEQ ID NO 39
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 39

Gly Lys Pro Ile Pro Asn Pro Leu Leu Gly Leu Asp Ser Thr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 40

Tyr Thr Asp Ile Glu Met Asn Arg Leu Gly Lys
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 41

Asp Leu Tyr Asp Asp Asp Asp Lys
1               5

<210> SEQ ID NO 42
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 42

Thr Asp Lys Asp Met Thr Ile Thr Phe Thr Asn Lys Lys Asp Ala Glu
1               5                   10                  15

<210> SEQ ID NO 43
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 43

Ala His Ile Val Met Val Asp Ala Tyr Lys Pro Thr Lys
1               5                   10

<210> SEQ ID NO 44
<211> LENGTH: 6
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MISC_FEATURE
<222> LOCATION: (1)..(1)
<223> OTHER INFORMATION: Residue sidechain modified with Pbf
<220> FEATURE:
<221> NAME/KEY: MISC_FEATURE
<222> LOCATION: (3)..(3)
<223> OTHER INFORMATION: Residue sidechain modified with OtBu
<220> FEATURE:
<221> NAME/KEY: MISC_FEATURE
<222> LOCATION: (5)..(5)
<223> OTHER INFORMATION: Residue sidechain modified with OtBu
<220> FEATURE:
<221> NAME/KEY: MOD_RES
<222> LOCATION: (6)..(6)
<223> OTHER INFORMATION: AMIDATION

<400> SEQUENCE: 44

Arg Gly Ser Gly Ser Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MISC_FEATURE
<222> LOCATION: (1)..(1)
<223> OTHER INFORMATION: Residue sidechain modified with Pbf
<220> FEATURE:
<221> NAME/KEY: MISC_FEATURE
<222> LOCATION: (2)..(2)
<223> OTHER INFORMATION: Residue sidechain modified with Pbf
<220> FEATURE:
<221> NAME/KEY: MISC_FEATURE
<222> LOCATION: (4)..(4)
<223> OTHER INFORMATION: Residue sidechain modified with OtBu
<220> FEATURE:
<221> NAME/KEY: MISC_FEATURE
<222> LOCATION: (6)..(6)
<223> OTHER INFORMATION: Residue sidechain modified with OtBu
<220> FEATURE:
<221> NAME/KEY: MOD_RES
<222> LOCATION: (7)..(7)
<223> OTHER INFORMATION: AMIDATION

<400> SEQUENCE: 45

Arg Arg Gly Ser Gly Ser Gly
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAHa
<220> FEATURE:
<221> NAME/KEY: MISC_FEATURE
```

```
<222> LOCATION: (2)..(2)
<223> OTHER INFORMATION: Residue sidechain modified with OtBu
<220> FEATURE:
<221> NAME/KEY: MISC_FEATURE
<222> LOCATION: (4)..(4)
<223> OTHER INFORMATION: Residue sidechain modified with OtBu
<220> FEATURE:
<221> NAME/KEY: MISC_FEATURE
<222> LOCATION: (6)..(6)
<223> OTHER INFORMATION: Residue sidechain modified with Pbf
<220> FEATURE:
<221> NAME/KEY: MOD_RES
<222> LOCATION: (6)..(6)
<223> OTHER INFORMATION: AMIDATION

<400> SEQUENCE: 46

Gly Ser Gly Ser Gly Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MISC_FEATURE
<222> LOCATION: (2)..(2)
<223> OTHER INFORMATION: Residue sidechain modified with OtBu
<220> FEATURE:
<221> NAME/KEY: MISC_FEATURE
<222> LOCATION: (4)..(4)
<223> OTHER INFORMATION: Residue sidechain modified with OtBu
<220> FEATURE:
<221> NAME/KEY: MISC_FEATURE
<222> LOCATION: (6)..(6)
<223> OTHER INFORMATION: Residue sidechain modified with Pbf
<220> FEATURE:
<221> NAME/KEY: MISC_FEATURE
<222> LOCATION: (7)..(7)
<223> OTHER INFORMATION: Residue sidechain modified with Pbf
<220> FEATURE:
<221> NAME/KEY: MOD_RES
<222> LOCATION: (7)..(7)
<223> OTHER INFORMATION: AMIDATION

<400> SEQUENCE: 47

Gly Ser Gly Ser Gly Arg Arg
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MISC_FEATURE
<222> LOCATION: (2)..(2)
<223> OTHER INFORMATION: Residue sidechain modified with OtBu
<220> FEATURE:
<221> NAME/KEY: MISC_FEATURE
<222> LOCATION: (4)..(4)
<223> OTHER INFORMATION: Residue sidechain modified with OtBu
<220> FEATURE:
<221> NAME/KEY: MISC_FEATURE
<222> LOCATION: (6)..(6)
```

<223> OTHER INFORMATION: Residue sidechain modified with Boc
<220> FEATURE:
<221> NAME/KEY: MOD_RES
<222> LOCATION: (6)..(6)
<223> OTHER INFORMATION: AMIDATION

<400> SEQUENCE: 48

Gly Ser Gly Ser Gly Lys
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha

<400> SEQUENCE: 49

Gly Ser Gly Ser Gly Lys Lys
1               5

<210> SEQ ID NO 50
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MOD_RES
<222> LOCATION: (14)..(14)
<223> OTHER INFORMATION: AMIDATION

<400> SEQUENCE: 50

Lys Leu Ala Lys Leu Ala Lys Lys Leu Ala Lys Leu Ala Lys
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MOD_RES
<222> LOCATION: (7)..(7)
<223> OTHER INFORMATION: AMIDATION

<400> SEQUENCE: 51

Lys Leu Ala Lys Leu Ala Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE

```
<222> LOCATION: (1)..(1)
<223> OTHER INFORMATION: Residue saidechain modified with Flu
<220> FEATURE:
<221> NAME/KEY: MOD_RES
<222> LOCATION: (7)..(7)
<223> OTHER INFORMATION: AMIDATION

<400> SEQUENCE: 52

Lys Arg Gly Ser Gly Ser Gly
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (8)..(8)
<223> OTHER INFORMATION: AMIDATION

<400> SEQUENCE: 53

Lys Arg Arg Gly Ser Gly Ser Gly
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (7)..(7)
<223> OTHER INFORMATION: AMIDATION

<400> SEQUENCE: 54

Lys Gly Ser Gly Ser Gly Arg
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (8)..(8)
<223> OTHER INFORMATION: AMIDATION

<400> SEQUENCE: 55

Lys Gly Ser Gly Ser Gly Arg Arg
1               5

<210> SEQ ID NO 56
<211> LENGTH: 7
<212> TYPE: PRT
```

```
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (7)..(7)
<223> OTHER INFORMATION: AMIDATION

<400> SEQUENCE: 56

Lys Gly Ser Gly Ser Gly Lys
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (8)..(8)
<223> OTHER INFORMATION: AMIDATION

<400> SEQUENCE: 57

Lys Gly Ser Gly Ser Gly Lys Lys
1               5

<210> SEQ ID NO 58
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (15)..(15)
<223> OTHER INFORMATION: AMIDATION

<400> SEQUENCE: 58

Lys Lys Leu Ala Lys Leu Ala Lys Leu Ala Lys Leu Ala Lys
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with 5/6-Flu
<220> FEATURE:
<221> NAME/KEY: MOD_RES
<222> LOCATION: (12)..(12)
<223> OTHER INFORMATION: AMIDATION

<400> SEQUENCE: 59

Lys Tyr Gly Arg Lys Lys Arg Arg Gln Arg Arg Arg
1               5                   10
```

```
<210> SEQ ID NO 60
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with 5/6-Flu
<220> FEATURE:
<221> NAME/KEY: MOD_RES
<222> LOCATION: (7)..(7)
<223> OTHER INFORMATION: AMIDATION

<400> SEQUENCE: 60

Lys Arg Arg Arg Arg Arg Arg
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with 5/6-Flu
<220> FEATURE:
<221> NAME/KEY: MOD_RES
<222> LOCATION: (6)..(6)
<223> OTHER INFORMATION: AMIDATION

<400> SEQUENCE: 61

Lys Gly Ser Gly Ser Gly
1               5

<210> SEQ ID NO 62
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MOD_RES
<222> LOCATION: (11)..(11)
<223> OTHER INFORMATION: AMIDATION

<400> SEQUENCE: 62

Tyr Gly Arg Lys Lys Arg Arg Gln Arg Arg Arg
1               5                   10

<210> SEQ ID NO 63
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MISC_FEATURE
<222> LOCATION: (1)..(1)
<223> OTHER INFORMATION: Residue sidechain modified with Pbf
```

```
<220> FEATURE:
<221> NAME/KEY: MISC_FEATURE
<222> LOCATION: (2)..(2)
<223> OTHER INFORMATION: Residue sidechain modified with Pbf
<220> FEATURE:
<221> NAME/KEY: MISC_FEATURE
<222> LOCATION: (3)..(3)
<223> OTHER INFORMATION: Residue sidechain modified with Pbf
<220> FEATURE:
<221> NAME/KEY: MISC_FEATURE
<222> LOCATION: (4)..(4)
<223> OTHER INFORMATION: Residue sidechain modified with Pbf
<220> FEATURE:
<221> NAME/KEY: MISC_FEATURE
<222> LOCATION: (5)..(5)
<223> OTHER INFORMATION: Residue sidechain modified with Pbf
<220> FEATURE:
<221> NAME/KEY: MISC_FEATURE
<222> LOCATION: (6)..(6)
<223> OTHER INFORMATION: Residue sidechain modified with Pbf
<220> FEATURE:
<221> NAME/KEY: MISC_FEATURE
<222> LOCATION: (7)..(7)
<223> OTHER INFORMATION: Residue sidechain modified with Pbf
<220> FEATURE:
<221> NAME/KEY: MISC_FEATURE
<222> LOCATION: (8)..(8)
<223> OTHER INFORMATION: Residue sidechain modified with Pbf
<220> FEATURE:
<221> NAME/KEY: MOD_RES
<222> LOCATION: (8)..(8)
<223> OTHER INFORMATION: AMIDATION

<400> SEQUENCE: 63

Arg Arg Arg Arg Arg Arg Arg Arg
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MOD_RES
<222> LOCATION: (5)..(5)
<223> OTHER INFORMATION: AMIDATION

<400> SEQUENCE: 64

Gly Ser Gly Ser Gly
1               5

<210> SEQ ID NO 65
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorGly
<220> FEATURE:
<221> NAME/KEY: MISC_FEATURE
<222> LOCATION: (1)..(1)
<223> OTHER INFORMATION: Residue sidechain modified with EDANS

<400> SEQUENCE: 65

Glu Arg Pro Ala His
1               5
```

```
<210> SEQ ID NO 66
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: Residue sidechain modified with DABCYL
<220> FEATURE:
<221> NAME/KEY: MOD_RES
<222> LOCATION: (11)..(11)
<223> OTHER INFORMATION: AMIDATION

<400> SEQUENCE: 66

Leu Arg Asp Ser Gly Lys Gly Ser Gly Ser Gly
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAHa
<220> FEATURE:
<221> NAME/KEY: MOD_RES
<222> LOCATION: (8)..(8)
<223> OTHER INFORMATION: AMIDATION

<400> SEQUENCE: 67

Arg Arg Arg Arg Arg Arg Arg Arg
1               5

<210> SEQ ID NO 68
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MOD_RES
<222> LOCATION: (11)..(11)
<223> OTHER INFORMATION: AMIDATION

<400> SEQUENCE: 68

Tyr Gly Arg Lys Lys Arg Arg Gln Arg Arg Arg
1               5                   10

<210> SEQ ID NO 69
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorAha
<220> FEATURE:
<221> NAME/KEY: MOD_RES
<222> LOCATION: (5)..(5)
<223> OTHER INFORMATION: AMIDATION
```

```
<400> SEQUENCE: 69

Gly Ser Gly Ser Gly
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (9)..(9)
<223> OTHER INFORMATION: AMIDATION

<400> SEQUENCE: 70

Lys Arg Arg Arg Arg Arg Arg Arg
1               5

<210> SEQ ID NO 71
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (11)..(11)
<223> OTHER INFORMATION: AMIDATION

<400> SEQUENCE: 71

Lys Tyr Gly Arg Lys Lys Arg Arg Gln Arg Arg
1               5                   10

<210> SEQ ID NO 72
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: Residue sidechain modified with Flu
<220> FEATURE:
<221> NAME/KEY: MOD_RES
<222> LOCATION: (6)..(6)
<223> OTHER INFORMATION: AMIDATION

<400> SEQUENCE: 72

Lys Gly Ser Gly Ser Gly
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 73
```

```
Gly Ala Leu Val Pro Arg Gly Ser
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 74

Gly Glu Arg Asp Gly
1               5

<210> SEQ ID NO 75
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 75

Cys Arg Pro Ala His Leu Arg Asp Ser Gly
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (10)..(10)
<223> OTHER INFORMATION: Residue sidechain modified with DABCYL
<220> FEATURE:
<221> NAME/KEY: MOD_RES
<222> LOCATION: (15)..(15)
<223> OTHER INFORMATION: AMIDATION

<400> SEQUENCE: 76

Arg Pro Ala His Leu Arg Asp Ser Gly Lys Gly Ser Gly Ser Gly
1               5                   10                  15

<210> SEQ ID NO 77
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: Residue modified with NorGly
<220> FEATURE:
<221> NAME/KEY: misc_feature
<222> LOCATION: (1)..(1)
<223> OTHER INFORMATION: Residue sidechain modified by EDANS

<400> SEQUENCE: 77

Glu Arg Pro Ala His
1               5
```